US007795262B2

(12) United States Patent
Gao et al.

(10) Patent No.: US 7,795,262 B2
(45) Date of Patent: Sep. 14, 2010

(54) PIPERAZINYL OXOALKYL TETRAHYDROISOQUINOLINES AND RELATED ANALOGUES

(75) Inventors: Yang Gao, Madison, CT (US); Bingsong Han, North Haven, CT (US); Linghong Xie, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 226 days.

(21) Appl. No.: 11/716,354

(22) Filed: Mar. 8, 2007

(65) Prior Publication Data

US 2007/0232591 A1    Oct. 4, 2007

Related U.S. Application Data

(60) Provisional application No. 60/781,516, filed on Mar. 10, 2006.

(51) Int. Cl.
*A61K 31/497* (2006.01)
*C07D 241/04* (2006.01)
*C07D 295/00* (2006.01)

(52) U.S. Cl. .................. 514/252.12; 544/358
(58) Field of Classification Search .......... None
See application file for complete search history.

(56) References Cited

U.S. PATENT DOCUMENTS

| | | | |
|---|---|---|---|
| 6,417,195 | B1 | 7/2002 | Lebl |
| 6,723,730 | B2 | 4/2004 | Bakthavatchalam et al. |
| 6,908,926 | B1 | 6/2005 | Dorwald et al. |
| 6,992,085 | B2 | 1/2006 | Goldstein et al. |
| 7,067,507 | B2 * | 6/2006 | Pulley et al. ............. 514/183 |
| 7,208,497 | B2 | 4/2007 | Dorwald et al. |
| 2004/0019039 | A1 | 1/2004 | Dorwald et al. |
| 2004/0053956 | A1 | 3/2004 | Bromidge et al. |

FOREIGN PATENT DOCUMENTS

| | | | |
|---|---|---|---|
| EP | 441226 | * | 8/1998 |
| WO | 9823593 | A1 | 6/1998 |
| WO | WO 9823593 | * | 6/1998 |
| WO | 0063208 | A1 | 10/2000 |
| WO | WO 03/031432 | A1 | 4/2003 |
| WO | WO 2004/018432 | A1 | 3/2004 |
| WO | WO 2004/026837 | A2 | 4/2004 |
| WO | WO 2004/054973 | A2 | 7/2004 |
| WO | WO 2005005392 | * | 1/2005 |
| WO | WO 2005/035495 | A2 | 4/2005 |
| WO | WO 2005/058837 | A1 | 6/2005 |
| WO | WO 2005/082893 | A2 | 9/2005 |
| WO | WO 2005/111036 | A1 | 11/2005 |
| WO | WO 2006/018260 | A1 | 2/2006 |
| WO | 2008012010 | A1 | 1/2008 |
| WO | 2008068174 | A1 | 6/2008 |

OTHER PUBLICATIONS

Chavez et al. Brain Research, 2005, 1064, 1-9.*
Witjmans et al. Expert Opinion on Investigational Drugs, 2007, 16(7), 967-85.*
Hancock et al. Expert Opinion on Investigational Drugs, 2006, 71, 1103-13.*
"Type 1 Diabetes prevention", http://diabetes.webmd.com/tc/type-1-diabetes-prevention, accessed May 26, 2009.*
"Eating Disorders", http://www.nlm.nih.gov/cgi/mesh/2009/MB_cgi, accessed Jun. 2, 2009.*
"Schizophrenia-Prevention", http://www.webmd.com/schizophrenia/tc/schizophrenia- prevention, accessed Dec. 12, 2008.*
International Search Report and Written Opinion in corresponding PCT Application No. PCT/US2007/005762.
Supplemental European Search Report for 07752458.5—1211/1998620.
Batey, et al., "Parallel Synthesis of Tri- and Tetrasubstituted Ureas from Carbamoyl Imidazolium Salts," Combinatorial Chemistry and High Throughput Screening, vol. 5(3), 2002, pp. 219-232.
Hromatka, et al., "Piperazine-substituted isoquinoline derivatives," Monatshefte Fuer Chemie, vol. 97(1), 1966, pp. 19-31. (Translation of Abstract Only).
Lau, et al., "Ureas with Histamine H3-antagonist receptor activity—A new scaffold discovered by lead-hopping crom cimmanic acid amides," Bioorganic & Medicinal Chemistry Letters, vol. 16(20), 2006, pp. 5303-5308.
Stark, "Recent advances in histamine H3/H4 receptor ligands," Expert Opinion on Therapeutic Patents, vol. 13(6), 2003, pp. 851-865.

* cited by examiner

*Primary Examiner*—James O Wilson
*Assistant Examiner*—Noble Jarrell
(74) *Attorney, Agent, or Firm*—Cantor Colburn LLP

(57) ABSTRACT

Piperazinyl oxoalkyl tetrahydroisoquinolines and related analogues of the Formula:

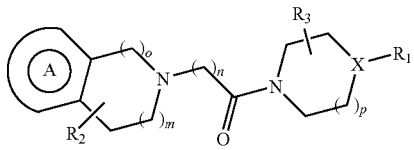

are provided, in which variables are as described herein. Such compounds may be used to modulate ligand binding to histamine H3 receptors in vivo or in vitro, and are particularly useful in the treatment of a variety of central nervous system (CNS) and other disorders in humans, domesticated companion animals and livestock animals. Compounds provided herein may be administered alone or in combination with one or more other CNS agents to potentiate the effects of the other CNS agent(s). Pharmaceutical compositions and methods for treating such disorders are provided, as are methods for using such ligands for detecting histamine H3 receptors (e.g., receptor localization studies).

21 Claims, No Drawings

PIPERAZINYL OXOALKYL TETRAHYDROISOQUINOLINES AND RELATED ANALOGUES

CROSS-REFERENCE TO RELATED APPLICATIONS

This application claims the benefit of U.S. provisional patent application No. 60/781,516, filed Mar. 10, 2006, the contents of which are hereby incorporated by reference in their entirety.

FIELD OF THE INVENTION

This invention relates generally to piperazinyl oxoalkyl tetrahydroisoquinolines and related analogues, and to the use of such compounds for treating conditions responsive to histamine H3 receptor modulation. The invention further relates to the use of such compounds as probes for the detection and localization of histamine H3 receptors.

BACKGROUND OF THE INVENTION

Hormones and neurotransmitters regulate a wide variety of biological functions, often via specific receptor proteins located on the surface of living cells. Many of these receptors carry out intracellular signaling via the activation of coupled guanosine triphosphate-binding proteins (G proteins); such receptors are collectively called G protein-coupled receptors or GPCRs. The important role of GPCRs in the regulation of cell and organ function has attracted attention to these receptors as targets for new pharmaceutical agents.

Histamine is a multifunctional chemical transmitter that signals through specific cell surface GPCRs. To date, four histamine receptor subtypes have been identified: H1, H2, H3 and H4. Histamine H3 receptor is a presynaptic GPCR that is found primarily in the central nervous system, although lower levels are also found in the peripheral nervous system. Genes encoding the H3 receptor have been reported in various organisms, including humans (see Lovenberg et al. (1999) *Molecular Pharmacology* 55:1101-07), and alternative splicing of this gene appears to result in multiple isoforms. The histamine H3 receptor is an auto- and hetero-receptor whose activation leads to a decreased release of neurotransmitters (including histamine, acetylcholine, norepinephrine and glutamate) from neurons in the brain. Histamine H3 receptor is involved in the regulation of processes such as sleep and wakefulness, feeding and memory.

Antagonists of histamine H3 receptor increase synthesis and release of cerebral histamine and other neurotransmitters, inducing an extended wakefulness, an improvement in cognitive processes, a reduction in food intake and a normalization of vestibular reflexes. Such antagonists are useful, for example, as therapeutics for central nervous system disorders such as Alzheimer's disease, Parkinson's disease, schizophrenia, mood and attention alterations including attention deficit hyperactivity disorder and attention deficit disorder, memory and learning disorders, cognitive disorders (such as mild cognitive impairment and cognitive deficits in psychiatric pathologies), epilepsy, migraine, and disorders associated with the regulation of sleep and wakefulness, as well as in the treatment and prevention of conditions such as obesity, eating disorders, diabetes, vertigo, motion sickness and allergic rhinitis.

Accordingly, there is a need for new H3 receptor modulators. The present invention fulfills this need, and provides further related advantages.

SUMMARY OF THE INVENTION

In certain aspects, the present invention provides piperazinyl oxoalkyl tetrahydroisoquinolines of Formula I:

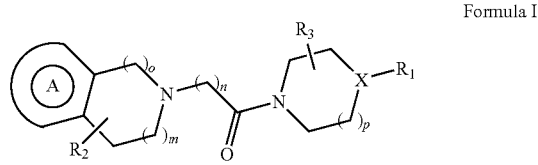

Formula I and pharmaceutically acceptable salts, solvates and esters of such compounds. Within Formula I:

n and p are independently 0, 1, 2 or 3;

m and o are independently 1, 2 or 3;

X is CH or N, such that if p is 0 then X is CH;

$R_1$ is $C_1$-$C_6$alkyl, $C_2$-$C_6$alkenyl, $C_2$-$C_6$alkynyl, mono- or di-($C_1$-$C_6$alkyl)amino, ($C_3$-$C_8$cycloalkyl)$C_0$-$C_2$alkyl or (3- to 8-membered heterocycloalkyl)$C_0$-$C_2$alkyl, each of which is optionally substituted and each of which is preferably substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl;

or $R_1$ and $R_3$ are taken together (with the ring atoms to which they are attached) to form a fused 5- to 7-membered cycloalkyl or heterocycloalkyl ring, each of which is optionally substituted and each of which is preferably substituted with from 0 to 3 substituents independently chosen from oxo, $C_1$-$C_6$alkyl, $C_1$-$C_6$haloalkyl and $C_1$-$C_6$alkoxy;

$R_2$ represents optional substituents of the indicated ring; preferably $R_2$ represents from 0 to 4 substituents independently chosen from:

(i) $C_1$-$C_6$alkyl, $C_2$-$C_6$alkenyl, $C_2$-$C_6$alkynyl, ($C_3$-$C_8$cycloalkyl)$C_0$-$C_2$alkyl, and $C_1$-$C_6$haloalkyl; or two $R_2$ groups are taken together to form a $C_1$-$C_3$alkylene bridge; and (ii) phenyl$C_0$-$C_4$alkyl that is substituted with from 0 to 3 substituents independently chosen from halogen and $C_1$-$C_6$alkyl; or two $R_2$ groups are taken together with a ring atom to which they are attached to form a spiro $C_3$-$C_7$cycloalkyl or a spiro 4- to 7-membered heterocycloalkyl, each of which is substituted with from 0 to 3 substituents independently chosen from $C_1$-$C_6$alkyl;

$R_3$ represents optional substituents of the indicated ring; preferably $R_3$ represents from 0 to 4 substituents independently chosen from $C_1$-$C_6$alkyl and $C_1$-$C_6$haloalkyl; or two $R_3$ groups are taken together to form a $C_1$-$C_3$alkylene bridge; or two $R_3$ groups are taken together to form a fused 5- to 7-membered cycloalkyl or heterocycloalkyl ring, each of which is substituted with from 0 to 3 substituents independently chosen from oxo, $C_1$-$C_6$alkyl, and $C_1$-$C_6$alkoxy;

represents a phenyl ring or a 5- or 6-membered heteroaryl ring, each of which rings is optionally substituted; and each of which rings is preferably substituted with (i) zero or one $R_x$, and (ii) from 0 to 3 substituents independently chosen from $R_y$;

$R_x$ is:
(i) halogen, cyano, aminocarbonyl or COOH; or
(ii) $C_1$-$C_6$alkyl, $C_2$-$C_6$alkenyl, $C_2$-$C_6$alkynyl, $C_1$-$C_6$alkoxy, $C_1$-$C_6$-aminoalkyl, $C_1$-$C_6$alkanoyl, $C_1$-$C_6$alkoxycarbonyl, $C_1$-$C_6$alkylsulfonyl, mono- or di-($C_1$-$C_6$alkyl)aminocarbonyl, mono- or di-($C_1$-$C_6$alkyl)amino$C_0$-$C_4$alkyl, ($C_3$-$C_{10}$cycloalkyl)-J-$C_0$-$C_4$alkyl, (3- to 10-membered heterocycloalkyl)-J-$C_0$-$C_4$alkyl, phenyl-J-$C_0$-$C_4$alkyl, naphthyl-J-$C_0$-$C_4$alkyl or (5- to 14-membered heteroaryl)-J-$C_0$-$C_4$alkyl, each of which is substituted with from 0 to 4 substituents independently chosen from:
(a) oxo, halogen, cyano, hydroxy, amino, nitro and aminocarbonyl; and
(b) groups of the formula D-J-E-
wherein:
D represents $C_1$-$C_6$alkyl, $C_2$-$C_6$alkenyl, $C_2$-$C_6$alkynyl, $C_3$-$C_7$cycloalkyl, 3- to 7-membered heterocycloalkyl, phenyl or 5- or 6-membered heteroaryl, each of which is substituted with from 0 to 6 substituents independently chosen from halogen, cyano, hydroxy, amino, nitro, $C_1$-$C_4$alkyl, $C_1$-$C_4$haloalkyl and $C_1$-$C_4$alkoxy;
Each J is independently absent, O, $CH_2$O, OCH$_2$, C(=O), OC(=O), C(=O)O, S(O)$_m$, N($R_z$), C(=O)N($R_z$), N($R_z$)C(=O), N($R_z$)S(O)$_m$ or S(O)$_m$N($R_z$), wherein each m is independently 0, 1 or 2 and each $R_z$ is independently hydrogen or $C_1$-$C_6$alkyl; and
E is absent or represents $C_1$-$C_6$alkylene or $C_1$-$C_6$alkoxy; and Each $R_y$ is independently oxo, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, phenyl$C_0$-$C_2$alkyl or (5- or 6-membered heteroaryl)$C_0$-$C_2$alkyl.

Within certain aspects, piperazinyl oxoalkyl tetrahydroisoquinolines provided herein are histamine H3 receptor modulators that exhibit a $K_i$ at a histamine H3 receptor, preferably a human H3 receptor, that is no greater than 4 micromolar, 1 micromolar, 500 nanomolar, 100 nanomolar, 50 nanomolar or 10 nanomolar, as determined using a histamine-induced H3 receptor GTP binding assay.

Within certain aspects, compounds provided herein are labeled with a detectable marker (e.g., radiolabeled or fluorescein conjugated).

The present invention further provides, within other aspects, pharmaceutical compositions comprising at least one piperazinyl oxoalkyl tetrahydroisoquinoline as provided herein in combination with a physiologically acceptable carrier or excipient.

Within further aspects, methods are provided for modulating H3 receptor activity, comprising contacting a cell (e.g., neuronal) expressing H3 receptor with at least one H3 receptor modulator as described herein. Such contact may occur in vivo or in vitro and is generally performed using a concentration of compound that is sufficient to alter H3 receptor GTP binding in vitro (e.g., using an assay provided in Example 7 or Example 8, herein).

The present invention further provides methods for treating a condition responsive to H3 receptor modulation in a patient, comprising administering to the patient a therapeutically effective amount of at least one H3 receptor modulator. Such conditions include, for example, attention deficit disorder, attention deficit hyperactivity disorder, dementia, schizophrenia, cognitive disorders (including mild cognitive impairment), epilepsy, migraine, excessive daytime sleepiness (EDS) and related disorders such as shift work sleep disorder, jet lag, narcolepsy, sleep apnea, allergic rhinitis, vertigo, motion sickness, memory disorders such as Alzheimer's disease, Parkinson's disease, obesity, eating disorders and diabetes.

Within further aspects, the present invention provides methods for determining the presence or absence of H3 receptor in a sample, comprising: (a) contacting a sample with a H3 receptor modulator as described herein under conditions that permit binding of the H3 receptor modulator to H3 receptor; and (b) detecting a level of the H3 modulator bound to H3 receptor.

The present invention also provides packaged pharmaceutical preparations, comprising: (a) a pharmaceutical composition as described herein in a container; and (b) instructions for using the composition to treat one or more conditions responsive to H3 receptor modulation, such as the conditions recited herein.

In yet another aspect, the present invention provides methods of preparing the compounds disclosed herein, including the intermediates.

These and other aspects of the present invention will become apparent upon reference to the following detailed description.

DETAILED DESCRIPTION

As noted above, the present invention provides piperazinyl oxoalkyl tetrahydroisoquinolines and related analogues. Such compounds may be used in vitro or in vivo, to modulate H3 receptor activity in a variety of contexts.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, X, n). Unless otherwise specified, each variable within such a formula is defined independently of any other variable, and any variable that occurs more than one time in a formula is defined independently at each occurrence.

The phrase "piperazinyl oxoalkyl tetrahydroisoquinolines and related analogues," as used herein, encompasses all compounds of Formula I (as well as compounds Formulas II-V and subformulas thereof), including any enantiomers, racemates and stereoisomers, as well as pharmaceutically acceptable salts, solvates and esters of such compounds.

A "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutically acceptable anions for use in salt formation include, but are not limited to, acetate, 2-acetoxybenzoate, ascorbate, benzoate, bicarbonate, bitartrate, bromide, calcium edetate, carbonate, chloride, citrate, dihydrochloride, diphosphate, edetate, estolate (ethylsuccinate), formate, fumarate, gluceptate, gluconate, glutamate, glycolate, glycollylarsanilate, hexylresorcinate, hydrabamine, hydrobromide, hydrochloride, hydroiodide, hydroxymaleate, hydroxynaphthoate, iodide, isethionate, lactate, lactobionate, malate, maleate, mandelate, methylbromide, methylnitrate, methylsulfate, mucate, napsylate, nitrate, pamoate, pantothenate, phenylacetate, phosphate, polygalacturonate, propionate, salicylate, stearate, subacetate, succinate, sulfamate, sulfanilate, sulfate, sulfonates including besylate (benzenesulfonate), camsylate (camphorsulfonate), edisylate (ethane-1,2-disulfonate), esylate (ethanesulfonate) 2-hydroxyethylsulfonate, mesylate (methanesulfonate), triflate (trifluoromethanesulfonate) and tosylate (p-toluenesulfonate), tannate, tartrate, teoclate and triethiodide. Similarly, pharmaceutically acceptable cations for use in salt formation include, but are not limited to ammonium, benzathine, chloroprocaine, choline, diethanolamine, ethylenediamine, meglumine, procaine, and metals such as aluminum, calcium, lithium, magnesium, potassium, sodium and zinc. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, methanol, isopropanol or acetonitrile, is preferred.

It will be apparent that each compound provided herein may, but need not, be formulated as a solvate (e.g., hydrate) or non-covalent complex. In addition, the various crystal forms and polymorphs are within the scope of the present invention. Also provided herein are prodrugs of the compounds of the recited Formulas. A "prodrug" is a compound that may not fully satisfy the structural requirements of the compounds provided herein, but is modified in vivo, following administration to a patient, to produce a compound a formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_4$alkyl" refers to a single covalent bond ($C_0$) or an alkylene group having from 1 to 4 carbon atoms.

"Alkylene" refers to a divalent alkyl group. $C_1$-$C_4$alkylene is an alkylene group having from 1 to 4 carbon atoms. $C_0$-$C_4$alkylene is a single covalent bond or an alkylene group having from 1 to 4 carbon atoms.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. A "($C_3$-$C_8$cycloalkyl)$C_0$-$C_2$alkyl" is a $C_3$-$C_8$cycloalkyl group linked via a single covalent bond or a methylene or ethylene group.

By "alkoxy," as used herein, is meant an alkyl group attached via an oxygen bridge. Alkoxy groups include $C_1$-$C_8$alkoxy and $C_1$-$C_4$alkoxy groups, which have from 1 to 8 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups. Similarly, "alkylthio" refers to an alkyl group attached via a sulfur bridge.

The term "oxo" is used herein to refer to an oxygen substituent of a carbon atom that results in the formation of a carbonyl group (C=O). An oxo group that is a substituent of a nonaromatic carbon atom results in a conversion of —$CH_2$— to —C(=O). An oxo group that is a substituent of an aromatic carbon atom results in a conversion of —CH— to —C(=O)— and may result in a loss of aromaticity.

The term "alkanoyl" refers to an acyl group (e.g., —C=O) alkyl), in which carbon atoms are in a linear or branched alkyl arrangement and where attachment is through the carbon of the carbonyl group. Alkanoyl groups have the indicated number of carbon atoms, with the carbonyl carbon being included in the numbered carbon atoms. For example a $C_2$alkanoyl group is an acetyl group having the formula —(C=O)$CH_3$; "$C_1$alkanoyl" refers to —(C=O)H. Alkanoyl groups include, for example, $C_1$-$C_8$alkanoyl, $C_1$-$C_6$alkanoyl and $C_1$-$C_4$alkanoyl groups, which have from 1 to 8, from 1 to 6 or from 1 to 4 carbon atoms, respectively.

An "alkanone" is a ketone group in which carbon atoms are in a linear or branched alkyl arrangement. "$C_3$-$C_8$alkanone," "$C_3$-$C_6$alkanone" and "$C_3$-$C_4$alkanone" refer to an alkanone having from 3 to 8, 6 or 4 carbon atoms, respectively. By way of example, a $C_3$alkanone group has the structure —$CH_2$—(C=O)—$CH_3$.

Similarly, "alkyl ether" refers to a linear or branched ether substituent (i.e., an alkyl group that is substituted with an alkoxy group). Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. A $C_2$alkyl ether has the structure —$CH_2$—O—$CH_3$ The term "alkoxycarbonyl" refers to an alkoxy group attached through a keto (—C(=O)—) bridge (i.e., a group having the general structure —C(=O)—O-alkyl). Alkoxycarbonyl groups include $C_1$-$C_8$, $C_1$-$C_6$ and $C_1$-$C_4$alkoxycarbonyl groups, which have from 1 to 8, 6 or 4 carbon atoms, respectively, in the alkyl portion of the group (i.e., the carbon of the keto bridge is not included in the indicated number of carbon atoms). "$C_1$alkoxycarbonyl" refers to —C(=O)—$OCH_3$; $C_3$alkoxycarbonyl indicates —C(=O)—O—$(CH_2)_2CH_3$ or —C(=O)—O—(CH)$(CH_3)_2$.

"Alkylsulfonyl" refers to groups of the formula —$(SO_2)$-alkyl, in which the sulfur atom is the point of attachment. Alkylsulfonyl groups include, for example, $C_1$-$C_6$alkylsulfonyl and $C_1$-$C_4$alkylsulfonyl groups, which have from 1 to 6 or from 1 to 4 carbon atoms, respectively.

"Aminosulfonyl" refers to groups of the formula —$(SO_2)NH_2$, in which the sulfur atom is the point of attachment. The term "mono- or di-($C_1$-$C_6$alkyl)aminosulfonyl" refers to groups that satisfy the formula —$(SO_2)NR_2$, in which the sulfur atom is the point of attachment, and in which one R is $C_1$-$C_6$alkyl and the other R is hydrogen or an independently chosen $C_1$-$C_6$alkyl.

The term "aminocarbonyl" refers to an amide group (i.e., —C(=O)$NH_2$). The term "mono- or di-($C_1$-$C_6$alkyl)aminocarbonyl" refers to groups of the formula —(C=O)—N$(R)_2$, in which the carbonyl is the point of attachment, one R is $C_1$-$C_6$alkyl and the other R is hydrogen or an independently chosen $C_1$-$C_6$alkyl.

"Alkylamino" refers to a secondary or tertiary amine that has the general structure —NH-alkyl or —N(alkyl)(alkyl), wherein each alkyl is selected independently from alkyl, cycloalkyl and (cycloalkyl)alkyl groups. Such groups include, for example, mono- and di-($C_1$-$C_8$alkyl)amino groups, in which each $C_1$-$C_8$alkyl may be the same or different, as well as mono- and di-($C_1$-$C_6$alkyl)amino groups and mono- and di-($C_1$-$C_4$alkyl)amino groups.

"Alkylaminoalkyl" refers to an alkylamino group linked via an alkylene group (i.e., a group having the general structure -alkylene-NH-alkyl or -alkylene-N(alkyl)(alkyl)) in which each alkyl is selected independently from alkyl, cycloalkyl and (cycloalkyl)alkyl groups. Alkylaminoalkyl groups include, for example, mono- and di-($C_1$-$C_8$alkyl)amino$C_1$-$C_4$alkyl.

"Mono- or di-($C_1$-$C_8$alkyl)amino$C_0$-$C_4$alkyl" refers to a mono- or di-($C_1$-$C_8$alkyl)amino group linked via a single covalent bond or a $C_1$-$C_4$alkylene group. The following are representative alkylaminoalkyl groups:

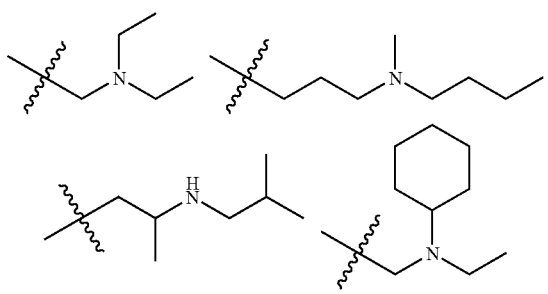

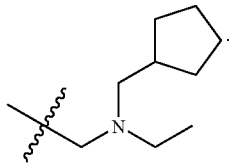

It will be apparent that the definition of "alkyl" as used in the terms "alkylamino" and "alkylaminoalkyl" differs from the definition of "alkyl" used for all other alkyl-containing groups, in the inclusion of cycloalkyl and (cycloalkyl)alkyl groups (e.g., ($C_3$-$C_7$cycloalkyl)$C_0$-$C_6$alkyl).

The term "halogen" refers to fluorine, chlorine, bromine or iodine.

A "haloalkyl" is an alkyl group that is substituted with 1 or more halogen atoms (e.g., "$C_1$-$C_4$haloalkyl" groups have from 1 to 4 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above attached via an oxygen bridge. "$C_1$-$C_4$haloalkoxy" groups have 1 to 4 carbon atoms.

A dash ("-") that is not between two letters or symbols is used to indicate a point of attachment for a substituent. For example, —COOH is attached through the carbon atom.

A "heteroatom," as used herein, is oxygen, sulfur or nitrogen.

A "carbocycle" or "carbocyclic group" comprises at least one ring formed entirely by carbon-carbon bonds (referred to herein as a carbocyclic ring), and does not contain a heterocycle. Certain representative carbocycles are cycloalkyl as described above. Other carbocycles are aryl (i.e., contain at least one aromatic ring).

A "heterocycle" or "heterocyclic group" has from 1 to 3 fused, pendant or spiro rings, at least one of which is a heterocyclic ring (i.e., one or more ring atoms is a heteroatom independently chosen from O, S and N, with the remaining ring atoms being carbon). Additional rings, if present, may be heterocyclic or carbocyclic. Typically, a heterocyclic ring comprises 1, 2, 3 or 4 heteroatoms; within certain embodiments each heterocyclic ring has 1 or 2 heteroatoms per ring. Each heterocyclic ring generally contains from 4 to 8 ring members (rings having from 4 or 5 to 7 ring members are recited in certain embodiments) and heterocycles comprising fused, pendant or spiro rings typically contain from 9 to 14 ring members. Certain heterocycles comprise a sulfur atom as a ring member; in certain embodiments, the sulfur atom is oxidized to SO or $SO_2$. Heterocycles may be optionally substituted with a variety of substituents, as indicated. Unless otherwise specified, a heterocycle may be a heterocycloalkyl group (i.e., each ring is saturated or partially saturated) or a heteroaryl group (i.e., at least one ring within the group is aromatic), and may be linked via any ring atom, provided that a stable compound results. A nitrogen-containing (or N-containing) heterocycle comprises at least one nitrogen ring atom. Additional ring heteroatoms may, but need not, be present. A nitrogen-linked (or N-linked) heterocycle is linked by a single covalent bond at one ring nitrogen atom. Additional heteroatoms may, but need not, be present.

Certain heterocyclic groups include, for example, acridinyl, azepanyl, azocinyl, benzimidazolyl, benzimidazolinyl, benzisothiazolyl, benzisoxazolyl, benzofuranyl, benzothiofuranyl, benzothiophenyl, benzoxazolyl, benzothiazolyl, benzotriazolylcarbazolyl, benztetrazolyl, NH-carbazolyl, carbolinyl, chromanyl, chromenyl, cinnolinyl, decahydroquinolinyl, dihydrofuro[2,3-b]tetrahydrofuran, dihydroisoquinolinyl, dihydrotetrahydrofuranyl, 1,4-dioxa-8-aza-spiro[4,5]dec-8-yl, dithiazinyl, furanyl, furazanyl, imidazolinyl, imidazolidinyl, imidazolyl, indazolyl, indolenyl, indolinyl, indolizinyl, indolyl, isobenzofuranyl, isochromanyl, isoindazolyl, isoindolinyl, isoindolyl, isothiazolyl, isoxazolyl, isoquinolinyl, morpholinyl, naphthyridinyl, octahydroisoquinolinyl, oxadiazolyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, piperidonyl, pteridinyl, purinyl, pyranyl, pyrazinyl, pyrazolidinyl, pyrazolinyl, pyrazolyl, pyridazinyl, pyridoimidazolyl, pyridooxazolyl, pyridothiazolyl, pyridyl, pyrimidyl, pyrrolidinyl, pyrrolidonyl, pyrrolinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienothiazolyl, thienooxazolyl, thienoimidazolyl, thienyl, thiophenyl, thiomorpholinyl and variants thereof in which the sulfur atom is oxidized, triazinyl, xanthenyl and any of the foregoing that are substituted with from 1 to 4 substituents as described above.

Certain heterocycles are 5- to 12-membered heteroaryl groups, or 5- or 6-membered heteroaryl rings (e.g., pyridyl, pyrimidyl and pyridazinyl), each of which may be substituted as indicated. Other heterocycles are 9- or 10-membered heteroaryl groups, which may be substituted as indicated, and comprise two fused rings, at least one of which comprises a heteroatom and at least one of which is aromatic. Representative such groups include, for example, quinolinyl, quinazolinyl, isoquinolinyl, pyridoimidazolyl and pyridopyrazinyl. It will be apparent that the aromatic ring and the heterocycle may, but need not, be the same; for example, the term "heteroaryl" encompasses groups that comprise a phenyl ring and a heterocycloalkyl ring, such as 2,3-dihydro-1,4-benzodioxinyl and 1,3-benzodioxol-5-yl. Other heterocycles are 4- to 8-membered heterocycloalkyl groups, which are saturated or partially saturate heterocyclic rings as described above, containing 4, 5, 6, 7 or 8 ring members.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or substituted by other than hydrogen at one or more available positions, typically 1, 2, 3, 4, 5 or 6 positions, by one or more suitable groups (which may be the same or different). Optional substitution is also indicated by the phrase "substituted with from 0 to X substituents," where X is the maximum number of permissible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents).

Unless otherwise specified, the term "H3 receptor" is used herein to refer to any histamine H3 subtype receptor, including human H3 receptor (see, e.g., U.S. Pat. No. 6,136,559), H3 receptor found in other mammals and chimeric receptors retaining H3 function, including the chimeric H3 receptor described as SEQ ID NO:8 in U.S. patent application Ser. No. 11/355,711, which published as US 2006/0188960.

A "H3 receptor modulator" is a compound that modulates H3 receptor GTP binding. A H3 receptor modulator may be a H3 receptor agonist or antagonist. A H3 receptor modulator binds with "high affinity" if the $K_i$ at H3 receptor is less than 4 micromolar, preferably less than 1 micromolar, 500 nanomolar, 100 nanomolar, 50 nanomolar or 10 nanomolar. Representative assays for evaluating an effect on H3 receptor GTP binding are provided in Examples 7 and 8, herein.

Unless otherwise specified, the terms "$IC_{50}$" and "$EC_{50}$," as used herein, refer to values obtained using the assay as described in Example 7.

A H3 receptor modulator is considered an "antagonist" if it detectably inhibits H3 receptor agonist-stimulated GTP binding (using, for example, the representative assay provided in Example 7); in general, such an antagonist inhibits such GTP binding with a $IC_{50}$ value of less than 4 micromolar, preferably less than 1 micromolar, 500 nanomolar, 100 nanomolar, 50 nanomolar or 10 nanomolar. H3 receptor antagonists include neutral antagonists and inverse agonists.

An "inverse agonist" of H3 receptor is a compound that reduces the GTP binding activity of H3 receptor below its basal activity level in the absence of added agonist. Inverse agonists of H3 receptor may also inhibit the activity in the presence of agonist. The basal activity of H3 receptor, as well as the reduction in H3 receptor GTP binding activity due to the presence of H3 receptor antagonist, may be determined using an assay provided in Example 7 or Example 8.

A "neutral antagonist" of H3 receptor is a compound that inhibits the activity of H3 receptor agonist, but does not significantly change the basal activity of the receptor (i.e., within the assay of Example 7 or Example 8 performed in the absence of agonist, H3 receptor activity is reduced by no more than 10%, preferably by no more than 5%, and more preferably by no more than 2%; most preferably, there is no detectable reduction in activity). The basal activity is the level of GTP binding observed in the assay in the absence of added histamine or any other agonist, and in the further absence of any test compound. Neutral antagonists of H3 receptor may, but need not, inhibit the binding of agonist to H3 receptor.

As used herein a "H3 receptor agonist" is a compound that elevates the activity of the receptor above the basal activity level of the receptor. H3 receptor agonist activity may be identified using the representative assays provided in Example 7 and Example 8. In general, such an agonist has an $EC_{50}$ value of less than 4 micromolar, preferably less than 1 micromolar, 500 nanomolar, 100 nanomolar, 50 nanomolar or 10 nanomolar within the assay provided in Example 7. If the GTP binding activity brought about by a test compound attains the same level to that of histamine, it is defined as a full agonist. If the level of GTP binding activity brought about by a test compound is above baseline but below the level attained by histamine, it is defined as a partial agonist. Preferred antagonist compounds provided herein do not elevate GTP binding activity under such conditions more than 10% above baseline, preferably not more than 5% above baseline, and most preferably not more than 2% above baseline.

A "therapeutically effective amount" (or dose) is an amount that, upon administration to a patient, results in a discernible patient benefit (e.g., provides detectable relief from a condition being treated). Such relief may be detected using any appropriate criteria, including alleviation of one or more symptoms characteristic of the condition. A therapeutically effective amount or dose generally results in a concentration of compound in a body fluid (such as blood, plasma, serum, CSF, synovial fluid, lymph, cellular interstitial fluid, tears or urine) that is sufficient to alter H3 receptor GTP binding in vitro.

A "patient" is any individual treated with a compound or pharmaceutically acceptable salt thereof provided herein. Patients include humans, as well as other animals such as companion animals (e.g., dogs and cats) and livestock. Patients may be experiencing one or more symptoms of a condition responsive to H3 receptor modulation, or may be free of such symptom(s) (e.g., treatment may be prophylactic).

Piperazinyl Oxoalkyl Tetrahydroisoquinolines and Related Analogues

As noted above, the present invention provides piperazinyl oxoalkyl tetrahydroisoquinolines and related analogues of Formula I. Within certain aspects, such compounds are H3 receptor modulators that may be used in a variety of contexts, including in the therapeutic treatment of human and animal patients as discussed below. H3 receptor modulators may also be used within in vitro assays (e.g., assays for receptor activity), and as probes for detection and localization of H3 receptor.

Within Formula I,

represents a phenyl ring or a 5- or 6-membered heteroaryl ring, each of which rings is optionally substituted as described above. If

is a heteroaryl, the heteroatom(s) may appear at any position(s) in the ring provided that the resulting compound is stable. Compounds in which a ring nitrogen atom is shared by the two fused rings (e.g., at the positions indicated by the arrows below:

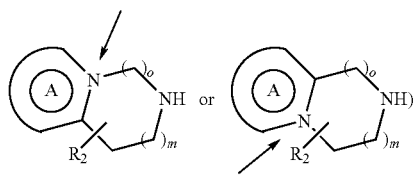

are specifically included within the scope of Formula I.

Within certain compounds of Formula I, and other Formulas and subformulas provided herein, variables satisfy one or more of the following:

(i)

represents a phenyl ring or a 5- or 6-membered heteroaryl ring, each of which rings is substituted with exactly one $R_x$, and each of which rings is further substituted with 0 or 1 substituent chosen from $R_y$;

(ii) n is 1;

(iii) p is 1;

(iv) o is 1 or 2; and/or (v) $R_2$ and $R_3$ independently represent 0 substituents or 1 or 2 methyl substituents.

Within certain embodiments, piperazinyl oxoalkyl tetrahydroisoquinolines and related analogues of Formula I further satisfy (are represented by) Formula II or Formula III:

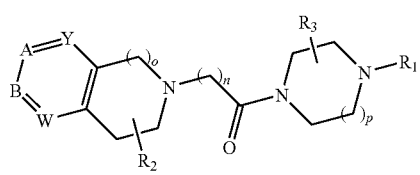

Formula II

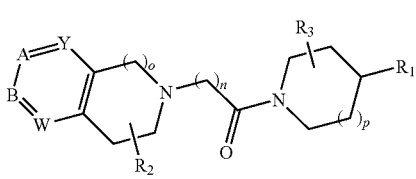

Formula III

Within Formula II:

$R_1$ is $C_1$-$C_6$alkyl, $C_2$-$C_6$alkenyl, $C_2$-$C_6$alkynyl, ($C_3$-$C_8$cycloalkyl)$C_0$-$C_2$alkyl or (4- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl;

Within Formula III:

$R_1$ is $C_1$-$C_6$-aminoalkyl, mono- or di-($C_1$-$C_6$alkyl)amino$C_0$-$C_2$alkyl, ($C_3$-$C_8$cycloalkyl)$C_0$-$C_2$alkyl that is substituted with amino or mono- or di-($C_1$-$C_6$alkyl)amino, or a N-containing (3- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl;

Within Formulas II and III:

n, o and p are independently 1 or 2;

Exactly one of A, B and Y is CRC; and the others of A, B and Y are independently $CR_4$ or N;

W is $CR_4$ or N;

each $R_4$ is independently hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, mono- or di-($C_1$-$C_6$alkyl)amino, phenyl$C_0$-$C_2$alkyl or (5- or 6-membered heteroaryl)$C_0$-$C_2$alkyl;

and the remaining variables are as described for Formula I.

Certain piperazinyl oxoalkyl tetrahydroisoquinolines and related analogues of Formula II further satisfy one or more of Formulas IIa-IIf, in which W, Y and Z are independently $CR_4$ or N; $R_5$ is hydrogen, $C_1$-$C_6$alkyl, ($C_3$-$C_8$cycloalkyl)$C_0$-$C_2$alkyl or phenyl$C_0$-$C_4$alkyl; and the remaining variables are as described for Formula II:

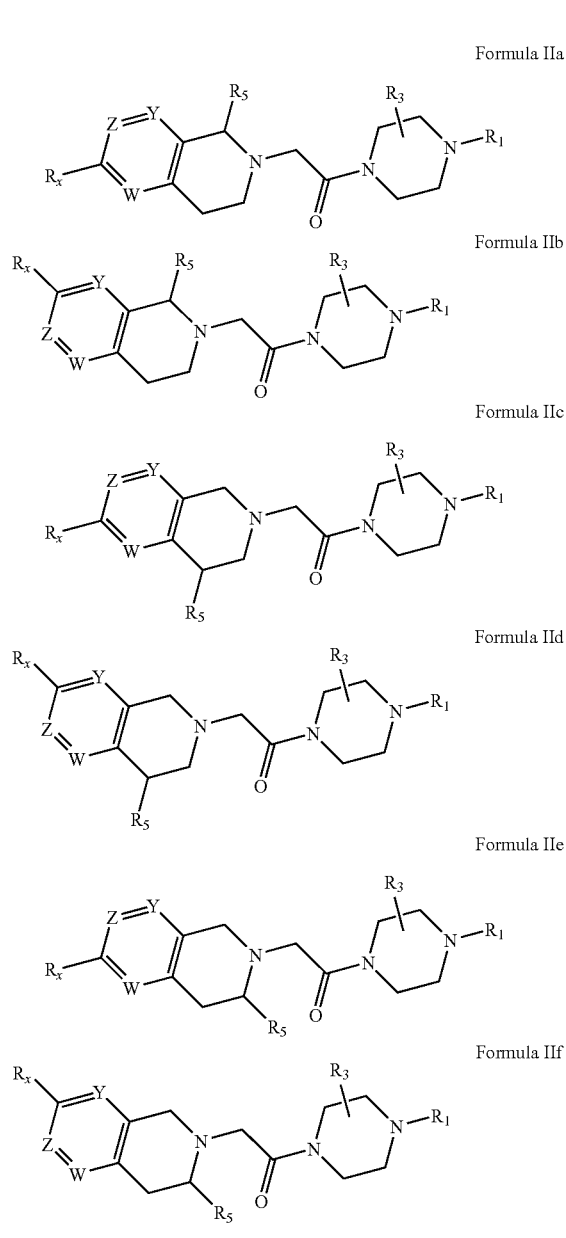

Other piperazinyl oxoalkyl tetrahydroisoquinolines and related analogues of Formula II satisfy Formula IIg, in which all variables are as described for Formula II:

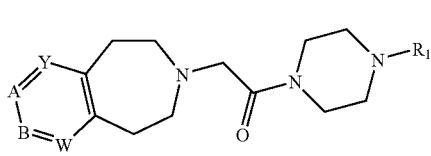

Still further piperazinyl oxoalkyl tetrahydroisoquinolines and related analogues of Formula IIg satisfy Formula IIh or Formula IIi, in which W is CH or N, Z is N or $CR_4$, and the remaining variables are as described for Formula II:

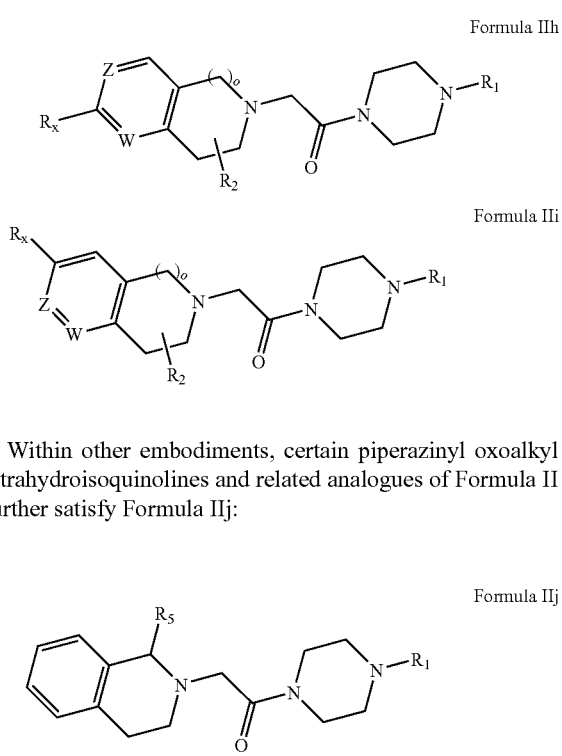

Within other embodiments, certain piperazinyl oxoalkyl tetrahydroisoquinolines and related analogues of Formula II further satisfy Formula IIj:

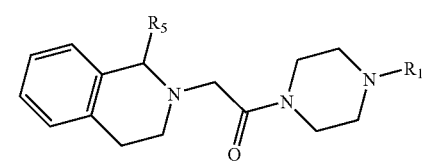

in which $R_5$ is hydrogen, $C_1$-$C_6$alkyl, ($C_3$-$C_8$cycloalkyl)$C_0$-$C_2$alkyl or phenyl$C_0$-$C_4$alkyl, and $R_1$ is as described for Formula II.

Within further embodiments, certain piperazinyl oxoalkyl tetrahydroisoquinolines and related analogues of Formula II further satisfy one or more of Formulas IIk-IIo:

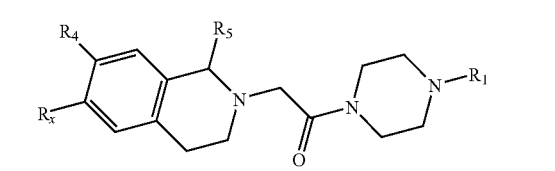

-continued

Formula III
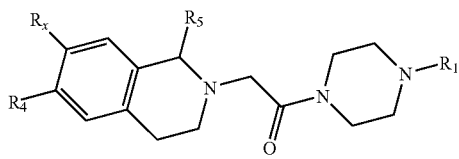

Formula IIm
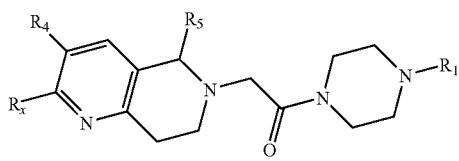

Formula IIn
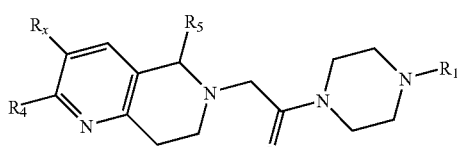

Formula IIo
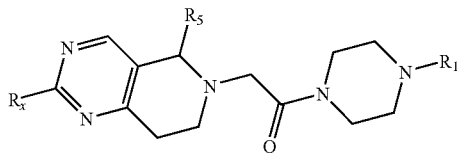

Within Formulas IIk-IIo:

$R_x$ is:
  (i) halogen, cyano, $C_1$-$C_6$alkoxy, $C_1$-$C_6$alkanoyl, $C_1$-$C_6$alkylsulfonyl, mono- or di-($C_1$-$C_6$alkyl)aminosulfonyl, mono- or di($C_1$-$C_6$alkyl)aminocarbonyl; or
  (ii) phenyl or 5- or 6-membered heteroaryl, each of which is substituted with from 0 to 3 substituents independently chosen from $C_1$-$C_6$alkyl, $C_1$-$C_6$alkanoyl, $C_1$-$C_6$alkylsulfonyl, mono- or di-($C_1$-$C_6$alkyl)aminosulfonyl, and mono- or di($C_1$-$C_6$alkyl)aminocarbonyl;

$R_4$ is hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, mono- or di-($C_1$-$C_6$alkyl)amino, phenyl$C_0$-$C_2$alkyl or (5- or 6-membered heteroaryl)$C_0$-$C_2$alkyl; and $R_5$ is hydrogen or $C_1$-$C_6$alkyl.

$R_1$, within certain compounds of Formula II, and subformulas thereof, is $C_3$-$C_6$alkyl or ($C_3$-$C_6$cycloalkyl)$C_0$-$C_2$alkyl. Representative $R_1$ groups for Formula II and subformulas thereof include, for example, isopropyl, cyclobutyl, cyclopentyl and cyclohexyl.

Certain piperazinyl oxoalkyl tetrahydroisoquinolines and related analogues of Formula III further satisfy one or more of formulas IIIa-IIIf, in which W, Y and Z are independently $CR_4$ or N; $R_5$ is hydrogen, $C_1$-$C_6$alkyl, ($C_3$-$C_8$cycloalkyl)$C_0$-$C_2$alkyl or phenyl$C_0$-$C_4$alkyl; and the remaining variables are as described for Formula III:

Formula IIIa
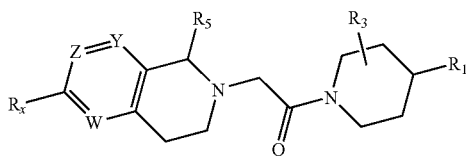

Formula IIIb
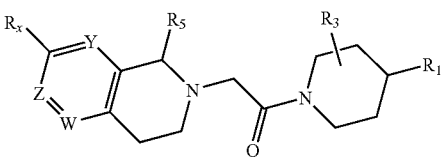

Formula IIIc
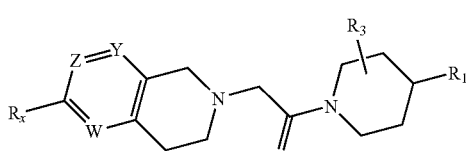

Formula IIId
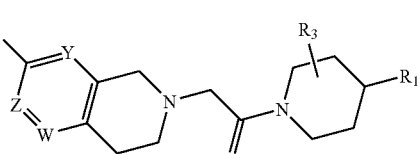

Formula IIIe

Formula IIIf
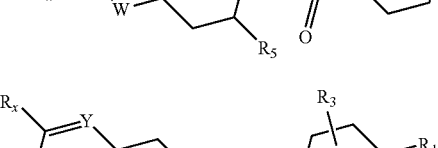

Other piperazinyl oxoalkyl tetrahydroisoquinolines and related analogues of Formula III satisfy Formula IIIg, in which all variables are as described for Formula III.

Formula IIIg
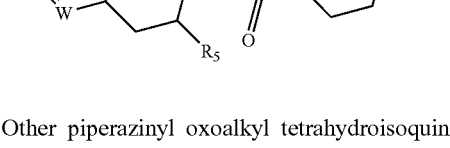

Still further piperazinyl oxoalkyl tetrahydroisoquinolines and related analogues of Formula IIIg satisfy Formula IIIh or Formula IIIi, in which W is CH or N, Z is N or $CR_4$, and the remaining variables are as described for Formula III:

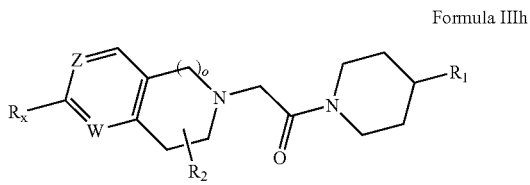

Formula IIIh

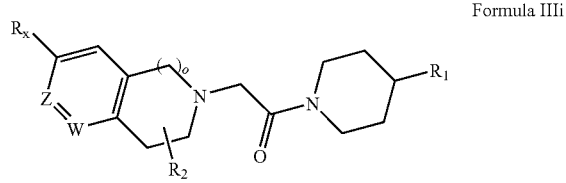

Formula IIIi

Within other embodiments, certain piperazinyl oxoalkyl tetrahydroisoquinolines and related analogues of Formula III satisfy Formula IIIj:

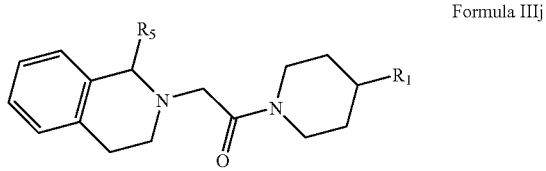

Formula IIIj in which $R_5$ is hydrogen, $C_1$-$C_6$alkyl, ($C_3$-$C_8$cycloalkyl)$C_0$-$C_2$alkyl or phenyl$C_0$-$C_4$alkyl, and $R_1$ is as described for Formula III.

Within further embodiments, certain piperazinyl oxoalkyl tetrahydroisoquinolines and related analogues of Formula III satisfy one or more of Formulas IIIk-IIIo:

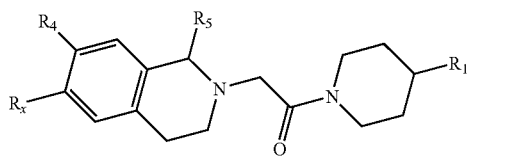

Formula IIIk

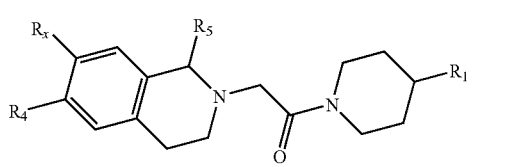

Formula IIIl

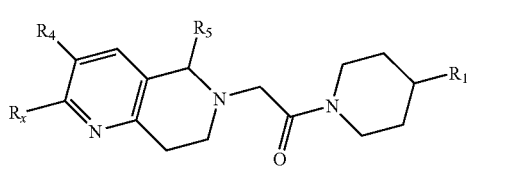

Formula IIIm

-continued

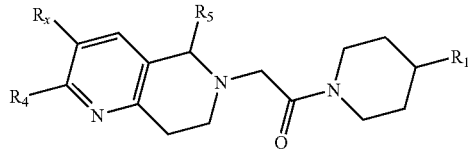

Formula IIIn

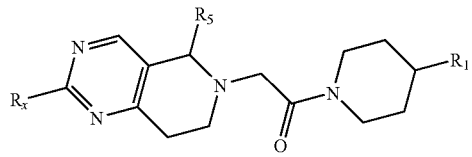

Formula IIIo

Within Formulas IIIk-IIIo:

$R_x$ is:
(i) halogen, cyano, $C_1$-$C_6$alkoxy, $C_1$-$C_6$alkanoyl, $C_1$-$C_6$alkylsulfonyl, mono- or di-($C_1$-$C_6$alkyl)amino, mono- or di-($C_1$-$C_6$alkyl)aminosulfonyl, mono- or di($C_1$-$C_6$alkyl)aminocarbonyl; or
(ii) $C_1$-$C_8$alkyl, $C_3$-$C_8$cycloalkyl, 4- to 7-membered heterocycloalkyl, phenyl, naphthyl, or 5- to 10-membered heteroaryl, each of which is substituted with from 0 to 3 substituents independently chosen from:
  (a) hydroxy, cyano, halogen and oxo; and
  (b) $C_1$-$C_8$alkyl, $C_1$-$C_8$haloalkyl, $C_1$-$C_8$cyanoalkyl, $C_1$-$C_8$alkoxy, $C_1$-$C_8$haloalkoxy, $C_1$-$C_8$alkylthio, $C_2$-$C_8$alkyl ether, $C_1$-$C_6$alkylsulfonyl, mono- or di($C_1$-$C_6$alkyl)amino$C_0$-$C_4$alkyl, mono- or di-($C_1$-$C_6$alkyl)aminosulfonyl, phenoxy, phenyl, and 4- to 7-membered heterocycloalkyl, each of which is unsubstituted or substituted with 1 or 2 substituents independently chosen from oxo, $C_1$-$C_4$alkyl and $C_1$-$C_4$alkoxy;

$R_4$ is hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, mono- or di-($C_1$-$C_6$alkyl)amino, phenyl$C_0$-$C_2$alkyl or (5- or 6-membered heteroaryl)$C_0$-$C_2$alkyl; and $R_5$ is hydrogen or $C_1$-$C_6$alkyl.

Within certain embodiments of Formulas IIIk-IIIo, $R_1$ is mono- or di-($C_1$-$C_6$alkyl)amino, 4- to 7-membered heterocycloalkyl, phenyl, naphthyl, or 5- to 10-membered heteroaryl, each of which is substituted with from 0 to 3 substituents independently chosen from: (a) hydroxy, cyano, halogen and oxo; and (b) $C_1$-$C_8$alkyl, $C_1$-$C_8$haloalkyl, $C_1$-$C_8$cyanoalkyl, $C_1$-$C_8$alkoxy, $C_1$-$C_8$haloalkoxy, $C_1$-$C_8$alkylthio, $C_2$-$C_8$alkyl ether, $C_1$-$C_6$alkylsulfonyl, mono- or di($C_1$-$C_6$alkyl)amino$C_0$-$C_4$alkyl, mono- or di-($C_1$-$C_6$alkyl)aminosulfonyl, phenoxy, phenyl, and 4- to 7-membered heterocycloalkyl, each of which is unsubstituted or substituted with 1 or 2 substituents independently chosen from oxo, $C_1$-$C_4$alkyl and $C_1$-$C_4$alkoxy; and $R_1$ is $C_3$-$C_8$cycloalkyl$C_0$-$C_2$alkyl, 4- to 7-membered heterocycloalkyl or $C_2$-$C_8$alkyl, each of which is unsubstituted or substituted with 1 or 2 substituents independently chosen from $C_1$-$C_4$alkyl and $C_1$-$C_4$alkoxy.

Within further such compounds of Formulas IIIk-IIIo, $R_1$ is: (i) $C_1$-$C_6$alkanoyl, $C_1$-$C_6$alkylsulfonyl, mono- or di-($C_1$-$C_6$alkyl)aminosulfonyl, or mono- or di($C_1$-$C_6$alkyl)aminocarbonyl; or (ii) phenyl or 5- or 6-membered heteroaryl, each of which is substituted with from 0 to 3 substituents independently chosen from halogen, cyano, $C_1$-$C_6$alkyl, $C_1$-$C_4$alkoxy, $C_1$-$C_6$alkanoyl, $C_1$-$C_6$alkylsulfonyl, mono- or di-($C_1$-$C_6$alkyl)aminosulfonyl, and mono- or di($C_1$-$C_6$alkyl) aminocarbonyl; $R_4$ is hydrogen; and $R_5$ is hydrogen.

Representative $R_x$ groups include phenyl, pyridyl and pyrimidinyl, each of which is substituted with one substituent chosen from halogen, cyano, $C_1$-$C_4$alkyl, $C_1$-$C_4$alkoxy, and $C_1$-$C_4$alkanoyl.

$R_1$, within certain compounds of Formula III, and subformulas thereof, is di-($C_1$-$C_6$alkyl)amino or a N-containing (e.g., N-linked) 5- to 7-membered heterocycloalkyl.

Representative $R_1$ groups for Formula III and subformulas thereof include, for example, dimethylamino, diethylamino and piperidin-1-yl.

Within other embodiments, certain compounds of Formula I further satisfy Formula IV or Formula V:

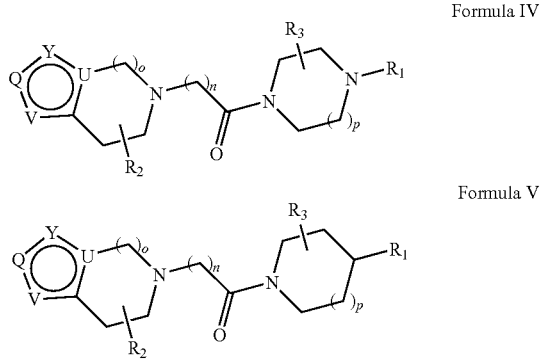

Formula IV

Formula V in which

is a 5-membered heteroaryl, wherein:
U is N or C; and V, Q and Y are independently chosen from $CR_x$, $CR_4$, N, $NR_x$, $NR_4$, O and S, such that: (i) at least one of V, Q and Y is N, $NR_x$, $NR_4$, O or S; (ii) no more than one of V, Q and Y is O or S; and (iii) exactly one of V, Q and Y comprises an $R_x$ moiety (i.e., one of V, Q and Y is $CR_x$ or $NR_x$, and the others of V, Q and Y are independently $CR_4$, N, $NR_4$, O or S);
n, o and p are independently 1 or 2;
$R_1$ for Formula IV is $C_1$-$C_6$alkyl, $C_2$-$C_6$alkenyl, $C_2$-$C_6$alkynyl, ($C_3$-$C_8$cycloalkyl)$C_0$-$C_2$alkyl or (3- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl;
$R_1$ for Formula V is $C_1$-$C_6$-aminoalkyl, mono- or di-($C_1$-$C_6$alkyl)amino$C_0$-$C_2$alkyl, ($C_3$-$C_8$cycloalkyl)$C_0$-$C_2$alkyl that is substituted with amino or mono- or di-($C_1$-$C_6$alkyl) amino, or a N-containing (e.g., N-linked) (3- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl; and each $R_4$ is independently hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl or mono- or di-($C_1$-$C_6$alkyl)amino.

Within certain compounds of Formulas IV and V, the group designated:

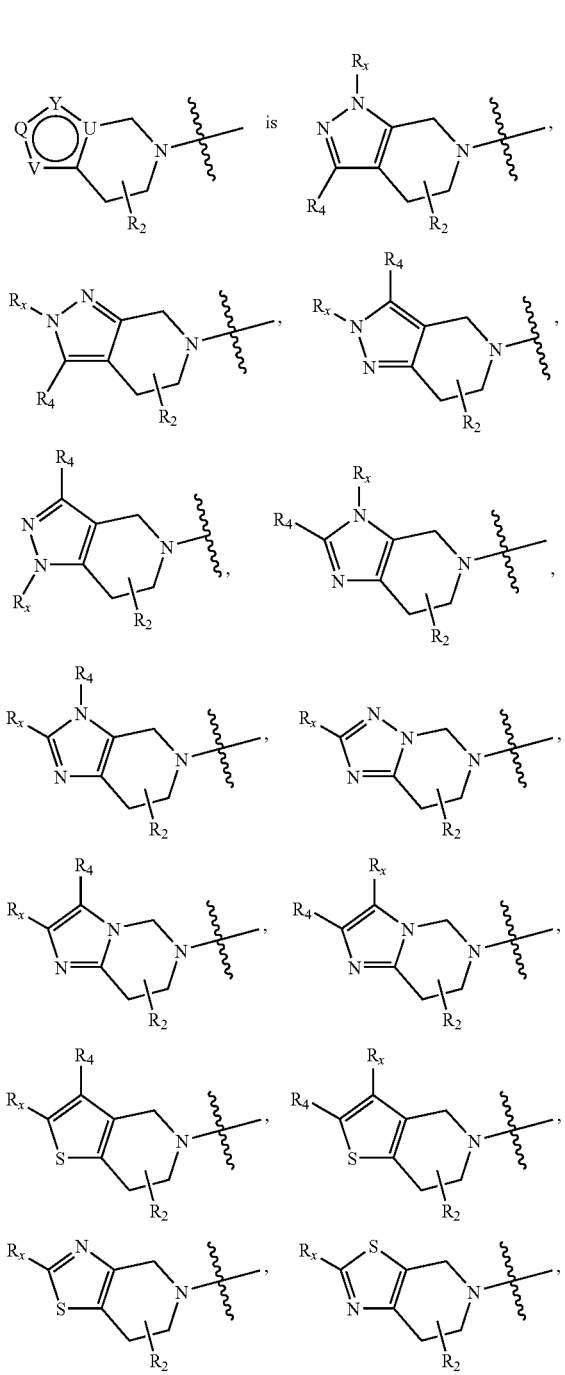

-continued

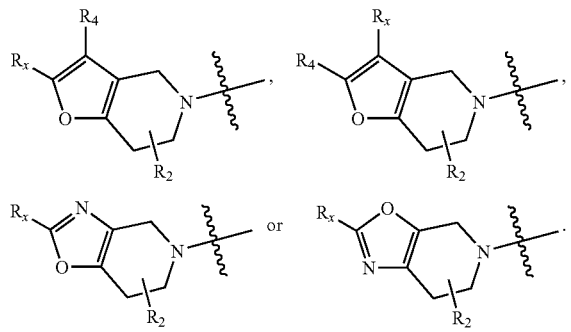

Certain piperazinyl oxoalkyl tetrahydroisoquinolines and related analogues of Formula IV further satisfy one of Formulas IVa-IVg, in which variables are as described for Formula IV:

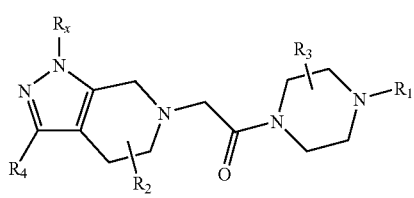
Formula IVa

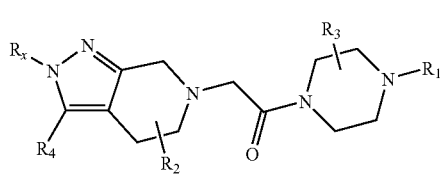
Formula IVb

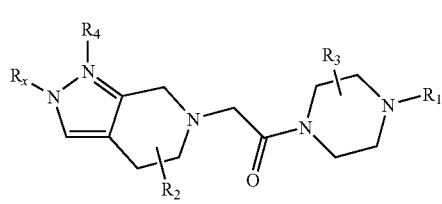
Formula IVc

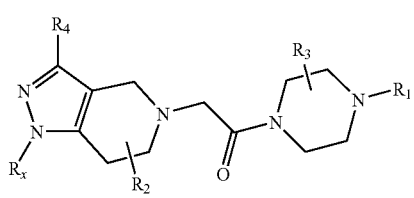
Formula IVd

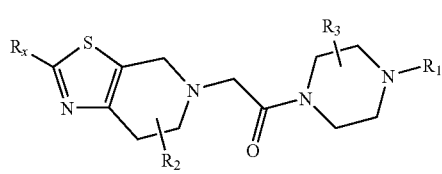
Formula IVe

Formula IVf

Formula IVg

Still other compounds of Formula I further satisfy Formula VI or Formula VII:

Formula VI

Formula VII in which

is a 5-membered heteroaryl, in which V, Q and Y are independently chosen from $CR_x$, $CR_4$, N, $NR_x$, $NR_4$, O and S, such that: (i) at least one of V, Q and Y is N, $NR_x$, $NR_4$, O or S; (ii) no more than one of V, Q and Y is O or S; and (iii) exactly one of V, Q and Y comprises an $R_x$ moiety; and the remaining variables are as described for Formulas IV and V, respectively.

Within certain compounds of Formulas VI and VII, the group designated:

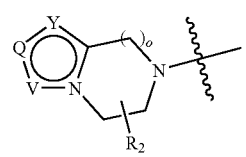

is

-continued

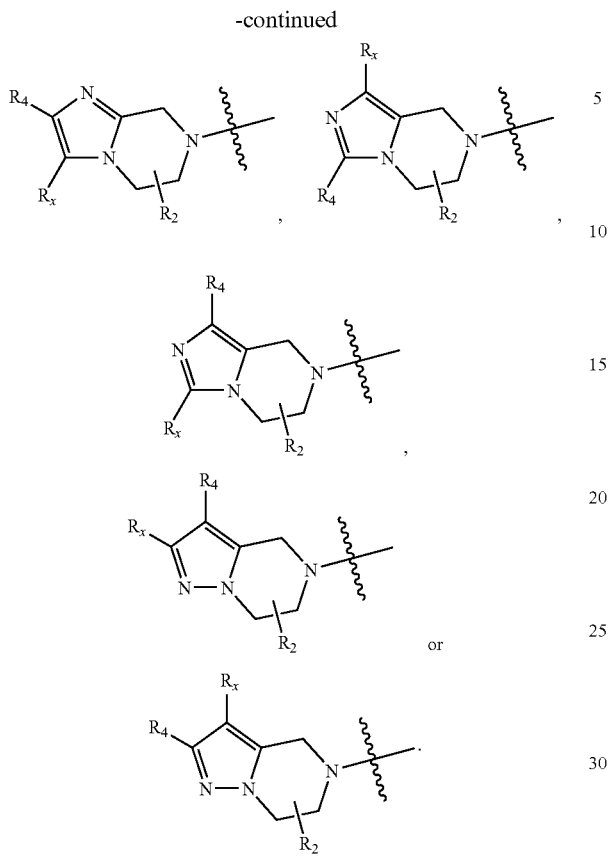

Certain piperazinyl oxoalkyl tetrahydroisoquinolines and related analogues of Formula VI further satisfy any one of Formulas VIa-VId, in which variables are as described for Formula VI:

Formula VIa
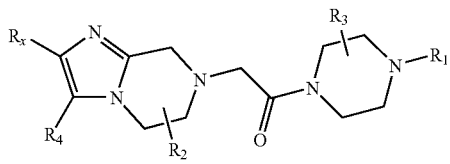

Formula VIb
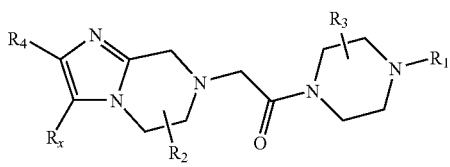

Formula VIc
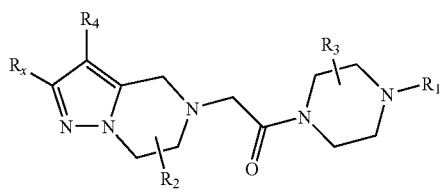

-continued

Formula VId
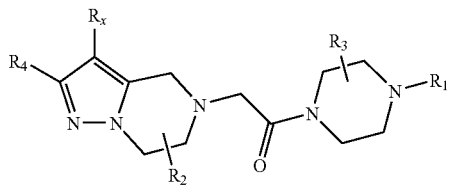

Within certain compounds of Formula IV, V, VI or VII (and the subformulas thereof), $R_x$ is: (i) halogen, cyano, $C_1$-$C_6$alkoxy, $C_1$-$C_6$alkanoyl, $C_1$-$C_6$alkylsulfonyl, mono- or di-($C_1$-$C_6$alkyl)amino, mono- or di-($C_1$-$C_6$alkyl)aminosulfonyl, mono- or di($C_1$-$C_6$alkyl)aminocarbonyl; or (ii) $C_1$-$C_8$alkyl, $C_3$-$C_8$cycloalkyl, 4- to 7-membered heterocycloalkyl, phenyl, naphthyl, or 5- to 10-membered heteroaryl, each of which is substituted with from 0 to 3 substituents independently chosen from: (a) hydroxy, cyano, halogen and oxo; and (b) $C_1$-$C_8$alkyl, $C_1$-$C_8$haloalkyl, $C_1$-$C_8$cyanoalkyl, $C_1$-$C_8$alkoxy, $C_1$-$C_8$haloalkoxy, $C_1$-$C_8$alkylthio, $C_2$-$C_8$alkyl ether, $C_1$-$C_6$alkylsulfonyl, mono- or di($C_1$-$C_6$alkyl)amino$C_0$-$C_4$alkyl, mono- or di-($C_1$-$C_6$alkyl)aminosulfonyl, phenoxy, phenyl, and 4- to 7-membered heterocycloalkyl, each of which is unsubstituted or substituted with 1 or 2 substituents independently chosen from oxo, $C_1$-$C_4$alkyl and $C_1$-$C_4$alkoxy; and $R_4$ is hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, mono- or di-($C_1$-$C_6$alkyl)amino, phenyl$C_0$-$C_2$alkyl or (5- or 6-membered heteroaryl)$C_0$-$C_2$alkyl.

Within further such compounds, $R_x$ is mono- or di-($C_1$-$C_6$alkyl)amino, 4- to 7-membered heterocycloalkyl, phenyl, naphthyl, or 5- to 10-membered heteroaryl, each of which is substituted with from 0 to 3 substituents independently chosen from: (a) hydroxy, cyano, halogen and oxo; and (b) $C_1$-$C_8$alkyl, $C_1$-$C_8$haloalkyl, $C_1$-$C_8$cyanoalkyl, $C_1$-$C_8$alkoxy, $C_1$-$C_8$haloalkoxy, $C_1$-$C_8$alkylthio, $C_2$-$C_8$alkyl ether, $C_1$-$C_6$alkylsulfonyl, mono- or di($C_1$-$C_6$alkyl)amino$C_0$-$C_4$alkyl, mono- or di-($C_1$-$C_6$alkyl)aminosulfonyl, phenoxy, phenyl, and 4- to 7-membered heterocycloalkyl, each of which is unsubstituted or substituted with 1 or 2 substituents independently chosen from oxo, $C_1$-$C_4$alkyl and $C_1$-$C_4$alkoxy; and $R_1$ is $C_3$-$C_8$cycloalkyl$C_0$-$C_2$alkyl, 4- to 7-membered heterocycloalkyl or $C_2$-$C_8$alkyl, each of which is unsubstituted or substituted with 1 or 2 substituents independently chosen from $C_1$-$C_4$alkyl and $C_1$-$C_4$alkoxy.

Within still further such compounds, $R_1$ is (i) $C_1$-$C_6$alkanoyl, $C_1$-$C_6$alkylsulfonyl, mono- or di-($C_1$-$C_6$alkyl)aminosulfonyl, or mono- or di($C_1$-$C_6$alkyl)aminocarbonyl; or (ii) phenyl or 5- or 6-membered heteroaryl, each of which is substituted with from 0 to 3 substituents independently chosen from halogen, cyano, $C_1$-$C_6$alkyl, $C_1$-$C_4$alkoxy, $C_1$-$C_6$alkanoyl, $C_1$-$C_6$alkylsulfonyl, mono- or di-($C_1$-$C_6$alkyl)aminosulfonyl, and mono- or di($C_1$-$C_6$alkyl)aminocarbonyl; and $R_4$ is hydrogen. Representative $R_x$ groups include, for example, phenyl, pyridyl or pyrimidinyl, each of which is substituted with one substituent chosen from halogen, cyano, $C_1$-$C_4$alkyl, $C_1$-$C_4$alkoxy, and $C_1$-$C_4$alkanoyl.

$R_1$, within certain compounds of Formula IV, VI, and subformulas thereof, is $C_3$-$C_6$alkyl or ($C_3$-$C_6$cycloalkyl)$C_0$-$C_2$alkyl. Representative $R_1$ groups for Formulas IV and VI and subformulas thereof include, for example, isopropyl, cyclobutyl, cyclopentyl and cyclohexyl.

R$_1$, within certain compounds of Formula V and VII, and subformulas thereof, is di-(C$_1$-C$_6$alkyl)amino or a N-containing (e.g., N-linked) 5- to 7-membered heterocycloalkyl. Representative R$_1$ groups for Formula V, VII and subformulas thereof include, for example, dimethylamino, diethylamino and piperidin-1-yl.

Representative compounds provided herein include, but are not limited to, those specifically described in Examples 1-3. It will be apparent that the specific compounds recited herein are representative only, and are not intended to limit the scope of the present invention. Further, as noted above, all compounds of the present invention may be present as a free acid or base or as a pharmaceutically acceptable salt or solvate (e.g., hydrate).

In certain aspects, compounds provided are H3 receptor modulators, as determined using an assay for H3 receptor GTP binding. References herein to a "histamine-induced H3 receptor GTP binding assay" are intended to refer to either of the in vitro GTP binding assays provided in Examples 7 and 8, which may be performed in the presence or absence of added agonist. Briefly, to assess H3 receptor agonist-stimulated GTP binding, a H3 receptor preparation is incubated with a H3 receptor agonist (e.g., histamine or an analogue thereof such as R-alpha-methylhistamine), labeled (e.g., $^{35}$S) GTP and unlabeled test compound. Within the assays provided herein, the H3 receptor used is preferably mammalian H3 receptor (e.g., human or rat H3 receptor, and preferably human H3 receptor), and more preferably a chimeric human H3 receptor such as a receptor having the sequence provided in SEQ ID NO:8 of U.S. patent application Ser. No. 11/355,711, which published as US 2006/0188960. The H3 receptor may be recombinantly expressed or naturally expressed. The H3 receptor preparation may be, for example, a membrane preparation from cells that recombinantly express H3 receptor. Incubation with a H3 receptor modulator results in a decrease or increase in the amount of label bound to the H3 receptor preparation, relative to the amount of label bound in the absence of the compound.

As noted above, compounds that are H3 receptor antagonists are preferred within certain embodiments. When agonist-contacted cells are contacted with a compound that is a H3 receptor antagonist, the response is preferably reduced by at least 20%, more preferably at least 50% and still more preferably at least 80%, as compared to cells that are contacted with the agonist in the absence of test compound. The IC$_{50}$ for H3 receptor antagonists provided herein is preferably less than 4 micromolar, less than 1 micromolar, less than 500 nM, less than 100 nM, less than 50 nM or less than 10 nM. In certain embodiments, H3 receptor antagonists provided herein exhibit no detectable agonist activity in the assay of Example 7 at a concentration of compound equal to the IC$_{50}$. Certain preferred antagonists exhibit no detectable agonist activity in the assay at a concentration of compound that is 100-fold higher than the IC$_{50}$.

In certain embodiments, preferred H3 receptor modulators provided herein are non-sedating. In other words, a dose of H3 receptor modulator that is twice the minimum therapeutically effective dose causes only transient (i.e., lasting for no more than ½ the time that the therapeutic effect lasts) or preferably no statistically significant sedation in an animal model assay of sedation (using the method described by Fitzgerald et al. (1988) *Toxicology* 49(2-3):433-9). Preferably, a dose that is any of 5, 10, 20, 30, 40, 50, 60, 70, 80, 90 or 100 times the minimum therapeutically effective dose does not produce statistically significant sedation.

If desired, H3 receptor modulators provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, and still more preferably less than 1 mg/kg), toxicity (a preferred H3 receptor modulator is nontoxic when a therapeutically effective amount is administered to a subject), side effects (a preferred H3 receptor modulator produces side effects comparable to placebo when a therapeutically effective amount of the compound is administered to a subject), serum protein binding and in vitro and in vivo half-life (a preferred H3 receptor modulator exhibits an in vivo half-life allowing for Q.I.D. dosing, preferably T.I.D. dosing, more preferably B.I.D. dosing, and most preferably once-a-day dosing). In addition, differential penetration of the blood brain barrier may be desirable for certain H3 receptor modulators. Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays or whole serum binding assays. In vitro half-lives of compounds may be predicted from assays of microsomal half-life as described within Example 8 of PCT Publication Number WO 06/089076.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 9 of PCT Publication Number WO 06/089076. In other words, cells treated as described in Example 9 therein with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the EC$_{50}$ or IC$_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ for the compound does not elevate serum levels of ALT, LDH or AST in laboratory rodents by more than 100% over matched mock-treated controls. In more highly preferred embodiments, such doses do not elevate such serum levels of ALT, LDH or AST by more than 75% or 50% over matched controls. Alternatively, a H3 receptor modulator does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the $EC_{50}$ or $IC_{50}$ for the compound.

In other embodiments, certain preferred compounds do not substantially inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred H3 receptor modulators do not induce sister chromatid exchange (e.g., in Chinese hamster ovary cells) at such concentrations.

For detection purposes, as discussed in more detail below, H3 receptor modulators provided herein may be isotopically-labeled or radiolabeled. For example, compounds may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., 2H) can afford certain therapeutic advantages resulting from greater metabolic stability, for example increased in vivo half-life or reduced dosage requirements and, hence, may be preferred in some circumstances.

Preparation of Piperazinyl Oxoalkyl Tetrahydroisoquinolines and Related Analogues Compounds provided herein may generally be prepared using standard synthetic methods. Starting materials illustrated in the schemes and in the examples are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein. $R_3'$ and $R_3''$ have the same definition as $R_3$.

Certain abbreviations used in the following Schemes and elsewhere herein are:

BINAP rac-2,2-bis(diphenylphosphino)-1,1-binaphthyl

BOC tert-Butyl carboxyl

BOP benzotriazol-1-yl-oxy-tris(dimethylamino)phosphonium hexafluorophosphate

Bn benzyl n-BuLi n-butyl lithium

Bu butyl

CDI N,N'-carbonyldiimidazole

δ chemical shift

DCC dicyclohexylcarbodiimide

DCM dichloromethane

DMC 2-chloro-1,3-dimethylimidazolinium chloride

DME 1,2-dimethoxyethane

DMF dimethylformamide

DIEA N,N-diisopropylethylamine

DPPP 1,3-bis(diphenylphosphino)propane $Et_2O$ diethyl ether

EtOAc ethyl acetate

EtOH ethanol

Eq. equivalent(s)

HPLC high pressure liquid chromatography hr hour(s)

Hz hertz

LCMS liquid chromatography/mass spectrometry (M+1) mass+1 mCPBA m-chloroperoxybenzoic acid

MS mass spectrometry

Me methyl

MeOH methanol min minute(s)

NBS N-bromosuccinimide $PdCl_2$(dppf) [1,1'-bis(diphenylphosphino)ferrocene]dichloropalladium(II)

$Pd_2$(dba)$_3$ tris(dibenzylideneacetone)dipalladium(0)

Pd(PPh₃)₄ tetrakis(triphenylphosphine)palladium(0)

Pd(OAc)₂ Palladium acetate

PG protecting group, such as BOC or a benzyl group

PTLC preparative thin layer chromatography

PTSA p-toluenesulfonic acid rt room temperature t-BuXPhos 2-di-tert-butylphosphino-2',4',6'-triisopropylbiphenyl t-BuONa sodium tert-butoxide t-BuOK potassium tert-butoxide TEA triethylamine TfO trifluoromethane sulfonate Tf₂O trifluoromethanesulfonic anhydride THF tetrahydrofuran TLC thin layer chromatography Xantphos 4,5-bis(diphenylphosphino)-9,9-dimethyl-xanthene

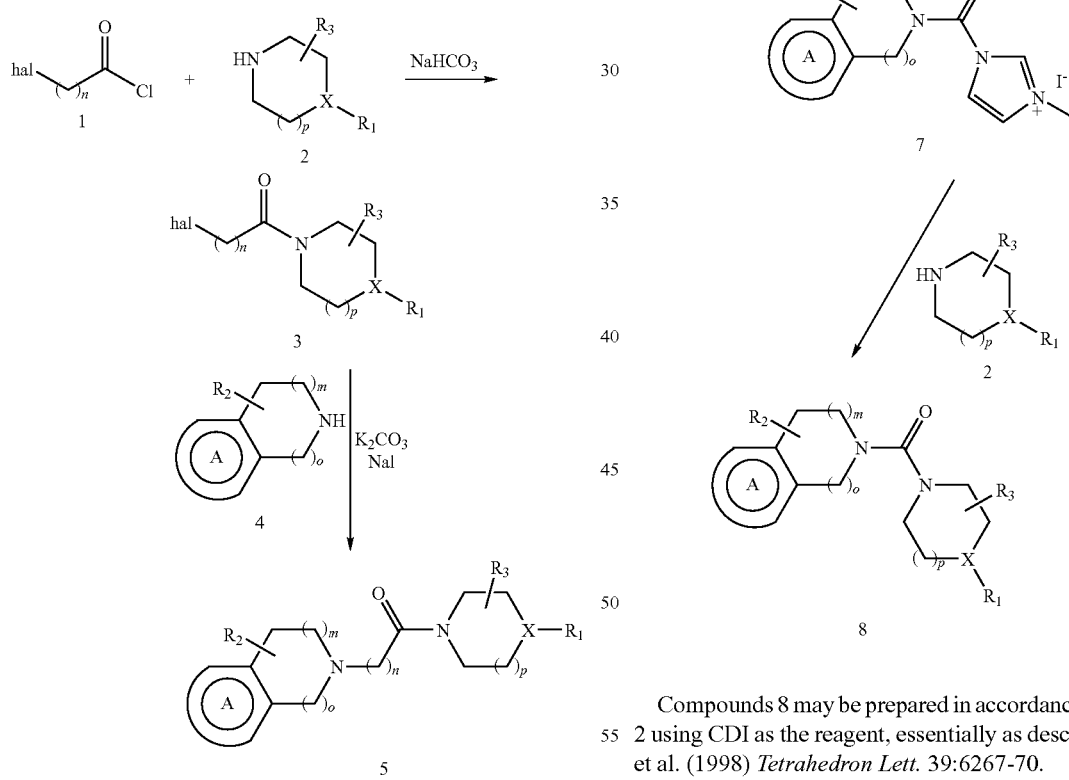

Compounds 5 may be prepared in accordance with Scheme 1. Cyclic amine 2 is reacted with halogen substituted acylchloride 1 in the presence of a base such as sodium bicarbonate to afford halogen substituted carboxamide 3, which is treated with an amine 4 in the presence of a base such as potassium carbonate to produce 5. Cyclic amine 2 is available from commercial sources such as Aldrich (St Louis, Mo.) or may be synthesized from commercially available precursors using established protocols known in the art of synthetic organic chemistry, or variations thereon as appreciated by those skilled in the art. Suitable tetrahydroisoquinoline or related amine analogues for use as compound 4 are available from commercial sources such as Aldrich or may be synthesized as described in the following Schemes.

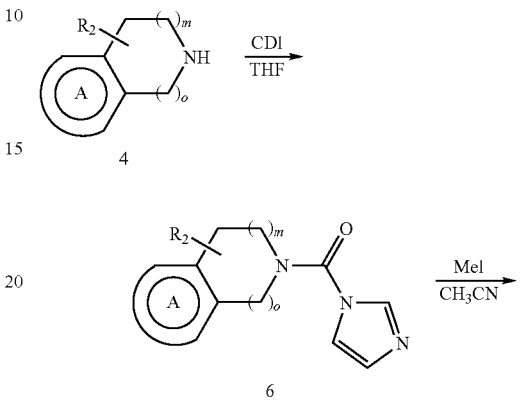

Compounds 8 may be prepared in accordance with Scheme 2 using CDI as the reagent, essentially as described by Batey et al. (1998) *Tetrahedron Lett.* 39:6267-70.

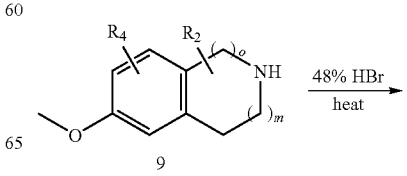

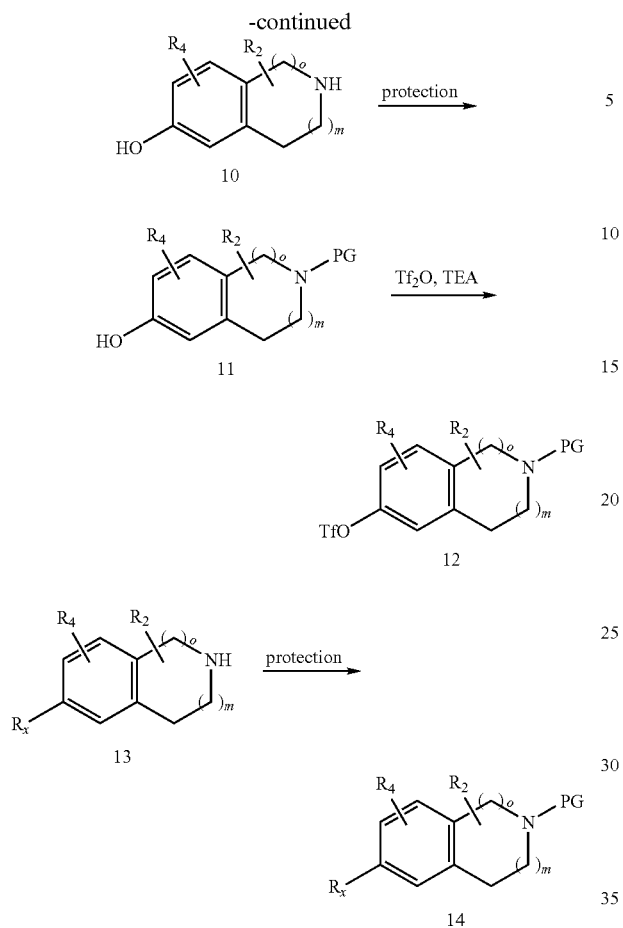

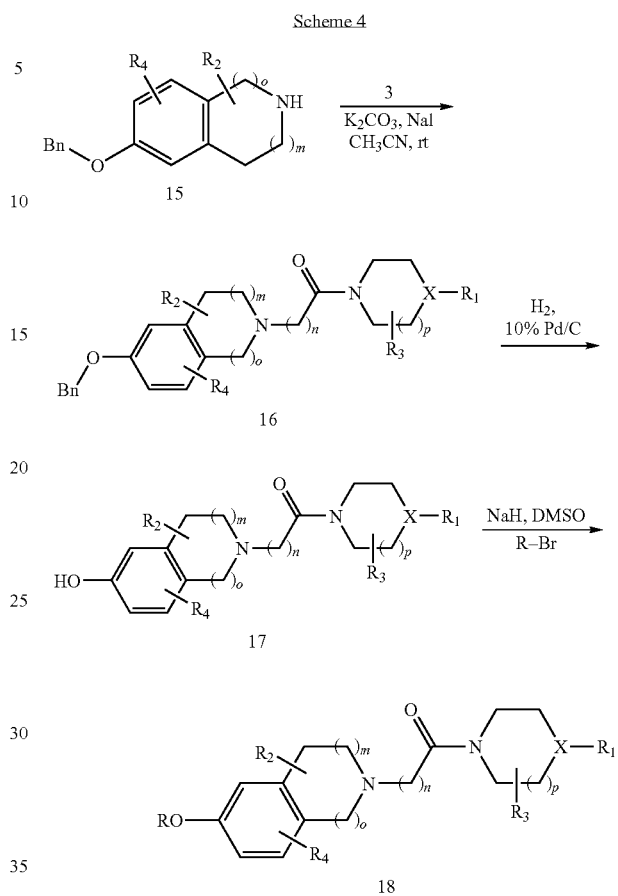

Compounds 12 and 14 may be prepared in accordance with Scheme 3. Amines 9 and 13 are commercially available or may be prepared from suitable amine through Pictet-Spengler cyclization, Friedel-Crafts reaction or other well established protocols based on the nature of $R_2$ and $R_4$, and the ring size. Demethylation of 9 with hydrobromic acid gives 10, which is selectively protected to afford 11. Treatment of 11 with $Tf_2O$ provides 12. Similarly, protection of amine 13 gives 14 which is used as a starting material for the preparation of some compounds as described below.

Scheme 4 illustrates the synthesis of ether analogues of formula 18. Compound 15 is commercially available, known in the literature or conveniently prepared by a variety of methods familiar to those skilled in the art. Treatment of 15 with compound 3 in the presence of a base such as potassium carbonate produces compound 16, which is deprotected under hydrogenolysis condition to provide compound 17. Treatment of compound 17 with NaH followed by reaction with alkyl halide R—Br provides compound 18.

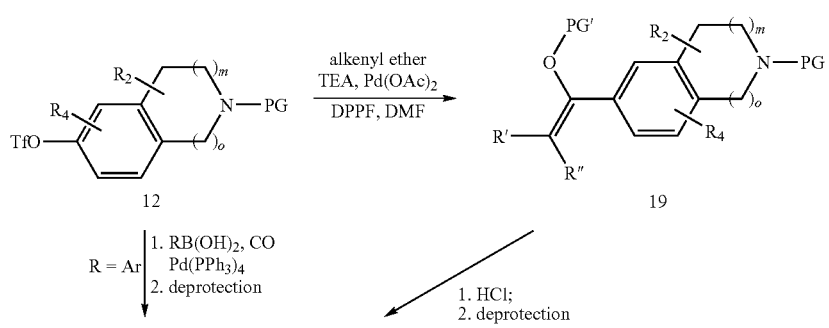

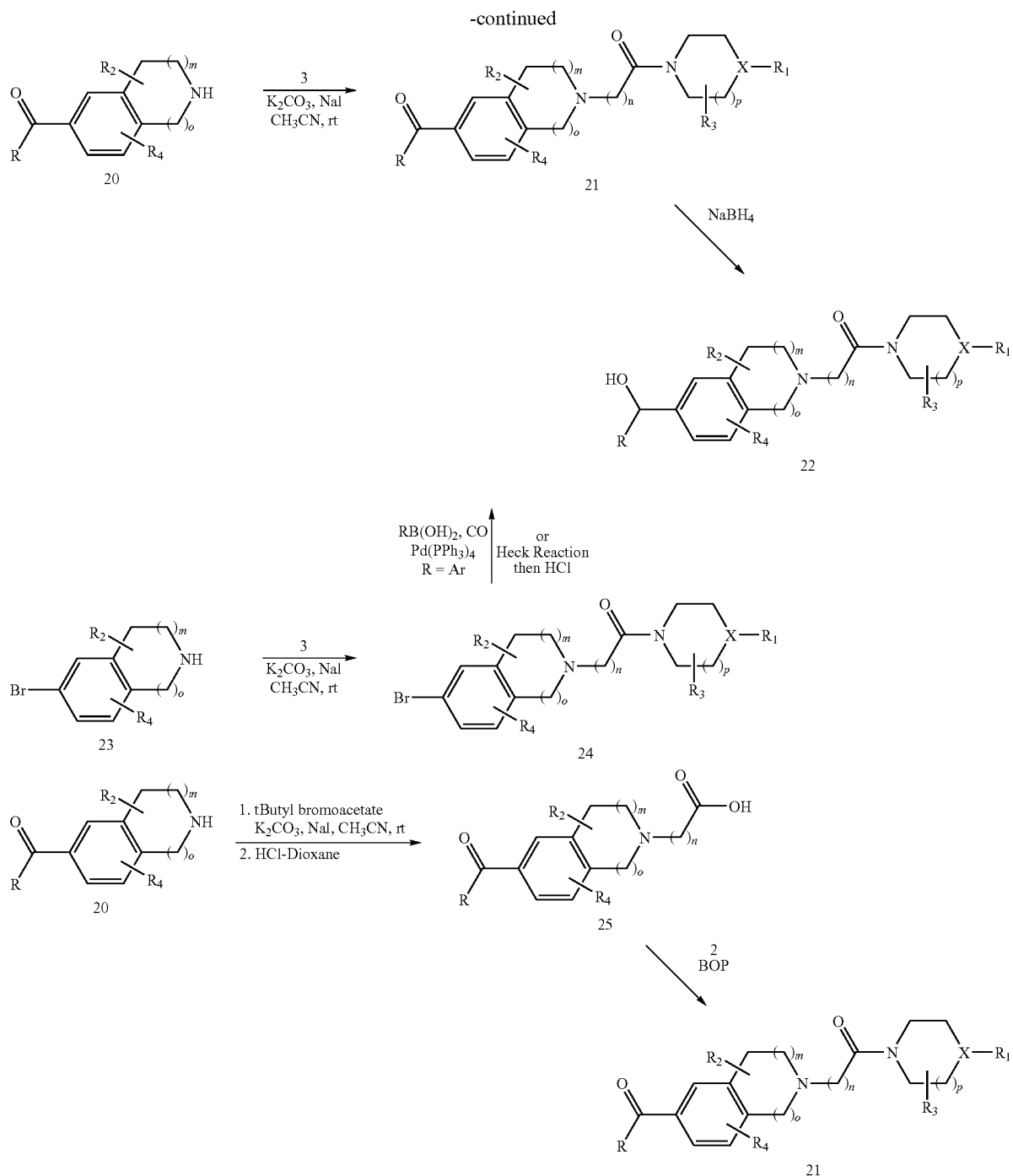

Scheme 5 illustrates the preparation of ketone analogues of formula 21 and alcohol 22. The conversion of compound 12 to enol ether 19 is achieved under Heck reaction conditions in the presence of a catalyst such as palladium acetate and TEA as base. Enol ether 19 is treated with a suitable acid followed by deprotection to give amine 20, which is alkylated with halogen substituted carboxamide 3 to furnish the final product 21. When R is an aryl or heteroaryl group, 12 couples with a corresponding boronic acid in the presence of carbon monoxide and a catalyst such as Pd(PPh$_3$)$_4$ to give amine 20 directly after removing the protective group. Alternatively, the bromo-substituted amine 23 couples with 3 first to give 24, which is then converted to 21 through Heck reaction and deprotection or palladium coupling reaction with a corresponding boronic acid and carbon monoxide, based on the nature of R. Alternatively, amine 20 reacts with t-butyl bromoacetate in the presence of a base such as potassium carbonate followed by deprotection to give acid 25, which couples with amine 2 in the presence of a coupling reagent such as BOP or EDCI to afford compound 21.

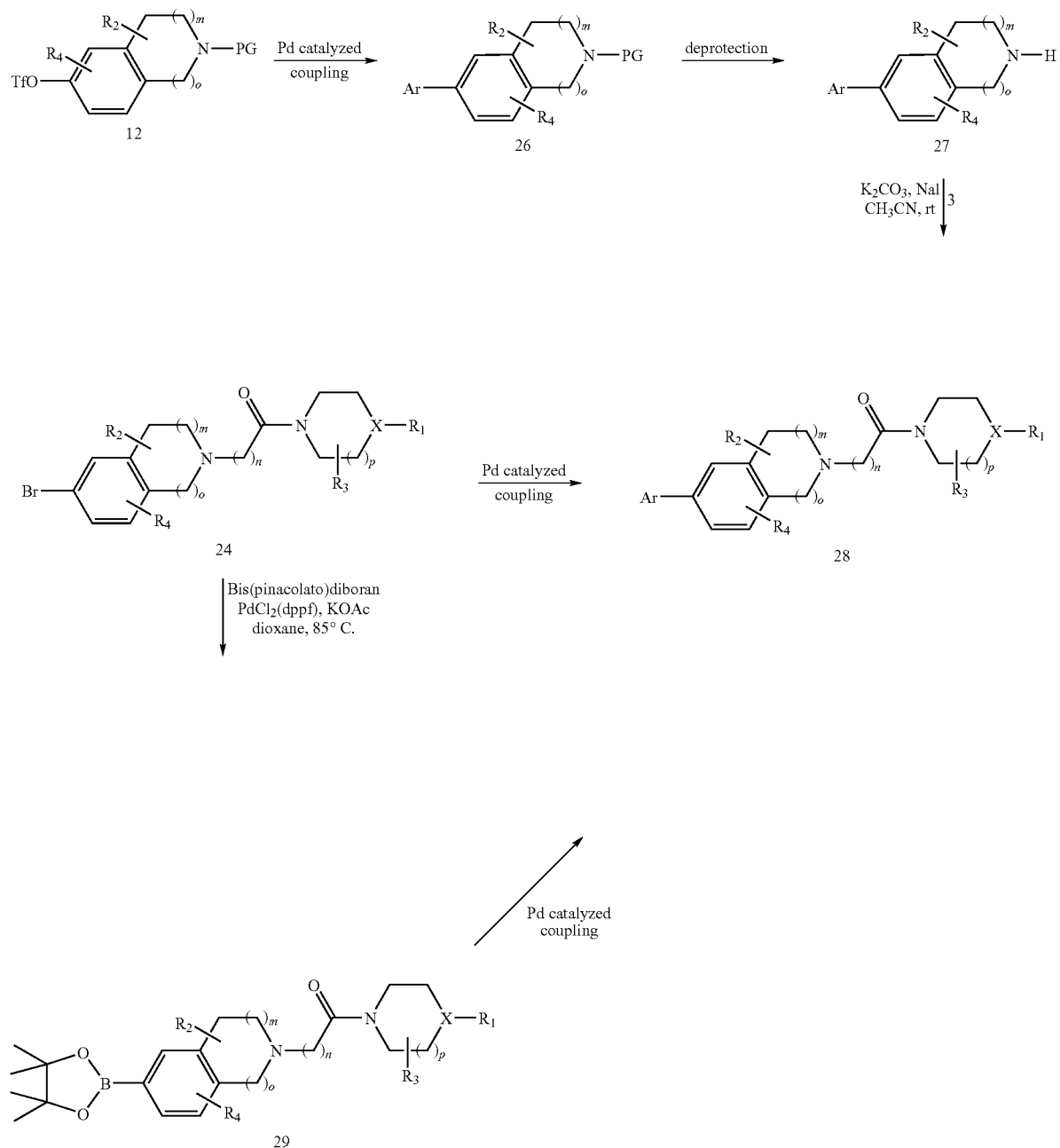

Scheme 6 illustrates the preparation of biaryl analogues of formula 28. Compound 12 is converted to biaryl intermediate 26 by palladium-catalyzed coupling reaction, such as Suzuki coupling, Nigishi coupling or Stille coupling. After deprotection, the resulting amine 27 is alkylated with halogen-substituted carboxamide 3 to furnish 28. Alternatively, 28 is synthesized from the bromo-substituted analogue 24 by palladium coupling reaction with corresponding boronic acids, zinc reagents or tin reagents. Upon coupling with bis (pinacolato)diboran in the presence of a palladium catalyst such as $PdCl_2(dppf)$ and potassium acetate as base, 24 is converted to compound 29 which leads to biaryl compounds 28 by palladium-catalyzed coupling, such as Suzuki coupling.

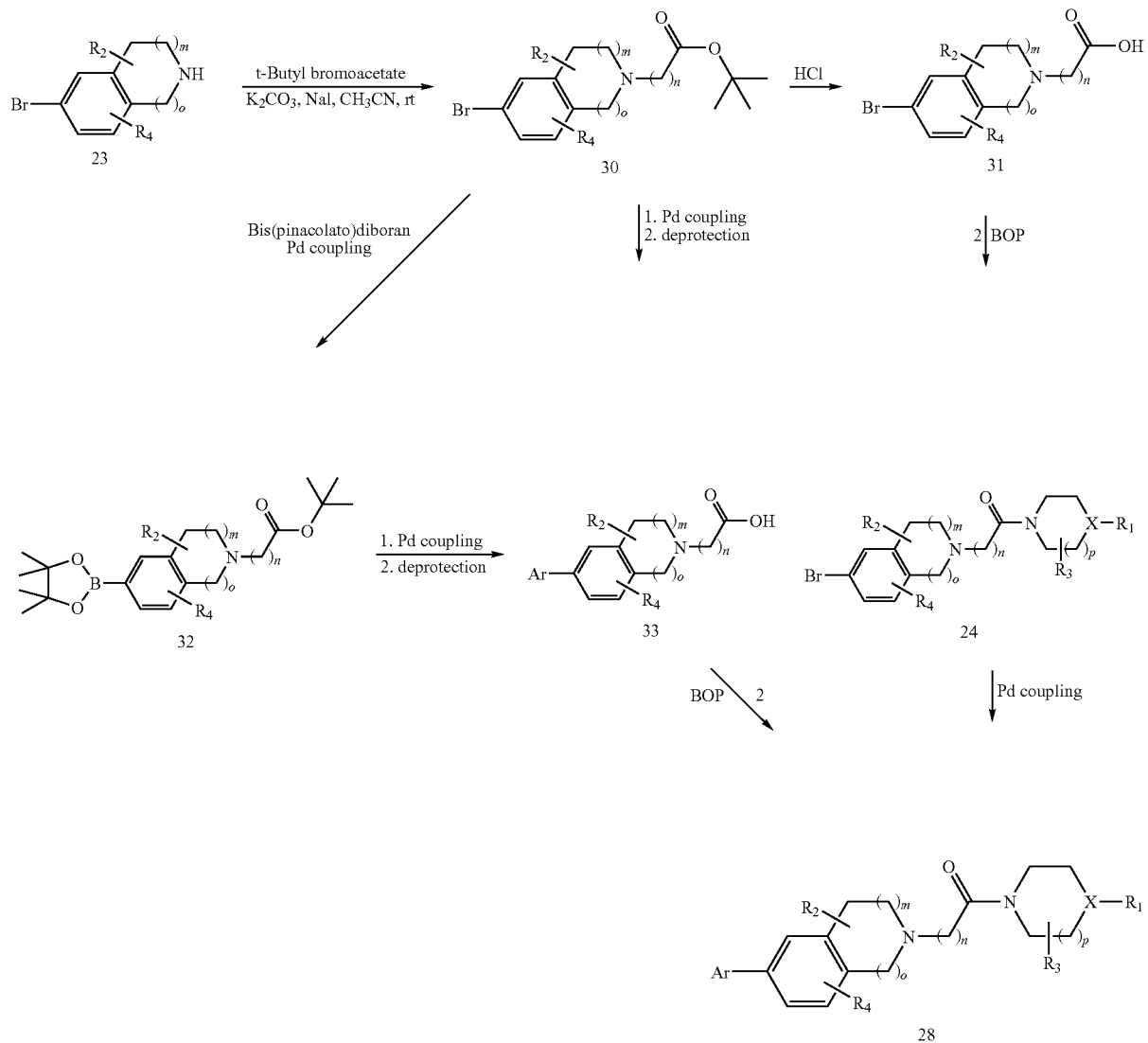

Scheme 7

Scheme 7 illustrates an alternative method for preparing biaryl analogues of formula 28. Alkylation of compound 23 with t-butyl bromoacetate in the presence of a base such as potassium carbonate provides intermediate 30. 30 is treated with hydrogen chloride to give acid 31, which is coupled with amine 2 to afford compound 24. Compound 24 is converted to 28 by palladium-catalyzed coupling, such as Suzuki coupling, Nigishi coupling or Stille coupling. Alternatively, intermediate 30 is converted to borate 32 by palladium coupling reaction with bis(pinacolato)diboran. 32 is transformed into acid 33 through Suzuki coupling followed by deprotection. Compound 30 may also be converted to acid 33 directly through palladium catalyzed coupling, such as Suzuki coupling, Nigishi coupling or Stille coupling followed by removal of the t-butyl group. Acid 33 is converted to compound 28 after coupling with amine 2 in the presence of a coupling reagent, such as BOP or EDCI.

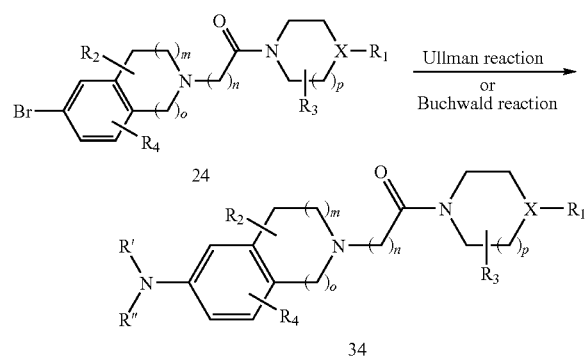

Scheme 8

Scheme 8 illustrates the preparation N-substituted THIQ analogues 34. Compound 24 is converted to 34 by a copper-catalyzed coupling reaction (Ullman reaction), or by a palladium-catalyzed coupling reaction (Buchwald reaction).

Scheme 9

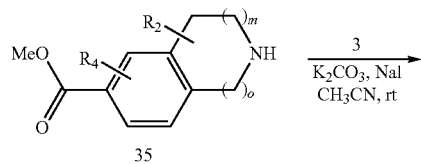

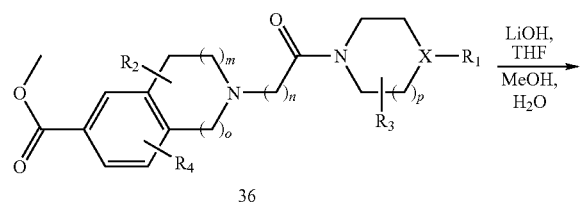

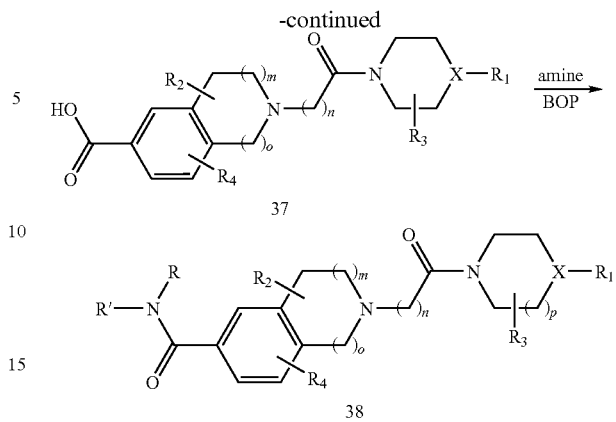

Scheme 9 illustrates the preparation of amide analogues of formula 38. Compound 35 is commercially available, known in the literature or conveniently prepared by a variety of methods familiar to those skilled in the art. Alkylation of 35 with halogen-substituted carboxamide 3 furnishes 36. Hydrolysis of 36 with LiOH-THF-MeOH—H$_2$O system gives acid 37, which leads to amide 38 upon coupling with an appropriate amine in the presence of a coupling reagent such as BOP, DCC or CDI.

Scheme 10

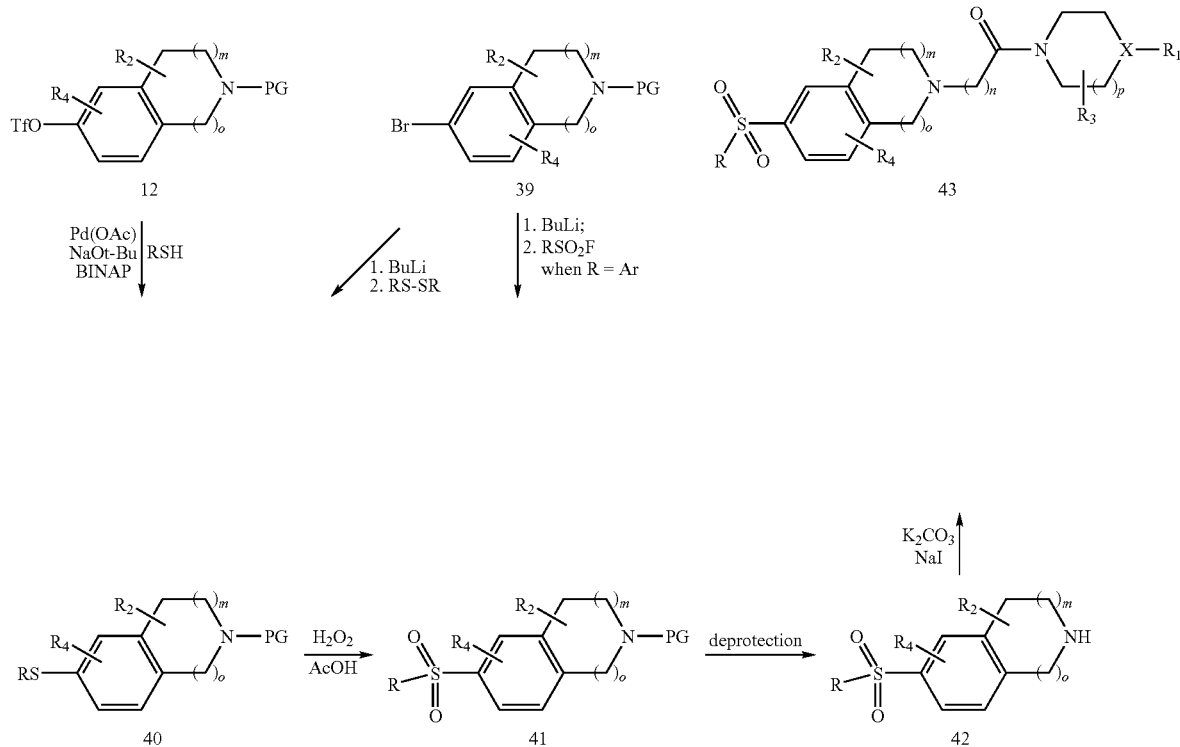

Scheme 10 illustrates the preparation of compounds of formula 43. Compound 12 couples with a thiol RSH in the presence of Pd(OAC)$_2$, NaOt-Bu and BINAP to give sulfanyl compound 40. Treatment of 40 with hydroxyperoxide in acetic acid furnishes sulfone 41. Alternatively, both 40 and 41 are prepared from 39. 39 is treated with BuLi at −78° C., and the resulting anion is quenched with dialkyldisulfide to give compound 40. If R is a substituted phenyl or heteroaryl group, the anion is quenched with sulfonyl halide to give sulfone compound 41 directly. Compound 41 is converted to amine 42 through deprotection. Alkylation of 42 with carboxamide 3 under standard alkylation conditions provides 43.

Scheme 11

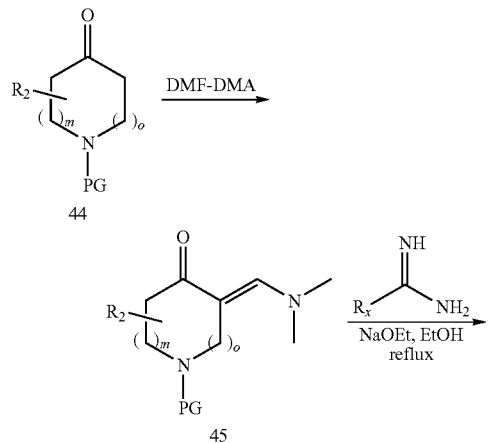

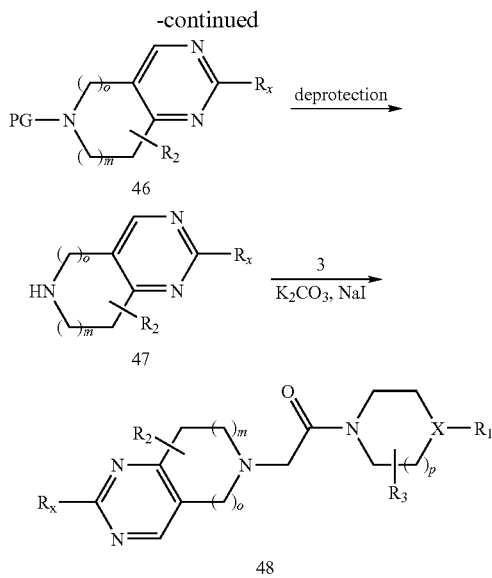

Scheme 11 illustrates the synthesis of compounds of formula 48. Treatment of N-protected piperidin-4-one 44 with N,N-dimethylformamide dimethyl acetal or a related reagent furnishes compound 45. Condensation of 45 with an appropriate amidine in EtOH in the presence of sodium ethoxide provides 46, which is then converted to amine 47 upon deprotection. Alkylation of 47 with carboxamide 3 under standard alkylation conditions provides 48.

Scheme 12

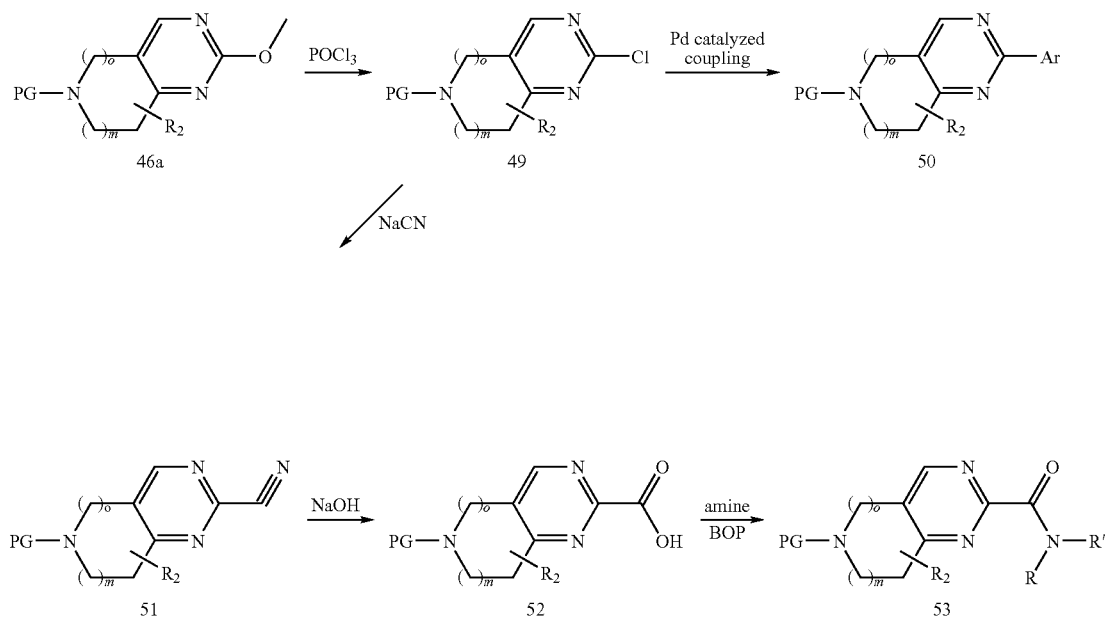

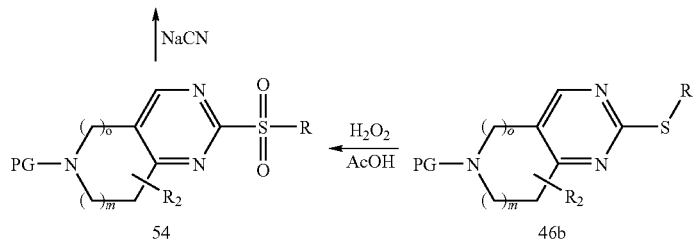

Scheme 12 illustrates the conversion of compound 46 to biaryl (50), cyano (51), carboxylic acid (52), amide (53), and sulfone (54) analogues. When $R_x$ of 46 is a methoxy group upon treatment with hydroxyperoxide in acetic acid. Alternatively, 54 may be converted to 51, which is then converted to acid 52 and amide 53 using a similar procedure.

Scheme 13

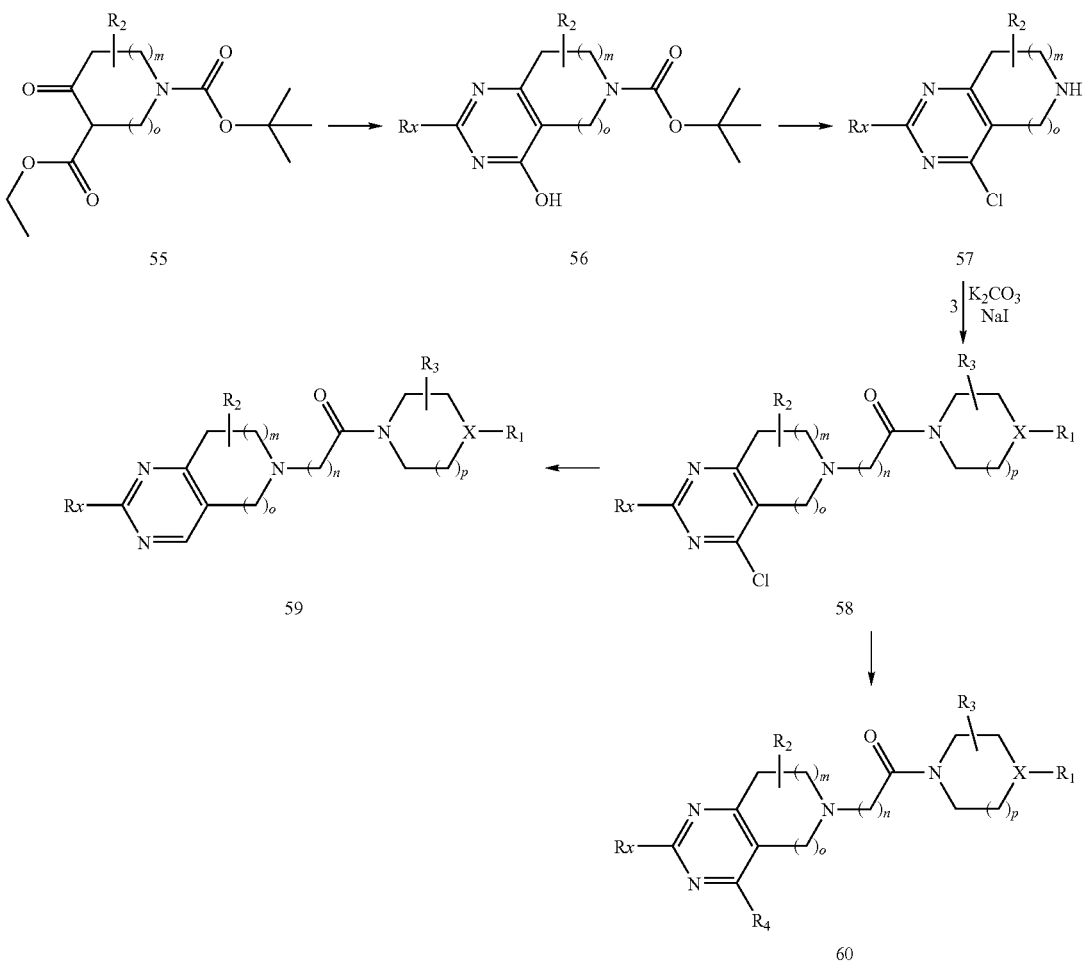

(46a), the compound is treated with phosphorous oxychloride to give 49. 49 is converted to biaryl-compound 50 through palladium catalyzed reaction such as Suzuki coupling, or to nitrile compound 51 upon heating with sodium cyamide. Basic hydrolysis of 51 provides acid 52, which is further converted to amide 53 upon coupling with an appropriate amine in the presence of a coupling reagent such as BOP. Compound 46b (when $R_x$ is SR) can be oxidized to sulfone 54

Scheme 13 illustrates an alternative synthesis of compounds 59 and 60. Condensation of 55 with a suitable formamidine in the presence of a suitable base such as NaOEt or NaH affords 56, which is reacted with a chlorination reagent such as $POCl_3$ to give 57. Treatment of 57 with compound 3 in the presence of a base such as potassium carbonate produces 58, which is hydrogenated over palladium on charcoal to afford 59. Alternatively, 58 is reacted with an organic metallic reagent such as boronic acid under Suzuki conditions, or organic tin under Stille conditions, to give 60.

coupling or Stille coupling. Conversion of 61 to nitrile 63 is achieved by reaction with Zn(CN)$_2$ under Stille reaction conditions. Hydrolysis of 63 provides acid 64, which is further

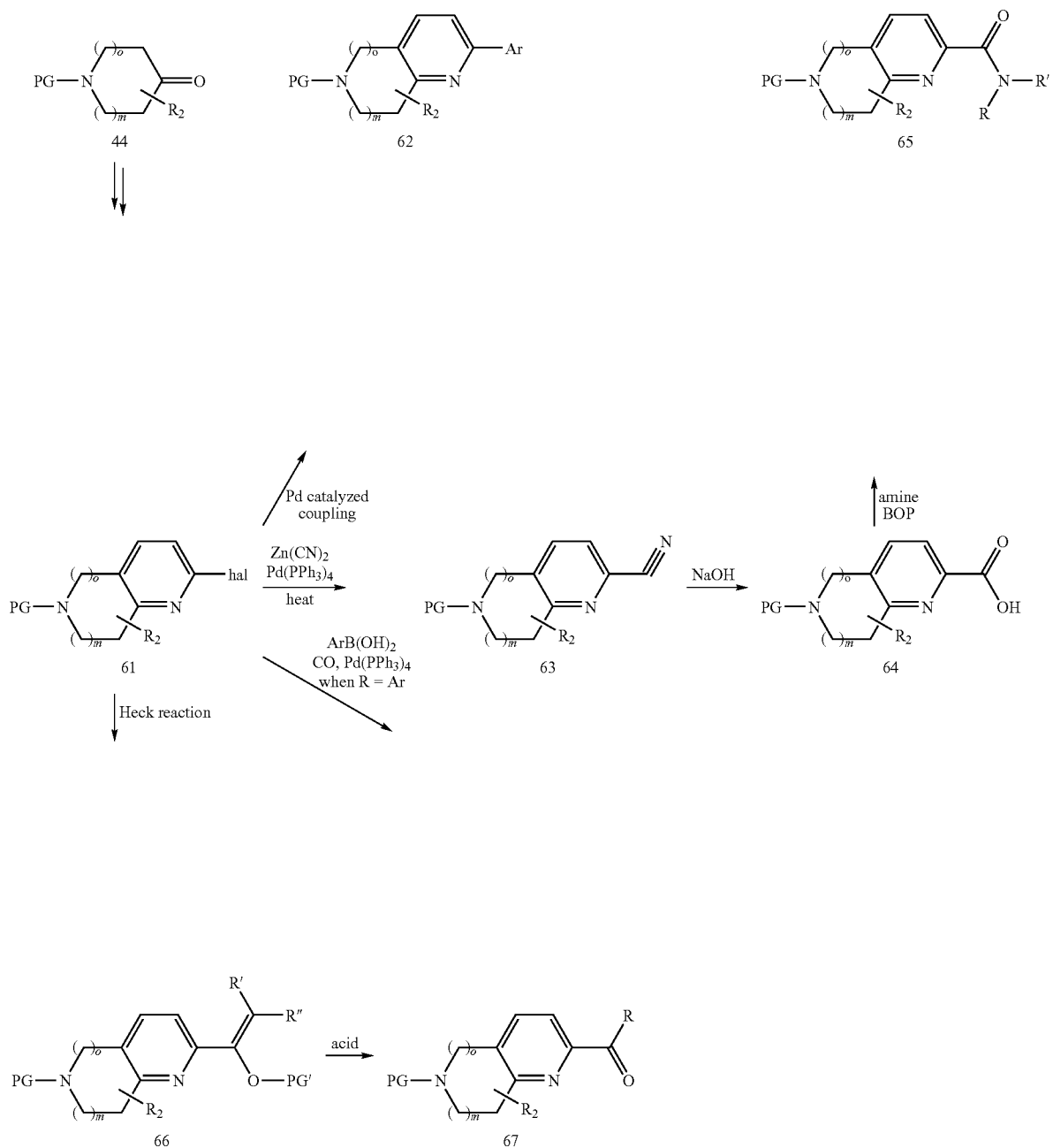

Scheme 14 illustrates the preparation of 5,6,7,8-tetrahydro-[1,6]naphthyridine intermediates 62-67. Compound 61, in which "hal" is a halogen such as bromo or chloro, is prepared from 44 essentially as described in PCT International Application Publication Number WO 03/076427A1, or by other methods familiar to those skilled in the art. Conversion of 61 to biaryl compound 62 is achieved through palladium-catalyzed coupling, such as Suzuki coupling, Nigishi transformed to amide 65 upon coupling with an appropriate amine in the presence of a coupling reagent such as BOP. Compound 66 may be prepared from 61 by reaction with a suitable enol ether under Heck reaction conditions in the presence of a catalyst such as palladium acetate and TEA as base. Hydrolysis of 66 yields 67. When R is an aryl or a heteroaryl group, 67 is alternatively prepared directly from 61 by coupling with a corresponding boronic acid and carbon monoxide in the presence of catalyst such as Pd(PPh$_3$)$_4$.

Scheme 15

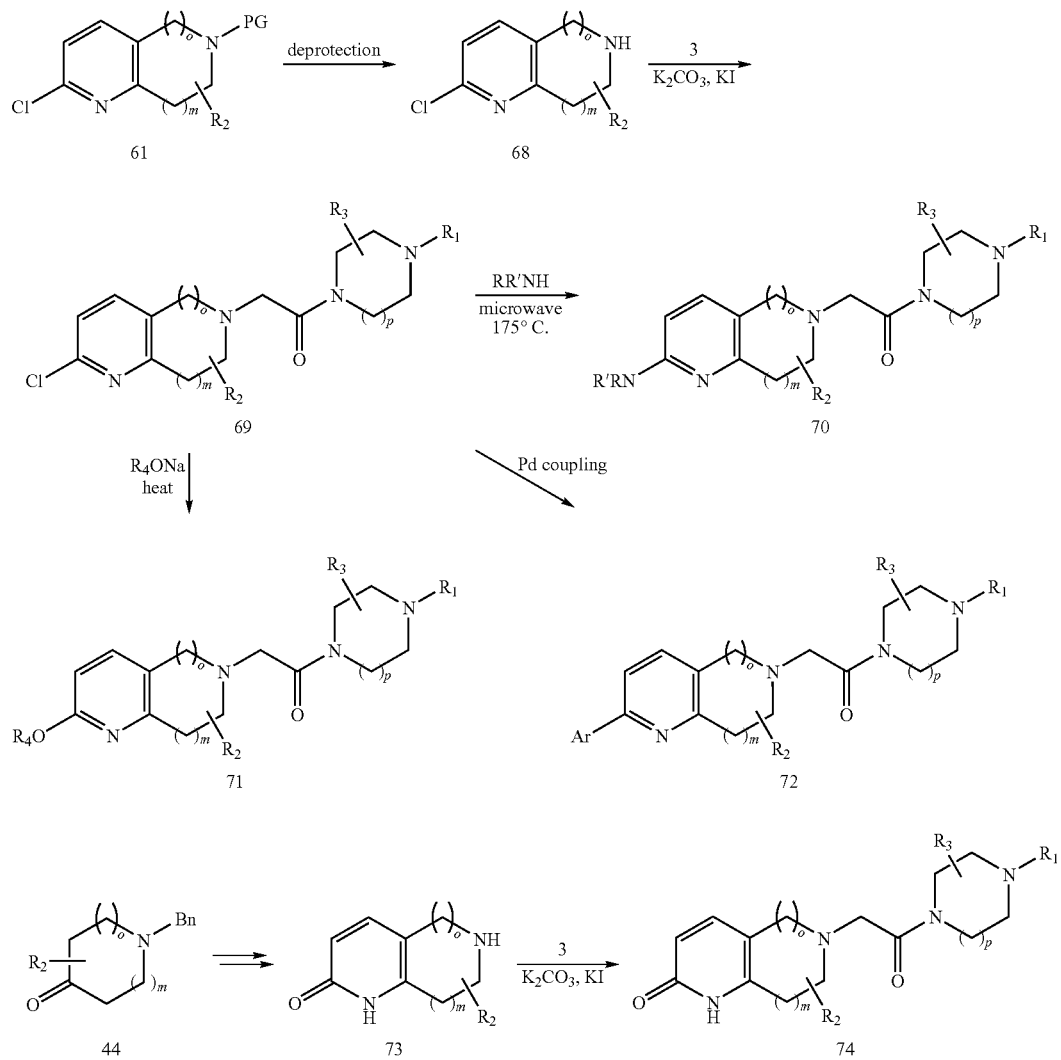

Scheme 15 illustrates the preparation of compounds 70, 71, 72, and 74. Compound 61 is deprotected to give 68. Alkylation of 68 with 3 provides compounds 69. Compounds 70, 71 and 72 are prepared from chloride 69 by Stille/Suzuki reaction, microwave amination and alkoxylation, respectively.

Compound 73 is alternatively prepared from 44 essentially as described in PCT International Application Publication Number WO 03/076427A1, or by other methods familiar to those skilled in the art. Alkylation of 73 with 3 under standard alkylation condition provides 74.

Scheme 16

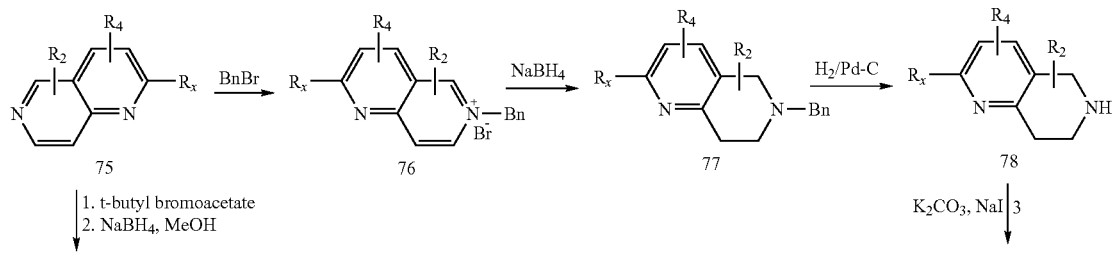

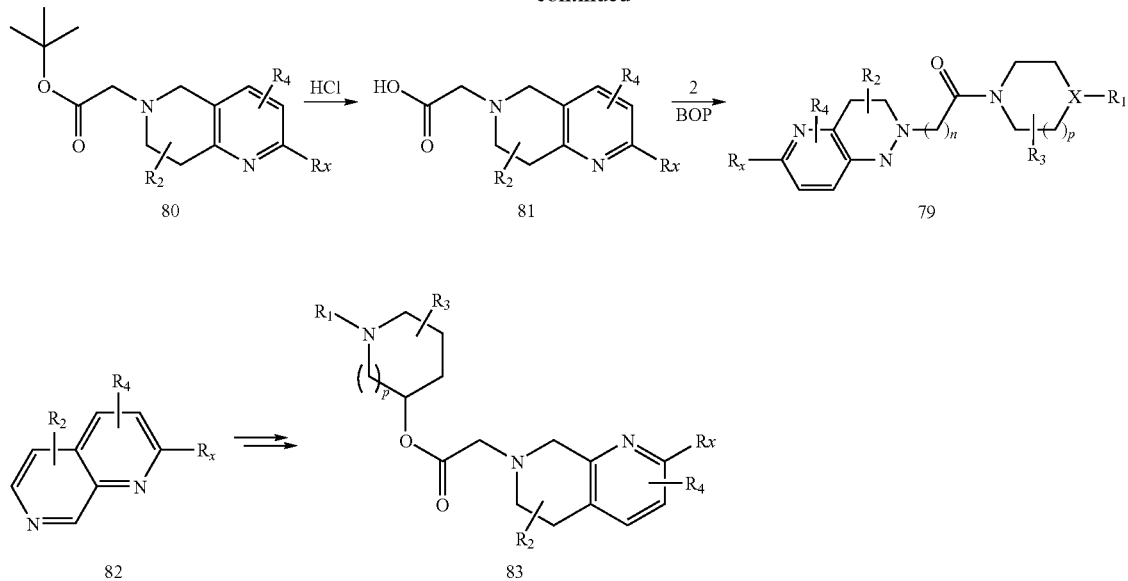

Scheme 16 illustrates an alternative method for preparing 79 and related analogues 83. Naphthyridine 75 and 82 are commercially available, known in the literature (e.g., *Bioorg. Med. Chem. Lett.* (1999) 17:2583-86) or conveniently prepared by a variety of methods familiar to those skilled in the art. Naphthyridine 75 is refluxed with benzyl bromide in acetonitrile to give the quaternary salt 76, which is converted to benzyl protected amine 77 upon treatment with sodium borohydride. The benzyl group in 77 is removed by hydrogenation in the presence of palladium on charcoal to give amine 78, which is transformed to 79 using a standard alkylation reaction. Alternatively, treatment of naphthyridine 75 with tert-butyl bromoacetate followed by reduction of the resultant quaternary salt with NaBH$_4$ gives tetrahydro-naphthyridine 80. Deprotection with HCl provides acid 81, which undergoes BOP coupling with diamine 2 to afford 79. By a similar sequence of reactions, 83 is prepared from 1,7-naphthyridine 82.

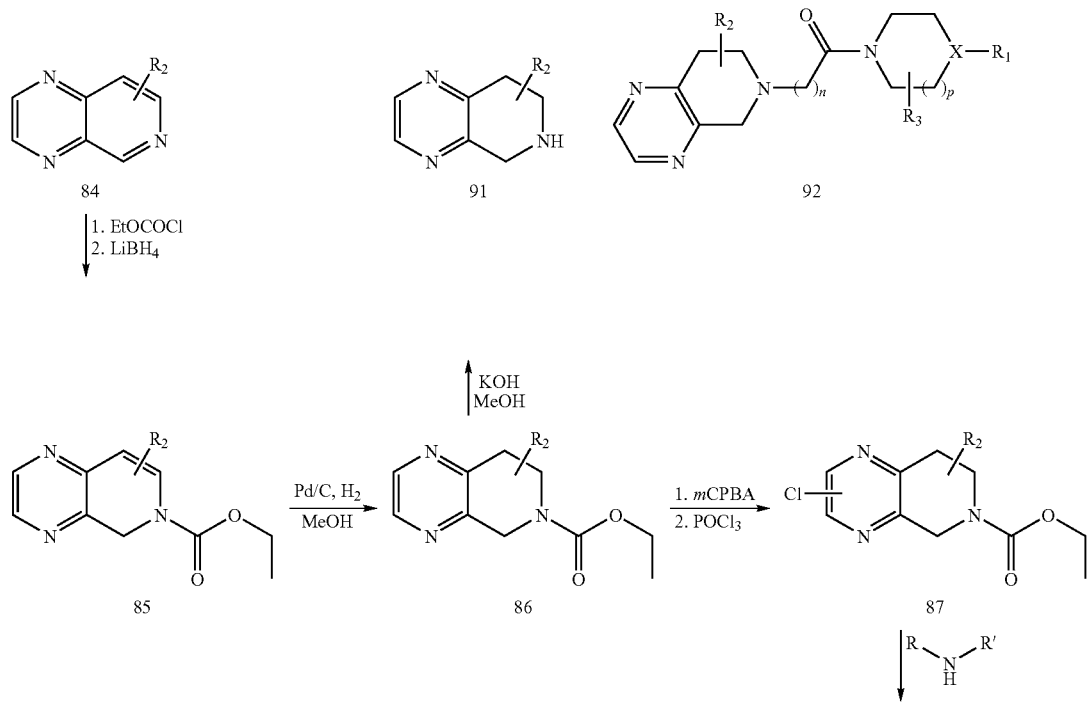

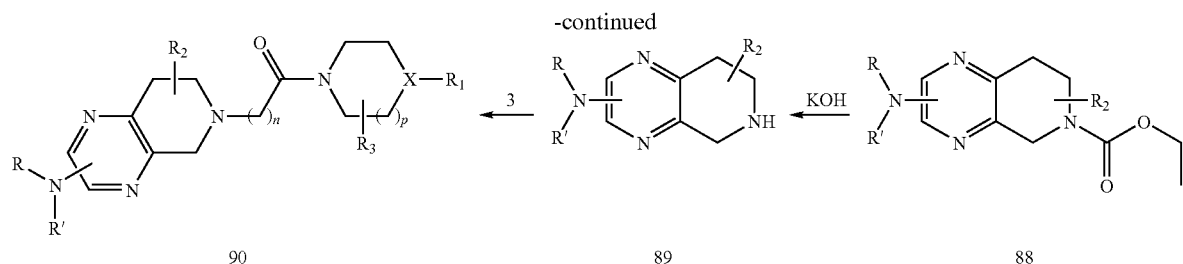

Scheme 17 illustrates the preparation of pyrazine analogues 90 and 92. Pyrido-pyrazine 84 is reacted with ethyl chloroformate followed by in situ reduction to form intermediate 85. Compound 85 is converted to tetrahydropyridine pyrazine intermediate 86 by palladium-catalyzed hydrogenation. Formation of the N-oxide of 86 followed by treatment with phosphorous oxychloride yields chloropyrazine intermediate 87. Treatment of 87 with an appropriate amine gives the amino pyrazine 88. Hydrolysis of carbamate ester 86 or 88 with potassium hydroxide yields intermediates 89 and 91, respectively, which are alkylated to yield tetrahydropyridopyrazine analogues 90 and 92.

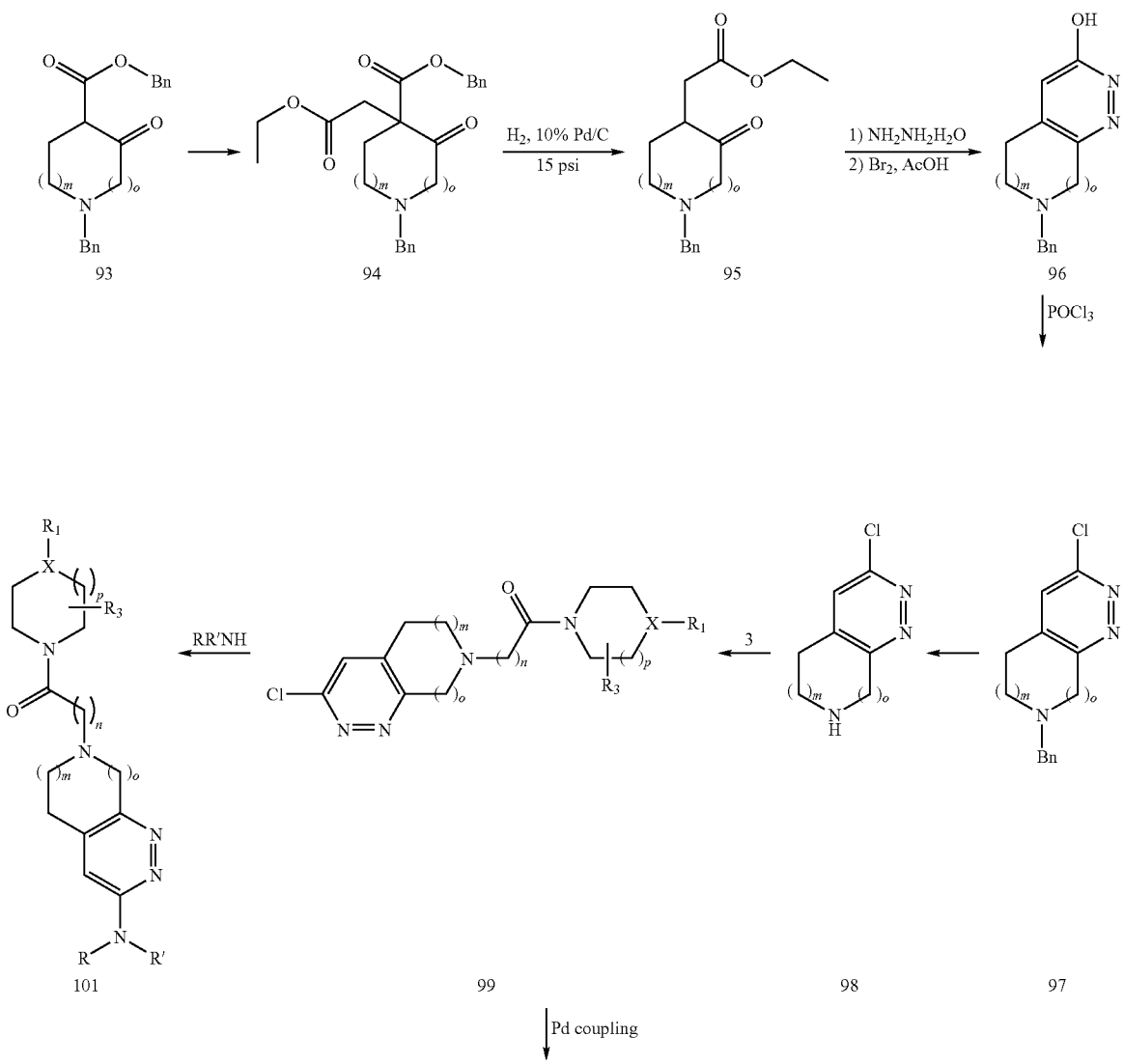

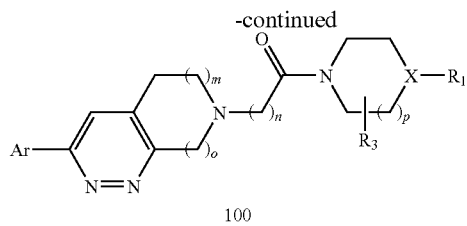

100

Scheme 18 illustrates the preparation of compounds 100 and 101. Alkylation of benzyl ester 93 with ethyl bromoacetate affords compound 94. Hydrogenolysis of benzyl ester 94 followed by concomitant decarboxylation produces ketoester 95. Cyclization of this ketoester with hydrazine monohydrate followed by dehydration with bromine in acetic acid affords compound 96. Treatment of 96 with $POCl_3$ provides compound 97, which is deprotected with 1-chloroethyl chloroformate to afford 98 as a HCl salt. Alkylation of 98 with halogen-substituted carboxamide 3 furnishes 99, which undergoes a coupling reaction such as Suzuki coupling, Stille coupling to give 100. Reaction of 99 with an amine under thermal, or Pd catalyzed coupling conditions to gives 101.

Scheme 19 illustrates the synthesis of compounds 105, 106 and 107. Compound 102 is commercially available, known in the literature (e.g., *Heterocycles*; EN; 63; 7; (2004) 63: 1555-1562), or conveniently prepared by a variety of methods familiar to those skilled in the art. Deprotection of 102 gives 103, which is treated with 3 in the presence of a base such as $K_2CO_3$ to give bromide 104. 104 is converted to 105, 106 and 107 by Pd catalyzed coupling reactions, such as Nigishi reaction, Heck reaction, Stille reaction or Suzuki reaction.

Scheme 19

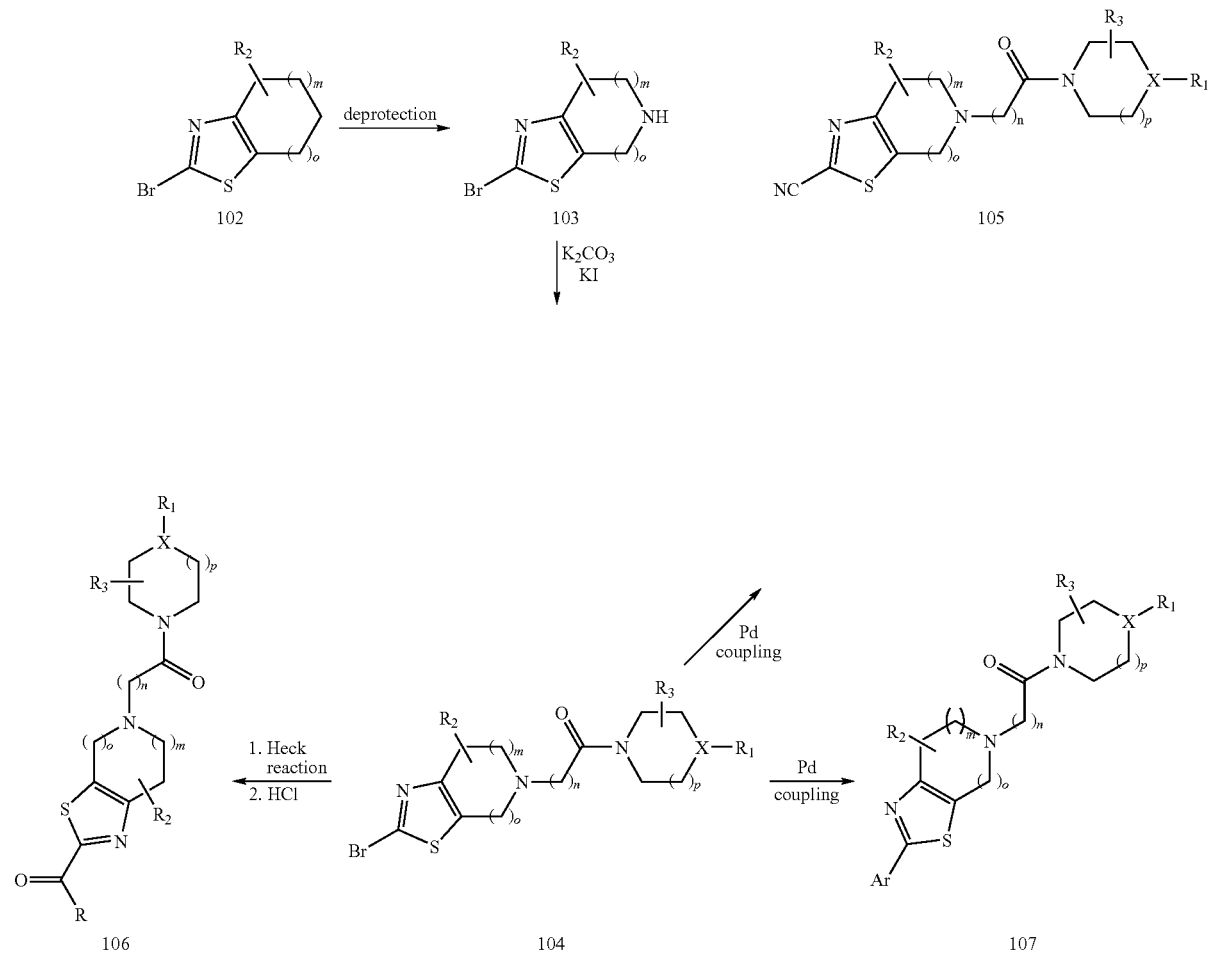

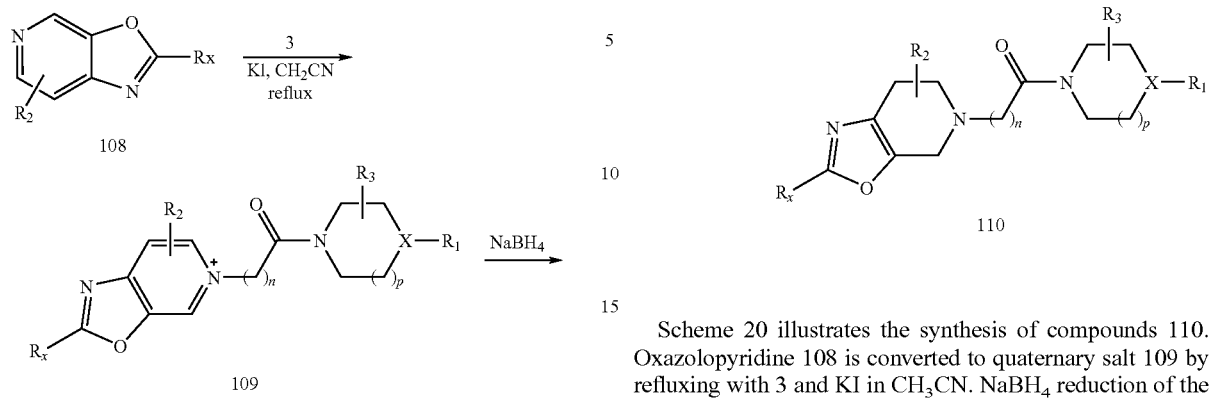
Scheme 20 illustrates the synthesis of compounds 110. Oxazolopyridine 108 is converted to quaternary salt 109 by refluxing with 3 and KI in CH$_3$CN. NaBH$_4$ reduction of the salt in a polar solvent such as MeOH provides 110.
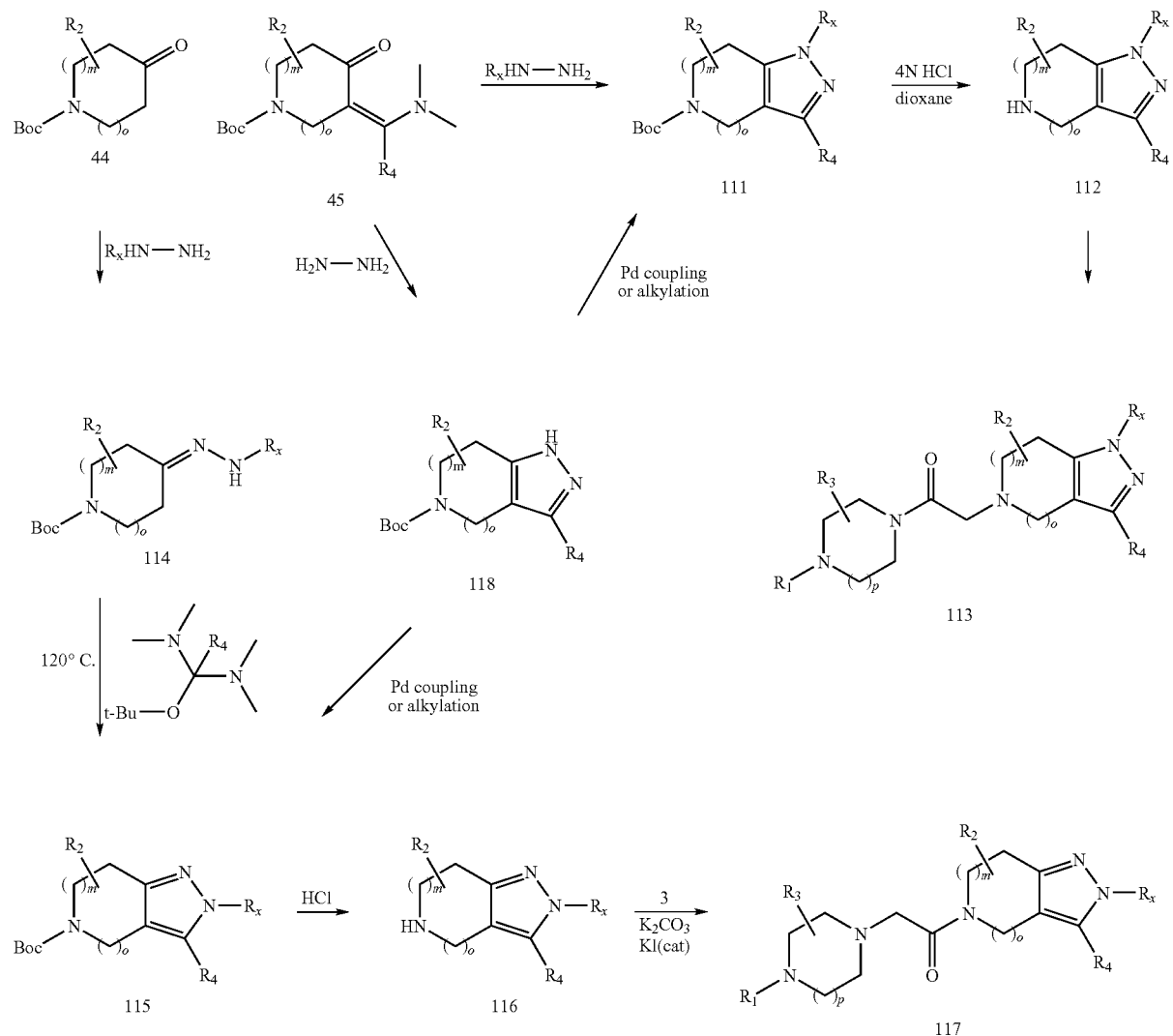

Scheme 21 illustrates the synthesis of compounds 113 and 117. Compound 45 reacts with a suitable hydrazine to provide 111. Deprotection of 111 furnishes 112, which is alkylated with 3 to give 113. Alternatively, the substituted hydrazine condenses with protected piperidone 44 first to provide hydrazone 114, which is converted to 115 by refluxing in Brederick reagent at elevated temperature. Deprotection of 115 gives 116, which is alkylated with 3 to provide 117.

Alternatively, reacting compound 45 with hydrazine provides pyrazole 118, which is reacted with an aryl halide under modified Buchwald reaction condition in the presence of tBuXPhos, Pd$_2$(dba)$_3$, tBuONa to give substituted pyrazoles 111 and 115 as a 1:5 to 1:3 mixture. The isomers are separated by recrystallization, and then, as described in Scheme 21, be converted to 113 and 117.

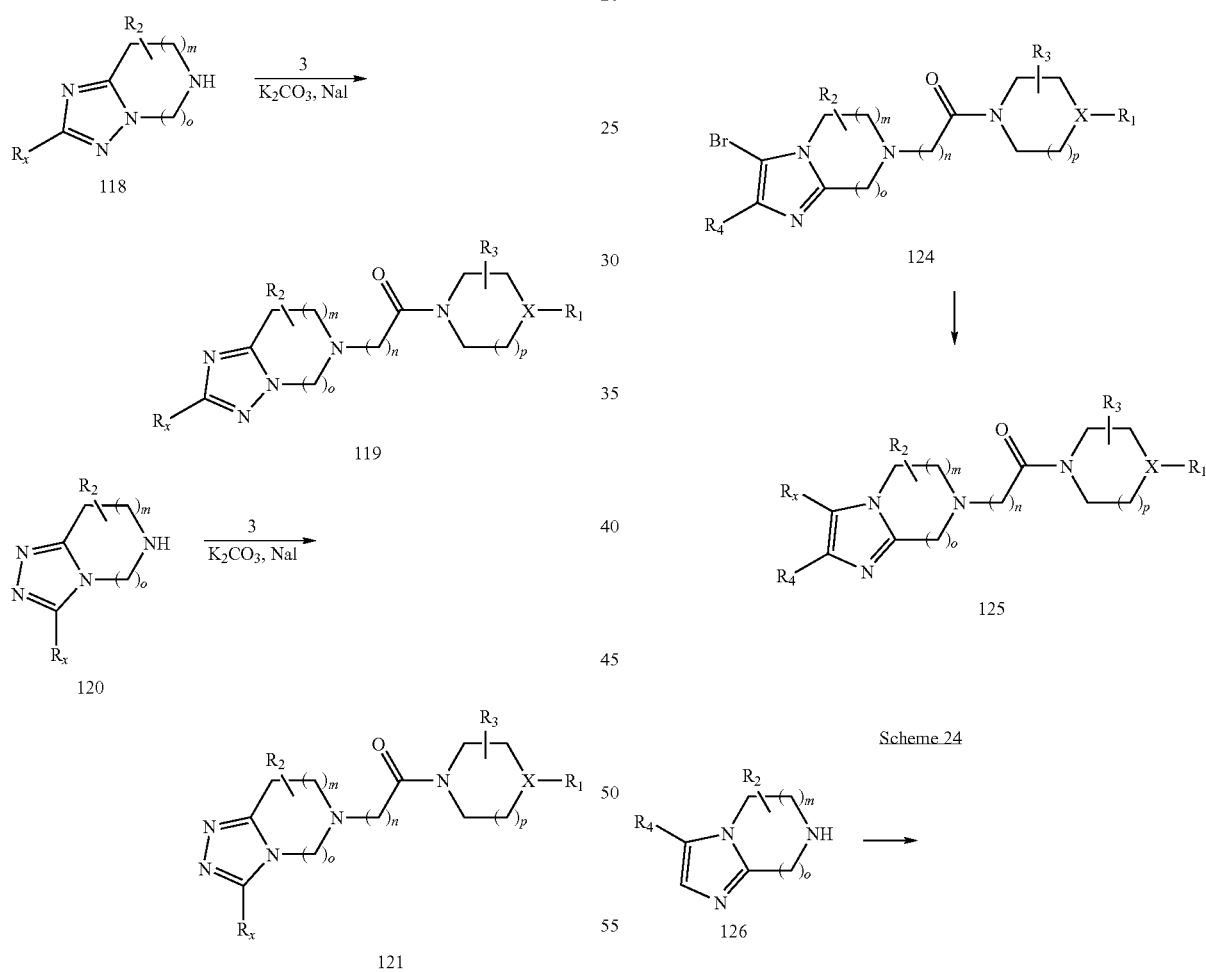

Scheme 22 illustrates the synthesis of compounds 119 and 121. Compounds 118 and 120 are commercially available, known in the literature (e.g., PCT International Application Publication Numbers WO 2004/032836 and WO 2003/004498), or conveniently prepared by a variety of methods familiar to those skilled in the art. Treatment of 118 and 120 with 3 in the presence of a base such as potassium carbonate provides, respectively, 119 and 121.

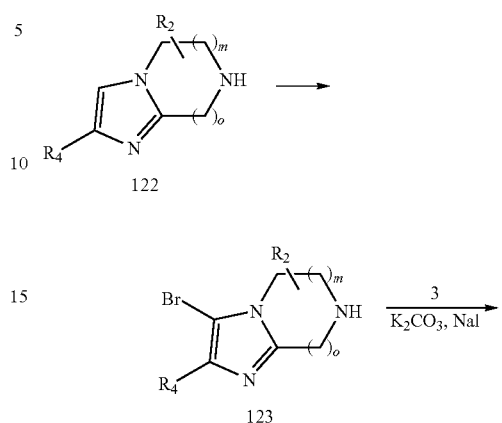

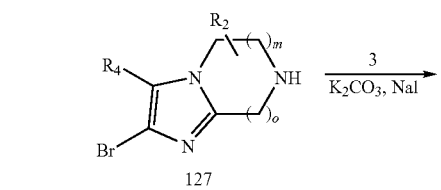

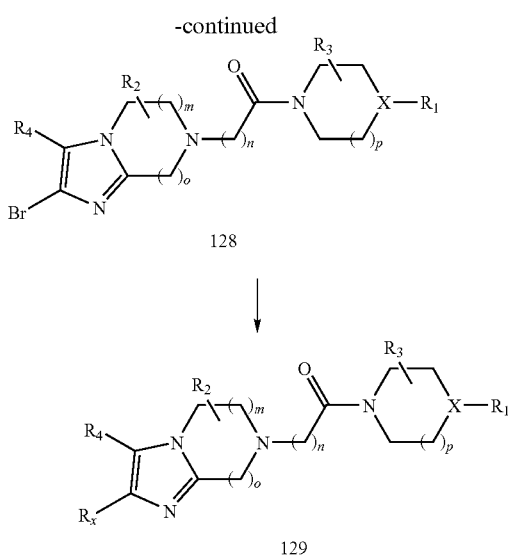

128

↓

129

Schemes 23 and 24 illustrate the synthesis of imidazole compounds 125 and 129, respectively. Compounds 122 and 126 are commercially available, known in the literature (e.g., PCT International Application Publication Number WO 2003/004498) or conveniently prepared by a variety of methods familiar to those skilled in the art. 122 and 126 are brominated using standard methods, with a bromination agent (such as NBS) to give compounds 123 and 127, respectively. Treatment of 123 and 127 with 3 in the presence of a base such as potassium carbonate produces 124 and 128, respectively, which are reacted with an organic metallic reagent such as boronic acid under Suzuki conditions, or organic tin under Stille conditions, to give 125 and 129, respectively.

130 with di-t-butyl dicarbonate or other reagents gives 131, which is brominated with NBS in acetonitrile to give 132. 132 reacts with an organic metallic reagent such as boronic acid under Suzuki conditions, or organic tin under Stille conditions, to give 133. Deprotection of 133 followed by alkylation with 3 in the presence of a base such as potassium carbonate produces 134.

In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$) or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

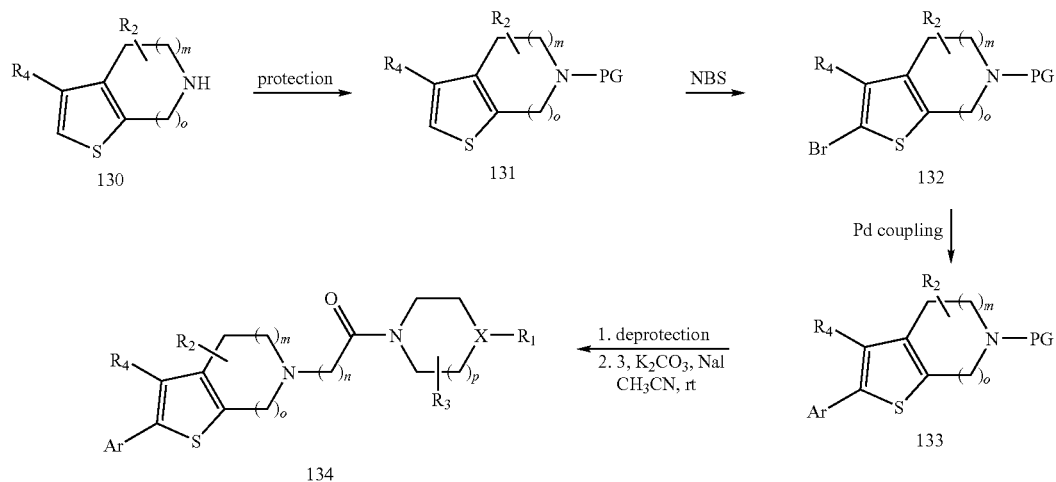

Scheme 25

Scheme 25 illustrates the synthesis of thiophene compounds 134. Compounds of formula 130 are commercially available, known in the literature (e.g., *Chem. Pharm. Bull.*, (1994) 42: 1676-1678) or conveniently prepared by a variety of methods familiar to those skilled in the art. Protection of The present invention also provides pharmaceutical compositions comprising one or more compounds provided herein, together with at least one physiologically acceptable carrier or excipient. Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs or cats). In addition, other active ingredients may (but need not) be included in the pharmaceutical compositions provided herein.

Pharmaceutical compositions may be formulated for any appropriate manner of administration, including, for example, inhalation (e.g., nasal or oral), topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents to increase the bulk weight of the material to be tableted (e.g., calcium carbonate, sodium carbonate, lactose, calcium phosphate or sodium phosphate), granulating and disintegrating agents that modify the disintegration rate in the environment of use (e.g., corn starch, starch derivatives, alginic acid and salts of carboxymethylcellulose), binding agents that impart cohesive qualities to the powdered material(s) (e.g., starch, gelatin, acacia and sugars such as sucrose, glucose, dextrose and lactose) and lubricating agents (e.g., magnesium stearate, calcium stearate, stearic acid or talc). Tablets may be formed using standard techniques, including dry granulation, direct compression and wet granulation. The tablets may be uncoated or they may be coated by known techniques.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active material(s) in admixture with one or more suitable excipients, such as suspending agents (e.g., sodium carboxymethylcellulose, methylcellulose, hydroxypropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The active ingredient(s), depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the body temperature and will therefore melt in the body to release the drug. Suitable excipients include, for example, cocoa butter and polyethylene glycols.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Pharmaceutical compositions may be formulated for release at a pre-determined rate. Instantaneous release may be achieved, for example, via sublingual administration (i.e., administration by mouth in such a way that the active ingredient(s) are rapidly absorbed via the blood vessels under the tongue rather than via the digestive tract). Controlled release formulations (i.e., formulations such as a capsule, tablet or coated tablet that slows and/or delays release of active ingredient(s) following administration) may be administered by, for example, oral, rectal or subcutaneous implantation, or by implantation at a target site. In general, a controlled release formulation comprises a matrix and/or coating that delays disintegration and absorption in the gastrointestinal tract (or implantation site) and thereby provides a delayed action or a sustained action over a longer period. One type of controlled-release formulation is a sustained-release formulation, in which at least one active ingredient is continuously released over a period of time at a constant rate. Preferably, the therapeutic agent is released at such a rate that blood (e.g., plasma) concentrations are maintained within the therapeutic range, but below toxic levels, over a period of time that is at least 4 hours, preferably at least 8 hours, and more preferably at least 12 hours. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of H3 receptor modulator release. The amount of H3 receptor modulator contained within a sustained release formulation depends upon, for example, the site of implantation, the rate and expected duration of release and the nature of the condition to be treated or prevented.

Controlled release may be achieved by combining the active ingredient(s) with a matrix material that itself alters release rate and/or through the use of a controlled-release coating. The release rate can be varied using methods well known in the art, including (a) varying the thickness or composition of coating, (b) altering the amount or manner of addition of plasticizer in a coating, (c) including additional ingredients, such as release-modifying agents, (d) altering the composition, particle size or particle shape of the matrix, and (e) providing one or more passageways through the coating. The amount of H3 receptor modulator contained within a sustained release formulation depends upon, for example, the method of administration (e.g., the site of implantation), the rate and expected duration of release and the nature of the condition to be treated or prevented.

The matrix material, which itself may or may not serve a controlled-release function, is generally any material that supports the active ingredient(s). For example, a time delay material such as glyceryl monosterate or glyceryl distearate may be employed. Active ingredient(s) may be combined with matrix material prior to formation of the dosage form (e.g., a tablet). Alternatively, or in addition, active ingredient(s) may be coated on the surface of a particle, granule, sphere, microsphere, bead or pellet that comprises the matrix material. Such coating may be achieved by conventional means, such as by dissolving the active ingredient(s) in water or other suitable solvent and spraying. Optionally, additional ingredients are added prior to coating (e.g., to assist binding of the active ingredient(s) to the matrix material or to color the solution). The matrix may then be coated with a barrier agent prior to application of controlled-release coating. Multiple coated matrix units may, if desired, be encapsulated to generate the final dosage form.

In certain embodiments, a controlled release is achieved through the use of a controlled release coating (i.e., a coating that permits release of active ingredient(s) at a controlled rate in aqueous medium). The controlled release coating should be a strong, continuous film that is smooth, capable of supporting pigments and other additives, non-toxic, inert and tack-free. Coatings that regulate release of the H3 receptor modulator include pH-independent coatings, pH-dependent coatings (which may be used to release H3 receptor modulator in the stomach) and enteric coatings (which allow the formulation to pass intact through the stomach and into the small intestine, where the coating dissolves and the contents are absorbed by the body). It will be apparent that multiple coatings may be employed (e.g., to allow release of a portion of the dose in the stomach and a portion further along the gastrointestinal tract). For example, a portion of active ingredient(s) may be coated over an enteric coating, and thereby released in the stomach, while the remainder of active ingredient(s) in the matrix core is protected by the enteric coating and released further down the GI tract. pH dependent coatings include, for example, shellac, cellulose acetate phthalate, polyvinyl acetate phthalate, hydroxypropylmethylcellulose phthalate, methacrylic acid ester copolymers and zein.

In certain embodiments, the coating is a hydrophobic material, preferably used in an amount effective to slow the hydration of the gelling agent following administration. Suitable hydrophobic materials include alkyl celluloses (e.g., ethylcellulose or carboxymethylcellulose), cellulose ethers, cellulose esters, acrylic polymers (e.g., poly(acrylic acid), poly (methacrylic acid), acrylic acid and methacrylic acid copolymers, methyl methacrylate copolymers, ethoxy ethyl methacrylates, cyanoethyl methacrylate, methacrylic acid alkamide copolymer, poly(methyl methacrylate), polyacrylamide, ammonio methacrylate copolymers, aminoalkyl methacrylate copolymer, poly(methacrylic acid anhydride) and glycidyl methacrylate copolymers) and mixtures of the foregoing. Representative aqueous dispersions of ethylcellulose include, for example, AQUACOAT® (FMC Corp., Philadelphia, Pa.) and SURELEASE® (Colorcon, Inc., West Point, Pa.), both of which can be applied to the substrate according to the manufacturer's instructions. Representative acrylic polymers include, for example, the various EUDRAGIT® (Rohm America, Piscataway, N.J.) polymers, which may be used singly or in combination depending on the desired release profile, according to the manufacturer's instructions.

The physical properties of coatings that comprise an aqueous dispersion of a hydrophobic material may be improved by the addition or one or more plasticizers. Suitable plasticizers for alkyl celluloses include, for example, dibutyl sebacate, diethyl phthalate, triethyl citrate, tributyl citrate and triacetin. Suitable plasticizers for acrylic polymers include, for example, citric acid esters such as triethyl citrate and tributyl citrate, dibutyl phthalate, polyethylene glycols, propylene glycol, diethyl phthalate, castor oil and triacetin.

Controlled-release coatings are generally applied using conventional techniques, such as by spraying in the form of an aqueous dispersion. If desired, the coating may comprise pores or channels or to facilitate release of active ingredient. Pores and channels may be generated by well known methods, including the addition of organic or inorganic material that is dissolved, extracted or leached from the coating in the environment of use. Certain such pore-forming materials include hydrophilic polymers, such as hydroxyalkylcelluloses (e.g., hydroxypropylmethylcellulose), cellulose ethers, synthetic water-soluble polymers (e.g., polyvinylpyrrolidone, cross-linked polyvinylpyrrolidone and polyethylene oxide), water-soluble polydextrose, saccharides and polysaccharides and alkali metal salts. Alternatively, or in addition, a controlled release coating may include one or more orifices, which may be formed my methods such as those described in U.S. Pat. Nos. 3,845,770; 4,034,758; 4,077,407; 4,088,864;

4,783,337 and 5,071,607. Controlled-release may also be achieved through the use of transdermal patches, using conventional technology (see, e.g., U.S. Pat. No. 4,668,232).

Further examples of controlled release formulations, and components thereof, may be found, for example, in U.S. Pat. Nos. 4,572,833; 4,587,117; 4,606,909; 4,610,870; 4,684,516; 4,777,049; 4,994,276; 4,996,058; 5,128,143; 5,202,128; 5,376,384; 5,384,133; 5,445,829; 5,510,119; 5,618,560; 5,643,604; 5,891,474; 5,958,456; 6,039,980; 6,143,353; 6,126,969; 6,156,342; 6,197,347; 6,387,394; 6,399,096; 6,437,000; 6,447,796; 6,475,493; 6,491,950; 6,524,615; 6,838,094; 6,905,709; 6,923,984; 6,923,988; and 6,911,217; each of which is hereby incorporated by reference for its teaching of the preparation of controlled release dosage forms.

In addition to or together with the above modes of administration, a compound provided herein may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Compounds provided herein are generally present within a pharmaceutical composition at levels providing a therapeutically effective amount upon administration, as described above. Dosage forms providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms generally contain between from about 0.1 mg to about 2 g, preferably 0.5 mg to 1 g, and more preferably 1 mg to 500 mg, of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing and procedures that are well known in the art.

Pharmaceutical compositions may be packaged for treating conditions responsive to H3 receptor modulation, including those specifically recited herein (e.g., attention deficit disorder, attention deficit hyperactivity disorder, schizophrenia, a cognitive disorder (such as mild cognitive impairment), epilepsy, migraine, narcolepsy, allergic rhinitis, vertigo, motion sickness, a memory disorder such as Alzheimer's disease, Parkinson's disease, obesity, an eating disorder or diabetes). Packaged pharmaceutical preparations comprise a container holding one or more dosage units comprising a therapeutically effective amount of at least one H3 receptor modulator as described herein and instructions (e.g., labeling) indicating that the contained composition is to be used for treating a condition responsive to H3 receptor modulation in the patient.

Methods of Use

H3 receptor modulators provided herein may be used to alter activity and/or activation of H3 receptors in a variety of contexts, both in vitro and in vivo. Within certain aspects, H3 receptor modulators may be used to inhibit or enhance (preferably to inhibit) H3 receptor activity in vitro or in vivo. In general, such methods comprise the step of contacting a H3 receptor with one or more H3 receptor modulators provided herein, in aqueous solution and under conditions otherwise suitable for binding of the H3 receptor modulator(s) to H3 receptor. The H3 receptor modulator(s) are generally present at a concentration that is sufficient to alter H3 receptor GTP binding activity in vitro (using the assay provided in Example 7). The H3 receptor may be present in solution or suspension (e.g., in an isolated membrane or cell preparation), or in a cultured or isolated cell. Within certain embodiments, the H3 receptor is present in a patient (e.g., expressed by a neuronal cell), and the aqueous solution is a body fluid. Preferably, one or more H3 receptor modulators are administered to a patient in an amount such that each H3 receptor modulator is present in at least one body fluid of the patient at a therapeutically effective concentration that is 1 micromolar or less; preferably 500 nanomolar or less; more preferably 100 nanomolar or less, 50 nanomolar or less, 20 nanomolar or less, or 10 nanomolar or less. For example, such compounds may be administered at a dose that is less than 20 mg/kg body weight, preferably less than 5 mg/kg and, in some instances, less than 1 mg/kg. In vivo, modulation of H3 receptor activity may be assessed by detecting an alteration of a symptom (e.g., memory or attention) in a patient being treated with one or more H3 receptor modulators provided herein.

The present invention further provides methods for treating conditions responsive to H3 receptor modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to H3 receptor modulation" if it is characterized by inappropriate activity of H3 receptor, regardless of the amount of H3 receptor ligand present locally, and/or if modulation of H3 receptor activity results in alleviation of the condition or a symptom thereof. Such conditions may be diagnosed and monitored using criteria that have been established in the art. Patients may include humans, domesticated companion animals and livestock, with dosages as described above.

Conditions that are responsive to H3 receptor modulation include, for example:

Cardiovascular disorders, including atherosclerosis, hypertension, myocardial infarction, coronary heart disease and stroke;

Cancer (e.g., endometrial, breast, prostate and colon cancer, cutaneous carcinoma, medullary thyroid carcinoma and melanoma);

Metabolic disorders including impaired glucose tolerance, dyslipidaemia, and diabetes (e.g., non-insulin dependent diabetes mellitus);

Immune conditions and disorders including osteoarthritis, allergy (e.g., allergic rhinitis), and inflammation;

Respiratory conditions including nasal congestion, upper airway allergic response, asthma and chronic obstructive pulmonary disease;

Disorders associated with the regulation of sleep and wakefulness, or arousal and vigilance, including narcolepsy, jet lag, sleep apnea, and sleep disorders, such as excessive daytime sleepiness (EDS) (e.g., shift work sleep disorder), insomnia (e.g., primary insomnia), idiopathic hypersomnia, circadian rhythm sleep disorder, dyssomnia NOS, parasomnias including nightmare disorder, sleep terror disorder, sleep disorders secondary to depression, anxiety and/or other mental disorders and substance-induced sleep disorder;

Eating disorders (e.g., bulimia, binge eating and anorexia) and obesity;

Digestive system and gastrointestinal disorders including gallbladder disease, ulcer, hyper- and hypo-motility of the gastrointestinal tract and irritable bowel syndrome;

CNS disorders including hyper- and hypo-activity of the central nervous system, migraine, epilepsy, seizures, convulsions, mood disorders, attention deficit disorder, attention deficit hyperactivity disorder, bipolar disorder, depression, manic disorders, obsessive compulsive disorder, schizophrenia, migraine, vertigo, motion sickness, dementia, cognitive deficit (e.g., in psychiatric disorder, such as mild cognitive impairment), learning deficit, memory deficit (e.g., age-related memory dysfunction), multiple sclerosis, Parkinson's disease, Alzheimer's disease and other neurodegenerative disorders, addiction (e.g., resulting from drug abuse), neurogenic inflammation and Tourette's syndrome;

Vestibular dysfunction (e.g., Meniere's disease, dizziness and motion sickness);

Pain (e.g., inflammatory pain or neuropathic pain) and itch;

Septic shock; and

Glaucoma.

H3 receptor modulators may further be used to enhance a patient's cognitive ability.

In certain embodiments, compounds provided herein are used to treat attention deficit disorder, attention deficit hyperactivity disorder, schizophrenia, a cognitive disorder (such as mild cognitive impairment), epilepsy, migraine, narcolepsy, allergic rhinitis, vertigo, motion sickness, a memory disorder such as Alzheimer's disease, Parkinson's disease, obesity, an eating disorder or diabetes. Treatment regimens may vary depending on the compound used and the particular condition to be treated. However, for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Within other aspects, H3 receptor modulators provided herein may be used within combination therapy for the treatment of conditions that are responsive to H3 receptor modulation, as described above. Within such combination therapy, a H3 receptor modulator is administered to a patient along with a second therapeutic agent that is not a H3 receptor modulator. The H3 receptor modulator and second therapeutic agent may be present in the same pharmaceutical composition, or may be administered separately in either order. It will be apparent that additional therapeutic agents may, but need not, also be administered.

Second therapeutic agents suitable for use in such combination therapy include, for example, antiobesity agents, antidiabetics, antihypertensive agents, antidepressants, antipsychotic agents and anti-inflammatory agents. In certain combinations, the second therapeutic agent is a compound for the treatment of attention deficit disorder or attention deficit hyperactivity disorder, an antipsychotic agent or an anti-obesity agent.

Histamine H1 receptor modulators represent one class of second therapeutic agents. Combination with H1 receptor modulators may be used, for example, in the treatment of Alzheimer's disease, inflammatory diseases and allergic conditions. Representative H1 receptor antagonists include, for example, loratadine (CLARITIN™), desloratadine (CLARINEX™), fexofenadine (ALLEGRA™) and cetirizine (ZYRTEC™). Other H1 receptor antagonists include ebastine, mizolastine, acrivastine, astemizole, azatadine, azelastine, brompheniramine, chlorpheniramine, clemastine, cyproheptadine, dexchlorpheniramine, diphenhydramine, hydroxyzine, levocabastine, promethazine and tripelennamine.

Antiobesity therapeutic agents for use in combination therapy include, for example, leptin, leptin receptor agonists, melanin concentrating hormone (MCH) receptor antagonists, melanocortin receptor 3 (MC3) agonists, melanocortin receptor 4 (MC4) agonists, melanocyte stimulating hormone (MSH) agonists, cocaine and amphetamine regulated transcript (CART) agonists, dipeptidyl aminopeptidase inhibitors, a growth hormone secretagogue, beta-3 adrenergic agonists, 5HT-2 agonists, orexin antagonists, neuropeptide $Y_1$ or $Y_5$ antagonists, tumor necrosis factor (TNF) agonists, galanin antagonists, urocortin agonists, cholecystokinin (CCK) agonists, GLP-1 agonists, serotonin (5HT) agonists, bombesin agonists, CB1 antagonists such as rimonabant, growth hormone, growth factors such as prolactin or placental lactogen, growth hormone releasing compounds, thyrotropin (TRH) agonists, uncoupling protein 2 or 3 (UCP 2 or 3) modulators, dopamine agonists, agents that modify lipid metabolism such as antilipidemic agents (e.g., cholestyramine, colestipol, clofibrate, gemfibrozil, lovastatin, pravastatin, simvastatin, probucol or dextrothyroxine), lipase/amylase inhibitors, peroxisome proliferator-activated receptor (PPAR) modulators, retinoid X receptor (RXR) modulators, TR-beta agonists, agouti-related protein (AGRP) inhibitors, opioid antagonists such as naltrexone, exendin-4, GLP-1, ciliary neurotrophic factor, corticotropin-releasing factor binding protein (CRF BP) antagonists and/or corticotropin-releasing factor (CRF) agonists. Representative such agents include, for example, sibutramine, dexfenfluramine, dextroamphetamine, amphetamine, orlistat, mazindol, phentermine, phendimetrazine, diethylpropion, fluoxetine, bupropion, topiramate and ecopipam.

Antihypertensive therapeutic agents for use in combination therapy include, for example, beta-blockers such as alprenolol, atenolol, timolol, pindolol, propranolol and metoprolol, angiotensin converting enzyme (ACE) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, alpha-blockers such as doxazosin, urapidil, prazosin and terazosin, and angiotensin receptor blockers such as losartan.

CNS-active agents for use in combination therapy include, but are not limited to the following: for anxiety, depression, mood disorders or schizophrenia-serotonin receptor (e.g., $5\text{-HT}_{1A}$) agonists and antagonists, neurokinin receptor antagonists, GABAergic agents, and corticotropin releasing factor receptor ($CRF_1$) antagonists; for sleep disorders—melatonin receptor agonists; and for neurodegenerative disorders—such as Alzheimer's dementia, nicotinic agonists, muscarinic agents, acetylcholinesterase inhibitors and dopamine receptor agonists. For example, such combination therapy may include a selective serotonin reuptake inhibitor (SSRI) or a non-selective serotonin, dopamine and/or norepinephrine reuptake inhibitor. Such agents include, for example, fluoxetine, sertraline, paroxetine, amitriptyline, seroxat and citalopram. For cognitive disorders, representative agents for use in combination therapy include GABAergic agents.

Other therapeutic agents suitable for combination therapy include, for example, agents that modify cholinergic transmission (e.g., 5-$HT_6$ antagonists), M1 muscarinic agonists, M2 muscarinic antagonists and acetylcholinesterase inhibitors.

Suitable doses for H3 receptor modulator within such combination therapy are generally as described above. Doses and methods of administration of other therapeutic agents can be found, for example, in the manufacturer's instructions in the *Physician's Desk Reference*. In certain embodiments, the combination administration of a H3 receptor modulator with the second therapeutic agent results in a reduction of the dosage of the second therapeutic agent required to produce a therapeutic effect (i.e., a decrease in the minimum therapeutically effective amount). Thus, preferably, the dosage of second therapeutic agent in a combination or combination treatment method is less than the maximum dose advised by the manufacturer for administration of the second therapeutic agent without combination administration of a H3 receptor modulator. More preferably this dosage is less than ¾, even more preferably less than ½, and highly preferably, less than ¼ of the maximum dose, while most preferably the dose is less than 10% of the maximum dose advised by the manufacturer for the second therapeutic agent when administered without combination administration of a H3 receptor modulator. It will be apparent that the dosage amount of H3 receptor modulator component(s) of the combination needed to achieve the desired effect may similarly be affected by the dosage amount and potency of the other therapeutic component(s) of the combination.

In certain preferred embodiments, the combination administration of a H3 receptor modulator with other therapeutic agent(s) is accomplished by packaging one or more H3 receptor modulators and one or more other therapeutic agents in the same package, either in separate containers within the package or in the same contained as a mixture of one or more H3 receptor modulators and one or more other therapeutic agents. Preferred mixtures are formulated for oral administration (e.g., as pills, capsules, tablets or the like). In certain embodiments, the package comprises a label bearing indicia indicating that the one or more H3 receptor modulators and one or more other therapeutic agents are to be taken together for the treatment of attention deficit disorder, attention deficit hyperactivity disorder, schizophrenia, a cognitive disorder (such as mild cognitive impairment), epilepsy, migraine, narcolepsy, allergic rhinitis, vertigo, motion sickness, a memory disorder such as Alzheimer's disease, Parkinson's disease, obesity, an eating disorder or diabetes.

Within separate aspects, the present invention provides a variety of non-pharmaceutical in vitro and in vivo uses for the compounds provided herein. For example, such compounds may be labeled and used as probes for the detection and localization of H3 receptor (in samples such as cell preparations or tissue sections, preparations or fractions thereof). In addition, compounds provided herein that comprise a suitable reactive group (such as an aryl carbonyl, nitro or azide group) may be used in photoaffinity labeling studies of receptor binding sites. In addition, compounds provided herein may be used as positive controls in assays for receptor activity, as standards for determining the ability of a candidate agent to bind to H3 receptor, or as radiotracers for positron emission tomography (PET) imaging or for single photon emission computerized tomography (SPECT). Such methods can be used to characterize H3 receptors in living subjects. For example, a H3 receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of H3 receptor in the sample. Detection assays, including receptor autoradiography (receptor mapping) of H3 receptor in cultured cells or tissue samples may be performed as described by Kuhar in sections 8.1.1 to 8.1.9 of Current Protocols in Pharmacology (1998) John Wiley & Sons, New York.

Compounds provided herein may also be used within a variety of well known cell separation methods. For example, H3 receptor modulators may be linked to the interior surface of a tissue culture plate or other support, for use as affinity ligands for immobilizing and thereby isolating, H3 receptors (e.g., isolating receptor-expressing cells) in vitro. Within one preferred embodiment, a H3 receptor modulator linked to a fluorescent marker, such as fluorescein, is contacted with the cells, which are then analyzed (or isolated) by fluorescence activated cell sorting (FACS).

H3 receptor modulators provided herein may further be used within assays for the identification of other agents that bind to H3 receptor. In general, such assays are standard competition binding assays, in which bound, labeled H3 receptor modulator is displaced by a test compound. Briefly, such assays are performed by: (a) contacting H3 receptor with a radiolabeled H3 receptor modulator as described herein, under conditions that permit binding of the H3 receptor modulator to H3 receptor, thereby generating bound, labeled H3 receptor modulator; (b) detecting a signal that corresponds to the amount of bound, labeled H3 receptor modulator in the absence of test agent; (c) contacting the bound, labeled H3 receptor modulator with a test agent; (d) detecting a signal that corresponds to the amount of bound labeled H3 receptor modulator in the presence of test agent; and (e) detecting a decrease in signal detected in step (d), as compared to the signal detected in step (b).

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Mass spectroscopy data in the following Examples is Electrospray MS, obtained in positive ion mode using a Micromass Time-of-Flight LCT (Waters Corp.; Milford, Mass.), equipped with a Waters 600 pump (Waters Corp.; Milford, Mass.), Waters 996 photodiode array detector (Waters Corp.; Milford, Mass.), and a Gilson 215 autosampler (Gilson, Inc.; Middleton, Wis.). MassLynx™ (Waters Corp.; Milford, Mass.) version 4.0 software with OpenLynx Global Server™, OpenLynx™ and AutoLynx™ processing is used for data collection and analysis. MS conditions are as follows: capillary voltage=3.5 kV; cone voltage=30 V, desolvation and source temperature=350° C. and 120° C., respectively; mass range=181-750 with a scan time of 0.22 seconds and an interscan delay of 0.05 seconds.

Analyses are performed using one of the following procedures:

Method 1: Sample volume of I microliter is injected onto a 30×4.6 mm XBridge™ C18, 5μ, column (Waters Corp.; Milford, Mass.), and eluted using a 2-phase linear gradient at a flow rate of 6 ml/min. Sample is detected using total absorbance count over the 220-340 nm UV range. The elution conditions are: Mobile Phase A—95% water, 5% MeOH with 0.025% ammonium hydroxide; Mobile Phase B—5% water, 95% MeOH with 0.025% ammonium hydroxide. The following gradient is used: 0-0.5 min 5-100% B, hold at 100% B to 1.2 min, return to 5% B at 1.21 min. Inject to inject cycle is 2.15 min.

Method 2: Sample volume of 1 microliter is injected onto a 50×4.6 mm Chromolith SpeedROD RP-18e column (Merck KGaA, Darmstadt, Germany), and eluted using a 2-phase linear gradient at a flow rate of 6 ml/min. Sample is detected using total absorbance count over the 220-340 nm UV range. The elution conditions are: Mobile Phase A—95% water, 5% MeOH with 0.05% TFA; Mobile Phase B—5% water, 95% MeOH with 0.025% TFA. The following gradient is used: 0-0.5 min 5-100% B, hold at 100% B to 1.2 min, return to 5% B at 1.21 min. Inject to inject cycle is 2.15 min.

Method 3: Sample volume of 1 microliter is injected onto a 50×4.6 mm Chromolith SpeedROD RP-18e column (Merck KGaA, Darmstadt, Germany), and eluted using a 2-phase linear gradient at a flow rate of 6 ml/min. Sample is detected using total absorbance count over the 220-340 nm UV range. The elution conditions are: Mobile Phase A—95% water, 5% MeOH with 0.05% TFA; Mobile Phase B—5% water, 95% MeOH with 0.025% TFA. The following gradient is used: 0-0.5 min 10-100% B, hold at 100% B to 1.2 min, return to 10% B at 1.21 min. Inject to inject cycle is 2.15 min.

Example 1

Preparation of Representative Compounds

I. 1-(4-Cyclobutyl-Piperazin-1-Yl)-2-(6-Methoxy-3,4-Dihydro-1H-Isoquinolin-2-Yl)-Ethanone (Schemes 1 and 3)

Compound 1

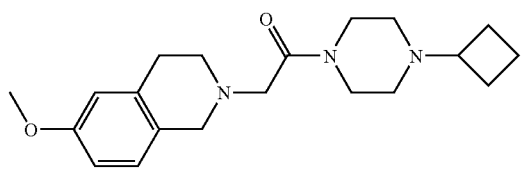

Step 1. Preparation of 2-chloro-1-(4-cyclobutyl-piperazin-1-yl)-ethanone

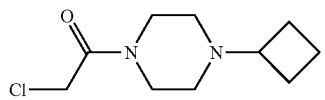

To a solution of sodium bicarbonate (15 mmol) in water (5 mL) and DCM (30 mL) at 0° C. is added chloroacetyl bromide (12 mmol), followed by immediate addition of 1-cyclobutylpiperazine (10 mmol). The mixture is stirred at 0° C. for an additional 40 min. To the mixture is added aqueous sodium bicarbonate (15 mL) and DCM (30 mL). The layers are separated and the organic layer is dried (MgSO$_4$) and solvent is removed in vacuo to give 2-chloro-1-(4-cyclobutyl-piperazin-1-yl)-ethanone, which is used in the next step without further purification. $^1$H NMR (300 MHz, CDCl$_3$) δ 4.07 (2H, s), 3.64 (2H, t), 3.52 (2H, t), 2.74 (1H, m), 2.36 (2H, t), 2.31 (2H, t), 1.72-2.08 (6H, m); MS (+VE) m/z 217.1 (M$^+$+1).

Step 2. Preparation of 6-methoxy-1,2,3,4-tetrahydroisoquinoline

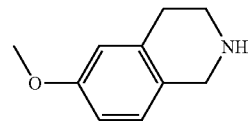

To the solution of 3-methoxylphenethylamine (15.1 g, 0.1 mol) in formic acid (100 ml) at rt is added paraformaldehyde (3.0 g, 0.1 mol, 1.0 eq.). The resulting mixture is stirred at 40~50° C. for 24 hr. After the reaction is completed, the formic acid is evaporated and the residue is diluted with water (200 ml), basified with sodium hydroxide solution (10.0N, 10.5 ml) to pH=10, and extracted with EtOAc. The combined organic layers are washed with water and brine and dried over sodium sulfate, and the solvent is removed under reduced pressure to give the title compound. MS (+VE) m/z 164.1 (M$^+$+1).

Step 3. Preparation of 1-(4-cyclobutyl-piperazin-1-yl)-2-(6-methoxy-3,4-dihydro-1H-isoquinolin-2-yl)-ethanone

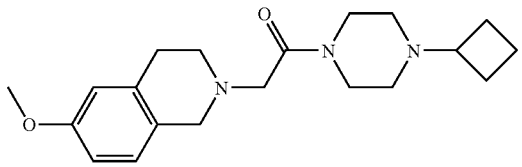

To a stirred solution of 6-methoxy-1,2,3,4-tetrahydroisoquinoline (163 mg, 1.0 mmol) in acetonitrile (5.0 ml) is added 2-chloro-(4-cyclobutyl-piperazine)-acetamide (216 mg, 1.0 mmol, 1.0 eq.), K$_2$CO$_3$ (376 mg, 2.0 mmol, 2.0 eq.), and NaI (30 mg). The resulting mixture is stirred at rt overnight. Water (10.0 ml) is added to quench the reaction, and then the acetonitrile is evaporated. The residue is extracted with DCM (10 ml×3). The extracts are dried over sodium sulfate, and the solvent is removed under reduced pressure to yield a residue that is purified through PTLC (EtOAc/4% TEA) to give the title compound. ¹H NMR (300 MHz, CDCl₃) δ 6.92 (1H, d), 6.70 (1H, dd), 6.63 (1H, d), 3.77 (3H, s), 3.58~3.68 (6H, m), 3.33 (2H, s), 2.86 (2H, t), 2.74 (2H, t), 2.65 (1H, m), 2.27 (4H, m), 1.62~2.06 (6H, m); MS (+VE) m/z 344.2 (M⁺+1).

II. 2-[2-(4-Cyclobutylpiperazin-1-Yl)-2-Oxoethyl]-6-(Cyclopentyloxy)-1,2,3,4-Tetrahydroisoquinoline (Scheme 4)

Compound 2

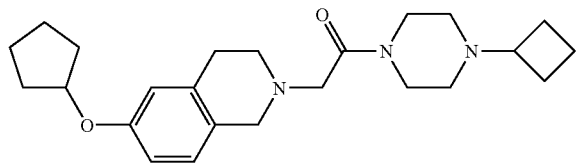

Step 1. Preparation of 6-(benzyloxy)-2-[2-(4-cyclobutylpiperazin-1-yl)-2-oxoethyl]-1,2,3,4-tetrahydroisoquinoline

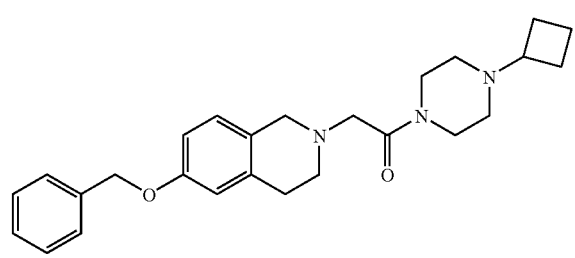

To a stirred solution of 6-benzyloxy-1,2,3,4-tetrahydroisoquinoline (1.5 g, 6.26 mmol) in acetonitrile (20.0 ml) is added 2-chloro-(4-cyclobutyl-piperazine)-acetamide (1.36 g, 6.26 mmol, 1.0 eq.), K₂CO₃ (1.73 g, 12.5 mmol, 2.0 eq.), and NaI (180 mg). The resulting mixture is stirred at rt overnight. Water (20.0 ml) is added to quench the reaction, and then the acetonitrile is evaporated. The residue is extracted with DCM (20 ml×3). The combined organic phase is dried over sodium sulfate, and the solvent is removed under reduced pressure to give a residue that is purified by PTLC (EtOAc/4% TEA) to give the title compound. ¹H NMR (300 MHz, CDCl₃) δ 7.30-7.44 (5H, m), 6.84-6.94 (1H, m), 6.70-6.80 (2H, 1 m), 5.20 (2H, s), 3.60-3.74 (6H, m), 3.56 (2H, s), 2.62-2.92 (5H, m), 2.22-2.32 (4H, m), 1.60~2.10 (6H, m); MS (+VE) m/z 420.2 (M⁺+1).

Step 2. Preparation of 2-[2-(4-cyclobutylpiperazin-1-yl)-2-oxoethyl]-1,2,3,4-tetrahydroisoquinolin-6-ol

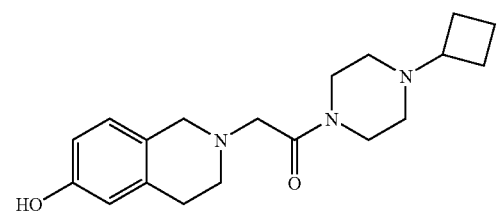

To a mixture of 6-(benzyloxy)-2-[2-(4-cyclobutylpiperazin-1-yl)-2-oxoethyl]-1,2,3,4-tetrahydroisoquinoline (2.5 g, 5.96 mmol) in EtOH (30 ml) is added 10% Pd(OH)₂/C (0.5 g). The mixture is hydrogenated at 45 psi for 2 hr. The mixture is filtered through celite and washed with EtOH. The solvent is removed under reduced pressure to give the title compound. MS (+VE) m/z 330.2 (M+1).

Step 3. Preparation of 2-[2-(4-cyclobutylpiperazin-1-yl)-2-oxoethyl]-6-(cyclopentyloxy)-1,2,3,4-tetrahydroisoquinoline

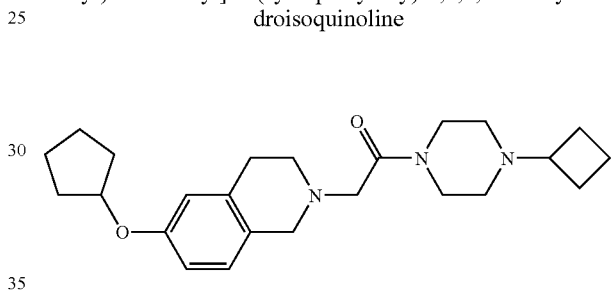

To a stirred solution of 2-[2-(4-cyclobutylpiperazin-1-yl)-2-oxoethyl]-1,2,3,4-tetrahydroisoquinolin-6-ol (145 mg, 0.44 mmol) in DMF (10.0 ml) is added 1-bromo-cyclopentane (72 mg, 0.48 mmol), and K₂CO₃ (60 mg, 0.44 mmol). The resulting mixture is stirred at 50° C. overnight. Water (10.0 ml) is added to quench the reaction, and the mixture is extracted with DCM (10 ml×3). The combined organic phase is dried over sodium sulfate, and the solvent is removed under reduced pressure to give a residue that is purified by PTLC (EtOAc/4% TEA) to give the title compound. ¹H NMR (300 MHz, CDCl₃) δ 6.84-6.94 (1H, m), 6.60-6.70 (2H, m), 4.68-4.74 (1H, m), 3.60-3.74 (6H, m), 3.36 (2H, s), 2.62-2.86 (5H, m), 2.22-2.34 (4H, m), 1.56~2.10 (14H, m); MS (+VE) m/z 398.3 (M⁺+1).

III. 2-[2-(4-Cyclobutylpiperazin-1-Yl)-2-Oxoethyl]-6-{[5-(Trifluoromethyl)-Pyridin-2-Yl]Oxy}-1,2,3,4-Tetrahydroisoquinoline (Scheme 4)

Compound 3

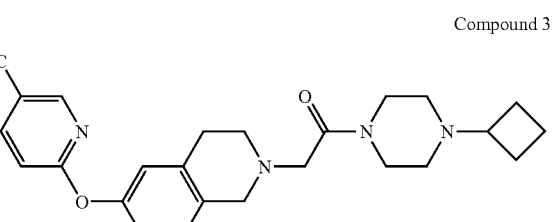

To a stirred solution of 2-[2-(4-cyclobutylpiperazin-1-yl)-2-oxoethyl]-1,2,3,4-tetrahydroisoquinolin-6-ol (50 mg, 0.15 mmol) in DMSO (10.0 ml) is added NaH (10 mg, 0.23 mmol). The mixture is stirred for 30 min, and then 2-chloro-3-trifluoropyridine (34 mg, 0.15 mmol) is added. The resulting mixture is stirred at 50° C. overnight. Water (10.0 ml) is added to quench the reaction, and the mixture is extracted with DCM (10 ml×3). The combined organic phase is dried over sodium sulfate, and the solvent is removed under reduced pressure to give a residue that is purified by PTLC (EtOAc/ 4% TEA) to give the title compound. $^1$H NMR (300 MHz, CDCl$_3$) δ 8.42 (1H, s), 7.90 (1H, d), 7.12 (1H, d), 6.84-6.94 (3H, m), 3.60-3.74 (6H, m), 3.38 (2H, s), 2.62-2.94 (5H, m), 2.22-2.32 (4H, m), 1.62~2.10 (6H, m); MS (+VE) m/z 475.3 (M$^+$+1).

IV. 1-(4-{2-[2-(4-Cyclobutylpiperazin-1-Yl)-2-Oxoethyl]-1,2,3,4-Tetrahydroisoquinolin-6-Yl}Phenyl) Ethanone (Schemes 1, 3, and 5)

Compound 4

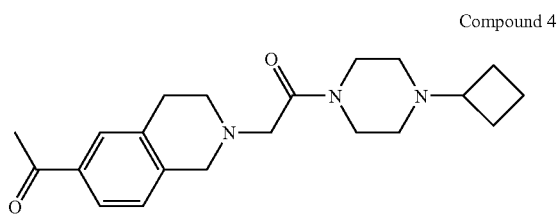

Step 1. Preparation of 6-hydroxy-1,2,3,4-Tetrahydroisoquinoline

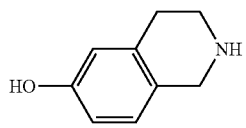

6-Methoxy-1,2,3,4-tetrahydroisoquinoline (14.7 g, 90 mmol) is dissolved into hydrobromic acid (48%, 300 ml), and the mixture is heated at 120° C. for 16 hr. The solvent is removed under reduced pressure to give the title compound as the hydrobromate.

Step 2. Preparation of 6-hydroxy-3,4-dihydro-1H-isoquinoline-2-carboxylic acid tert-butyl ester

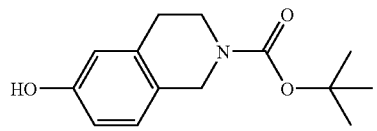

To a suspension of 6-hydroxy-1,2,3,4-tetrahydroisoquinoline hydrobromate (19.51 g, 85.5 mmol) in DCM (300 ml) is added TEA (28.6 ml, 205 mmol, 2.4 eq). The reaction mixture is stirred at rt for 30 min, and then cooled to 0° C., followed by the addition of di-tert-butyl dicarbonate (20.53 g, 94.05 mmol, 1.1 eq.). The reaction mixture is stirred at rt overnight. Water (200 ml) is added to quench the reaction. The organic layer is collected, washed with water and brine, and dried over sodium sulfate. Concentration and purification through silica gel chromatography (hexane/EtOAc 4:1) provides the title compound. MS (+VE) m/z 250.1 (M$^+$+1).

Step 3. Preparation of 6-trifluoromethanesulfonyloxy-3,4-dihydro-1H-isoquinoline-2-carboxylic acid tert-butyl ester

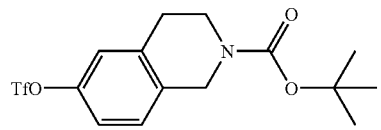

To a solution of 6-hydroxy-3,4-dihydro-1H-isoquinoline-2-carboxylic acid tert-butyl ester (12.46 g, 50 mmol) in anhydrous DCM (150 ml) cooled to 0° C. is added TEA (10.45 ml, 75 mmol, 1.5 eq.), followed by trifluoromethanesulfonic anhydride (15.51 g, 55 mmol, 1.1 eq.) added dropwise. After the addition is complete, 4-dimethylaminopyridine is added (100 mg). The reaction mixture is stirred at 0° C. for 1 hr, then warmed to rt and stirred for an additional 1 hr. Water (200 ml) is added to quench the reaction. The DCM layer is collected, washed with water and brine, and dried over sodium sulfate, and the solvent is removed under reduced pressure. Purification of the residue through silica gel flash chromatography (hexane/EtOAc 10:1) gives the title compound. MS (+VE) m/z 382.2 (M$^+$+1).

Step 4. Preparation of 1-(1,2,3,4-tetrahydro-isoquinolin-6-yl)-ethanone

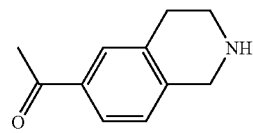

To a stirred solution of 6-trifluoromethanesulfonyloxy-3,4-dihydro-1H-isoquinoline-2-carboxylicacid tert-butyl ester (3.81 g, 10 mmol) in dry DMF (30 ml) are added n-butylvinyl ether (6.01 g, 60 mmol, 6.0 eq.), TEA (1.67 ml, 12 mmol, 1.2 eq.), 1,3-bis(diphenylphosphino)propane (144 mg, 0.276 mmol, 0.0276 eq.), and palladium acetate (56.1 mg, 0.25 mmol, 0.025 eq.) under nitrogen. The resulting mixture is stirred at 80° C. for 7 hr. Water (100 ml) is added to quench the reaction, and the mixture is extracted with EtOAc (30 ml×3). The combined organic layer is washed with water and brine, dried over sodium sulfate, and concentrated. The crude product is purified through silica gel flash chromatography (hexane/EtOAc 10:1) to give a mixture of the vinyl ether and the ketone product, which is dissolved in EtOAc (50 ml), and then treated with concentrated hydrochloric acid (3.0 ml). The mixture is stirred at rt for 2 hr, and then basified with saturated sodium carbonate solution. The organic phase is collected, and the aqueous phase is extracted with EtOAc twice. The combined organic phase is dried with sodium sulfate and concentrated to give the title compound. MS (+VE) m/z 176.1 (M$^+$+1).

Step 5. Preparation of 1-(1,2,3,4-tetrahydro-isoquinolin-6-yl)-ethanone

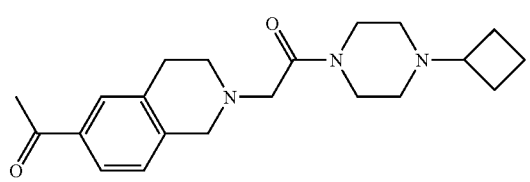

To a stirred solution of 6-acetyl-1,2,3,4-tetrahydroisoquinoline (350 mg, 2.0 mmol) in acetonitrile (10.0 ml) is added 2-chloro-(4-cyclobutyl-piperazine)-acetamide (433 mg, 2.0 mmol, 1.0 eq.), K$_2$CO$_3$ (552 mg, 4.0 mmol, 2.0 eq.), and NaI (50 mg). The resulting mixture is stirred at rt overnight. Water (10.0 ml) is added to quench the reaction, and then the acetonitrile is evaporated. The residue is extracted with DCM (10 ml×3). The combined organic phase is dried over sodium sulfate, and the solvent is removed under reduced pressure to give a residue that is purified by PTLC (EtOAc/4% TEA) to give the title compound. $^1$H NMR (300 MHz, CDCl$_3$) δ 7.68~7.74 (2H, m), 7.09 (1H, d), 3.74 (2H, s), 3.59~3.68 (4H, m), 3.37 (2H, s), 2.94 (2H, t), 2.81 (2H, t), 2.68 (1H, m), 2.57 (3H, s), 2.28 (4H, m), 1.60~2.10 (6H, m); MS (+VE) m/z 356.2 (M$^+$+1).

V. 1-{2-[2-(4-Cyclobutylpiperazin-1-Yl)-2-Oxoethyl]-1,2,3,4-Tetrahydroisoquinolin-6-Yl}Ethanol (Scheme 5)

Compound 5

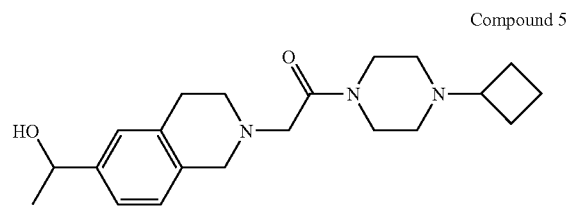

To a stirred solution of 1-(4-{2-[2-(4-cyclobutylpiperazin-1-yl)-2-oxoethyl]-1,2,3,4-tetrahydroisoquinolin-6-yl}phenyl)ethanone (153 mg) in EtOH (10 mL) is added sodium borohydride (20 mg). The resulting mixture is stirred at rt for 2 hr. Water (10.0 ml) is added to quench the reaction, and then the EtOH is evaporated. The residue is extracted with DCM (10 ml×3). The combined organic phase is dried over sodium sulfate, and the solvent is removed under reduced pressure to give a residue that is purified by PTLC (EtOAc/4% TEA) to give the title compound. $^1$H NMR (300 MHz, CDCl$_3$) δ 7.08~7.14 (2H, m), 6.92-6.98 (1H, m), 4.82 (1H, q), 3.58-3.64 (6H, m), 3.28 (2H, s), 2.60-2.84 (6H, m), 2.20-2.28 (4H, m), 1.60-2.20 (6H, m), 1.42 (3H, d); MS (+VE) m/z 358.2 (M$^+$+1).

VI. 2-[6-Bromo-1-(2-Chloro-Phenyl)-3,4-Dihydro-1H-Isoquinolin-2-Yl]-1-(4-Cyclobutyl-Piperazin-1-Yl)-Ethanone (Scheme 5)

Compound 6

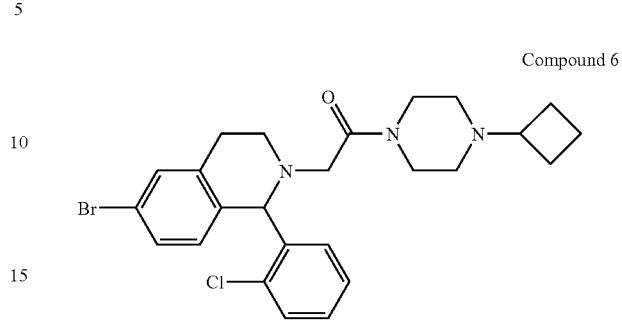

Step 1. Preparation of N-[2-(3-bromo-phenyl)-ethyl]-2-chloro-benzamide

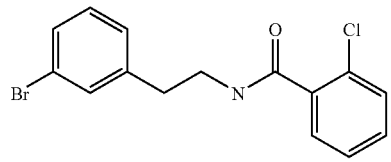

To a solution of 3-bromophenethylamine (10.0 g, 50 mmol) in DCM (100 ml) containing TEA (8.36 g, 60 mmol, 1.2 eq.) cooled to 0° C. is added 2-chlorobenzoylchloride (8.75 g, 50 mmol, 1.0 eq.) portionwise. The resulting mixture is stirred at rt for 1 hr. Water (100 ml) is added to quench the reaction. The organic layer is collected, washed with water and brine, dried over sodium sulfate, and concentrated to give the title compound.

Step 2. Preparation of 6-bromo-1-(2-chloro-phenyl)-1,2,3,4-tetrahydroisoquinoline

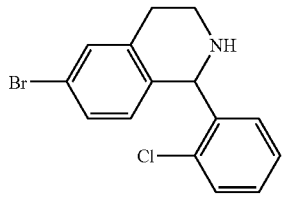

To a suspension of N-[2-(3-bromo-phenyl)-ethyl]-4-chloro-benzamide (16.94 g, 50 mmol) in toluene (200 ml) is added phosphorous pentaoxide (14.19 g, 2.0 eq) and phosphorous oxychloride (15.3 g, 2.0 eq). The resulting mixture is refluxed overnight, and then poured onto crushed ice. The resulting solid is collected, washed with ether, and dried under vacuum to give the cyclized product as a brown solid, which is dissolved in EtOH (160 ml). To the solution at 0° C. is added sodium borohydride (3.78 g, 0.1 mol, about 2.0 eq.). The resulting mixture is then warmed to rt, and stirred overnight until all the imine is reduced. The organic solvent is evaporated, and the residue is dissolved in DCM (150 ml). The solution is washed with water and brine, dried over sodium sulfate, and concentrated to give the crude product, which is dissolved in EtOAc (100 ml) and treated with dioxane-HCl solution (4.0 N, 25 ml). The resulting solid precipitate is collected, washed with ether, and dried under vacuum to give the title compound as the HCl salt. MS (+VE) m/z 321.9 (M$^+$+1).

Step 3. Preparation of 2-[6-bromo-1-(2-chloro-phenyl)-3,4-dihydro-1H-isoquinolin-2-yl]-1-(4-cyclobutyl-piperazin-1-yl)-ethanone

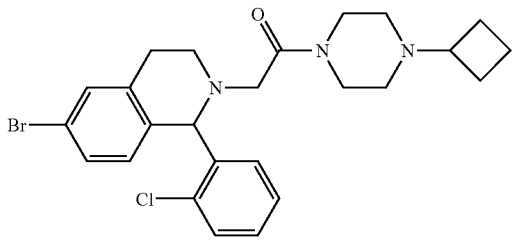

To a stirred suspension of 6-bromo-1-(2-chloro-phenyl)-1,2,3,4-tetrahydroisoquinoline HCl salt (400 mg, 1.11 mmol) in acetonitrile (10.0 ml) is added 2-chloro-(4-cyclobutyl-piperazine)-acetamide (241 mg, 1.11 mmol, 1.0 eq.), K$_2$CO$_3$ (306 mg, 2.22 mmol, 2.0 eq.), and NaI (50 mg). The resulting mixture is stirred at rt overnight. Water (10.0 ml) is added to quench the reaction, and the acetonitrile is evaporated. The residue is extracted with DCM (10 ml×3), and the combined extracts are dried over sodium sulfate. The solvent is removed under reduced pressure, and the residue is purified through PTLC (EtOAc/4% TEA) to give the title compound. $^1$H NMR (300 MHz, CDCl$_3$) δ 7.40 (1H, dd), 7.18~7.32 (5H, m), 6.49 (1H, d), 5.10 (1H, s), 3.81 (1H, m), 3.46 (1H, m), 3.04~3.40 (6H, m), 2.60~2.88 (3H, m), 2.41 (1H, m), 2.27 (1H, m), 1.96~2.14 (4H), 1.60~1.92 (4H); MS (+VE) m/z 503.9 (M$^+$+1).

VII. 2-[6-Acetyl-1-(2-Chloro-Phenyl)-3,4-Dihydro-1H-Isoquinolin-2-Yl]-1-(4-Cyclobutyl-Piperazin-1-Yl)-Ethanone (Scheme 5)

Compound 7

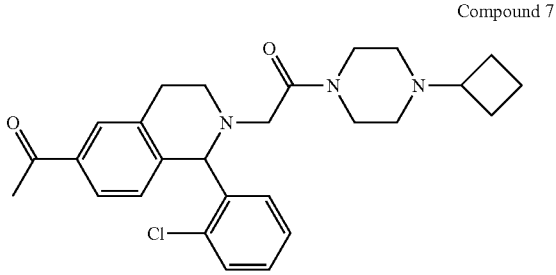

To a solution of 2-[6-bromo-1-(2-chloro-phenyl)-3,4-dihydro-1H-isoquinolin-2-yl]-1-(4-cyclobutyl-piperazin-1-yl)-ethanone (310 mg, 0.62 mmol) in dry DMF (5.0 ml) is added n-butylvinyl ether (310 mg, 3.98 mmol, 5.0 eq.), TEA (75 mg, 0.74 mmol, 1.2 eq.), 1,3-bis(diphenylphosphino)propane (7 mg, 0.0017 mmol, 0.0276 eq.), and palladium acetate (3.5 mg, 0.015 mmol, 0.025 eq.) under nitrogen. The resulting mixture is stirred at 80° C. for 7 hr. Water (20 ml) is added to quench the reaction, and the mixture is extracted with EtOAc (10 ml×3). The combined organic phase is washed with water, and treated with concentrated HCl (1.0 ml). The mixture is stirred at rt for 2 hr, and then basified with saturated sodium carbonate solution. The organic phase is collected, and the aqueous phase is extracted with EtOAc (10 ml×2). The combined organic phase is dried over sodium sulfate, and concentrated. The residue is purified by PTLC (EtOAc/4% TEA) to give the title compound. $^1$H NMR (300 MHz, CDCl$_3$) δ 7.74 (1H, s), 7.59 (1H, dd), 7.41 (1H, dd), 7.10~7.25 (3H, m), 6.72 (1H, d), 5.22 (1H, s), 3.81 (1H, m), 3.04~3.52 (7H, m), 2.78~2.98 (2H, m), 2.67 (1H, m), 2.55 (3H, s), 2.41 (1H, m), 2.27 (1H, m), 1.96~2.14 (4H), 1.60~1.92 (4H); MS (+VE) m/z 466.00 (M$^+$).

VIII. 1-(4-Cyclobutyl-Piperazin-1-Yl)-2-(7-Methoxy-1,2,4,5-Tetrahydro-Benzo[D]Azepin-3-Yl)-Ethanone (Schemes 1 and 3)

Compound 8

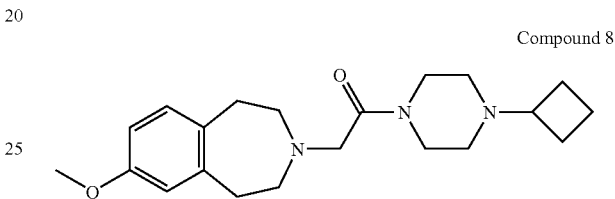

Step 1. Preparation of 7-methoxy-3-(toluene-4-sulfonyl)-2,3,4,5-tetrahydro-1H-benzo[d]azepine

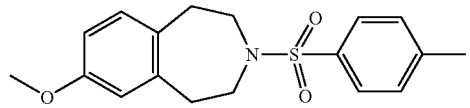

7-Methoxy-3-(toluene-4-sulfonyl)-2,3,4,5-tetrahydro-benzo[d]azepin-1-one (6.91 g, 20 mmol) (prepared essentially as described by Kanao et al. (1982) *Chem. Pharm. Bull.* 30:180-88) is added to a mixture of acetic acid (20 ml), 37% hydrochloric acid (8 ml), EtOH (8 ml) and dioxane (80 ml). 1.0 g of 10% palladium-carbon is added to the mixture, and the resulting mixture is hydrogenated under 30-55 psi at rt overnight. The palladium-carbon is removed by filtration, and the filtering cake is washed with MeOH (30 ml×3). The combined organic phase is evaporated to dryness under reduced pressure to give the title compound as a white solid. MS (+VE) m/z 332.1 (M$^+$).

Step 2. Preparation of 7-methoxy-2,3,4,5-tetrahydro-1H-benzo[d]azepine

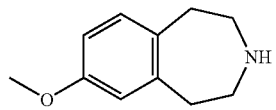

To a solution of 7-methoxy-3-(toluene-4-sulfonyl)-2,3,4,5-tetrahydro-1H-benzo-[d]azepine (6.62 g, 20 mmol) in anhydrous THF (150 ml) is added a solution of LiAlH$_4$ in THF (1.0 M, 40 ml, 2.0 eq.). The resulting mixture is refluxed under N₂ for 24 hr. To the solution at 0° C. is added water (1.52 g) very carefully with stirring, followed by the addition of sodium hydroxide solution (10.0 N, 1.52 ml) and then water (3.04 g). The mixture is stirred at rt for an additional 1 hr, then diluted with EtOAc (300 ml), and dried with magnesium sulfate (40.0 g). After filtration, and washing the filtering cake with EtOAc (100 ml×3), the combined organic phase is evaporated to dryness under reduced pressure to give the title compound. MS (+VE) m/z 178.1 (M⁺+1).

Step 3. Preparation of 1-(4-cyclobutyl-piperazin-1-yl)-2-(7-methoxy-1,2,4,5-tetrahydro-benzo[d]azepin-3-yl)-ethanone

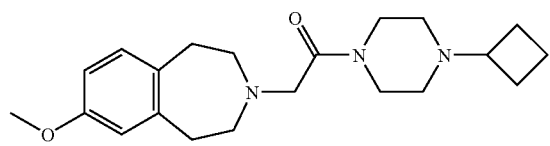

To a stirred solution of 7-methoxy-2,3,4,5-tetrahydro-1H-benzo[d]azepine (177 mg, 1.0 mmol) in acetonitrile (5.0 ml) is added 2-chloro-(4-cyclobutyl-piperazine)-acetamide (216 mg, 1.0 mmol, 1.0 eq.), K₂CO₃ (376 mg, 2.0 mmol, 2.0 eq.) and NaI (30 mg). The resulting mixture is stirred at rt overnight. Water (10.0 ml) is added to quench the reaction, and the acetonitrile is evaporated. The residue is extracted with DCM (10 ml×3). The combined extracts are dried over sodium sulfate, and the solvent is removed under reduced pressure. The resulting residue is purified by PTLC (EtOAc/4% TEA) to give the title compound. ¹H NMR (300 MHz, CDCl₃) δ 6.99 (1H, d), 6.60~6.66 (2H, m), 3.77 (3H, s), 3.60~3.73 (4H, m), 3.26 (2H, s), 2.80~3.00 (4H, m), 2.58~2.73 (5H, m), 2.25~2.40 (4H, m), 1.65~2.10 (6H, m); MS (+VE) m/z 358.4 (M⁺+1).

IX. 2-[2-(4-Cyclobutyl-Piperazin-1-Yl)-2-Oxo-Ethyl]-1,2,3,4-Tetrahydro-Isoquinoline-7-Carboxylic Acid Methylamide (Scheme 1)

Compound 9

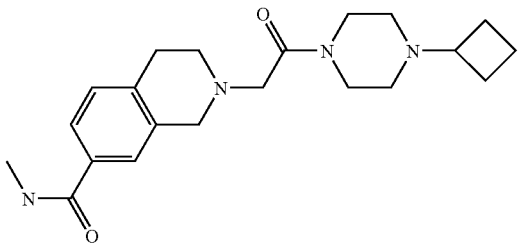

Step 1. Preparation of 1,2,3,4-tetrahydro-isoquinoline-7-carboxylic acid methylamide

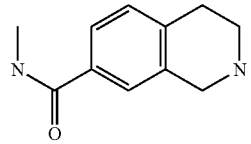

1,2,3,4-Tetrahydro-isoquinoline-7-carboxylic acid methyl ester hydrochloride (113 mg, 0.5 mmol) is dissolved in aqueous methylamine (40%, 5.0 ml)) and heated at 100° C. overnight. Upon cooling to rt, the reaction mixture is evaporated to dryness under reduced pressure. The residue is taken up in water (1.0 ml), and treated with sodium hydroxide solution (1.0 N, 1.0 ml). The mixture is extracted with DCM (10 ml×3). The combined organic phase is dried over sodium sulfate, and concentrated to give the title compound. MS (+VE) m/z 191.1 (M⁺+1).

Step 2. Preparation of 2-[2-(4-cyclobutyl-piperazin-1-yl)-2-oxo-ethyl]-1,2,3,4-tetrahydro-isoquinoline-7-carboxylic acid methylamide

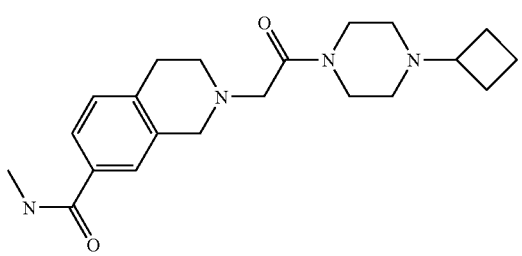

To a stirred solution of 1,2,3,4-tetrahydro-isoquinoline-7-carboxylic acid methylamide (96 mg, 0.5 mmol) in acetonitrile (3.0 ml) is added 2-chloro-(4-cyclobutyl-piperazine)-acetamide (109 mg, 0.5 mmol, 1.0 eq.), K₂CO₃ (138 mg, 1.0 mmol, 2.0 eq.), and NaI (10 mg). The resulting mixture is stirred at rt overnight. Water (10.0 ml) is added to quench the reaction, and the acetonitrile is evaporated. The residue is extracted with DCM (10 ml×3), and the combined organic phase is dried over sodium sulfate and concentrated. The residue is purified by PTLC (EtOAc/4% TEA plus 4% EtOH) to give the title compound. MS (+VE) m/z 371.1 (M⁺+1).

X. 2-[6-(4-Acetyl-Phenyl)-3,4-Dihydro-1H-Isoquinolin-2-Yl]-1-(4-Cyclobutyl-Piperazin-1-Yl)-Ethanone (Scheme 6)

Compound 10

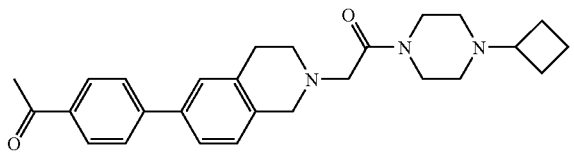

Step 1. Preparation of 1-[4-(1,2,3,4-tetrahydro-isoquinolin-6-yl)-phenyl]-ethanone

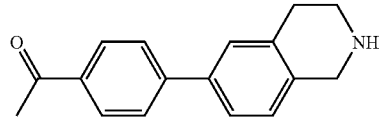

To a mixture of 6-trifluoromethanesulfonyloxy-3,4-dihydro-1H-isoquinoline-2-carboxylic acid t-butyl ester (350 mg, 0.92 mmol), 4-acetylphenylboronic acid (200 mg, 1.22 mmol, 1.3 eq.), Pd(PPh$_3$)$_4$ (8.4 mg, 0.001 mmol, 0.01 eq.) under nitrogen are added dioxane (10.0 ml) and sodium carbonate aqueous solution (2.0 N, 1.0 ml). The resulting mixture is stirred at 100° C. for 16 hr. The reaction mixture is diluted with EtOAc (30 ml), washed with water and brine, dried over sodium sulfate, and concentrated. The crude product is purified through silica gel flash chromatography (hexane/EtOAc 10:1) to give the vinyl ether, which is dissolved in dioxane (10.0 ml), and then treated with concentrated hydrochloric acid (1.0 ml). The mixture is stirred at 50° C. for 1 hr, and basified with saturated sodium carbonate solution. The organic layer is collected, and the aqueous phase is extracted with EtOAc twice. The combined organic phase is dried over sodium sulfate, and concentrated to give the title compound. MS (+VE) m/z 252.1 (M$^+$+1).

Step 2. Preparation of 2-[6-(4-acetyl-phenyl)-3,4-dihydro-1H-isoquinolin-2-yl]-1-(4-cyclobutyl-piperazin-1-yl)-ethanone

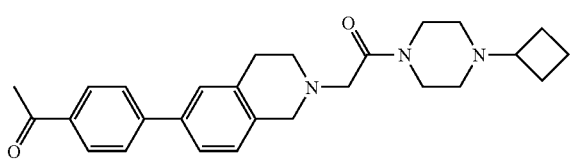

To a stirred solution of 1-[4-(1,2,3,4-tetrahydro-isoquinolin-6-yl)-phenyl]-ethanone (216 mg, 0.86 mmol) in acetonitrile (5.0 ml) is added 2-chloro-(4-cyclobutyl-piperazine)-acetamide (186 mg, 0.86 mmol, 1.0 eq.), K$_2$CO$_3$ (238 mg, 1.72 mmol, 2.0 eq.) and NaI (50 mg). The resulting mixture is stirred at 50° C. overnight. Water (10.0 ml) is added to quench the reaction, and the acetonitrile is evaporated. The residue is extracted with DCM (10 ml×3). The combined organic phase is dried over sodium sulfate and concentrated. The residue is purified by PTLC (EtOAc/4% TEA) to give the title compound. $^1$H NMR (300 MHz, CDCl$_3$) δ 8.01 (2H, d), 7.66 (2H, d), 7.36~7.44 (2H, m), 7.12 (1H, d), 3.74 (2H, s), 3.60~3.70 (4H, m), 3.38 (2H, s), 2.97 (2H, t), 2.83 (2H, t), 2.66 (1H, m), 2.64 (3H, s), 2.29 (4H, m), 1.60~2.08 (6H); MS (+VE) m/z 432.2 (M$^+$+1).

XI. 1-(4-Cyclobutyl-Piperazin-1-Yl)-2-(6-Pyridazin-3-Yl-3,4-Dihydro-1H-Isoquinolin-2-Yl)-Ethanone (Scheme 6)

Compound 11

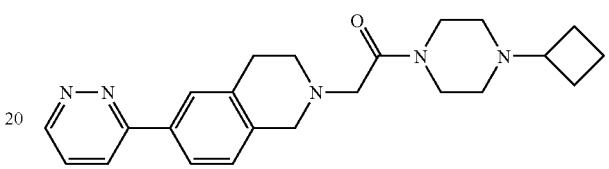

Step 1. Preparation of 2-(6-bromo-3,4-dihydro-1H-isoquinolin-2-yl)-1-(4-cyclobutyl-piperazin-1-yl)-ethanone

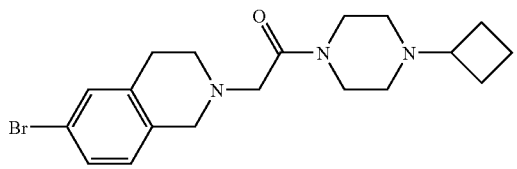

To a stirred solution of 6-bromo-1,2,3,4-tetrahydro-isoquinoline hydrochloride (3.09 g, 12.4 mmol) in acetonitrile (50.0 ml) is added 2-chloro-(4-cyclobutyl-piperazine)-acetamide (2.69 mg, 12.4 mmol, 1.0 eq.), K$_2$CO$_3$ (5.14 g, 37.3 mmol, 3.0 eq.), and NaI (400 mg). The resulting mixture is stirred at rt overnight. Water (40.0 ml) is added to quench the reaction, and then the acetonitrile is evaporated. The residue is extracted with DCM (40 ml×3). The combined organic phase is dried over sodium sulfate, and the solvent is removed under reduced pressure to give a residue that is purified by flash silica gel chromatography (EtOAc/4% TEA) to give the title compound. MS (+VE) m/z 392.2 (M$^+$+1).

Step 2. Preparation of 2-(6-bromo-3,4-dihydro-1H-isoquinolin-2-yl)-1-(4-cyclobutyl-piperazin-1-yl)-ethanone

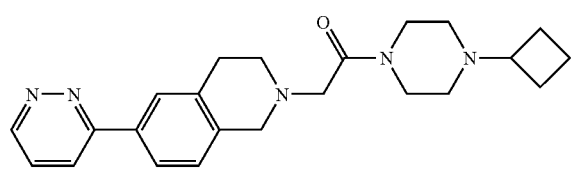

To a mixture of 2-(6-bromo-3,4-dihydro-1H-isoquinolin-2-yl)-1-(4-cyclobutyl-piperazin-1-yl)-ethanone (100 mg, 0.25 mmol), 3-tributylstannanyl-pyridazine (122 mg, 0.33 mmol, 1.3 eq.) and Pd(PPh₃)₄ (14 mg, 0.0125 mmol, 0.05 eq.) under nitrogen is added toluene (5.0 ml). The resulting mixture is stirred at 120° C. for 36 hr. The reaction mixture is diluted with EtOAc (20 ml), washed with water and brine, dried over sodium sulfate, and concentrated. The crude product is purified through silica gel flash chromatography (EtOAc/4% TEA) to give the title compound. $^1$H NMR (300 MHz, CDCl₃) δ 7.85 (1H, s), 9.43 (1H, s), 9.19 (1H, dd), 7.61 (1H, dd), 7.42~7.46 (2H, overlapped), 7.18 (1H, d), 3.76 (2H, s), 3.65 (4H, m), 3.39 (2H, s), 2.99 (2H, t), 2.85 (2H, t), 2.69 (1H, m), 2.29 (4H, m), 1.64~2.05 (6H, m); MS (+VE) m/z 392.1 (M⁺+1).

XII. 3-{2-[2-(4-Cyclobutylpiperazin-1-Yl)-2-Oxoethyl]-1,2,3,4-Tetrahydro-Isoquinolin-6-Yl}-1,3-Oxazolidin-2-One (Scheme 6)

Compound 12

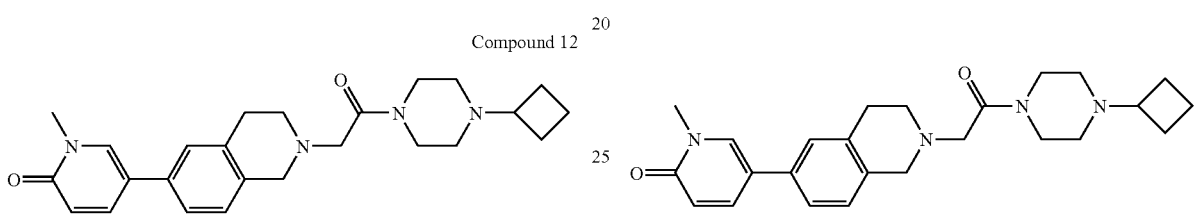

Step 1. Preparation of 5-bromo-1-methylpyridin-2(1H)-one

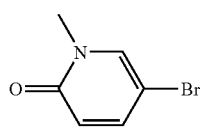

To a solution of 2-hydroxy-5-bromo-pyridine (3.00 g, 17.3 mmol) in anhydrous DMF (25 mL) is added MeI (2.95 g, 20.76 mmol, 1.2 eq.). The mixture is stirred overnight at rt. The solution is diluted with EtOAc (200 mL) and extracted with H₂O (4×100 mL). The organic extract is dried over Na₂SO₄ and the solvent removed under reduced pressure. The crude product is purified by silica gel chromatography eluting first with hexane/acetone (4:1) followed by elution with hexane/acetone (1:1) to yield the title compound. MS (+VE) m/z 188.02 (M⁺+1).

Step 2. Preparation of 2-[2-(4-cyclobutylpiperazin-1-yl)-2-oxoethyl]-6-(4,4,5,5-tetramethyl-1,3,2-dioxaborolan-2-yl)-1,2,3,4-tetrahydroisoquinoline

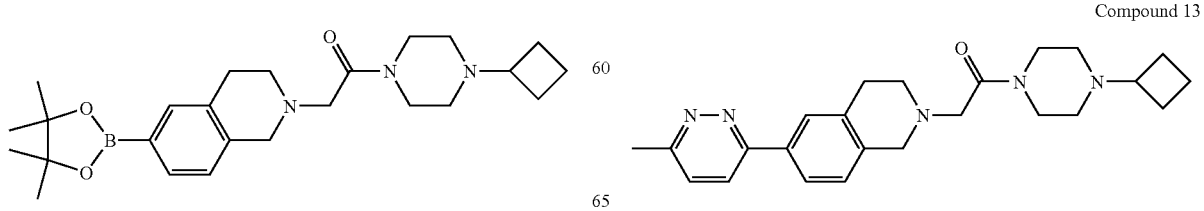

To a sealed tube charged with 6-bromo-2-[2-(4-cyclobutylpiperazin-1-yl)-2-oxoethyl]-1,2,3,4-tetrahydroisoquinoline (3.01 g, 10.3 mmol), bis(pinacolato)diboron (2.88 g, 11.3 mmol, 1.1 eq.), PdCl₂dppf.CHCl₃ (252 mg, 0.309 mmol, 0.03 eq.) and KOAc (3.04 g, 30.9 mmol, 3.0 eq.) is added anhydrous dioxane (65 ml). The mixture is degassed with nitrogen for 5 min. The tube is sealed and heated at 85° C. overnight. The mixture is cooled to rt and filtered through Celite. The Celite bed is washed with EtOAc, and the combined organics are concentrated. The crude product is purified by silica gel chromatography eluting with EtOAc/NEt₃ (95:5) to yield the title compound. MS (+VE) m/z 440.51 (M⁺+1).

Step 3. Preparation of 3-{2-[2-(4-cyclobutylpiperazin-1-yl)-2-oxoethyl]-1,2,3,4-tetrahydro-isoquinolin-6-yl}-1,3-oxazolidin-2-one

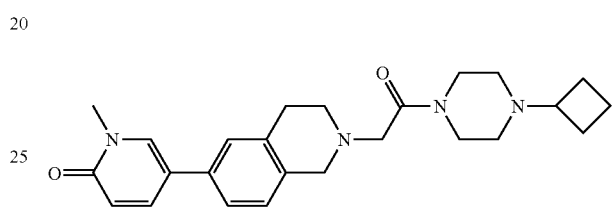

To a sealed tube charged with 2-[2-(4-cyclobutylpiperazin-1-yl)-2-oxoethyl]-6-(4,4,5,5-tetramethyl-1,3,2-dioxaborolan-2-yl)-1,2,3,4-tetrahydroisoquinoline (1.00 g, 2.28 mmol), 5-bromo-1-methylpyridin-2(1H)-one (513 mg, 2.73 mmol, 1.2 eq.), Pd(PPh₃)₄ (100 mg, 0.087 mmol, 0.04 eq.) and K₂CO₃ (945 mg, 6.84 mmol, 3.0 eq.), are added dioxane (20 ml) and water (3 mL). The mixture is degassed with nitrogen for 5 min. The tube is sealed and heated at 100° C. overnight. The reaction mixture is cooled and partitioned between DCM (150 mL) and 1N NaOH (100 mL). The mixture is extracted with DCM (2×150 mL). The combined organic extracts are dried and evaporated to yield the crude product which is purified by silica gel column chromatography eluting with EtOAc/MeOH/NEt₃ (95:5:3) to yield the title compound. $^1$H NMR (300 MHz, CDCl₃) δ 7.61 (1H, dd), 7.47 (1H, d), 7.15 (1H, s), 7.06 (1H, d), 6.66 (1H, d), 3.72 (2H, s), 3.67-3.64 (m, 4H), 3.62 (3H, s), 3.37 (2H, s), 2.94 (2H, t), 2.81 (2H, t), 2.69 (1H, m), 2.32-2.27 (4H, m), 2.03-1.67 (6H); MS (+VE) m/z 421.49 (M⁺+1).

XIII. 2-[2-(4-Cyclobutylpiperazin-1-Yl)-2-Oxoethyl]-6-(6-Methylpyridazin-3-Yl)-1,2,3,4-Tetrahydroisoquinoline (Scheme 7)

Compound 13

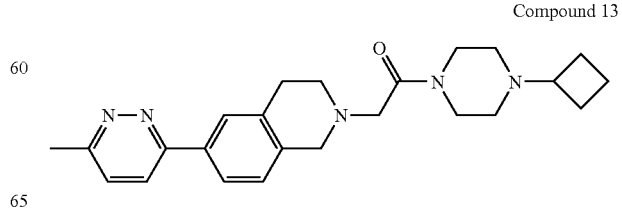

Step 1. Preparation of (6-bromo-3,4-dihydro-1H-isoquinolin-2-yl)-acetic acid tert-butyl ester

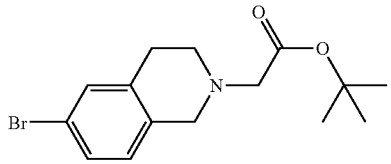

To a mixture of 6-bromo-1,2,3,4-tetrahydro-isoquinoline (10.60 g, 50 mmol) and t-butyl bromoacetate (9.95 g, 51 mmol, 1.02 eq.) in acetonitrile (100 ml) are added sodium carbonate (10.6 g, 100 mmol, 2.0 eq.) and NaI (375 mg, 2.5 mmol, 0.05 eq.). The resulting mixture is stirred at rt for 16 hr. Water (100 ml) is added to quench the reaction, and the acetonitrile is evaporated. The residue is extracted with EtOAc (100 ml×3), and the combined organic phase is dried over sodium sulfate and concentrated. The residue is purified by silica gel flash chromatography (EtOAc/hexane, 1:4) to give the title compound. MS (+VE) m/z 326.10 (M$^+$+1).

Step 2. Preparation of [6-(4,4,5,5-tetramethyl-[1,3,2] dioxaborolan-2-yl)-3,4-dihydro-1H-isoquinolin-2-yl]-acetic acid tert-butyl ester

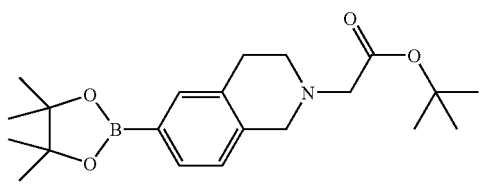

To a 100 ml round bottom flask charged with dry dioxane (30 ml) under nitrogen are added (6-bromo-3,4-dihydro-1H-isoquinolin-2-yl)-acetic acid tert-butyl ester (1.63 g, 5 mmol), bis(pinacolato)diboran (1.40 g, 5.5 mmol, 1.1 eq.), PdCl$_2$ (dppf) (122 mg, 0.15 mmol, 0.03 eq.), and potassium acetate (1.48 g, 15 mmol, 3.0 eq.). The resulting mixture is stirred at 85° C. for 18 hr. The reaction mixture is cooled, and filtered through Celite. The Celite bed is washed with EtOAc, and the combined organics are concentrated. The crude product is purified through silica gel flash chromatography (hexane/EtOAc 5:1) to give the title compound. MS (+VE) m/z 374.2 (M$^+$+1).

Step 3. Preparation of [6-(6-methyl-pyridazin-3-yl)-3,4-dihydro-1H-isoquinolin-2-yl]-acetic acid tert-butyl ester

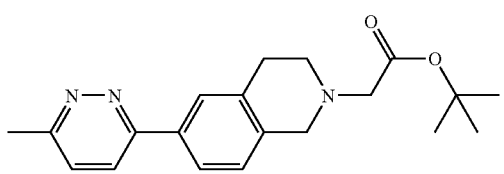

To a mixture of [6-(4,4,5,5-tetramethyl-[1,3,2]dioxaborolan-2-yl)-3,4-dihydro-1H-isoquinolin-2-yl]-acetic acid tert-butyl ester (1.12 g, 3 mmol), 3-chloro-6-methyl-pyridazine (501 mg, 3.9 mmol, 1.3 eq.), Pd(PPh$_3$)$_4$ (104 mg, 0.009 mmol, 0.03 eq.) under nitrogen, are added dioxane (30.0 ml) and sodium carbonate aqueous solution (2.0N, 3.0 ml). The resulting mixture is stirred at 90° C. for 16 hr. The reaction mixture is diluted with EtOAc (80 ml), washed with water and brine, dried over sodium sulfate, and concentrated. The crude product is purified by silica gel flash chromatography (hexane/EtOAc 1:1) to give the title compound. MS (+VE) m/z 340.20 (M$^+$+1).

Step 4. Preparation of [6-(6-methyl-pyridazin-3-yl)-3,4-dihydro-1H-isoquinolin-2-yl]-acetic acid

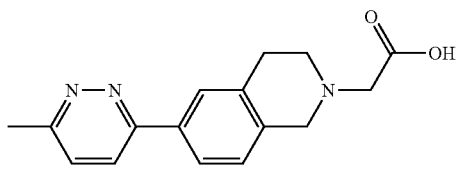

To a stirred solution of [6-(6-methyl-pyridazin-3-yl)-3,4-dihydro-1H-isoquinolin-2-yl]-acetic acid tert-butyl ester (957 mg, 2.82 mmol) in EtOAc (30 ml), is added the solution of hydrochloride in dioxane (4.0M, 10 ml, 40 mmol). The mixture is stirred at 50° C. overnight. The organic solvents are evaporated to give the title compound as dihydrochloric acid salt. MS (+VE) m/z 284.1 (M$^+$+1).

Step 5. Preparation of 2-[2-(4-cyclobutylpiperazin-1-yl)-2-oxoethyl]-6-(6-methylpyridazin-3-yl)-1,2,3,4-tetrahydroisoquinoline

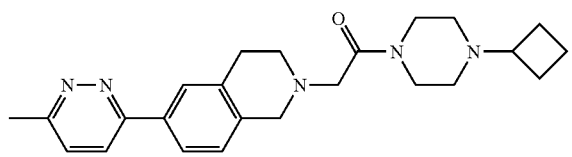

To a stirred solution of [6-(6-methyl-pyridazin-3-yl)-3,4-dihydro-1H-isoquinolin-2-yl]-acetic acid dihydrochloride (313 mg, 0.88 mmol) and 1-cyclobutyl-piperazine bistrifluoroacetate (356 mg, 0.97 mmol, 1.1 eq.) in DCM (10.0 ml) are added BOP (467 mg, 1.06 mmol, 1.2 eq.) and TEA (267 mg, 2.64 mmol, 3.0 eq.). The mixture is stirred at rt for 2 hr. Water (10.0 ml) is added to quench the reaction, and the organic layer is collected, dried over sodium sulfate, and concentrated. The residue is purified by PTLC (EtOAc/4% TEA) to give the title compound. $^1$H NMR (300 MHz, CDCl$_3$) δ 7.85 (1H, s), 7.78 (1H, dd), 7.72 (1H, d), 7.36 (1H, d), 7.15 (1H, d), 3.75 (2H, s), 3.65 (4H, m), 3.39 (2H, s), 2.99 (2H, t), 2.82 (2H, t), 2.74 (3H, s), 2.68 (1H, m), 2.28 (4H, m), 1.64-2.08 (6H, m); MS (+VE) m/z 406.2 (M$^+$+1).

XIV. 2-{2-[2-(4-Cyclobutylpiperazin-1-Yl)-2-Oxoethyl]-1,2,3,4-Tetrahydroiso-Quinolin-6-Yl}Pyridazin-3(2H)-One (Scheme 8)

Compound 14

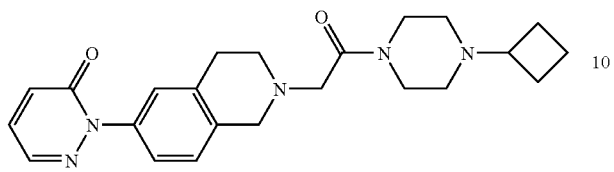

To a sealed tube charged with 6-bromo-2-[2-(4-cyclobutylpiperazin-1-yl)-2-oxoethyl]-1,2,3,4-tetrahydroisoquinoline (128 mg, 0.326 mmol), CuCl (3.2 mg, 0.0163 mmol, 0.05 eq.), pyridazin-3(2H)-one (47 mg, 0.489 mmol, 1.5 eq.), 8-hydroxyquinoline (9.5 mg, 0.0326 mmol, 0.1 eq.) and $K_2CO_3$ (90 mg, 0.652 mmol, 2.0 eq.) is added anhydrous DMF (3 ml). The mixture is degassed with nitrogen for 5 min. The tube is sealed and heated at 140° C. overnight. The mixture is cooled to rt and filtered through Celite. The Celite bed is washed with EtOAc, the combined organics are concentrated, and 5N HCl (30 mL) is added. The mixture is extracted with EtOAc (2×30 mL). The aqueous layer is basified with 10N NaOH, and extracted with DCM (3×40 mL), and the combined organics are dried and concentrated. The crude reaction mixture is purified by preparatory LC/MS to yield the title compound. $^1$H NMR (300 MHz, $CDCl_3$) δ 7.87 (1H, dd), 7.32 (2H, m), 7.24 (1H, d), 7.12 (1H, d), 7.04 (1H, d), 3.72 (2H, s), 3.67-3.63 (4H, m), 3.36 (2H, s), 2.94 (2H, t), 2.81 (2H, t), 2.69 (1H, m), 2.27 (4H, m), 1.66-2.08 (6H); MS (+VE) m/z 408.14 ($M^+$+1).

XV. 2,3-{2-[2-(4-Cyclobutylpiperazin-1-Yl)-2-Oxoethyl]-1,2,3,4-Tetrahydro-isoquinolin-6-yl}-1,3-oxazolidin-2-one (Scheme 8)

Compound 15

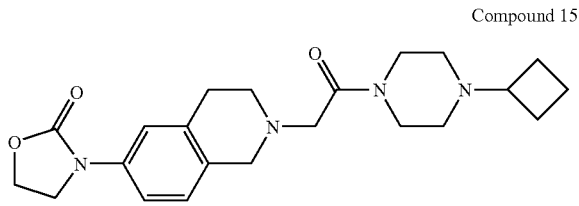

To a sealed tube charged with 6-bromo-2-[2-(4-cyclobutylpiperazin-1-yl)-2-oxoethyl]-1,2,3,4-tetrahydroisoquinoline (80 mg, 0.204 mmol), 1,3-oxazolidin-2-one (35 mg, 0.408 mmol, 2.0 eq.), $Pd_2dba_3$ (19 mg, 0.0204 mmol, 0.1 eq.), Xantphos (12 mg, 0.0204 mmol, 0.1 eq.) and $Cs_2CO_3$ (398 mg, 1.22 mmol, 6.0 eq), is added anhydrous dioxane (5 ml). The mixture is degassed with nitrogen for 5 min. The tube sealed and heated at 110° C. overnight. The mixture is cooled to rt and filtered through Celite. The Celite bed is washed with DCM. The combined organics are placed directly on SCX (ion exchange resin). The resin is washed with EtOAc/MeOH (95:5) (2×4 mL) to remove the non-basic fraction. The resin is then washed with EtOAc/MeOH/$NEt_3$ (90:10:10) and the wash is collected. The solvent is removed under vacuum to yield the title compound. $^1$H NMR (300 MHz, $CDCl_3$) δ 7.31 (1H, d), 7.25 (1H, dd), 7.01 (1H, d), 4.46 (2H, t), 4.02 (2H, t), 3.67-3.63 (6H, m), 3.34 (2H, s), 2.90 (2H, t), 2.77 (2H, t), 2.67 (1H, m), 2.30-2.23 (4H, m), 1.66-2.08 (6H); MS (+VE) m/z 399.13 ($M^+$+1).

XVI. 2-[2-(4-Cyclobutylpiperazin-1-Yl)-2-Oxoethyl]-6-(1H-Pyrazol-1-Yl)-1,2,3,4-Tetrahydroisoquinoline (Scheme 8)

Compound 16

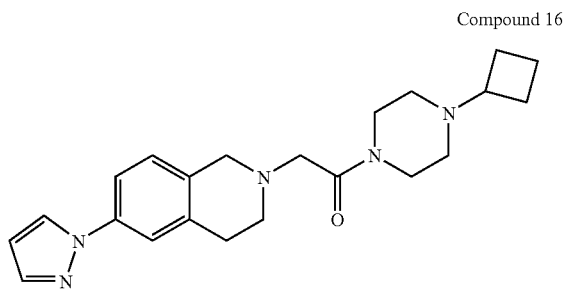

A mixture of 6-bromo-2-[2-(4-cyclobutylpiperazin-1-yl)-2-oxoethyl]-1,2,3,4-tetrahydroisoquinoline (120 mg, 0.307 mmol), pyrazole (31 mg, 0.46 mmol), $Cu_2O$ (4 mg, 0.03 mmol), salicylaldoxime (16 mg, 0.12 mmol) and $Cs_2CO_3$ (300 mg, 0.92 mmol) in $CH_3CN$ (8 mL) is degassed by argon and heated at 120° C. in a sealed tube overnight. EtOAc (10 mL) is added and the mixture is filtered. The organic layer is washed with brine (10 mL) and dried. Purification of the residue by PTLC gives title compound as a light yellow solid. MS (M+1): 380.2; $^1$H NMR (δ, $CDCl_3$): 7.88 (d, 1H), 7.70 (d, 1H), 7.47 (d, 1H), 7.41 (dd, 1H), 7.08 (d, 1H), 6.45 (dd, 1H), 3.71 (s, 2H), 3.65 (t, 4H), 3.38 (s, 2H), 2.96 (t, 2H), 2.81 (t, 2H), 2.63-2.72 (m, 1H), 2.28 (q, 4H), 1.64-2.08 (m, 6H).

XVII. 1-(4-Cyclobutyl-Piperazin-1-Yl)-2-[6-(Pyrrolidine-1-Carbonyl)-3,4-Dihydro-1H-Isoquinolin-2-Yl]-Ethanone (Scheme 9)

Compound 17

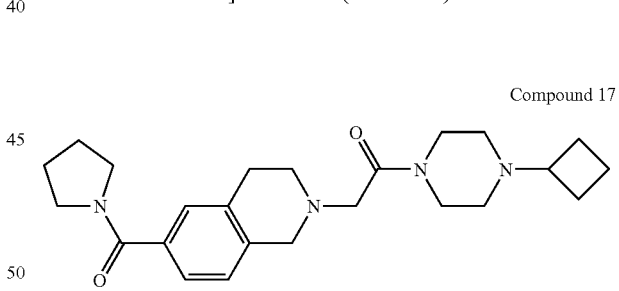

Step 1. Preparation of 2-[2-(4-cyclobutyl-piperazin-1-yl)-2-oxo-ethyl]-1,2,3,4-tetrahydro-isoquinoline-6-carboxylic acid ethyl ester

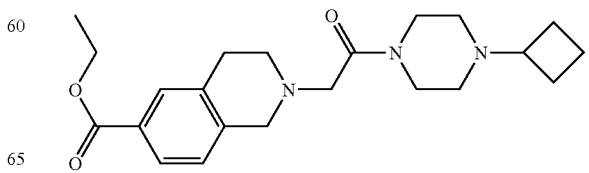

To a stirred solution of 1,2,3,4-tetrahydro-isoquinoline-6-carboxylic acid ethyl ester hydrochloride (530 mg, 2.20 mmol) in acetonitrile (20.0 ml) are added 2-chloro-(4-cyclobutyl-piperazine)-acetamide (474 mg, 2.20 mmol, 1.0 eq.), K$_2$CO$_3$ (608 mg, 4.40 mmol, 2.0 eq.) and NaI (100 mg). The resulting mixture is stirred at 40° C. overnight. Water (10.0 ml) is added to quench the reaction, and the acetonitrile is evaporated. The residue is extracted with DCM (20 ml×3), and the combined organic phase is dried over sodium sulfate and concentrated. The residue is purified by silica gel flash chromatography (EtOAc/4% TEA) to give the title compound. 386.1 (M$^+$+1).

Step 2. Preparation of 2-[2-(4-cyclobutyl-piperazin-1-yl)-2-oxo-ethyl]-1,2,3,4-tetrahydro-isoquinoline-6-carboxylic acid

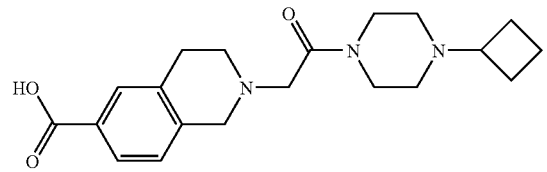

To a solution of 2-[2-(4-cyclobutyl-piperazin-1-yl)-2-oxo-ethyl]-1,2,3,4-tetrahydro-isoquinoline-6-carboxylic acid ethyl ester (610 mg, 1.58 mmol) in a mixture of THF-MeOH-water (3:1:1, 5 ml) cooled to 0° C. is added lithium hydroxide (76 mg, 3.16 mmol, 2.0 eq.). The mixture is stirred at rt overnight. The organic solvent is evaporated, and the residue is acidified to pH=5 with hydrochloric acid (2.0 N, about 1.58 ml). The resulting aqueous solution is evaporated to dryness, and the residue is extracted with a DCM-EtOH mixture (9:1, 10 ml×4). The combined organic solution is dried over sodium sulfate, and concentrated to give the title compound. MS (+VE) m/z 356.2 (M$^+$+1).

Step 3. Preparation of 1-(4-cyclobutyl-piperazin-1-yl)-2-[6-(pyrrolidine-1-carbonyl)-3,4-dihydro-1H-isoquinolin-2-yl]-ethanone

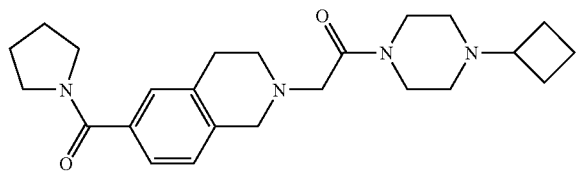

To a stirred solution of 2-[2-(4-cyclobutyl-piperazin-1-yl)-2-oxo-ethyl]-1,2,3,4-tetrahydro-isoquinoline-6-carboxylic acid (179 mg, 0.5 mmol) and pyrrolidine (71 mg, 1.0 mmol, 2.0 eq.) in DCM (5.0 ml) are added BOP (265 mg, 0.6 mmol, 1.2 eq.) and TEA (101 mg, 1 mmol, 2.0 eq.). The mixture is stirred at rt for 2 hr. Water (5.0 ml) is added to quench the reaction, and the organic layer is collected, dried over sodium sulfate, and concentrated. The residue is purified by PTLC (EtOAc/4% TEA) to give the title compound. $^1$H NMR (300 MHz, CDCl$_3$) δ 7.23-7.30 (2H, m), 7.01 (1H, d), 3.69 (2H, s), 3.55-3.66 (6H, m), 3.40 (2H, t), 3.35 (2H, s), 2.90 (2H, t), 2.78 (2H, t), 2.66 (1H, m), 2.26 (4H, m), 1.60-2.05 (10H, m); MS (+VE) m/z 411.1 (M$^+$+1).

XIII. 2-[2-(4-Acetyl-Phenyl)-7,8-Dihydro-5H-Pyrido[4,3-D]Pyrimidin-6-Yl]-1-(4-Cyclobutyl-Piperazin-1-Yl)-Ethanone (Scheme 11)

Compound 18

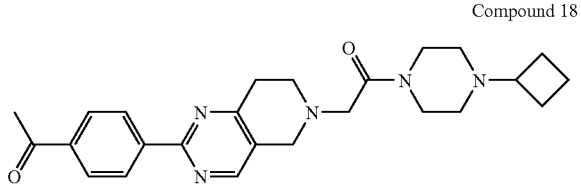

Step 1. Preparation of 3-dimethylaminomethylene-4-oxo-piperidine-1-carboxylic acid tert-butyl ester

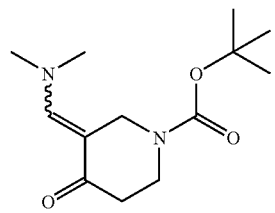

tert-Butyl-4-oxo-1-piperidinecarboxylate (10 g, 50 mmol) and N,N-dimethylformamide dimethyl acetal (7.3 ml, 55 mmol) are added to dry DMF (75 ml) under nitrogen and the mixture is heated at 90° C. for 16 hr. The reaction mixture is concentrated under reduced pressure, and the residue is partitioned between EtOAc (200 ml) and brine (200 ml). Layers are separated and the aqueous phase is extracted with EtOAc (200 ml). The combined organic extracts are dried over sodium sulfate and concentrated under reduced pressure to give a brown oil that solidifies on standing. The material is used for the next step reaction without further purification. $^1$H NMR (300 MHz, CDCl$_3$) δ 7.44 (1H, s), 4.54 (2H, s), 3.59 (2H, t), 3.06 (6H, s), 2.42 (2H, t), 1.44 (9H, s); MS (+VE) m/z 255.1 (M$^+$+1).

Step 2. Preparation of 2-(4-hydroxy-phenyl)-7,8-dihydro-5H-pyrido[4,3-d]pyrimidine-6-carboxylic acid tert-butyl ester

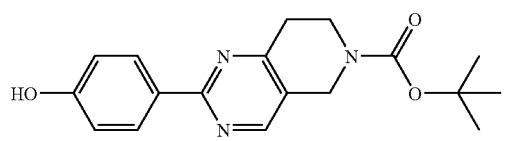

To a 250 ml round bottom flask charged with anhydrous EtOH (50 ml) under nitrogen at 0° C. is added sodium hydride (60% in mineral oil, 800 mg, 20 mmol, 2.0 eq.). The mixture is stirred at rt for 10 min, 4-hydroxyphenylamidine hydrochloric acid salt (1.72 g, 10 mmol) is added, and then tert-butyl-3-[(dimethylamino)methylene]-4-oxo-1-piperidinecarboxylate (2.54 g, 10 mmol, 1.0 eq.) is added. The resulting mixture is stirred at 75° C. for 16 hr. The solvent is evaporated under reduced pressure, and the residue is taken up in DCM (100 ml), washed with water and brine, dried (Na₂SO₄), and concentrated. The residue is purified by silica gel chromatography (Hexane/EtOAc 1:1) to give the title compound. MS (+VE) m/z 328.1 (M⁺+1).

Step 3. Preparation of 2-(4-trifluoromethanesulfonyloxy-phenyl)-7,8-dihydro-5H-pyrido[4,3-d]pyrimidine-6-carboxylic acid tert-butyl ester

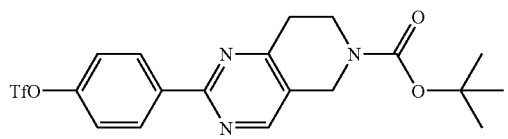

To a solution of 2-(4-hydroxy-phenyl)-7,8-dihydro-5H-pyrido[4,3-d]pyrimidine-6-carboxylic acid tert-butyl ester (1.31 g, 4.0 mmol) in anhydrous DCM (30 ml) cooled to 0° C. is added TEA (607 mg, 6.0 mmol, 1.5 eq.), followed by trifluoromethanesulfonic anhydride (1.24 g, 4.4 mmol, 1.1 eq.) added dropwise. After the addition is complete, 4-dimethylaminopyridine (30 mg) is added. The reaction mixture is stirred at 0° C. for 1 hr, then warmed to rt and stirred for an additional 1 hr. Water (30 ml) is added to quench the reaction. The DCM layer is collected, washed with water and brine, dried over sodium sulfate and concentrated. The residue is purified by silica gel flash chromatography (hexane/EtOAc 4:1) to give the title compound. MS (+VE) m/z 460.1 (M⁺+1).

Step 4. Preparation of 1-[4-(5,6,7,8-tetrahydro-pyrido[4,3-d]pyrimidin-2-yl)-phenyl]-ethanone

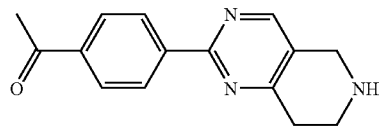

To a stirred solution of 2-(4-trifluoromethanesulfonyloxy-phenyl)-7,8-dihydro-5H-pyrido[4,3-d]pyrimidine-6-carboxylic acid tert-butyl ester (918 mg, 2.0 mmol) in dry DMF (10 ml) is added n-butylvinyl ether (1.02 g, 10 mmol, 5.0 eq.), TEA (404 mg, 4.0 mmol, 2.0 eq.), 1,3-bis(diphenylphosphino)propane (29 mg, 0.055 mmol, 0.0276 eq.) and palladium acetate (11.3 mg, 0.05 mmol, 0.025 eq.) under nitrogen. The resulting mixture is stirred at 80° C. for 7 hr. Water (30 ml) is added to quench the reaction, and the mixture is extracted with EtOAc (30 ml×3). The combined organic phase is washed with water and brine, dried over sodium sulfate, and concentrated. The crude product is purified by silica gel flash chromatography (hexane/EtOAc 5:1) to give a mixture of the vinyl ether and the ketone product, which is dissolved in EtOAc (30 ml), and then treated with concentrated hydrochloric acid (3.0 ml). The mixture is stirred at rt for 2 hr, and then basified with saturated sodium carbonate solution. The organic phase is collected, and the aqueous phase is extracted with DCM twice. The combined organic phase is dried over sodium sulfate, and concentrated to give the title compound. MS (+VE) m/z 254.1 (M⁺+1).

Step 5. Preparation of 2-[2-(4-acetyl-phenyl)-7,8-dihydro-5H-pyrido[4,3-d]pyrimidin-6-yl]-1-(4-cyclobutyl-piperazin-1-yl)-ethanone

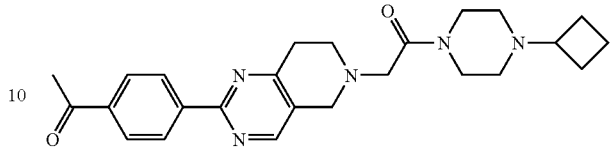

To a stirred solution of 1-[4-(5,6,7,8-tetrahydro-pyrido[4,3-d]pyrimidin-2-yl)-phenyl]-ethanone (253 mg, 1.0 mmol) in acetonitrile (5.0 ml) is added 2-chloro-(4-cyclobutyl-piperazine)-acetamide (216 mg, 1.0 mmol, 1.0 eq.), K₂CO₃ (276 mg, 2.0 mmol, 2.0 eq.) and NaI (50 mg). The resulting mixture is stirred at 50° C. overnight. Water (10.0 ml) is added to quench the reaction, and the acetonitrile is evaporated. The residue is extracted with DCM (10 ml×3), and the combined organic phase is dried over sodium sulfate and concentrated. The residue is purified by preparative silica gel flash chromatography (EtOAc/4% TEA) to give the title compound. ¹H NMR (300 MHz, CDCl₃) δ 8.52 (2H, d), 8.48 (1H, s), 8.05 (2H, d), 3.78 (2H, s), 3.58~3.72 (4H, m), 3.45 (2H, s), 3.09 (2H, t), 2.97 (2H, t), 2.69 (1H, m), 2.65 (3H, s), 2.29 (4H, m), 1.66~2.08 (6H); MS (+VE) m/z 434.2 (M⁺+1).

XIX. 6-[2-(4-Cyclobutylpiperazin-1-Yl)-2-Oxoethyl]-2-Morpholin-4-Yl-5,6,7,8-Tetrahydro-Pyrido[4,3-D]Pyrimidine (Scheme 11)

Compound 19

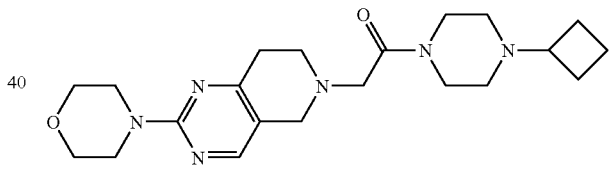

Step 1. Preparation 2-morpholin-4-yl-7,8-dihydro-5H-pyrido[4,3-d]pyrimidine-6-carboxylic acid tert-butyl ester

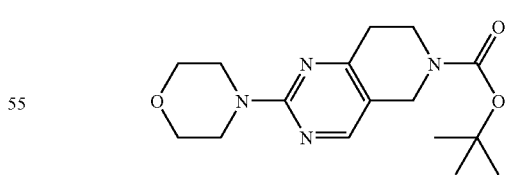

To a 500 ml round bottom flask charged with anhydrous EtOH (150 ml) under nitrogen at 0° C. are added morpholine-4-carboxamidine hydrobromide (10.50 g, 50 mmol), tert-butyl-3-[(dimethylamino)methylene]-4-oxo-1-piperidinecarboxylate (12.7 g, 50 mmol, 1.0 eq.), and potassium t-butoxide in t-butanol (11.0M, 100 ml, 100 mmol, 2.0 eq.). The resulting mixture is stirred at 75° C. for 16 hr. The solvent is evaporated under reduced pressure, and the residue is taken up in DCM (300 ml), washed with water and brine, dried (Na$_2$SO$_4$) and concentrated. The residue is purified by silica gel chromatography (Hexane/EtOAc 1:1) to give the title compound. MS (+VE) m/z 321.1 (M$^+$+1).

Step 2. Preparation of 2-morpholin-4-yl-5,6,7,8-tetrahydro-pyrido[4,3-d]pyrimidine

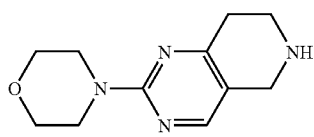

To a stirred solution of 2-(4-hydroxy-phenyl)-7,8-dihydro-5H-pyrido[4,3-d]pyrimidine-6-carboxylic acid tert-butyl ester (9.60 g, 30 mmol) in EtOH (100 ml) is added a solution of hydrochloride in dioxane (4.0M, 60 ml, 240 mmol, 8.0 eq.). The mixture is stirred at rt overnight. The organic solvents are evaporated to give the title compound as hydrochloric acid salt. MS (+VE) m/z 221.1 (M$^+$+1).

Step 3. Preparation of 6-[2-(4-cyclobutylpiperazin-1-yl)-2-oxoethyl]-2-morpholin-4-yl-5,6,7,8-tetrahydro-pyrido[4,3-d]pyrimidine

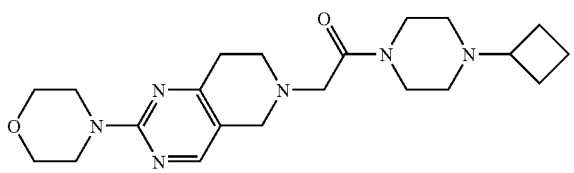

To a stirred solution of 2-morpholin-4-yl-5,6,7,8-tetrahydro-pyrido[4,3-d]pyrimidine (220 mg, 1.0 mmol) in acetonitrile (5.0 ml) is added 2-chloro-(4-cyclobutyl-piperazine)-acetamide (216 mg, 1.0 mmol, 1.0 eq.), K$_2$CO$_3$ (276 mg, 2.0 mmol, 2.0 eq.) and NaI (50 mg). The resulting mixture is stirred at 35° C. overnight. Water (10.0 ml) is added to quench the reaction, and the acetonitrile is evaporated. The residue is extracted with DCM (10 ml×3), and the combined organic phase is dried over sodium sulfate and concentrated. The residue is purified by preparative silica gel flash chromatography (EtOAc/4% TEA) to give the title compound. $^1$H NMR (300 MHz, CDCl$_3$) δ 7.99 (1H, s), 3.75 (8H, s), 3.63 (4H, m), 3.54 (2H, s), 3.36 (2H, s), 2.81 (4H, m), 2.67 (1H, m), 2.27 (4H, m), 1.64~2.07 (6H, m); MS (+VE) m/z 401.2 (M$^+$+1).

XX. 7-[2-(4-Cyclobutylpiperazin-1-Yl)-2-Oxoethyl]-4-Methoxy-6,7,8,9-Tetrahydro-5H-Pyrimido[4,5-D] Azepine (Scheme 13)

Compound 20

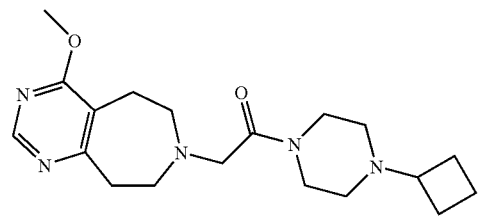

Step 1. Preparation of tert-butyl 4-hydroxy-5,6,8,9-tetrahydro-7H-pyrimido[4,5-d]azepine-7-carboxylate

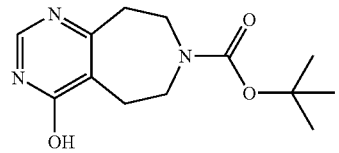

A solution of NaOMe in MeOH (13.6 mL, 25% in MeOH, 59.5 mmol) is added to a stirred solution of formamidine (2.2 g, 21 mmol) in MeOH (50 ml) at rt. The mixture is stirred for 15 min. 1-tert-Butyl 4-methyl 5-oxoazepane-1,4-dicarboxylate (5 g, 7.5 mmol) is added and the mixture is stirred at rt overnight. Acetic acid (2.33 g, 38.5 mmol) is added and the solvent is removed in vacuo. Water (30 ml) is added to the residue and the solution is extracted with DCM (3×30 ml). The combined extracts are washed with brine (40 ml), dried (Na$_2$SO$_4$) and evaporated, to provide a yellow solid that is used in the next step without further purification.

Step 2. Preparation of tert-butyl 4-chloro-5,6,8,9-tetrahydro-7H-pyrimido[4,5-d]azepine-7-carboxylate

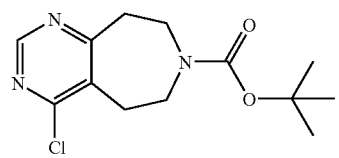

A mixture of tert-butyl 4-hydroxy-5,6,8,9-tetrahydro-7H-pyrimido[4,5-d]azepine-7-carboxylate (4.3 g, 16.2 mmol) and POCl$_3$ (2.3 ml) in toluene (30 mL) is heated at 90° C. for 1 hr. The solvent is removed in vacuo and EtOAc (30 ml) and water (30 ml) are added to the residue. NaHCO$_3$ is carefully added until the pH of the aqueous layer is greater than 7. The layers are separated and the aqueous layer is extracted with EtOAc (2×30 ml). The combined extracts are washed with brine (50 ml) and dried (Na$_2$SO$_4$), and the solvent is evaporated. Flash column purification of the residue with EtOAc/hexane (6:1) provides the title compound as a light yellow solid.

Step 3. Preparation of 4-chloro-6,7,8,9-tetrahydro-5H-pyrimido[4,5-d]azepine

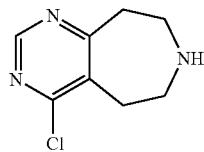

To a solution of tert-butyl 4-chloro-5,6,8,9-tetrahydro-7H-pyrimido[4,5-d]azepine-7-carboxylate (2.0 g, 7.1 mmol) in DCM, a solution of 4N HCl in dioxane (10 mL) is added. The mixture is stirred for 4 hr at rt. The solvent is removed under vacuum to give the title compound (dichloride salt) as a white solid.

Step 4. Preparation of 7-[2-(4-cyclobutylpiperazin-1-yl)-2-oxoethyl]-4-chloro-6,7,8,9-tetrahydro-5H-pyrimido[4,5-d]azepine

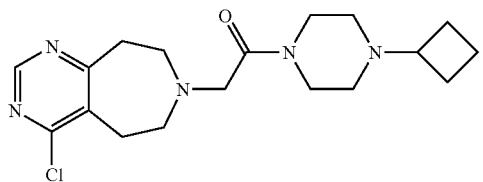

A mixture of 4-chloro-6,7,8,9-tetrahydro-5H-pyrimido[4,5-d]azepine dihydrochloride (0.57 g, 2.2 mmol), 2-chloro-1-(4-cyclobutyl-piperazin-1-yl)-ethanone (0.48 g, 2.2 mmol), $K_2CO_3$ (1 g, 7.2 mmol), and NaI (0.33 g, 2.2 mmol) in acetonitrile is stirred overnight at rt. The solvent is evaporated and water is added. The mixture is extracted with DCM. The combined organic layers are dried ($MgSO_4$) and solvent removed in vacuo to give the crude product, which is purified by PTLC (5% MeOH in DCM) to give the title compound.

Step 5. Preparation of 7-[2-(4-cyclobutylpiperazin-1-yl)-2-oxoethyl]-4-methoxy-6,7,8,9-tetrahydro-5H-pyrimido[4,5-d]azepine

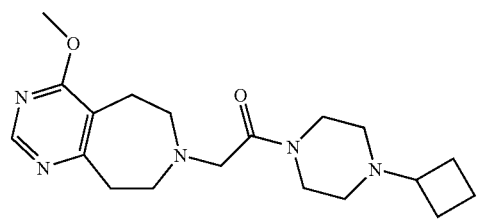

To a solution of 7-[2-(4-cyclobutylpiperazin-1-yl)-2-oxoethyl]-4-chloro-6,7,8,9-tetrahydro-5H-pyrimido[4,5-d]azepine (52 mg, 0.14 mmol) in MeOH, a solution of NaOMe in MeOH (0.3 ml, 25% in MeOH) is added. The mixture is stirred at rt overnight. The solvent is removed and water is added to the residue. The mixture is extracted with DCM. The organic layer is washed with brine, dried and solvent evaporated to give the crude product, which is purified by PTLC (5% TEA in EtOAc) to afford the title compound. $^1$H NMR (CDCl$_3$) δ 8.49 (s, 1H), 3.94 (s, 3H), 3.62 (m, 4H), 3.30 (s, 2H), 3.04 (m, 2H), 2.88 (m, 2H), 2.74-2.62 (m, 5H), 2.31 (m, 4H), 2.04 (m, 2H), 1.88 (m, 2H), 1.68 (m, 2H).

XXI. 1-(4-{7-[2-(4-Cyclobutylpiperazin-1-Yl)-2-Oxoethyl]-6,7,8,9-Tetrahydro-5H-Pyrimido[4,5-D]Azepin-4-Yl}Phenyl)Ethanone (Scheme 13)

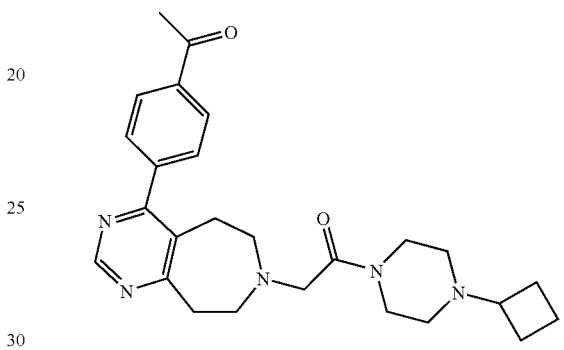

Compound 21

A mixture of 7-[2-(4-cyclobutylpiperazin-1-yl)-2-oxoethyl]-4-chloro-6,7,8,9-tetrahydro-5H-pyrimido[4,5-d]azepine (55 mg, 0.15 mmol), acetylphenylboronic acid (37 mg, 0.22 mmol), Pd(PPh)$_4$ (5.5 mg) and Na$_2$CO$_3$ (72 mg) in DME (3 mL) and water (1 mL) is heated overnight at 80° C. Water is added and the mixture is extracted with DCM. The combined organic layers are dried (MgSO$_4$) and solvent removed in vacuo to give the crude product, which is purified by PTLC (5% MeOH in DCM) to give the title compound. $^1$H NMR (CDCl$_3$) δ 8.99 (s, 1H), 8.04 (d, 2H), 7.55 (s, 2H), 3.54 (m, 4H), 3.33 (s, 2H), 3.20 (m, 2H), 2.97 (m, 2H), 2.94-2.66 (m, 5H), 2.64 (s, 3H), 2.26 (m, 4H), 2.04 (m, 2H), 1.88 (m, 2H), 1.68 (m, 2H).

XXII. 6-[2-(4-Cyclobutylpiperazin-1-Yl)-2-Oxoethyl]-5,6,7,8-Tetrahydro-1,6-Naphthyridin-2(1H)-One (Schemes 14 and 15)

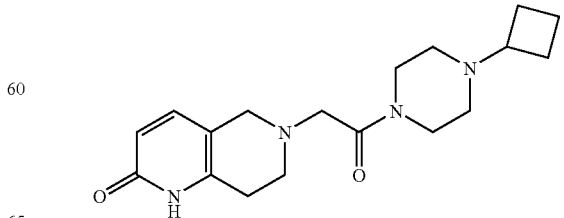

Compound 22

Step 1. Preparation of 1-benzyl-4-pyrrolidin-1-yl-1,2,3,6-tetrahydropyridine

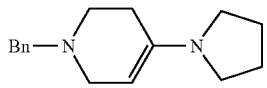

A mixture of 1-benzyl-4-piperidone (7.2 g, 39.64 mmol), and pyrrolidine (4.23 g, 59.5 mmol) in toluene (50 mL) is refluxed for 4 hr with a Dean-Stark trap to remove water. The mixture is cooled to rt and removal of solvent in vacuo provides the title compound as a light orange oil, which is used in the next step without further purification.

Step 2. Preparation of 6-benzyl-5,6,7,8-tetrahydro-1,6-naphthyridin-2(1H)-one

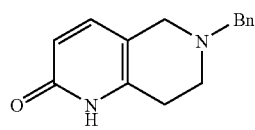

To a solution of 1-benzyl-4-pyrrolidin-1-yl-1,2,3,6-tetrahydropyridine (2.58 g, 10.65 mmol) in toluene (30 mL) is added propiolamide (1.47 g, 21.29 mmol) and the mixture is refluxed for 4 hr. The mixture is cooled to rt and the solvent is removed in vacuo. The residue is partitioned between NaHCO$_3$ (30 mL) and DCM (30 mL). The layers are separated and the aqueous layer is extracted with DCM (30 ml). The combined extracts are dried and evaporated and the residue is purified by flash column with 5% MeOH in DCM to give the title compound as a light yellow solid. MS (M+1): 241.1.

Step 3. Preparation of 5,6,7,8-tetrahydro-1,6-naphthyridin-2(1H)-one

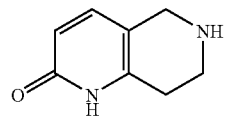

To a solution of 6-benzyl-5,6,7,8-tetrahydro-1,6-naphthyridin-2(1H)-one (400 mg, 1.66 mmol) in EtOH (30 mL) is added 20% Pd(OH)$_2$/C (20 mg) and the mixture is hydrogenated at 50 psi at rt overnight. The catalyst is filtered and the filtrate is concentrated to give the title compound as a light yellow solid. MS (M+1): 151.1

Step 4. Preparation of 6-[2-(4-cyclobutylpiperazin-1-yl)-2-oxoethyl]-5,6,7,8-tetrahydro-1,6-naphthyridin-2(1H)-one

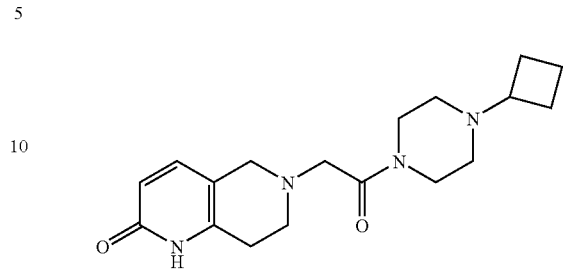

A mixture of 5,6,7,8-tetrahydro-1,6-naphthyridin-2(1H)-one (98 mg, 0.653 mmol), 1-(chloroacetyl)-4-cyclobutylpiperazine (142 mg, 0.653 mmol), K$_2$CO$_3$ (360 mg, 2.61 mmol) and KI (12 mg, 0.07 mmol) in CH$_3$CN (15 mL) is stirred at rt overnight. The solvent is removed in vacuo and the residue is partitioned between water (10 mL) and EtOAc (20 mL). The layers are separated and the aqueous layer is extracted with EtOAc (2×10 mL) and the combined extracts are dried and evaporated. The resulting oil is purified by PTLC with DCM/MeOH/NH$_4$OH (100:5:0.5) to give the title compound as a light yellow solid. MS (M+1): 331.2; $^1$H NMR ($\delta$, CDCl$_3$): 7.13 (d, 1H0, 6.38 (d, 1H), 3.60 (q, 4H), 3.44 (s, 2H), 3.35 (s, 2H), 2.79 (s, 2H), 2.63-2.75 (m, 1H), 2.26 (q, 4H), 1.63-2.06 (m, 6H).

XXIII. 2-Chloro-6-[2-(4-Cyclobutylpiperazin-1-Yl)-2-Oxoethyl]-5,6,7,8-Tetrahydro-1,6-Naphthyridine (Schemes 14 and 15)

Compound 23

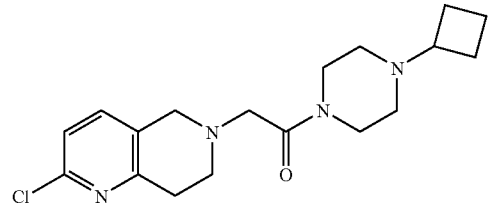

Step 1. Preparation of 6-benzyl-2-chloro-5,6,7,8-tetrahydro-1,6-naphthyridine

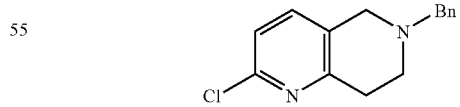

To POCl$_3$ (20 mL) is added 6-benzyl-5,6,7,8-tetrahydro-1,6-naphthyridin-2(1H)-one (1.21 g, 5.04 mmol) and the mixture is heated at 100° C. for 6 hr. Solvent is removed and the thick oil is poured onto crashed ice (60 g). Upon stirring, solid Na$_2$CO$_3$ is added to the suspension until pH>7. EtOAc (60 ml) is added and the layers are separated. The aqueous layer is extracted with EtOAc (30 ml) and the combined extracts are dried and evaporated. The residue is purified by flash silica gel column eluting with hexane/EtOAc (4:1) to give the title compound as a light yellow solid. MS (M+1): 259.1.

Step 2. Preparation of 2-chloro-5,6,7,8-tetrahydro-1,6-naphthyridine hydrochloride

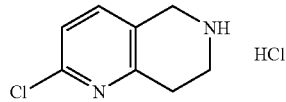

A mixture of 6-benzyl-2-chloro-5,6,7,8-tetrahydro-1,6-naphthyridine (98 mg, 0.38 mmol) and 1-chloroethyl chloroformate (0.05 mL, 0.46 mmol) in ClCH$_2$CH$_2$Cl (10 mL) is refluxed for 3 hr. The solvent is removed and the residue is dissolved in MeOH (10 mL) and the mixture is reflux for 30 min. Solvent is removed in vacuo and the residue is stirred with ether (10 mL) for 30 min at rt and filtered. The resulting light brown solid is used in the next step without further purification. MS (M+1): 169.1.

Step 3. Preparation of 2-chloro-6-[2-(4-cyclobutylpiperazin-1-yl)-2-oxoethyl]-5,6,7,8-tetrahydro-1,6-naphthyridine

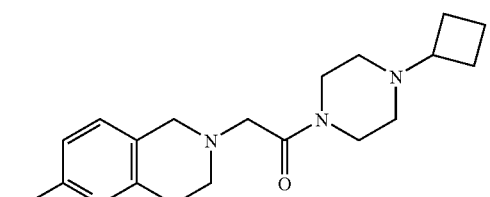

A mixture of 2-chloro-5,6,7,8-tetrahydro-1,6-naphthyridine hydrochloride (80 mg, 0.38 mmol), 1-(chloroacetyl)-4-cyclobutylpiperazine (82 mg, 0.38 mmol), K$_2$CO$_3$ (262 mg, 1.9 mmol) and KI (7 mg, 0.04 mmol) in CH$_3$CN (15 mL) is stirred at rt overnight. The solvent is removed in vacuo and the residue is partitioned between water (10 mL) and EtOAc (20 mL). The layers are separated and the aqueous layer is extracted with EtOAc (2×10 mL). The combined extracts are dried and evaporated. The resulting oil is purified by PTLC with 100:5:0.5 DCM:MeOH:NH$_4$OH to give the title compound as a white solid; MS (M+1): 349.2; $^1$H NMR (δ, CDCl$_3$): 7.27 (d, 1H), 7.09 (d, 1H), 3.59-3.67 (m, 6H), 3.38 (s, 2H), 3.01 (t, 2H), 2.87 (t, 2H), 2.64-2.73 (m, 1H), 2.28 (q, 4H), 1.64-2.06 (m, 6H).

XXIV. 6-[2-(4-Cyclobutylpiperazin-1-Yl)-2-Oxoethyl]-2-Pyridazin-3-Yl-5,6,7,8-Tetrahydro-1,6-Naphthyridine (Scheme 15)

Compound 24

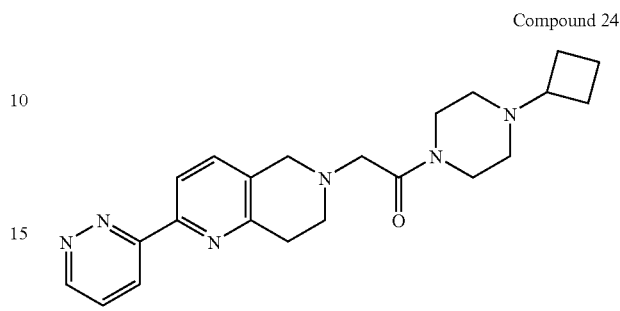

A mixture of 2-chloro-6-[2-(4-cyclobutylpiperazin-1-yl)-2-oxoethyl]-5,6,7,8-tetrahydro-1,6-naphthyridine (349 mg, 1 mmol), 3-(tributylstannyl)pyridazine (461 mg, 1.25 mmol) and Pd(PPh$_3$)$_4$ (116 mg, 0.1 mmol) in toluene (15 mL) is degassed by argon and heated at 110° C. in a sealed tube overnight. The mixture is cooled and saturated KF solution (10 mL) is added. The mixture is stirred at rt for 30 min, and then the layers are separated. The aqueous layer is extracted with EtOAc (15 ml) and the combined extracts are dried and evaporated. The residue is purified by PTLC to give the title compound as a white solid. MS (M+1): 393.2; $^1$H NMR (δ, CDCl$_3$): 9.77 (m, 1H), 9.26 (dd, 1H), 8.05 (dd, 1H), 7.64 (d, 1H), 7.48 (d, 1H), 3.79 (s, 2H), 3.65 (q, 4H), 3.43 (s, 2H), 3.13 (t, 2H), 2.96 (t, 2H), 2.64-2.74 (m, 1H), 2.30 (q, 4H), 1.64-2.06 (m, 6H).

XXV. 6-[2-(4-Cyclobutylpiperazin-1-Yl)-2-Oxoethyl]-2-Pyrrolidin-1-Yl-5,6,7,8-Tetrahydro-1,6-Naphthyridine (Scheme 15)

Compound 25

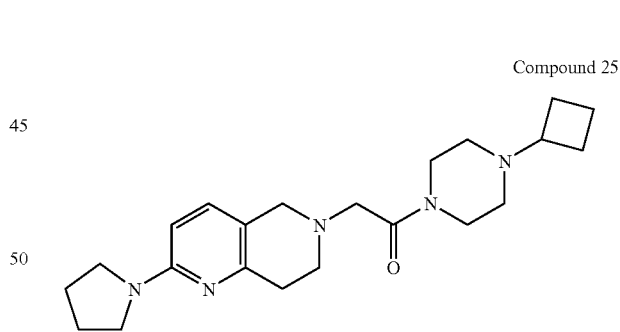

A mixture of 2-chloro-6-[2-(4-cyclobutylpiperazin-1-yl)-2-oxoethyl]-5,6,7,8-tetrahydro-1,6-naphthyridine (80 mg, 0.23 mmol) and pyrrolidine (2.5 mL) is heated by microwave (300 w) at 170° C. for 2 hr. Solvent is removed and the residue is partitioned between saturated NaHCO$_3$ solution (10 mL) and DCM (10 mL). The layers are separated and the aqueous layer is extracted with DCM (10 ml). The combined extracts are dried and evaporated. The residue is purified by PTLC to give the title compound as a light yellow oil. MS (M+1): 384.3; $^1$H NMR (δ, CDCl$_3$): 7.07 (d, 1H), 6.16 (d, 1H), 3.62-3.69 (m, 4H), 3.53 (s, 2H), 3.40-3.44 (m, 4H), 3.34 (s, 2H), 2.78-2.90 (m, 4H), 2.61-2.72 (m, 1H), 2.27 (q, 4H), 1.63-2.04 (m, 10H).

XXVI. 2-Cyclopentyloxy-6-[2-(4-Cyclobutylpiperazin-1-Yl)-2-Oxoethyl]-5,6,7,8-Tetrahydro-1,6-Naphthyridine (Scheme 15)

Compound 26

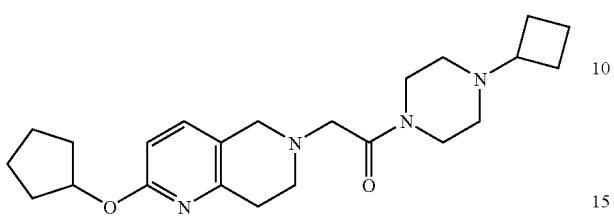

To a solution of cyclopentanol (99 mg, 1.15 mmol) in DMF (5 mL) is added NaH (60% in mineral oil, 18.4 mg, 0.46 mmol), and the mixture is stirred at rt for 30 min. 2-Chloro-6-[2-(4-cyclobutylpiperazin-1-yl)-2-oxoethyl]-5,6,7,8-tetrahydro-1,6-naphthyridine (80 mg, 0.23 mmol) is added and the mixture is heated at 100° C. for 2 hr. Solvent is removed and the residue is partitioned between water (10 mL) and DCM (10 mL). The layers are separated and the aqueous layer is extracted with DCM (10 ml). The combined extracts are dried and evaporated. The residue is purified by PTLC to give the title compound as a light yellow oil MS (M+1): 399.3; $^1$H NMR (δ, CDCl$_3$): 7.17 (d, 1H), 6.46 (d, 1H), 5.28 (m, 1H), 3.64 (q, 4H), 3.58 (s, 2H), 3.36 (s, 2H), 2.80-2.88 (m, 4H), 2.63-2.73 (m, 1H), 2.28 (q, 4H), 1.58-2.08 (m, 14H).

XXVI. 1-(4-Cyclobutyl-Piperazin-1-Yl)-2-(7,8-Dihydro-5H-[1,6]Naphthyridin-6-Yl)-Ethanone (Scheme 16)

Compound 27

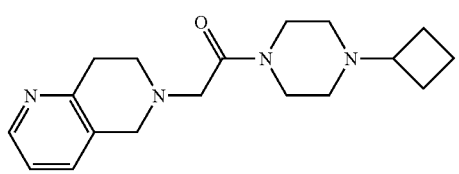

Step 1. Preparation of 6-benzyl-5,6,7,8-tetrahydro-[1,6]naphthyridine

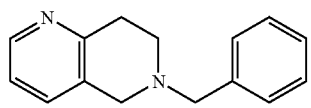

To a solution 1,6-naphthyridine (2.09 g, 16.05 mmol) in acetonitrile (50.0 ml) is added benzylbromide (3.30 g, 19.27 mmol, 1.2 eq) and NaI (50.0 mg). The resulting mixture is refluxed under nitrogen overnight. Acetonitrile is evaporated, and the residue is washed with ether (20 ml), and dried in vacuo to give the quaternary salt, which is dissolved in a mixture of MeOH (90 ml) and water (30 ml). To the solution at 0° C. is added sodium borohydride (2.28 g, 96.5 mmol, about 6.0 eq.). The resulting mixture is warmed to rt, and stirred overnight. The organic solvent is evaporated, and the residue is taken up in water (50 ml), extracted with EtOAc (50 ml×3). The combined organic phase is washed with brine, dried over sodium sulfate, and concentrated. The crude product is purified by silica gel chromatography (Hexane/EtOAc 1:1 plus 4% TEA) to give the title compound. MS (+VE) m/z 225.1 (M$^+$+1).

Step 2. Preparation of 5,6,7,8-tetrahydro-[1,6]naphthyridine

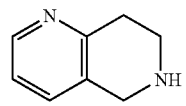

6-Benzyl-5,6,7,8-tetrahydro-[1,6]naphthyridine (3.10 g, 13.82 mmol) is dissolved in acetic acid (40 ml). To the solution is added Pd—C (10%, 500 mg). The resulting mixture is hydrogenated under 40-50 psi at 55-60° C. for 10 hr. The solid catalyst is removed by filtration, and the filtering cake is washed with MeOH (20 ml×2). The combined organic phase is evaporated to dryness. The residue is taken up into water (25.0 ml), basified with saturated sodium carbonate solution, and extracted with EtOAc (30 ml×3). The combined organic phase is dried with sodium sulfate, and concentrated to give the title compound. MS (+VE) m/z 135.1 (M$^+$+1).

Step 3. Preparation of 1-(4-cyclobutyl-piperazin-1-yl)-2-(7,8-dihydro-5H-[1,6]naphthyridin-6-yl)-ethanone

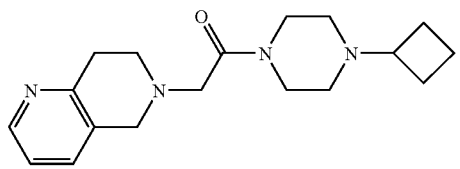

To a stirred solution of 5,6,7,8-tetrahydro-[1,6]naphthyridine (134 mg, 1.0 mmol) in acetonitrile (5.0 ml) is added 2-chloro-(4-cyclobutyl-piperazine)-acetamide (216 mg, 1.0 mmol, 1.0 eq.), K$_2$CO$_3$ (376 mg, 2.0 mmol, 2.0 eq.), and NaI (30 mg). The resulting mixture is stirred at rt overnight. Water (10.0 ml) is added to quench the reaction, and the acetonitrile is evaporated. The residue is extracted with DCM (10 ml×3). The combined organic phase is dried over sodium sulfate and concentrated. The residue is purified by PTLC (EtOAc/4% TEA/4% EtOH) to give the title compound. $^1$H NMR (300 MHz, CDCl$_3$) δ 8.40 (1H, dd), 7.30 (1H, dd), 7.06 (1H, dd), 3.70 (2H, s), 3.63 (4H, m), 3.38 (2H, s), 3.04 (2H, t), 2.89 (2H, t), 2.67 (1H, m), 2.27 (4H, m), 1.60-2.06 (6H, m); MS (+VE) m/z 315.2 (M$^+$+1).

XXVIII. N-Cyclobutyl-6-[2-(4-Cyclobutylpiperazin-1-Yl)-2-Oxoethyl)-5,6,7,8-Tetrahydro-1,6-Naphthyridine-2-Carboxamide (Scheme 16)

Compound 28

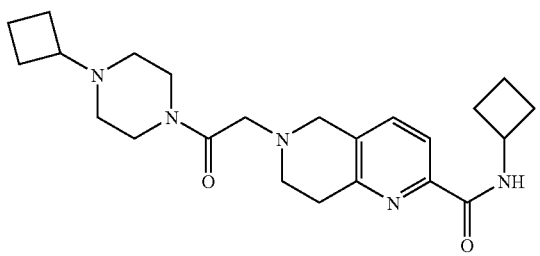

Step 1. Preparation of N-cyclobutyl-1,6-naphthyridine-2-carboxamide

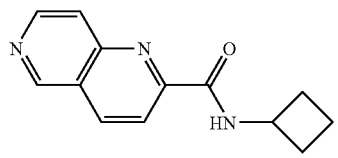

A mixture of 1,6-naphthyridine-2-carboxylic acid (188 mg, 1.08 mmol), cyclobutylamine (114 mg, 1.6 mmol), BOP (708 mg, 1.6 mmol) and TEA (0.45 ml, 3.2 mmol) in DCM (15 ml) is stirred at rt overnight. The solvent is removed in vacuo and the residue is partitioned between water (20 mL) and EtOAc (20 mL). The layers are separated and the aqueous layer is extracted with EtOAc (10 ml). The combined extracts are washed with brine (10 mL), dried and evaporated. The residue is purified by PTLC to give the title compound as a light yellow oil; MS (M+1): 228.2.

Step 2. Preparation of tert-butyl {2-[(cyclobutylamino)carbonyl]-7,8-dihydro-1,6-naphthyridin-6(5H)-yl}acetate

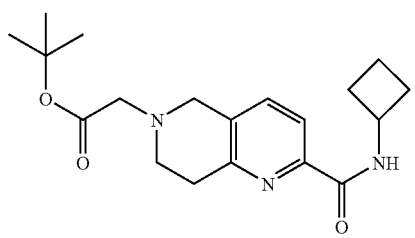

A mixture of N-cyclobutyl-1,6-naphthyridine-2-carboxamide (227 mg, 1 mmol), tert-butyl bromoacetate (234 mg, 1.2 mmol) in CH₃CN (15 mL) is refluxed overnight. Solvent is removed in vacuo and the residue is dissolve in MeOH (20 mL). To the solution is added NaBH₄ (181 mg, 4.8 mmol) and the mixture is refluxed for 4 hr. The solvent is removed in vacuo and the residue is partitioned between water (20 mL) and EtOAc (20 mL). The layers are separated and the aqueous layer is extracted with EtOAc (20 ml). The combined extracts are washed with brine (10 mL), dried and evaporated. The residue is purified by flash column to give the title compound as a light yellow oil. MS (M+1): 346.2.

Step 3. Preparation of {2-[(cyclobutylamino)carbonyl]-7,8-dihydro-1,6-naphthyridin-6(5H)-yl}acetic acid hydrochloride

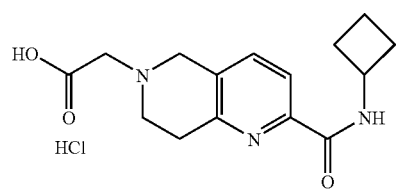

The oil obtained from step 2 is dissolved in dioxane (5 mL). 4 N HCl in dioxane (5 ml, 20 mmol) is added. The mixture is stirred at rt overnight. The solvent is removed and the residue is washed with ether to give the title compound as a white solid. MS (M+1): 290.1.

Step 4. Preparation of N-cyclobutyl-6-[2-(4-cyclobutylpiperazin-1-yl)-2-oxoethyl)-5,6,7,8-tetrahydro-1,6-naphthyridine-2-carboxamide

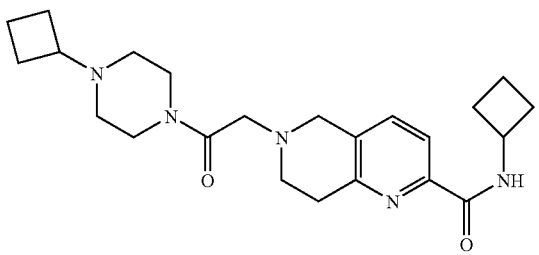

A mixture of {2-[(cyclobutylamino)carbonyl]-7,8-dihydro-1,6-naphthyridin-6(5H)-yl}acetic acid hydrochloride (37 mg, 0.11 mmol), 1-cyclobutylpiperazine (19 mg, 0.133 mmol), BOP (59 mg, 0.133 mmol) and TEA (0.075 ml, 0.532 mmol) in DCM (5 ml) is stirred at rt overnight. The solvent is removed in vacuo and the residue is partitioned between water (10 mL) and EtOAc (10 mL). The layers are separated and the aqueous layer is extracted with EtOAc (10 ml). The combined extracts are washed with brine (10 mL), dried and evaporated. The residue is purified by PTLC to give the title compound as a light yellow oil. MS (M+1): 412.4; $^1$H NMR (δ, CDCl₃): 8.11 (d, 1H), 7.94 (d, 1H), 7.43 (d, 1H), 4.53-4.61 (m, 1H), 3.75 (s, 2H), 3.58-3.66 (m, 4H), 3.45 (t, 2H), 3.40 (s, 2H), 3.04 (t, 2H), 2.92 (t, 2H), 2.63-2.76 (m, 1H), 2.36-2.46 (m, 2H), 2.25-2.32 (m, 6H), 1.63-2.06 (m, 6H).

XXIX. Ethyl 7-[2-(4-Cyclobutyl-3-Methylpiperazin-1-Yl)-2-Oxoethyl)-5,6,7,8-Tetrahydro-1,7-Naphthyridne-3-Carboxylate (Scheme 16)

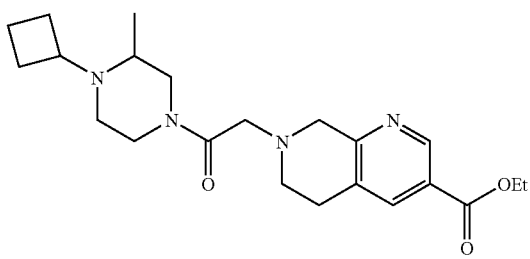

Compound 29

Step 1. Preparation of tert-butyl 4-formylpyridin-3-ylcarbamate

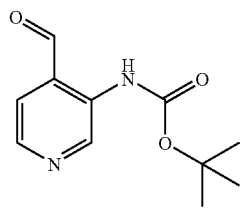

At −78° C., to a solution of tert-butyl pyridin-3-ylcarbamate (2.98 g, 15.34 mmol) in THF (60 mL) is added t-BuLi (1.7 N, 21.65 mL, 36.8 mmol) dropwise while maintaining the internal temperature below −70° C. Then, the mixture is allowed to warm to −20° C. for 2 hr and piperidine-1-carbaldehyde (5.11 mL, 46.02 mmol) is added dropwise and the mixture is stirred at −20° C. to rt overnight. Saturated NH$_4$Cl solution (30 mL) is added and the layers are separated. The aqueous layer is extracted with EtOAc (45 ml) and the combined extracts are dried and evaporated. The residue is purified by flash column with hexane/EtOAc (4:1) to give the title compound as a white solid. MS (M+1): 223.1.

Step 2. Preparation of ethyl 1,7-naphthyridine-3-carboxylate

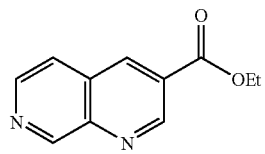

A mixture of tert-butyl 4-formylpyridin-3-ylcarbamate (1.7 g, 7.65 mmol), ethyl 3-ethoxyacrylate (1.27 g, 8.8 mmol) and TFA (5.9 mL, 76.5 mmol) in CHCl$_3$ (30 mL) is heated at reflux for 4 hr. The mixture is cooled and the solvent is removed in vacuo. The residue is dissolved in EtOAc (30 mL) and washed with saturated NaHCO$_3$ solution (20 mL). The organic layer is dried and evaporated. Purification of the residue with flash column with hexane/EtOAc (2:1) gives the title compound as a white solid. MS (M+1): 203.1.

Step 3. Preparation of ethyl 7-(2-tert-butoxy-2-oxoethyl)-5,6,7,8-tetrahydro-1,7-naphthyridine-3-carboxylate

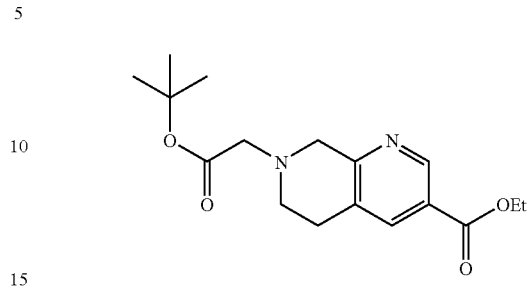

A mixture of ethyl 1,7-naphthyridine-3-carboxylate (905 mg, 4.476 mmol) and tert-butyl bromoacetate (1.0 g, 5.15 mmol) in CH$_3$CN (15 mL) is refluxed overnight. Solvent is removed in vacuo and the residue is dissolve in MeOH (20 mL). To the solution is added NaBH$_4$ (677 mg, 17.9 mmol) and the mixture is refluxed for 4 hr. The solvent is removed in vacuo and the residue is partitioned between water (30 mL) and EtOAc (30 mL). The layers are separated and the aqueous layer is extracted with EtOAc (20 ml). The combined extracts are washed with brine (20 mL), dried and evaporated. The residue is purified by flash column to give the title compound as a light yellow oil. MS (M+1): 321.2.

Step 4. Preparation of [3-(ethoxycarbonyl)-5,8-dihydro-1,7-naphthyridin-7(6H)-yl]acetic acid hydrochloride

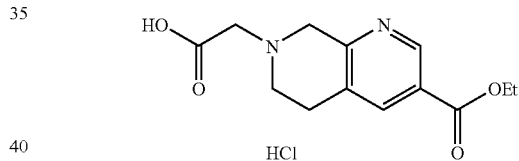

To a solution of ethyl 7-(2-tert-butoxy-2-oxoethyl)-5,6,7,8-tetrahydro-1,7-naphthyridine-3-carboxylate (657 mg, 2.05 mmol) in dioxane (10 mL) is added 4 N HCl in dioxane (5 ml, 20 mmol) and the mixture is stirred at rt overnight. The solvent is removed and the residue is washed with ether to give the title compound as a white solid. MS (M+1): 265.1.

Step 5. Preparation of ethyl 7-[2-(4-cyclobutyl-3-methylpiperazin-1-yl)-2-oxoethyl)-5,6,7,8-tetrahydro-1,7-naphthyridne-3-carboxylate A mixture of [3-(ethoxycarbonyl)-5,8-dihydro-1,7-naphthyridin-7(6H)-yl]acetic acid hydrochloride (40 mg, 0.134 mmol), 1-cyclobutyl-2-methylpiperazine (26 mg, 0.168 mmol), BOP (74 mg, 0.168 mmol) and TEA (0.075 ml, 0.54 mmol) in DCM (5 ml) is stirred at rt overnight. The solvent is removed in vacuo and the residue is partitioned between water (10 mL) and EtOAc (10 mL). The layers are separated and the aqueous layer is extracted with EtOAc (10 ml). The combined extracts are washed with brine (10 mL), dried and evaporated. The residue is purified by PTLC to give the title compound as a light yellow oil. MS (M+1): 401.3; $^1$H NMR (δ, CDCl$_3$): 8.95 (d, 1H), 8.02 (d, 1H), 4.38 (q, 2H), 3.84 (s, 2H), 3.53-3.75 (m, 4H), 3.26-3.43 (m, 4H), 2.59-3.07 (m, 6H), 1.58-2.26 (m, 6H), 1.39 (t, 3H), 0.97-1.03 (m, 3H).

XXX. N-Methyl-7-[2-(4-Cyclobutyl-3-Methylpiperazin-1-Yl)-2-Oxoethyl)-5,6,7,8-Tetrahydro-1,7-Naphthyridne-3-Carboxamide (Scheme 16)

Compound 30

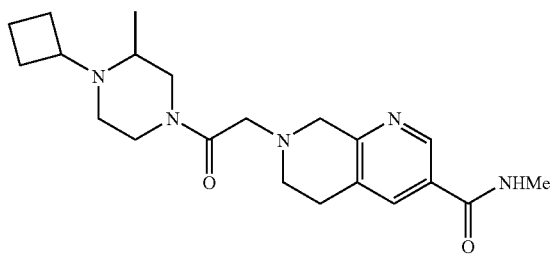

A solution of ethyl 7-[2-(4-cyclobutylpiperazin-1-yl)-2-oxoethyl)-5,6,7,8-tetrahydro-1,7-naphthyridine-3-carboxylate (30 mg, 0.75 mmol) in 40% MeNH$_2$ aqueous solution (3 ml) is heated at 100° C. overnight. The solvent is removed and the residue is purified by PTLC to give the title compound as a light yellow oil. MS (M+1): 386.3; $^1$H NMR (δ, CDCl$_3$): 8.68 (d, 1H), 7.86 (d, 1H), 6.17 (broad, 1H), 3.83 (s, 2H), 3.49-3.75 (m, 4H), 3.25-3.42 (m, 4H), 3.03 (d, 3H), 2.50-2.95 (m, 6H), 1.58-2.17 (m, 6H), 0.95-1.01 (m, 3H).

XXXI. 6-[2-(4-Cyclobutylpiperazin-1-Yl)-2-Oxoethyl]-5,6,7,8-Tetrahydro-pyrido[3,4-b]pyrazine (scheme 17)

Compound 31

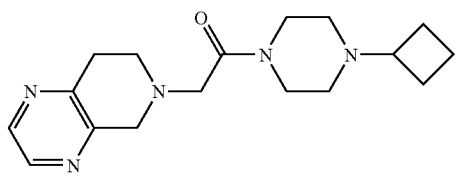

Step 1. Preparation of ethyl pyrido[3,4-b]pyrazine-6(5H)-carboxylate

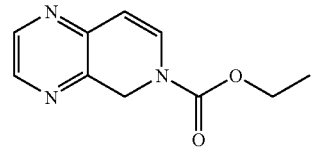

A solution of pyrido[3,4-b]pyrazine (20.0 g, 153 mmol) in anhydrous THF (250 mL) is cooled to −25° C. A solution of ethyl chloroformate (17.5 ml, 183 mmol) in THF (46 mL) is added dropwise. The mixture is stirred 1 hr at −25° C., and then LiBH$_4$ (2.0 M, 23 mL, 46 mmol) is added dropwise and the mixture is stirred for 1 hr. The reaction is quenched with the addition of 1N NaOH (100 mL) and extracted with Et$_2$O (3×100 mL). The organic extractions are combined, dried and evaporated. The crude product is purified by silica gel column chromatography eluting with hexane/EtOAc (3:2) to yield the title compound. MS (+VE) m/z 206.14 (M$^+$+1).

Step 2. Preparation of ethyl 7,8-dihydropyrido[3,4-b]pyrazine-6(5H)-carboxylate

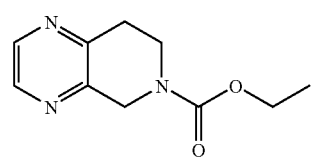

To a solution of ethyl pyrido[3,4-b]pyrazine-6(5H)-carboxylate (149 mg, 0.726 mmol) in EtOAc (25 mL) is added 10% Pd/C (100 mg). The mixture is hydrogenated at 30 psi. overnight. The mixture is filtered through Celite and the solvent removed under vacuum to yield the title compound. MS (+VE) m/z 208.16 (M$^+$+1).

Step 3. Preparation of 5,6,7,8-tetrahydropyrido[3,4-b]pyrazine

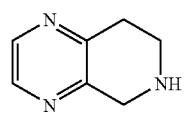

To a solution of ethyl 7,8-dihydropyrido[3,4-b]pyrazine-6 (5H)-carboxylate (150 mg, 0.724 mmol) in MeOH (20 mL)/H$_2$O (2 mL) is added KOH (500 mg, 8.91 mmol). The mixture is stirred overnight at rt and 4 hr at 65° C. The reaction mixture is cooled, and brine (50 mL) is added. The solution is extracted with DCM (3×100 mL). The combined organic extracts are dried and evaporated to yield the title compound. MS (+VE) m/z 136.20 (M$^+$+1).

Step 4. Preparation of 6-[2-(4-cyclobutylpiperazin-1-yl)-2-oxoethyl]-5,6,7,8-tetrahydropyrido-[3,4-b]pyrazine

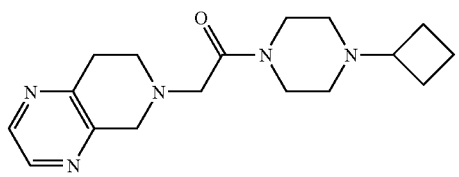

To a suspension of 5,6,7,8-tetrahydropyrido[3,4-b]pyrazine (70 mg, 0.518 mmol), NaI (50 mg, 0.333 mmol), and K$_2$CO$_3$ (200 mg, 1.45 mmol) in acetonitrile is added 2-chloro-1-(4-cyclobutyl-piperazin-1-yl)-ethanone (112 mg, 0.518 mmol). The mixture is stirred overnight at rt, diluted with DCM (20 mL) and filtered through Celite. The filtrate is evaporated and the crude product is purified by silica gel chromatography eluting with EtOAc/MeOH/NEt$_3$ (95:5:5) to yield the title compound. $^1$H NMR (300 MHz, CDCl$_3$) δ 8.35 (2H, dd), 3.85 (2H, s), 3.70-3.66 (m, 4H), 3.46 (2H, s), 3.09 (2H, t), 2.96 (2H, t), 2.75 (1H, m), 2.37-2.34 (4H, m), 2.09-1.67 (m, 6H); MS (+VE) m/z 316.21 (M$^+$+1).

XXXII. 6-[2-(4-Cyclobutylpiperazin-1-Yl)-2-Oxoethyl]-2-Morpholin-4-Yl-5,6,7,8-Tetrahydropyrido[3,4-b]Pyrazine (Scheme 17)

Compound 32

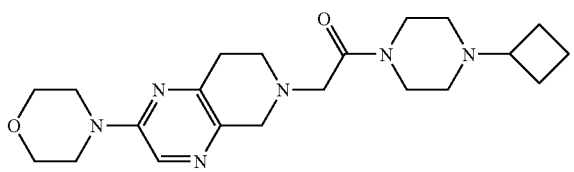

Step 1. Preparation of ethyl 2-chloro-7,8-dihydropyrido[3,4-b]pyrazine-6(5H)-carboxylate

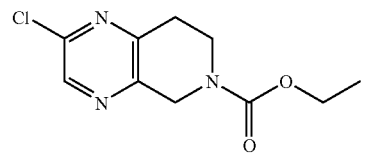

To a solution of ethyl 7,8-dihydropyrido[3,4-b]pyrazine-6(5H)-carboxylate (421 mg, 2.03 mmol) in anhydrous DCM (10 mL) is added mCPBA (520 mg, 3.01 mmol). The mixture is stirred at rt for 3 hr. Ammonia gas is bubbled through the solution for 5 min and the mixture is stirred for 1 hr. The resulting precipitate is filtered off and washed with DCM. The filtrate is evaporated to yield the crude N-oxide (453 mg, 2.03 mmol), which is dissolved in POCl$_3$ (8 mL) and heated at 100° C. for 3 hr. The mixture is cooled and excess POCl$_3$ is removed under reduced pressure. The residue is partitioned between EtOAc (20 mL) and saturated aqueous NaHCO$_3$ (20 mL). The mixture is extracted with EtOAc (3×20 mL) and the combined organic extracts are dried and evaporated. The crude product is purified by PTLC eluting with hexane/acetone (3:1) which yields two regioisomers. The title compound is the less polar regioisomer. MS (+VE) m/z 242.17 (M$^+$+1).

Step 2. Preparation of ethyl 2-morpholin-4-yl-7,8-dihydropyrido[3,4-b]pyrazine-6(5H)-carboxylate

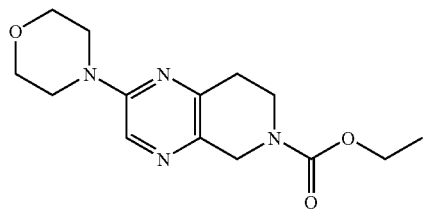

2-chloro-7,8-dihydropyrido[3,4-b]pyrazine-6(5H)-carboxylate (102 mg, 0.422 mmol) is dissolved in morpholine (2 mL). The reaction mixture is heated at 160° C. in a microwave reactor for 1 hr. The mixture is cooled and concentrated under reduced pressure. Toluene (10 mL) is added and the solution concentrated again. The crude residue is partitioned between DCM (50 mL) and a mixture of brine (25 mL) and 1 N NaOH (25 mL). The aqueous phase is extracted with DCM (3×50 mL). The organic extracts are combined, dried and evaporated to yield the title compound. MS (+VE) m/z 293.21 (M$^+$+1).

Step 3. Preparation of 2-morpholin-4-yl-5,6,7,8-tetrahydropyrido[3,4-b]pyrazine

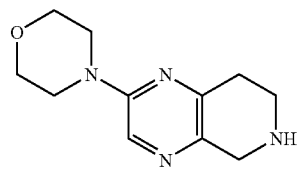

Ethyl 2-morpholin-4-yl-7,8-dihydropyrido[3,4-b]pyrazine-6(5H)-carboxylate (105 mg, 0.359 mmol) is dissolved in MeOH (5 mL) and H$_2$O (5 mL). KOH (1.00 g, 17.9 mmol) is added, and the reaction mixture is stirred overnight at 50° C. The mixture is cooled and partitioned between brine (50 mL) and DCM (50 mL). The mixture is extracted with DCM (2×50 mL). The combined organic extracts are dried and evaporated to yield the title compound. MS (+VE) m/z 221.21 (M$^+$+1).

Step 4. Preparation of 6-[2-(4-cyclobutylpiperazin-1-yl)-2-oxoethyl]-2-morpholin-4-yl-5,6,7,8-tetrahydropyrido[3,4-b]pyrazine

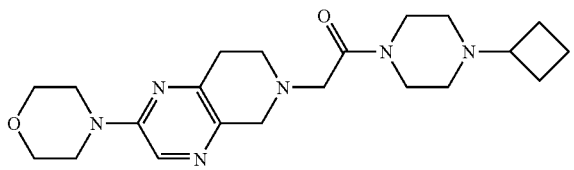

To a solution of 2-morpholin-4-yl-5,6,7,8-tetrahydropyrido[3,4-b]pyrazine (60 mg, 0.27 mmol) in acetonitrile (5 mL) is added NaI (50 mg, 0.333 mmol), K$_2$CO$_3$ (200 mg, 1.45 mmol) and 2-chloro-1-(4-cyclobutyl-piperazin-1-yl)-ethanone (100 mg, 0.463 mmol). The mixture is stirred overnight at rt. The mixture is diluted with DCM (25 mL) and filtered through Celite. The filtrate is concentrated and the residue is purified by PTLC eluting with EtOAc/MeOH/NEt$_3$ (90:10:10) to yield the title compound. $^1$H NMR (300 MHz, CDCl$_3$) δ 7.90 (1H, s), 3.85 (2H, m), 3.72 (4H, m), 3.63-3.60 (4H, m), 3.50 (2H, t), 3.40 (2H, s), 2.92-2.87 (3H, m), 2.74-2.69 (2H, m), 2.51 (2H, t), 2.34-2.26 (4H, m), 2.09-1.67 (m, 6H); MS (+VE) m/z 401.26 (M$^+$+1).

XXXIII. 7-[2-(4-Cyclobutylpiperazin-1-Yl)-2-Oxoethyl]-3-Morpholin-4-Yl-5,6,7,8-Tetrahydropyrido[3,4-C]Pyridazine (Scheme 18)

Compound 33

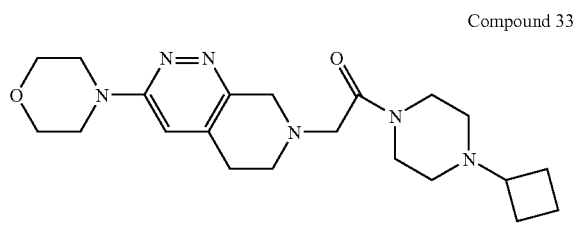

Step 1. Preparation of benzyl 1-benzyl-4-(2-ethoxy-2-oxoethyl)-3-oxopiperidine-4-carboxylate

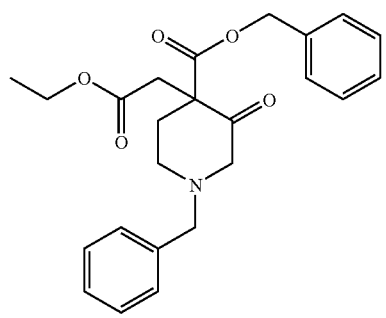

To a cooled (0° C.) solution of 1-benzyl-3-piperidone-4-carboxylic acid benzyl ester (24.9 g, 77 mmol) in dioxane (120 mL) is added NaH (3.7 g, 92.5 mmol, 1.2 eq.) portionwise. The cooling bath is removed and the resulting mixture is allowed to stir at 50° C. for one hour. The mixture is cooled to 0° C. and ethyl bromoacetate (14.1 g, 84.4 mmol, 1.1 eq) is added. The resulting mixture is stirred at rt overnight. Water (100.0 ml) is added to quench the reaction, and the mixture is extracted with EtOAc (100 ml×2). The combined organic phase is dried over sodium sulfate, and the solvent is removed under reduced pressure to give a residue that is purified by silica gel chromatography eluting with Hexane/EtOAc (2:1) to give the title compound.

Step 2. Preparation of ethyl (1-benzyl-3-oxopiperidin-4-yl)acetate

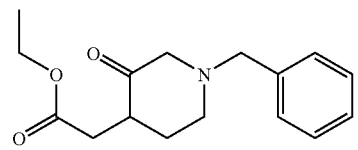

A mixture of benzyl 1-benzyl-4-(2-ethoxy-2-oxoethyl)-3-oxopiperidine-4-carboxylate (18.5 g, 45.2 mmol) and 10% palladium-on-carbon (1.5 g) in EtOAc (50 ml) is treated with 15 psi of hydrogen for 2 hours. The reaction mixture is filtered through a celite pad, washing with EtOAc (100 ml). The combined filtrate is concentrated in vacuo to afford the title compound.

Step 3. Preparation of 7-benzyl-5,6,7,8-tetrahydropyrido[3,4-c]pyridazin-3-ol

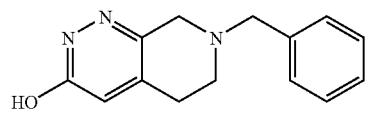

A mixture of ethyl (1-benzyl-3-oxopiperidin-4-yl)acetate (11.4 g, 41.4 mmol) and hydrazine monohydrate (3.1 g, 62 mmol) in EtOH (50 mL) is stirred at 80° C. for one hour. The resulting solution is cooled, and concentrated in vacuo to give a white solid. The white solid is dissolved in acetic acid (120 mL) and the mixture is heated at 85° C. To the reaction mixture is added bromine (6.62 g, 41.4 mmol) dropwise. The resulting mixture is heated for another 30 min. The solvent is removed in vacuo to give a residue. A saturated NaHCO$_3$ solution is added until pH ~8 while stirring. The formed solid is filtered and dried in air to afford the title compound.

Step 4. Preparation of 7-benzyl-3-chloro-5,6,7,8-tetrahydropyrido[3,4-c]pyridazine

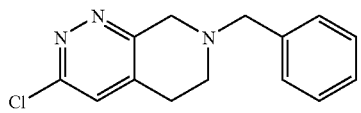

To a slurry of 7-benzyl-5,6,7,8-tetrahydropyrido[3,4-c]pyridazin-3-ol (7 g, 29.1 mmol) in toluene (50 ml) is added POCl$_3$ (7 ml). The resulting mixture is heated at 85° C. for 3 hr. The mixture is cooled to 0° C. and is neutralized with saturated NaHCO$_3$ solution. The mixture is extracted with EtOAc (100 ml×2). The combined organic phase is dried over sodium sulfate, and the solvent is removed under reduced pressure to give a residue that is purified by silica gel chromatography (EtOAc/4% TEA) to give the title compound.

Step 5. Preparation of 3-chloro-5,6,7,8-tetrahydropyrido[3,4-c]pyridazine

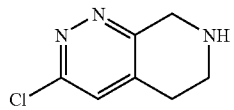

A mixture of 7-benzyl-3-chloro-5,6,7,8-tetrahydropyrido[3,4-c]pyridazine (1.3 g, 5.0 mmol) and 1-chloroethyl chloroformate (0.86 g, 10.0 mmol) in dichloroethane (30 ml) is heated at refluxing temperature overnight. The solvent is removed in vacuo and MeOH (30 ml) is added to the residue. The resulting mixture is refluxed for 30 min. The solvent is removed in vacuo to give the title compound as a hydrogen chloride salt, which is used in the next step without purification.

Step 6. Preparation of 7-[2-(4-cyclobutylpiperazin-1-yl)-2-oxoethyl]-3-chloro-5,6,7,8-tetrahydropyrido[3,4-c]pyridazine

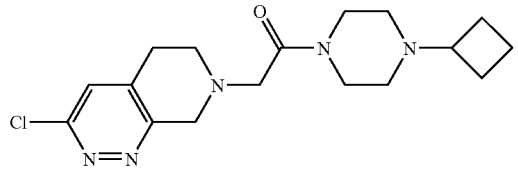

To a stirred solution of 3-chloro-5,6,7,8-tetrahydropyrido[3,4-c]pyridazine hydrogen chloride salt (0.9 g) in acetonitrile (10.0 ml) is added 2-chloro-(4-cyclobutyl-piperazine)-acetamide (1 g), $K_2CO_3$ (1.6 g), and NaI (50 mg). The resulting mixture is stirred at rt overnight. Water (20.0 ml) is added to quench the reaction, and then the acetonitrile is evaporated. The residue is extracted with DCM (20 ml×3). The combined organic phase is dried over sodium sulfate, and the solvent is removed under reduced pressure to give a residue which is purified by silica gel chromatography (EtOAc/4% TEA) to give the title compound.

Step 7. Preparation of 7-[2-(4-cyclobutylpiperazin-1-yl)-2-oxoethyl]-3-morpholin-4-yl-5,6,7,8-tetrahydropyrido[3,4-c]pyridazine

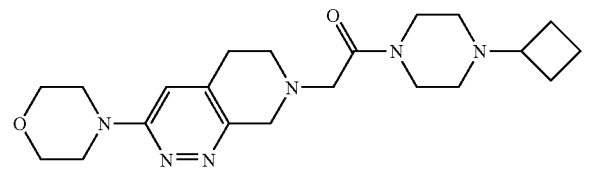

A solution of 7-[2-(4-cyclobutylpiperazin-1-yl)-2-oxoethyl]-3-chloro-5,6,7,8-tetrahydropyrido[3,4-c]pyridazine (0.2 g) in morpholine (5 ml) is heated at 200° C. in a microwave for 2 hr. The excess morpholine is removed in vacuo. The crude mixture is purified by PTLC (EtOAc/4% TEA) to give the title compound. $^1$H NMR (300 MHz, CDCl$_3$) δ 6.60 (1H, s), 3.86 (2H, s), 3.82 (4H, t), 3.50-3.70 (8H, m), 3.40 (2H, s), 2.62-2.84 (5H, m), 2.24-2.32 (4H, m), 1.60-2.06 (6H, m); MS (+VE) m/z 401.2 (M$^+$+1).

XXXIV. 7-[2-(4-Cyclobutylpiperazin-1-Yl)-2-Oxoethyl]-3-Pyrimidin-5-Yl-5,6,7,8-Tetrahydropyrido[3,4-c]pyridazine Compound 34

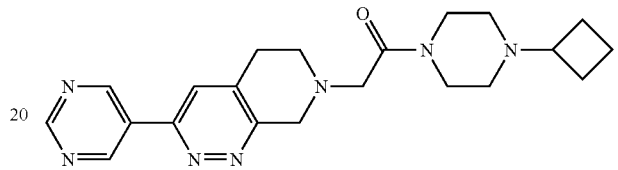

A mixture of 7-[2-(4-cyclobutylpiperazin-1-yl)-2-oxoethyl]-3-chloro-5,6,7,8-tetrahydropyrido-[3,4-c]pyridazine (22 mg, 0.06 mmol), 5-pyrimidineboronic acid (12 mg, 0.09 mmol), Pd(PPh$_3$)$_4$ (5.5 mg) and Na$_2$CO$_3$ (28 mg, 0.18 mmol) in DME (3 mL) and water (1 mL) is heated overnight at 80° C. Water is added and the mixture is extracted with DCM. The combined organic layers are dried (MgSO$_4$) and solvent is removed in vacuo to give the crude product, which is purified by PTLC (4% TEA in EA) to give the title compound. $^1$H NMR (300 MHz, CDCl$_3$) δ 9.40 (2H, s), 9.36 (1H, s), 7.64 (1H, s), 4.18 (2H, s), 3.84 (4H, m), 3.48 (2H, s), 3.84~3.16 (4H, m), 2.56-2.64 (1H, m), 2.04-2.20 (4H, m), 1.60-1.98 (6H, m); MS (+VE) m/z 394.2 (M$^+$+1).

XXXV. 2-Bromo-5-[2-(4-Cyclobutylpiperazin-1-Yl)-2-Oxoethyl]-4,5,6,7-Tetrahydro[1,3]Thiazolo[5,4-C]Pyridine (Scheme 19)

Compound 35

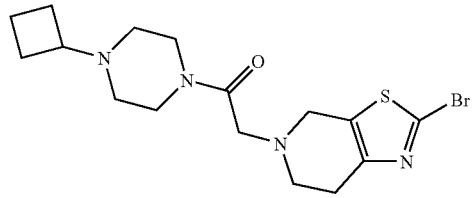

Step 1. Preparation of tert-butyl 4-pyrrolidin-1-yl-3,6-dihydropyridine-1(2H)-carboxylate

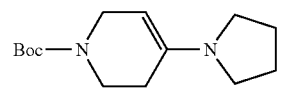

A mixture of Boc-4-piperidone (5.5 g, 27.6 mmol), pyrrolidine (2.42 ml, 29 mmol) and PTSA (30 mg) in cyclohexane (30 mL) is refluxed overnight with a Dean-Stark trap to remove water. The mixture is cooled to rt and the solvent is removed in vacuo and the thick oil obtained is used in the next step without further purification.

Step 2. Preparation of tert-butyl 2-amino-6,7-dihydro [1,3]thiazolo[5,4-c]pyridine-5(4H)-carboxylate

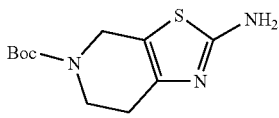

The oil from Step 1 is dissolved in anhydrous MeOH (7.5 mL) and a solution of cyanamide (1.16 g, 27.6 mmol) in MeOH (1 mL) is added, followed by addition of sulfur (885 mg, 27.6 mmol) in several small portions. The mixture is stirred at rt for 2 hr and filtered. The white solid is washed with cold MeOH (2 mL) and dried to give the title compound as a white solid. MS (M+1): 256.1.

Step 3. Preparation of tert-butyl 2-bromo-6,7-dihydro[1,3]thiazolo[5,4-c]pyridine-5(4H)-carboxylate

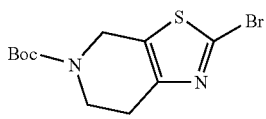

To a stirred suspension of $CuBr_2$ (4.6 g, 20.58 mmol) in DMF (12 mL) is added t-butyl nitrite (3.06 mL, 25.73 mmol). The mixture is gradually heated to 50° C., and then tert-butyl 2-amino-6,7-dihydro[1,3]thiazolo[5,4-c]pyridine-5(4H)-carboxylate (4.38 g, 17.15 mmol) is added carefully in several small portions while maintaining the internal temperature below 60° C. The mixture is then heated at 55° C. for 2 hr and cooled to rt. Water (100 ml) and EtOAc (100 mL) are added and the mixture is filtered. The layers are separated and the aqueous layer is extracted with EtOAc (100 mL). The combined extracts are washed with water (100 mL), dried and evaporated. The resulting oil is purified by flash column with hexane/EtOAc (5:1) to give the title compound as a yellow solid. MS (M+1): 319.0.

Step 4. Preparation of 2-bromo-4,5,6,7-tetrahydro[1,3]thiazolo[5,4-c]pyridine hydrochloride

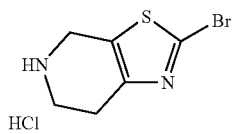

To a solution of tert-butyl 2-bromo-6,7-dihydro[1,3]thiazolo[5,4-c]pyridine-5(4H)-carboxylate (4.01 g, 12.56 mmol) in dioxane (20 ml) is added 4N HCl in dioxane (20 mL, 80 mmol), and the mixture is stirred at rt overnight. The solvent is removed and the residue is washed with ether to give a white solid. MS (M+1): 218.9.

Step 5. Preparation of 2-bromo-5-[2-(4-cyclobutylpiperazin-1-yl)-2-oxoethyl]-4,5,6,7-tetrahydro[1, 3]thiazolo[5,4-c]pyridine

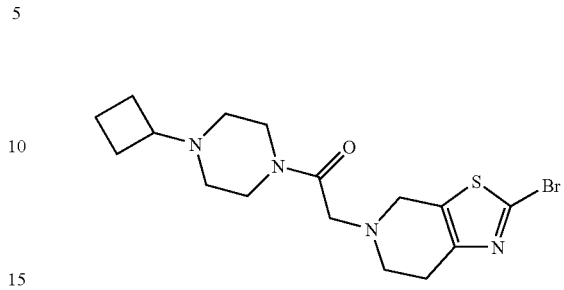

A mixture of 2-bromo-4,5,6,7-tetrahydro[1,3]thiazolo[5, 4-c]pyridine hydrochloride (3.03 g, 11.86 mmol), 1-(chloroacetyl)-4-cyclobutylpiperazine (2.57 g, 11.86 mmol), $K_2CO_3$ (4.91 g, 35.58 mmol) and KI (166 mg, 1 mmol) in $CH_3CN$ (20 ml) is stirred at rt overnight. The solvent is removed in vacuo and the residue is partitioned between water (20 mL) and EtOAc (20 mL). The layers are separated and the aqueous layer is extracted with EtOAc (3×30 mL). The combined extracts are washed with brine (50 μL), dried and evaporated. The resulting oil is purified by flash column with DCM/ MeOH/NH$_4$OH (100:5:0.5) to give the title compound as a light yellow solid. MS (M+1): 398.9; $^1$H NMR (δ, CDCl$_3$): 3.72 (s, 2H), 3.56-3.65 (m, 4H), 3.41 (s, 2H), 2.81-2.95 (m, 4H), 2.67-2.76 (m, 1H), 2.27-2.32 (m, 4H), 1.65-2.08 (m, 6H).

XXXVI. 5-[2-(4-Cyclobutylpiperazin-1-Yl)-2-Oxoethyl]-2-[3-(Methylsulfonyl)Phenyl]-4,5,6,7-Tetrahydro[1,3]Thiazolo[5,4-C]Pyridine (Scheme 19)

Compound 36

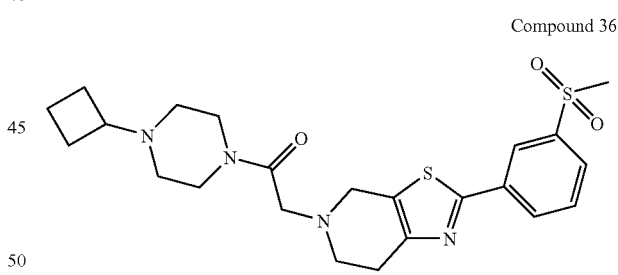

A mixture of 2-bromo-5-[2-(4-cyclobutylpiperazin-1-yl)-2-oxoethyl]-4,5,6,7-tetrahydro[1,3]thiazolo[5,4-c]pyridine (40 mg, 0.1 mmol), 3-methylsulfonyl-phenylboronic acid (40 mg, 0.2 mmol), $Na_2CO_3$ (42 mg, 0.4 mmol) and Pd(PPh$_3$)$_4$ (12 mg, 0.01 mmol) in DME (4 mL) and water (1 mL) is degassed with argon and heated at 110° C. in a sealed tube overnight. The mixture is cooled and the layers are separated. The aqueous layer is extracted with EtOAc (4 ml) and the combined extracts are dried and evaporated. The residue is purified by PTLC to give the title compound as a white solid. MS (M+1): 475.0; $^1$H NMR (δ, CDCl$_3$): 8.44 (t, 1H), 8.15 (td, 1H), 7.94 (td, 1H), 7.62 (t, 1H), 3.86 (s, 2H), 3.65 (q, 4H), 3.46 (d, 2H), 3.09 (s, 2H), 2.97 (s, 3H), 2.68-2.78 (m, 1H), 2.33 (q, 4H), 1.62-2.07 (m, 6H).

XXXVII. 2-Acetyl-5-[2-(4-Cyclobutylpiperazin-1-Yl)-2-Oxoethyl]-4,5,6,7-Tetrahydro[1,3]Thiazolo[5,4-C]Pyridine (Scheme 19)

Compound 37

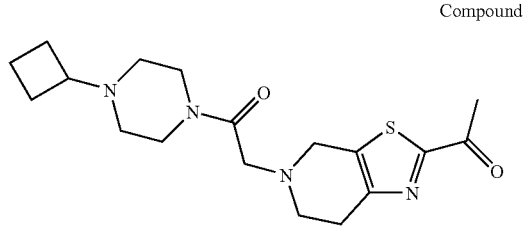

A mixture of 2-bromo-5-[2-(4-cyclobutylpiperazin-1-yl)-2-oxoethyl]-4,5,6,7-tetrahydro[1,3]thiazolo[5,4-c]pyridine (300 mg, 0.75 mmol), tributyl(1-ethoxy-vinyl)tin (361 mg, 1 mmol) and Pd(PPh$_3$)$_4$ (92 mg, 0.08 mmol) in toluene (15 mL) is degassed with argon and heated at 110° C. in a sealed tube overnight. The mixture is cooled and saturated KF solution (10 mL) is added. The mixture is stirred at rt for 30 min, and then the layers are separated. The aqueous layer is extracted with EtOAc (15 ml) and the combined extracts are dried and evaporated. The residue is dissolved in THF (10 mL), 2N HCl (10 mL) is added and the mixture is stirred at rt for 30 min. Solid Na$_2$CO$_3$ is added until pH>7 and the layers are separated. The aqueous layer is extracted with EtOAc (15 ml) and the combined extracts are dried and evaporated. The residue is purified by PTLC to give the title compound as a white solid. MS (M+1): 363.0; $^1$H NMR ($\delta$, CDCl$_3$): 3.88 (s, 2H), 3.52-3.62 (m, 4H), 3.41 (s, 2H), 2.99 (s, 4H), 2.62-2.77 (m, 4H), 2.29 (q, 4H), 1.66-2.08 (m, 6H).

XXXVIII. 2-Cyano-5-[2-(4-Cyclobutylpiperazin-1-Yl)-2-Oxoethyl]-4,5,6,7-Tetrahydro[1,3]Thiazolo[5,4-C]Pyridine (Scheme 19)

Compound 38

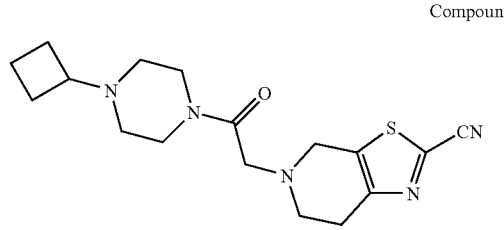

A mixture of 2-bromo-5-[2-(4-cyclobutylpiperazin-1-yl)-2-oxoethyl]-4,5,6,7-tetrahydro[1,3]thiazolo[5,4-c]pyridine (40 mg, 0.1 mmol), Zn(CN)$_2$ (15 mg, 0.2 mmol), Pd$_2$(dba)$_3$ (5 mg, 0.005 mmol) and dppf (6 mg, 0.01 mmol) in DMF (4 mL) is degassed with argon and heated at 110° C. in a sealed tube overnight. The mixture is cooled and solvent is removed in vacuo. The residue is partitioned between water (3 mL) and EtOAc (3 mL). The aqueous layer is extracted with EtOAc (4 ml) and the combined extracts are dried and evaporated. The residue is purified by PTLC to give the title compound as a light yellow solid. MS (M+1): 346.0; $^1$H NMR ($\delta$, CDCl$_3$): 3.92 (s, 2H), 3.55-3.67 (m, 4H), 3.45 (s, 2H), 3.00 (s, 4H), 2.66-2.77 (m, 1H), 2.31 (s, 4H), 1.63-2.08 (m, 6H).

XXXIX. 5-[2-(4-Cyclobutylpiperazin-1-Yl)-2-Oxoethyl]-2-Pyridazin-3-Yl-4,5,6,7-Tetrahydro[1,3]Thiazolo[5,4-C]Pyridine (Scheme 19)

Compound 39

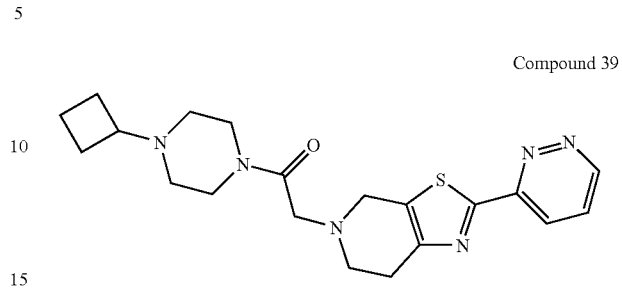

A mixture of 2-bromo-5-[2-(4-cyclobutylpiperazin-1-yl)-2-oxoethyl]-4,5,6,7-tetrahydro[1,3]thiazolo[5,4-c]pyridine (300 mg, 0.75 mmol), 3-(tributylstannyl)pyridazine (369 mg, 1 mmol) and Pd(PPh$_3$)$_4$ (92 mg, 0.08 mmol) in toluene (15 mL) is degassed by Ar and heated at 110° C. in a sealed tube overnight. The mixture is cooled and saturated KF solution (10 mL) is added. The mixture is stirred at rt for 30 min then the layers are separated. The aqueous layer is extracted with EtOAc (15 ml) and the combined extracts are dried and evaporated. The residue is purified by PTLC to give the title compound as white solid. MS (M+1): 399.2; $^1$H NMR ($\delta$, CDCl$_3$): 9.63-9.64 (m, 1H), 9.23 (dd, 1H), 7.84 (dd, 1H), 3.90 (s, 2H), 3.62 (td, 4H), 3.45 (s, 2H), 3.00 (s, 4H), 2.64-2.74 (m, 1H), 2.29 (t, 4H), 1.64-2.06 (m, 6H).

XL. 5-[2-(4-Cyclobutylpiperazin-1-Yl)-2-Oxoethyl]-2-Methylthio-4,5,6,7-Tetrahydro[1,3]Oxazolo[5,4-c]pyridine (Scheme 20)

Compound 40

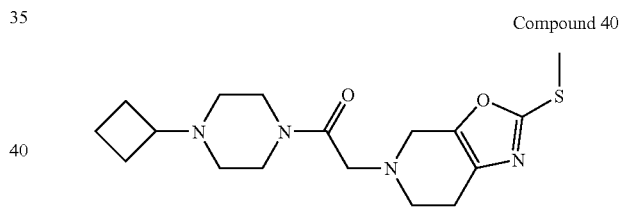

Step 1. Preparation of 5-[2-(4-cyclobutylpiperazin-1-yl)-2-oxoethyl]-2-methylthio-oxazolo[5,4-c]pyridine-5-ium iodide

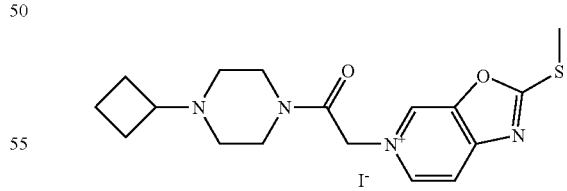

A mixture of 2-(methylthio)[1,3]oxazolo[5,4-c]pyridine (231 mg, 1.39 mmol), 1-(chloroacetyl)-4-cyclobutylpiperazine (301 mg, 1.39 mmol) and KI (230 mg, 1.39 mmol) in CH$_3$CN (15 mL) is heated at reflux overnight. The solvent is removed and the resulting orange solid is stirred with EtOAc (20 mL) for 30 min. The mixture is filtered and the solid is washed with EtOAc (10 mL) then dried. The orange solid obtained is used in the next step without further purification. MS (M+): 347.2

Step 2. Preparation of 5-[2-(4-cyclobutylpiperazin-1-yl)-2-oxoethyl]-2-methylthio-4,5,6,7-tetrahydro[1,3]oxazolo[5,4-c]pyridine

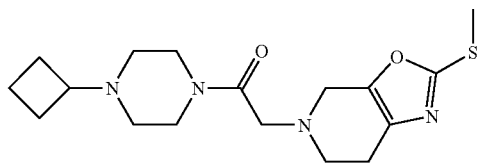

The solid from Step 1 is dissolved in MeOH and NaBH$_4$ (210 mg, 5.56 mmol) is added to the solution. The solution is heated at reflux for 4 hr, and then cooled to rt. The solvent is removed in vacuo and the residue is partitioned between water (6 mL) and EtOAc (6 mL). The layers are separated and aqueous layer is extracted with EtOAc (6 ml). The combined extracts are washed with brine (5 ml), dried and evaporated. The residue is purified by PTLC to give the title compound as a light yellow oil. MS (M+1): 351.0; $^1$H NMR (δ, CDCl$_3$): 3.55-3.65 (m, 6H), 3.40 (s, 2H), 2.87 (t, 2H), 2.65-2.76 (m, 1H), 2.54-2.62 (m, 5H), 2.28 (t, 4H), 1.64-2.06 (m, 6H)

XLI. 1-(6-Chloropyridazin-3-Yl)-5-[2-(4-Cyclobutylpiperazin-1-Yl)-2-Oxoethyl]-4,5,6,7-Tetrahydro-1H-Pyrazolo[4,3-C]Pyridine (Scheme 21)

Compound 41

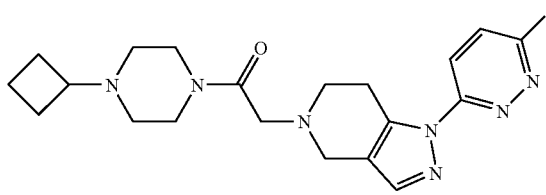

Step 1. Preparation of tert-butyl 1-(6-chloropyridazin-3-yl)-1,4,6,7-tetrahydro-5H-pyrazolo[4,3-c]pyridine-5-carboxylate

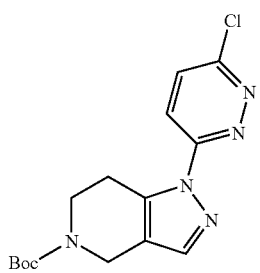

To a solution of tert-butyl-3-[(dimethylamino)methylene]-4-oxopiperidine-1-carboxylate (2.02 g, 7.94 mmol) in EtOH (20 mL) is added 3-hyrazino-6-chloropyridazine (1.15 g, 7.96 mmol), and the mixture is stirred at rt overnight. Solvent is evaporated in vacuo and residue is partitioned between EtOAc (60 mL) and water (40 mL). The layers are separated and the organic layer is washed with brine (20 mL), dried and evaporated. The residue is purified by flash column with hexane/EtOAc (3:1) to give the title compound as a white solid. MS (M+1): 336.1.

Step 2. Preparation of 1-(6-chloropyridazin-3-yl)-4,5,6,7-tetrahydro-1H-pyrazolo[4,3-c]pyridine hydrochloride

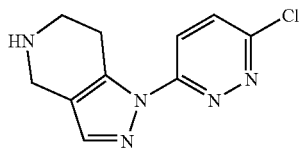

To a solution of tert-butyl 1-(6-chloropyridazin-3-yl)-1,4,6,7-tetrahydro-5H-pyrazolo[4,3-c]pyridine-5-carboxylate (2.14 g, 6.4 mmol) in dioxane (20 ml) is added 4N HCl in dioxane (20 mL, 80 mmol), and the mixture is stirred at rt overnight. The solvent is removed and the residue is washed with ether to give the title compound as a white solid. MS (M+1): 236.1.

Step 3. Preparation of 1-(6-chloropyridazin-3-yl)-5-[2-(4-cyclobutylpiperazin-1-yl)-2-oxoethyl]-4,5,6,7-tetrahydro-1H-pyrazolo[4,3-c]pyridine

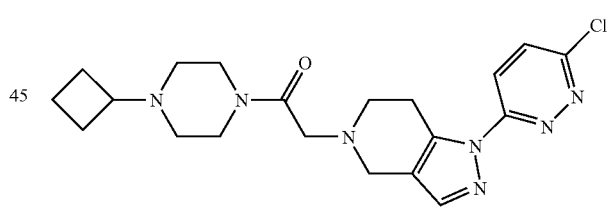

A mixture of 1-(6-chloropyridazin-3-yl)-4,5,6,7-tetrahydro-1H-pyrazolo[4,3-c]pyridine hydrochloride (1.05 g, 3.86 mmol), 1-(chloroacetyl)-4-cyclobutylpiperazine (840 mg, 3.86 mmol), K$_2$CO$_3$ (2.11 g, 15.4 mmol) and KI (66 mg, 0.4 mmol) in CH$_3$CN (20 mL) is stirred at rt overnight. The solvent is removed in vacuo and the residue is partitioned between water (20 mL) and EtOAc (20 mL). The layers are separated and the aqueous layer is extracted with EtOAc (3×20 mL). The combined extracts are washed with brine (30 μL), dried and evaporated. The resultant oil is purified by flash column with DCM/MeOH/NH$_4$OH (100:5:0.5) to give the title compound as a light yellow solid. $^1$H NMR (δ, CDCl$_3$): 8.16 (d, 1H), 7.57 (d, 1H), 7.51 (s, 1H), 3.58-3.62 (m, 6H), 3.40 (s, 2H), 3.35 (t, 2H), 2.86 (t, 2H), 2.62-2.72 (m, 1H), 2.27 (q, 4H), 1.62-2.02 (m, 6H). MS (M+1): 416.2.

XLII. 5-[(4-Cyclobutylpiperazin-1-Yl)-2-Oxoethyl]-2-(6-Methylpyridazin-3-Yl)-4,5,6,7Tetrahydro-2H-Pyrazolo[4,3-C]Pyridine (Scheme 21)

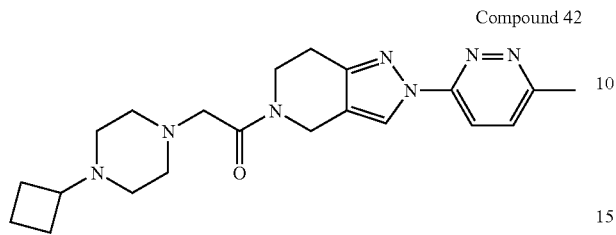

Compound 42

Step 1. Preparation of tert-butyl 1,4,6,7-tetrahydro-5H-pyrazolo[4,3-c]pyridine-5-carboxylate

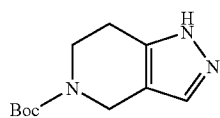

To a solution of tert-butyl-3-[(dimethylamino)methylene]-4-oxopiperidine-1-carboxylate (63.6 g, 250 mmol) in EtOH (200 mL) is added hydrazine (9.6 mL, 305 mmol) and the mixture is heated at reflux for 2 hr. Solvent is evaporated in vacuo and residue is purified by flash column with 5% MeOH in DCM to give the title compound as a white solid. MS (M+1): 224.1.

Step 2. Preparation of tert-butyl 2-(6-methylpyridazin-3-yl)-2,4,6,7-tetrahydro-5H-pyrazolo[4,3-c]pyridine-5-carboxylate

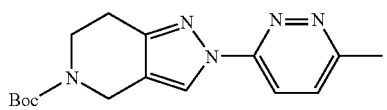

A mixture of tert-butyl 1,4,6,7-tetrahydro-5H-pyrazolo[4,3-c]pyridine-5-carboxylate (3.72 g, 16.67 mmol), 3-chloro-6-methylpyridazine (3.2 g, 24.92 mmol), Pd$_2$(dba)$_3$ (760 mg, 0.83 mmol), tBuXPhos (705 mg, 1.66 mmol) and tBuONa (1.99 g, 20.77 mmol) in toluene (90 mL) is degassed by argon and heated at 120° C. in a sealed tube overnight. EtOAc (200 mL) and water (250 mL) are added and the layers are separated. The organic layer is washed with water (200 mL) and then brine (200 mL), dried and evaporated. Purification of the residue by flash column with hexane/EtOAc (2:1) gives a white solid that is a mixture of two regioisomers. Recrystallization of the solid from hexane/EtOAc (1:1) gives the title compound as white needles. MS (M+1): 316.2.

Step 3. Preparation of 2-(6-methylpyridazin-3-yl)-2,4,6,7-tetrahydro-5H-pyrazolo[4,3-c]pyridine hydrochloride

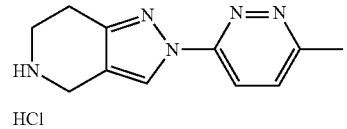

To a solution of tert-butyl 2-(6-methylpyridazin-3-yl)-2,4,6,7-tetrahydro-5H-pyrazolo[4,3-c]pyridine-5-carboxylate (2.38 g, 7.55 mmol) in dioxane (20 ml) is added 4N HCl in dioxane (20 mL, 80 mmol) and the mixture is stirred at rt overnight. The solvent is removed and the residue is washed with ether to give the title compound as a white solid. MS (M+1): 216.2.

Step 4. Preparation of 5-[(4-cyclobutylpiperazin-1-yl)-2-oxoethyl]-2-(6-methylpyridazin-3-yl)-4,5,6,7-tetrahydro-2H-pyrazolo[4,3-c]pyridine

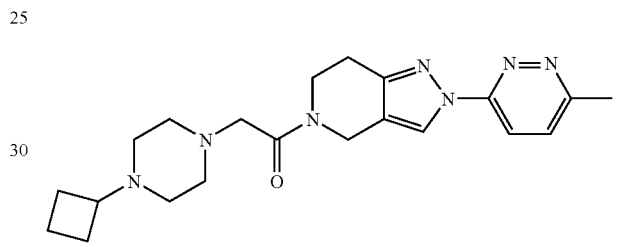

A mixture of 2-(6-methylpyridazin-3-yl)-2,4,6,7-tetrahydro-5H-pyrazolo[4,3-c]pyridine hydrochloride (920 mg, 3.65 mmol), 1-(chloroacetyl)-4-cyclobutylpiperazine (791 mg, 3.65 mmol), K$_2$CO$_3$ (2.52 g, 18.3 mmol) and KI (66 mg, 0.4 mmol) in CH$_3$CN (20 ml) is stirred at rt overnight. The solvent is removed in vacuo and the residue is partitioned between water (20 mL) and EtOAc (20 mL). The layers are separated and the aqueous layer is extracted with EtOAc (3×20 mL). The combined extracts are washed with brine (30 mL), dried and evaporated. The resulting oil is purified by flash column with DCM/MeOH/NH$_4$OH (100:5:0.5) to give the title compound as a light yellow solid. $^1$H NMR (δ, CDCl$_3$): 8.43 (s, 1H), 8.01 (d, 1H), 7.41 (d. 1H), 3.64-3.67 (m, 6H), 3.40 (s, 2H), 2.88 (s, 4H), 2.66-2.72 (m, 4H), 2.29 (q, 4H), 1.59-2.05 (m, 6H). MS (M+1): 396.2.

XLIII. 5-[(4-Cyclobutylpiperazin-1-Yl)-2-Oxoethyl]-2-Cyclopentyl-4,5,6,7-Tetrahydro-2H-Pyrazolo[4,3-C]Pyridine (Scheme 21)

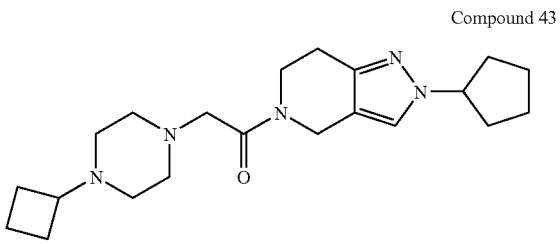

Compound 43

Step 1. Preparation of tert-butyl 2-cyclopentylidenehyrazinecarboxylate

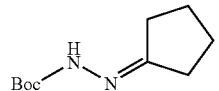

A mixture of cyclopentanone (4.0 g, 47.5 mmol) and tert-butyl hydrazinecarboxylate (6.28 g, 47.5 mmol) in MeOH (100 mL) is stirred at rt for 2 hr. The solvent is removed in vacuo to yield the title compound as a white solid, which is used in the next step without further purification. MS (M+1): 199.1.

Step 2. Preparation of tert-butyl 2-cyclopentylhyrazinecarboxylate

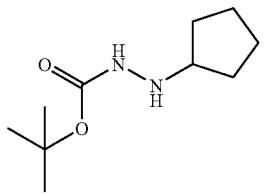

The white solid from Step 1 (4.74 g, 23.9 mmol) is dissolved in water (30 mL) and HOAc (30 mL), and NaCNBH$_3$ (1.5 g, 23.9 mmol) is added in several small portions over 30 min. The mixture is stirred at rt for 2 hr. 5 N NaOH is added until pH ~8. DCM (100 mL) is added, the layers are separated and the aqueous layer is extracted with DCM (100 mL). The combined extracts are washed with brine (80 mL), dried and evaporated to yield the title compound as white solid, which is used in the next step without further purification. MS (M+1): 201.1.

Step 3. Preparation of cyclopentylhydrazine hydrochloride

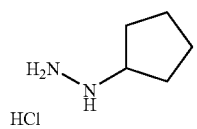

To a solution of tert-butyl 2-cyclopentylhyrazinecarboxylate (2.01 g, 10 mmol) in dioxane (20 mL) is added 4 N HCl in dioxane (20 mL) and the mixture is stirred at rt overnight. The solvent is removed in vacuo and the residue is washed with ether (40 mL) to give the title compound as a white solid, which is used in the next step without further purification. MS (M+1): 101.1

Step 4. Preparation of tert-butyl 4-(cyclopentylhydrazono)piperidine-1-carboxylate

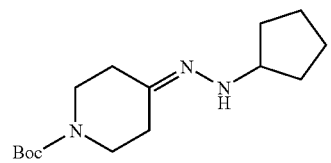

A mixture of cyclopentylhydrazine hydrochloride (1.07 g, 7.83 mmol), Boc-4-piperidone (1.57 g, 7.86 mmol) and K$_2$CO$_3$ (2.2 g, 16 mmol) in EtOH (20 mL) is heated at reflux for 3 hr. The mixture is filtered and the filtrated is concentrated to give the title compound as an oil that is used in the next step without further purification. MS (M+1): 282.2.

Step 5. Preparation of tert-butyl 2-cyclopentyl-2,4,6,7-tetrahydro-5H-pyrazolo[4,3-c]pyridine-5-carboxylate

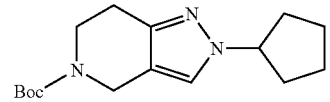

The oil from step 3 is dissolved in Bredereck's reagent (8 ml) and the mixture is heated at 120° C. overnight. The excess solvent is removed under high vacuum and the oil is partitioned between EtOAc (30 mL) and water (25 mL). The layers are separated and the aqueous layer is extracted with EtOAc (20 mL). The combined extracts are washed with brine (20 mL), dried and evaporated. Purification of the residue by flash column with hexane/EtOAc (2:1) gives title compound as a white solid. MS (M+1): 292.2

Step 6. Preparation of 2-cyclopentyl-2,4,6,7-tetrahydro-5H-pyrazolo[4,3-c]pyridine hydrochloride

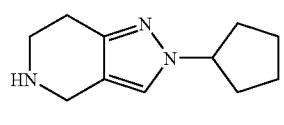

To a solution of tert-butyl 2-cyclopentyl-2,4,6,7-tetrahydro-5H-pyrazolo[4,3-c]pyridine-5-carboxylate (720 g, 2.47 mmol) in dioxane (5 mL) is added 4N HCl in dioxane

Step 3. Preparation of cyclopentylhydrazine hydrochloride

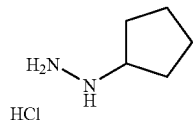

To a solution of tert-butyl 2-cyclopentylhyrazinecarboxylate (2.01 g, 10 mmol) in dioxane (20 mL) is added 4 N HCl in dioxane (20 mL) and the mixture is stirred at rt overnight. The solvent is removed in vacuo and the residue is washed with ether (40 mL) to give the title compound as a white solid, which is used in the next step without further purification. MS (M+1): 101.1

Step 4. Preparation of tert-butyl 4-(cyclopentylhydrazono)piperidine-1-carboxylate

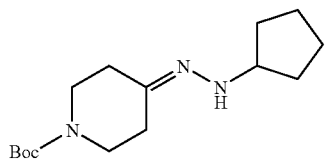

A mixture of cyclopentylhydrazine hydrochloride (1.07 g, 7.83 mmol), Boc-4-piperidone (1.57 g, 7.86 mmol) and K$_2$CO$_3$ (2.2 g, 16 mmol) in EtOH (20 mL) is heated at reflux for 3 hr. The mixture is filtered and the filtrated is concentrated to give the title compound as an oil that is used in the next step without further purification. MS (M+1): 282.2.

Step 5. Preparation of tert-butyl 2-cyclopentyl-2,4,6,7-tetrahydro-5H-pyrazolo[4,3-c]pyridine-5-carboxylate

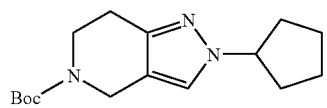

The oil from step 4 is dissolved in Bredereck's reagent (8 ml) and the mixture is heated at 120° C. overnight. The excess solvent is removed under high vacuum and the oil is partitioned between EtOAc (30 mL) and water (25 mL). The layers are separated and the aqueous layer is extracted with EtOAc (20 mL). The combined extracts are washed with brine (20 mL), dried and evaporated. Purification of the residue by flash column with hexane/EtOAc (2:1) gives title compound as a white solid. MS (M+1): 292.2

Step 6. Preparation of 2-cyclopentyl-2,4,6,7-tetrahydro-5H-pyrazolo[4,3-c]pyridine hydrochloride

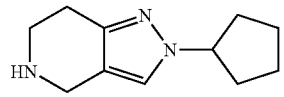

HCl

To a solution of tert-butyl 2-cyclopentyl-2,4,6,7-tetrahydro-5H-pyrazolo[4,3-c]pyridine-5-carboxylate (720 g, 2.47 mmol) in dioxane (5 mL) is added 4N HCl in dioxane (5 mL, 20 mmol) and the mixture is stirred at rt overnight. The solvent is removed and the residue is washed with ether to give the title compound as a white solid. MS (M+1): 192.1

Step 7. Preparation of 5-[(4-cyclobutylpiperazin-1-yl)-2-oxoethyl]-2-cyclopentyl-4,5,6,7-tetrahydro-2H-pyrazolo[4,3-c]pyridine

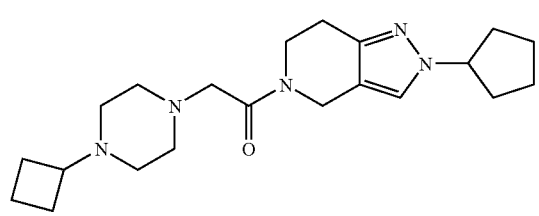

A mixture of 2-cyclopentyl-2,4,6,7-tetrahydro-5H-pyrazolo[4,3-c]pyridine hydrochloride (143 mg, 0.63 mmol), 1-(chloroacetyl)-4-cyclobutylpiperazine (136 mg, 0.63 mmol), K$_2$CO$_3$ (348 mg, 2.52 mmol) and KI (10 mg, 0.06 mmol) in CH$_3$CN (10 ml) is stirred at rt overnight. The solvent is removed in vacuo and the residue is partitioned between water (10 mL) and EtOAc (10 mL). The layers are separated and the aqueous layer is extracted with EtOAc (3×10 mL) and the combined extracts are washed with brine (20 mL), dried and evaporated. The resulting oil is purified by flash column with DCM/MeOH/NH$_4$OH (100:5:0.5) to give the title compound as a light yellow solid. MS (M+1): 372.3; $^1$H NMR (δ, CDCl$_3$): 7.10 (s, 1H), 4.51-4.60 (m, 1H), 3.64 (q, 4H), 3.54 (s, 2H), 3.36 (s, 2H), 2.77-2.83 (m, 4H), 2.64-2.74 (m, 1H), 2.25-2.32 (m, 4H), 1.62-2.62 (m, 14H).

XLIV. 1-(4-{7-[2-(4-Cyclobutylpiperazin-1-Yl)-2-Oxoethyl]-5,6,7,8-Tetrahydroimidazo[1,2-a]Pyrazin-3-Yl}Phenyl)Ethanone (Scheme 24)

Compound 44

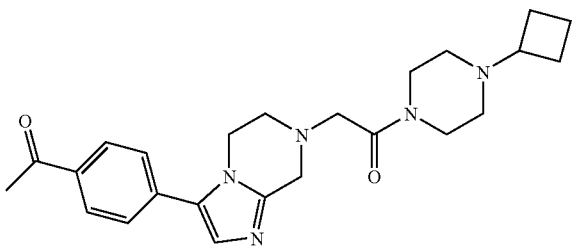

Step 1. Preparation of 5,6,7,8-tetrahydroimidazo[1,2-a]pyrazine

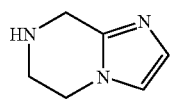

This compound is synthesized essentially as described in PCT International Application Publication Number WO 03/004498.

Step 2. Preparation of tert-butyl 5,6-dihydroimidazo[1,2-a]pyrazine-7(8H)-carboxylate

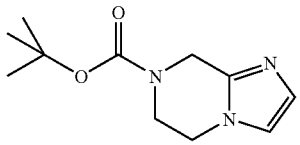

5,6,7,8-Tetrahydroimidazo[1,2-a]pyrazine (1 g, 6.2 mmol) is dissolved in DCM (10 mL). To this solution is added TEA (0.75 g, 7.42 mmol) and di-tert-butyl dicarbonate (1.63 g, 7.4 mmol). The reaction mixture is stirred overnight at rt The solvent is evaporated and the residue is purified by column with 5% MeOH in DCM to give the title compound. $^1$H NMR (CDCl$_3$) δ 7.01 (d, 1H), 6.83 (d, 1H), 4.67 (s, 2H), 3.97 (t, 2H), 3.82 (t, 2H), 1.45 (s, 9H).

Step 3. Preparation of tert-butyl 3-bromo-5,6-dihydroimidazo[1,2-a]pyrazine-7(8H)-carboxylate

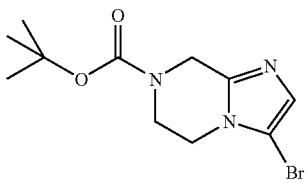

A mixture of tert-butyl 5,6-dihydroimidazo[1,2-a]pyrazine-7(8H)-carboxylate (2.23 g, 10 mmol) and NBS (1.78 g, 10 mmol) in benzene (10 mL) is heated at reflux for one hr. The solvent is evaporated and the residue is purified by column with 5% MeOH in DCM to give the title compound. $^1$H NMR (CDCl$_3$) δ 6.98 (s, 1H), 4.65 (s, 2H), 3.86 (s, 4H), 1.47 (s, 9H).

Step 4. Preparation of 3-bromo-5,6,7,8-dihydroimidazo[1,2-a]pyrazine

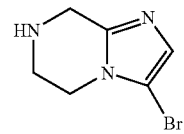

tert-Butyl 3-bromo-5,6-dihydroimidazo[1,2-a]pyrazine-7(8H)-carboxylate (2.1 g, 7 mmol) is dissolved in 4 N HCl in dioxane (10 mL). The mixture is stirred at 50° C. for 3 hr. The solvent is removed to give the title compound as dihydrochloride salt.

Step 5. Preparation of 3-bromo-7-[2-(4-cyclobutylpiperazin-1-yl)-2-oxoethyl]-5,6,7,8-dihydroimidazo[1,2-a]pyrazine

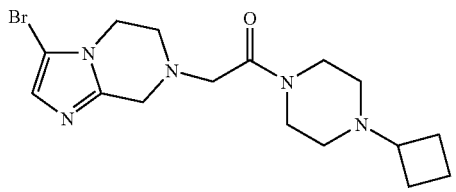

A mixture of 3-bromo-5,6,7,8-dihydroimidazo[1,2-a]pyrazine dihydrochloride (0.83 g, 3.0 mmol), 2-chloro-1-(4-cyclobutyl-piperazin-1-yl)-ethanone (0.65 g, 3.0 mmol), K$_2$CO$_3$ (1.46 g, 11 mmol), and NaI (0.45 g, 3.0 mmol) in acetonitrile is stirred overnight at rt. The solvent is evaporated and water is added. The mixture is extracted with DCM. The combined organic layers are dried (MgSO$_4$) and solvent removed in vacuo to give the crude product, which is purified by PTLC (5% MeOH in DCM) to give the title compound. $^1$H NMR (CDCl$_3$) δ 6.94 (s, 1H), 3.87-3.57 (m, 6H), 3.41 (s, 2H), 2.99 (m, 4H), 2.72 (m, 1H), 2.30 (m, 4H), 2.04 (m, 2H), 1.88 (m, 2H), 1.68 (m, 2H).

Step 6. Preparation of 1-(4-{7-[2-(4-cyclobutylpiperazin-1-yl)-2-oxoethyl]-5,6,7,8-tetrahydroimidazo[1,2-a]pyrazin-3-yl}phenyl)ethanone

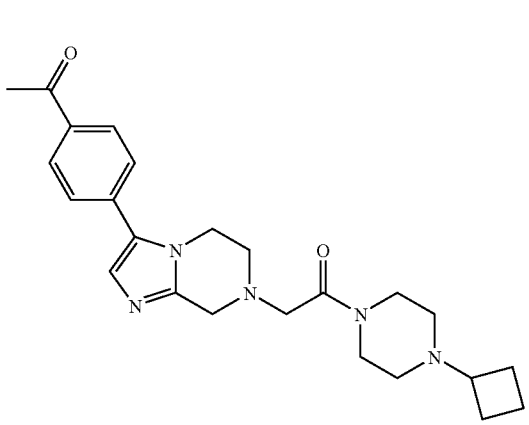

A mixture of 3-bromo-7-[2-(4-cyclobutylpiperazin-1-yl)-2-oxoethyl]-5,6,7,8-dihydroimidazo[1,2-a]pyrazine (37 mg, 0.1 mmol), acetylphenylboronic acid (24 mg, 0.15 mmol), Pd(PPh)₄ (5.5 mg) and Na₂CO₃ in DME (3 mL) and water (1 mL) is heated overnight at 80° C. The water is added and the mixture is extracted with DCM. The combined organic layers are dried (MgSO₄) and solvent removed in vacuo to give the crude product, which is purified by PTLC (5% MeOH in DCM) to give the title compound. ¹H NMR (CDCl₃) δ 7.99 (d, 2H), 7.48 (d, 2H), 7.19 (s, 1H), 3.91 (s, 2H), 3.65-3.54 (m, 4H), 3.45 (s, 2H), 2.99 (m, 4H), 2.72 (m, 1H), 2.61 (s, 3H), 2.30 (m, 4H), 2.04 (m, 2H), 1.88 (m, 2H), 1.68 (m, 2H).

XLV. 1-(4-Cyclobutyl-Piperazin-1-Yl)-2-(2-Pyrimidin-5-Yl-6,7-Dihydro-4H-Thieno[3,2-C]Pyridin-5-Yl)-Ethanone (Scheme 25)

Compound 45

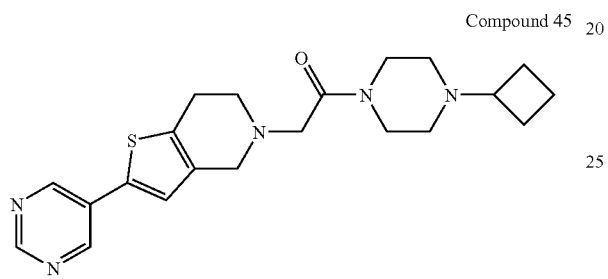

Step 1. Preparation of 6,7-dihydro-4H-thieno[3,2-c]pyridine-5-carboxylic acid tert-butyl ester

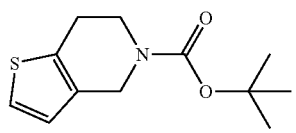

To a solution of 4,5,6,7-tetrahydro-thieno[3,2-c]pyridine hydrochloride (879 mg, 5 mmol) in DCM (20 ml) at 0° C. is added aqueous potassium solution (1.0N, 6 ml, 1.2 eq.), followed by the addition of di-t-butyl dicarbonate (1.35 g, 6.0 mmol, 1.2 eq.). The mixture is stirred at rt overnight. The organic phase is collected, washed with water (10 ml) and brine (10 ml), dried over sodium sulfate, and concentrated. The residue is purified by silica gel chromatography (hexane/EtOAc 10:1) to give the title compound. MS (+VE) m/z 240.10 (M⁺+1).

Step 2. Preparation of 2-bromo-6,7-dihydro-4H-thieno[3,2-c]pyridine-5-carboxylic acid tert-butyl ester

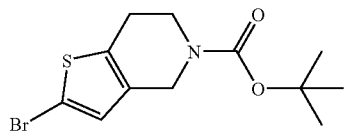

To a solution of 6,7-dihydro-4H-thieno[3,2-c]pyridine-5-carboxylic acid tert-butyl ester (240 mg, 1.0 mmol) in acetonitrile (5 ml) cooled to 0° C. is added NBS (183 mg, 1.03 mmol, 1.03 eq.). The mixture is stirred at rt overnight. The organic phase is collected, washed with water (10 ml) and brine (10 ml), dried over sodium sulfate, and concentrated. The residue is purified by silica gel chromatography (hexane/EtOAc 10:1) to give the title compound. MS (+VE) m/z 318.1 (M⁺+1).

Step 3. Preparation of 2-pyrimidin-5-yl-6,7-dihydro-4H-thieno[3,2-c]pyridine-5-carboxylic acid tert-butyl ester

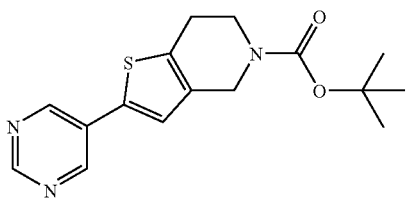

To a solution of 2-bromo-6,7-dihydro-4H-thieno[3,2-c]pyridine-5-carboxylic acid tert-butyl ester (235 mg, 0.74 mmol), 4-pyrimidinyllboronic acid (118 mg, 0.96 mmol, 1.3 eq.) and Pd(PPh₃)₄ (8.4 mg, 0.001 mmol, 0.013 eq.) under nitrogen are added dioxane (10.0 ml) and sodium carbonate aqueous solution (2.0N, 1.5 ml). The resulting mixture is stirred at 100° C. for 16 hr. The reaction mixture is diluted with EtOAc (30 ml), washed with water and brine, dried over sodium sulfate, and concentrated. The crude product is purified through silica gel flash chromatography (hexane/EtOAc 5:1) to give the title compound. MS (+VE) m/z 318.2 (M⁺+1).

Step 4. Preparation of 1-(4-cyclobutyl-piperazin-1-yl)-2-(2-pyrimidin-5-yl-6,7-dihydro-4H-thieno[3,2-c]pyridin-5-yl)-ethanone

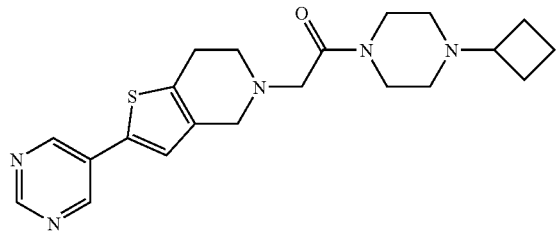

To a stirred solution of 2-pyrimidin-5-yl-6,7-dihydro-4H-thieno[3,2-c]pyridine-5-carboxylic acid tert-butyl ester (108 mg, 0.34 mmol) in EtOAc (5.0 ml) is added HCl-dioxane solution (4.0N, 2.0 ml). The resulting mixture is stirred at 50° C. overnight, and then organic solvents are evaporated. To the residue are added acetonitrile (5.0 ml), 2-chloro-(4-cyclobutyl-piperazine)-acetamide (74 mg, 0.34 mmol, 1.0 eq.), K₂CO₃ (94 mg, 0.68 mmol, 2.0 eq.), and NaI (30 mg). The resulting mixture is stirred at 40° C. overnight. Water (10.0 ml) is added to quench the reaction, and the acetonitrile is evaporated. The residue is extracted with DCM (10 ml×3), and the combined organic phase is dried over sodium sulfate and concentrated. The residue is purified by preparative silica gel flash chromatography (EtOAc/4% TEA) to give the title compound. $^1$H NMR (300 MHz, CDCl$_3$) δ 9.08 (1H, s), 8.87 (2H, s), 7.04 (1H, s), 3.60~3.65 (6H, m), 3.41 (2H, s), 3.09 (2H, t), 2.91 (4H, m), 2.70 (1H, m), 2.30 (4H, m), 1.66~2.08 (6H); MS (+VE) m/z 398.2 (M$^+$+1).

Example 2

Preparation of Additional Representative Compounds

Using routine modifications, the starting materials may be varied and additional steps employed to produce other compounds provided herein. Compounds listed in Tables I and II are prepared using such methods. A "*" in the column headed "K$_i$" in Table I and Table II indicates that the compound has a K$_i$ in an assay of Example 7 that is less than 1 micromolar. A "†" in the column headed "K$_i$" in Table II indicates that the percent inhibition of the signal obtained with 1 μM histamine using 4 μM of the compound, determined as described in Example 8, is at least 90%. The molecular weight (presented as M+1) obtained using one of the methods described above is shown in the column headed "MS." The retention time is provided in the column headed (RT) and is given in minutes, along with a number indicating the mass spectroscopy method used.

TABLE I

| Compound | Name | RT | MS | K$_i$ |
|---|---|---|---|---|
| 46 | 2-[2-(4-cyclopentylpiperazin-1-yl)-2-oxoethyl]-1,2,3,4-tetrahydroisoquinoline | 1.16 (1) | 328.19 | * |
| 47 | 2-[2-(4-cyclopentylpiperazin-1-yl)-2-oxoethyl]-6,7-dimethoxy-1,2,3,4-tetrahydroisoquinoline | 1.1 (1) | 388.17 | * |
| 48 | 2-[2-(4-cyclobutylpiperazin-1-yl)-2-oxoethyl]-6,7-dimethoxy-1,2,3,4-tetrahydroisoquinoline | 1.08 (1) | 374.15 | * |
| 49 | 2-[2-(4-isopropylpiperazin-1-yl)-2-oxoethyl]-6,7-dimethoxy-1,2,3,4-tetrahydroisoquinoline | 1.32 (1) | 362.26 | * |
| 50 | 2-[2-(4-cyclohexylpiperazin-1-yl)-2-oxoethyl]-6,7-dimethoxy-1,2,3,4-tetrahydroisoquinoline | 1.41 (1) | 402.29 | * |

TABLE I-continued

| Compound | | Name | RT | MS | $K_i$ |
|---|---|---|---|---|---|
| 51 | | 2-[2-(4-isopropylpiperazin-1-yl)-2-oxoethyl]-1-propyl-1,2,3,4-tetrahydroisoquinoline | 0.99 (3) | 344.37 | |
| 52 | | 2-[2-(4-isopropylpiperazin-1-yl)-2-oxoethyl]-1-phenyl-1,2,3,4-tetrahydroisoquinoline | 1.02 (3) | 378.36 | * |
| 53 | | 1-cyclohexyl-2-[2-(4-isopropylpiperazin-1-yl)-2-oxoethyl]-1,2,3,4-tetrahydroisoquinoline | 1.09 (3) | 384.42 | |
| 54 | | 1-(cyclopentylmethyl)-2-[2-(4-isopropylpiperazin-1-yl)-2-oxoethyl]-1,2,3,4-tetrahydroisoquinoline | 1.09 (3) | 384.41 | * |

TABLE I-continued

| Compound | | Name | RT | MS | $K_i$ |
|---|---|---|---|---|---|
| 55 | | 1-benzyl-2-[2-(4-isopropylpiperazin-1-yl)-2-oxoethyl]-1,2,3,4-tetrahydroisoquinoline | 1.07 (3) | 392.38 | * |
| 56 | | 1-ethyl-2-[2-(4-isopropylpiperazin-1-yl)-2-oxoethyl]-1,2,3,4-tetrahydroisoquinoline | | | * |
| 57 | | 1-isobutyl-2-[2-(4-isopropylpiperazin-1-yl)-2-oxoethyl]-1,2,3,4-tetrahydroisoquinoline | 1.06 (3) | 358.38 | * |
| 58 | | 1-(2-fluorophenyl)-2-[2-(4-isopropylpiperazin-1-yl)-2-oxoethyl]-1,2,3,4-tetrahydroisoquinoline | 1.04 (3) | 396.34 | * |

TABLE I-continued

| Compound | | Name | RT | MS | K$_i$ |
|---|---|---|---|---|---|
| 59 | | 1-(2-chlorophenyl)-2-[2-(4-isopropylpiperazin-1-yl)-2-oxoethyl]-1,2,3,4-tetrahydroisoquinoline | 1.09 (3) | 412.32 | * |
| 60 | | 2-[2-(4-cyclobutylpiperazin-1-yl)-2-oxoethyl]-6-methoxy-1,2,3,4-tetrahydroisoquinoline | 1.13 (1) | 344.19 | * |
| 61 | | 1-{2-[2-(4-cyclobutylpiperazin-1-yl)-2-oxoethyl]-1,2,3,4-tetrahydroisoquinolin-6-yl}ethanone | 1.08 (1) | 356.11 | * |
| 62 | | 1-(2-chlorophenyl)-2-[2-(4-cyclobutylpiperazin-1-yl)-2-oxoethyl]-6-methoxy-1,2,3,4-tetrahydroisoquinoline | 1.14 (3) | 454.00 | * |
| 63 | | 6-bromo-1-(2-chlorophenyl)-2-[2-(4-cyclobutylpiperazin-1-yl)-2-oxoethyl]-1,2,3,4-tetrahydroisoquinoline | 1.26 (3) | 503.87 | * |

TABLE I-continued

| Compound | | Name | RT | MS | $K_i$ |
|---|---|---|---|---|---|
| 64 | | 1-{1-(2-chlorophenyl)-2-[2-(4-cyclobutylpiperazin-1-yl)-2-oxoethyl]-1,2,3,4-tetrahydroisoquinolin-6-yl}ethanone | 1.14 (3) | 466.00 | * |
| 65 | | 6-{2-(4-cyclobutylpiperazin-1-yl)-2-oxoethyl]-5,6,7,8-tetrahydro-1,6-naphthyridine | 1.02 (1) | 315.15 | * |
| 66 | | 2-[2-(4-cyclobutylpiperazin-1-yl)-2-oxoethyl]-N-methyl-1,2,3,4-tetrahydroisoquinoline 7-carboxamide | 1.03 (1) | 371.12 | * |
| 67 | | 1-(4-{2-[2-(4-cyclobutylpiperazin-1-yl)-2-oxoethyl]-1,2,3,4-tetrahydroisoquinolin-6-yl}phenyl)ethanone | 0.97 (3) | 432.16 | * |
| 68 | | 2-[2-(4-cyclobutylpiperazin-1-yl)-2-oxoethyl]-6-(3,5-dimethylisoxazol-4-yl)-1,2,3,4-tetrahydroisoquinoline | 0.88 (3) | 409.16 | * |
| 69 | | 2-[2-(4-cyclobutylpiperazin-1-yl)-2-oxoethyl]-1,2,3,4-tetrahydroisoquinoline 6-carbonitrile | 1.07 (1) | 339.14 | * |

TABLE I-continued

| Compound | Name | RT | MS | K$_i$ |
|---|---|---|---|---|
| 70 | 2-[2-(4-cyclobutylpiperazin-1-yl)-2-oxoethyl]-6-pyrimidin-5-yl-1,2,3,4-tetrahydroisoquinoline | 1.06 (1) | 392.16 | * |
| 71 | 1-(4-{6-[2-(4-cyclobutylpiperazin-1-yl)-2-oxoethyl]-5,6,7,8-tetrahydropyrido[4,3-d]pyrimidin-2-yl}phenyl)ethanone | 0.99 (3) | 434.22 | * |
| 72 | 4-{2-[2-(4-cyclobutylpiperazin-1-yl)-2-oxoethyl]-1,2,3,4-tetrahydroisoquinolin-6-yl}-N-methylbenzamide | 0.97 (3) | 447.24 | * |
| 73 | 1-{2-[2-(4-cyclobutylpiperazin-1-yl)-2-oxoethyl]-1,2,3,4-tetrahydroisoquinolin-6-yl}propan-1-one | 0.49 (3) | 370.15 | * |
| 74 | 2-[2-(4-cyclobutylpiperazin-1-yl)-2-oxoethyl]-6-[3-(methylsulfonyl)phenyl]-1,2,3,4-tetrahydroisoquinoline | 0.91 (3) | 468.11 | * |

TABLE I-continued

| Compound | Name | RT | MS | K₁ |
|---|---|---|---|---|
| 75 | 2-[2-(4-cyclobutylpiperazin-1-yl)-2-oxoethyl]-6-pyridin-4-yl-1,2,3,4-tetrahydroisoquinoline | 1.11 (1) | 391.12 | * |
| 76 | 6-[2-(4-cyclobutylpiperazin-1-yl)-2-oxoethyl]-2-(4-methoxyphenyl)-5,6,7,8-tetrahydropyrido[4,3-d]pyrimidine | 0.97 (3) | 422.19 | * |
| 77 | 3-[2-(4-cyclobutylpiperazin-1-yl)-2-oxoethyl]-7-methoxy-2,3,4,5-tetrahydro-1H-3-benzazepine | 0.99 (1) | 358.25 | * |
| 78 | 7-[2-(4-cyclobutylpiperazin-1-yl)-2-oxoethyl]-4-methoxy-6,7,8,9-tetrahydro-5H-pyrimido[4,5-d]azepine | 1.06 (1) | 360.15 | * |
| 79 | 1-(4-{7-[2-(4-cyclobutylpiperazin-1-yl)-2-oxoethyl]-6,7,8,9-tetrahydro-5H-pyrimido[4,5-d]azepin-4-yl}phenyl)ethanone | 0.53 (3) | 448.09 | * |
| 80 | 7-[2-(4-cyclobutylpiperazin-1-yl)-2-oxoethyl]-6,7,8,9-tetrahydro-5H-pyrimido[4,5-d]azepine | 0.98 (1) | 330.15 | * |
| 81 | 3-bromo-7-[2-(4-cyclobutylpiperazin-1-yl)-2-oxoethyl]-5,6,7,8-tetrahydroimidazo[1,2-a]pyrazine | 1.05 (1) | 382.06 | * |

TABLE I-continued

| Compound | Name | RT | MS | $K_i$ |
|---|---|---|---|---|
| 82 | 7-[2-(4-cyclobutylpiperazin-1-yl)-2-oxoethyl]-5,6,7,8-tetrahydroimidazo[1,2-a]pyrazin-3-yl}phenyl)ethanone | 1.06 (1) | 422.21 | * |
| 83 | 7-[2-(4-cyclobutylpiperazin-1-yl)-2-oxoethyl]-5,6,7,8-tetrahydroimidazo[1,2-a]pyrazine | 0.96 (1) | 304.16 | * |

TABLE II

| Compound | Name | RT | MS | $K_i$ |
|---|---|---|---|---|
| 84 | 2-[2-(4-cyclobutylpiperazin-1-yl)-2-oxoethyl]-6-[3-(methylsulfonyl)phenyl]-1,2,3,4-tetrahydroisoquinoline | 1.11 (3) | 468.26 | * |
| 85 | 2-[2-(4-cyclobutylpiperazin-1-yl)-2-oxoethyl]-N-methyl-1,2,3,4-tetrahydroisoquinoline-6-carboxamide | 1.02 (1) | 371.14 | * |
| 86 | ethyl 2-[2-(4-cyclobutylpiperazin-1-yl)-2-oxoethyl]-1,2,3,4-tetrahydroisoquinoline-6-carboxylate | 0.84 (3) | 386.30 | * |
| 87 | 2-[2-(4-cyclobutylpiperazin-1-yl)-2-oxoethyl]-6-[(2-methylpyrrolidin-1-yl)carbonyl]-1,2,3,4-tetrahydroisoquinoline | 0.86 (3) | 425.26 | * |

TABLE II-continued

| Compound | Name | RT | MS | $K_i$ |
|---|---|---|---|---|
| 88 | 2-[2-(4-cyclobutylpiperazin-1-yl)-2-oxoethyl]-N-cyclopentyl-1,2,3,4-tetrahydroisoquinoline-6-carboxamide | 0.92 (3) | 425.25 | * |
| 89 | 2-[2-(4-cyclobutylpiperazin-1-yl)-2-oxoethyl]-6-(pyrrolidin-1-ylcarbonyl)-1,2,3,4-tetrahydroisoquinoline | 0.41 (3) | 411.25 | * |
| 90 | 1-(4-bromophenyl)-5-[2-(4-cyclobutylpiperazin-1-yl)-2-oxoethyl]-4,5,6,7-tetrahydro-1H-pyrazolo[4,3-c]pyridine | 1 (3) | 458.12 | * |
| 91 | 5-[2-(4-cyclobutylpiperazin-1-yl)-2-oxoethyl]-4,5,6,7-tetrahydro-2H-pyrazolo[4,3-c]pyridine | 0.97 (1) | 304.17 | * |
| 92 | 1-(4-{5-[2-(4-cyclobutylpiperazin-1-yl)-2-oxoethyl]-4,5,6,7-tetrahydro-1H-pyrazolo[4,3-c]pyridin-1-yl}phenyl)ethanone | 0.54 (3) | 422.25 | * |

TABLE II-continued

| Compound | Name | RT | MS | $K_i$ |
|---|---|---|---|---|
| 93 | 4-{5-[2-(4-cyclobutylpiperazin-1-yl)-2-oxoethyl]-4,5,6,7-tetrahydro-1H-pyrazolo[4,3-c]pyridin-1-yl}benzonitrile | 0.41 (3) | 405.24 | * |
| 94 | 1-(4-{5-[2-(4-cyclobutylpiperazin-1-yl)-2-oxoethyl]-4,5,6,7-tetrahydro-2H-pyrazolo[4,3-c]pyridin-2-yl}phenyl)ethanone | 0.86 (3) | 422.24 | * |
| 95 | 2-[2-(4-cyclobutylpiperazin-1-yl)-2-oxoethyl]-6-(6-methoxypyridin-3-yl)-1,2,3,4-tetrahydroisoquinoline | 0.99 (3) | 421.23 | * |
| 96 | 1-(6-{5-[2-(4-cyclobutylpiperazin-1-yl)-2-oxoethyl]-4,5,6,7-tetrahydro-2H-pyrazolo[4,3-c]pyridin-2-yl}pyridin-3-yl)ethanone | 0.61 (3) | 423.24 | * |

TABLE II-continued

| Compound | Name | RT | MS | K$_i$ |
|---|---|---|---|---|
| 97 | 2-bromo-5-[2-(4-cyclobutylpiperazin-1-yl)-2-oxoethyl]-4,5,6,7-tetrahydro[1,3]thiazolo[5,4-c]pyridine | 1.09 (1) | 399.02 | * |
| 98 | 1-(4-{5-[2-(4-cyclobutylpiperazin-1-yl)-2-oxoethyl]-4,5,6,7-tetrahydro[1,3]thiazolo[5,4-c]pyridin-2-yl}phenyl)ethanone | 0.96 (3) | 439.17 | * |
| 99 | 5-[2-(4-cyclobutylpiperazin-1-yl)-2-oxoethyl]-2-[3-(methylsulfonyl)phenyl]-4,5,6,7-tetrahydro[1,3]thiazolo[5,4-c]pyridine | 0.58 (3) | 475.16 | * |
| 100 | methyl 4-{5-[2-(4-cyclobutylpiperazin-1-yl)-2-oxoethyl]-4,5,6,7-tetrahydro[1,3]thiazolo[5,4-c]pyridin-2-yl}benzoate | 1.02 (3) | 455.18 | * |

TABLE II-continued

| Compound | Name | RT | MS | K_i |
|---|---|---|---|---|
| 101 | 1-{3-[2-(4-cyclobutylpiperazin-1-yl)-2-oxoethyl]-2,3,4,5-tetrahydro-1H-3-benzazepin-7-yl}ethanone | 0.43 (3) | 370.24 | * |
| 102 | 5-[2-(4-cyclobutylpiperazin-1-yl)-2-oxoethyl]-4,5,6,7-tetrahydro[1,3]thiazolo]5,4-c]pyridine-2-carbonitrile | 1.05 (1) | 346.11 | * |
| 103 | 1-{5-[2-(4-cyclobutylpiperazin-1-yl)-2-oxoethyl]-4,5,6,7-tetrahydro[1,3]thiazolo[5,4-c]pyridin-2-yl}ethanone | 1.06 (1) | 363.11 | * |
| 104 | 3-[2-(4-cyclobutylpiperazin-1-yl)-2-oxoethyl]-7-pyrimidin-5-yl-2,3,4,5-tetrahydro-1H-3-benzazepine | 0.65 (3) | 406.23 | * |
| 105 | 5-[2-(4-cyclobutylpiperazin-1-yl)-2-oxoethyl]-2-[4-(methylsulfonyl)phenyl]-4,5,6,7-tetrahydro[1,3]thiazolo[4,5-c]pyridine | 0.54 (3) | 475.48 | * |

TABLE II-continued

| Compound | | Name | RT | MS | $K_i$ |
|---|---|---|---|---|---|
| 106 | | 2-chloro-5-{2-oxo-2-[2-(pyrrolidin-1-yl)ethyl]-4,5,6,7-tetrahydro[1,3]thiazolo[5,4-c]pyridine | 1.09 (1) | 368.99 | |
| 107 | | 5-[2-(4-cyclobutylpiperazin-1-yl)-2-oxoethyl]-2-(methylthio)-4,5,6,7-tetrahydro[1,3]oxazolo[5,4-c]pyridine | 1.08 (1) | 351.04 | * |
| 108 | | 2-bromo-5-[2-(4-cyclobutylpiperazin-1-yl)-2-oxoethyl]-4,5,6,7-tetrahydro[1,3]thiazolo[4,5-c]pyridine | 1.1 (1) | 398.92 | * |
| 109 | | 2-chloro-5-[2-(4-cyclobutyl-3-methylpiperazin-1-yl)-2-oxoethyl]-4,5,6,7-tetrahydro[1,3]thiazolo[5,4-c]pyridine | 1.11 (1) | 369.00 | * |
| 110 | | 5-{2-oxo-2-[2-(pyrrolidin-1-ylmethyl)pyrrolidin-1-yl]ethyl}-2-pyrimidin-5-yl-4,5,6,7-tetrahydro[1,3]thiazolo[5,4-c]pyridine | 1.00 (1) | 413.20 | * |

TABLE II-continued

| Compound | Name | RT | MS | K_i |
|---|---|---|---|---|
| 111 | 5-[2-(4-cyclobutyl-3-methylpiperazin-1-yl)-2-oxoethyl]-2-pyrimidin-5-yl-4,5,6,7-tetrahydro[1,3]thiazolo[5,4-c]pyridine | 1.06 (1) | 413.03 | * |
| 112 | 1-(2-{2-oxo-2-[2-(pyrrolidin-1-ylmethyl)pyrrolidin-1-yl]ethyl}-1,2,3,4-tetrahydroisoquinolin-6-yl)ethanone | 1.09 (1) | 370.07 | |
| 113 | 5-[2-(4-cyclobutyl-3-methylpiperazin-1-yl)-2-oxoethyl]-2-(1,3-thiazol-4-yl)-4,5,6,7-tetrahydro[1,3]thiazolo[5,4-c]pyridine | 0.38 (3) | 418.13 | * |
| 114 | 5-[2-(4-cyclobutyl-3-methylpiperazin-1-yl)-2-oxoethyl]-2-pyridin-4-yl-4,5,6,7-tetrahydro[1,3]thiazolo[5,4-c]pyridine | 1.09 (1) | 412.04 | * |
| 115 | 5-[2-(4-cyclobutyl-3-methylpiperazin-1-yl)-2-oxoethyl]-2-(1,3-thiazol-2-yl)-4,5,6,7-tetrahydro[1,3]thiazolo[5,4-c]pyridine | 0.46 (3) | 418.12 | * |

TABLE II-continued

| Compound | Name | RT | MS | K_i |
|---|---|---|---|---|
| 116 | ethyl 7-[2-(4-cyclobutylpiperazin-1-yl)-2-oxoethyl]-5,6,7,8-tetrahydro-1,7-naphthyridine-3-carboxylate | 1.1 (1) | 387.08 | * |
| 117 | ethyl 7-[2-(4-cyclobutyl-3-methylpiperazin-1-yl)-2-oxoethyl]-5,6,7,8-tetrahydro-1,7-naphthyridine-3-carboxylate | 1.12 (1) | 401.09 | * |
| 118 | 6-bromo-2-[2-(4-cyclobutylpiperazin-1-yl)-2-oxoethyl]-1,2,3,4-tetrahydroisoquinoline | 1.2 (1) | 391.98 | * |
| 119 | 2-[2-(4-cyclobutylpiperazin-1-yl)-2-oxoethyl]-6-(1,3-thiazol-4-yl)-1,2,3,4-tetrahydroisoquinoline | 0.64 (3) | 397.27 | * |
| 120 | 2-[2-(4-cyclobutylpiperazin-1-yl)-2-oxoethyl]-6-(1,3-thiazol-2-yl)-1,2,3,4-tetrahydroisoquinoline | 0.8 (3) | 397.24 | * |

TABLE II-continued

| Compound | | Name | RT | MS | $K_i$ |
|---|---|---|---|---|---|
| 121 | | 7-[2-(4-cyclobutyl-3-methylpaperazin-1-yl)-2-oxoethyl]-N-methyl-5,6,7,8-tetrahydro-1,7-naphthyridine-3-carboxamide | 1 (1) | 386.22 | * |
| 122 | | 2-[2-(4-cyclobutylpiperazin-1-yl)-2-oxoethyl]-6-(1H-pyrazol-1-yl)-1,2,3,4-tetrahydroisoquinolin | 0.48 (3) | 380.29 | * |
| 123 | | 6-[2-(4-cyclobutylpiperazin-1-yl)-2-oxoethyl]-2-pyridin-3-yl-4,5,6,7-tetrahydro-2H-pyrazolo[3,4-c]pyridine | 1.03 (1) | 381.22 | * |
| 124 | | 6-[2-(4-cyclobutylpiperazin-1-yl)-2-oxoethyl]-2-pyrimidin-5-yl-4,5,6,7-tetrahydro-2H-pyrazolo[3,4-c]pyridine | 1.01 (1) | 382.22 | * |
| 125 | | N-cyclobutyl-6-[2-(4-cyclobutylpiperazin-1-yl)-2-oxoethyl]-5,6,7,8-tetrahydro-1,6-naphthyridine-2-carboxamide | 0.63 (3) | 412.27 | * |
| 126 | | N-cyclobutyl-6-[2-(4-cyclobutyl-3-methylpiperazin-1-yl)-2-oxoethyl]-5,6,7,8-tetrahydro-1,6-naphthyridine-2-carboxamide | 0.82 (3) | 426.30 | * |

TABLE II-continued

| Compound | | Name | RT | MS | $K_i$ |
|---|---|---|---|---|---|
| 127 | | 2-[2-(4-cyclobutylpiperazin-1-yl)-2-oxoethyl]-6-(1-methyl-1H-pyrazol-4-yl)-1,2,3,4-tetrahydroisoquinoline | 0.46 (3) | 394.28 | * |
| 128 | | 2-[2-(4-cyclobutylpiperazin-1-yl)-2-oxoethyl]-6-pyrazin-2-yl-1,2,3,4-tetrahydroisoquinoline | 1.11 (1) | 392.23 | * |
| 129 | | 2-[2-(4-cyclobutylpiperazin-1-yl)-2-oxoethyl]-6-pyridazin-3-yl-1,2,3,4-tetrahydroisoquinoline | 1.05 (1) | 392.22 | * |
| 130 | | 2-[2-(4-cyclobutylpiperazin-1-yl)-2-oxoethyl]-6-pyridin-2-yl-1,2,3,4-tetrahydroisoquinoline | 1.12 (1) | 391.23 | * |
| 131 | | 2-[2-(4-cyclobutylpiperazin-1-yl)-2-oxoethyl]-6-pyrimidin-2-yl-1,2,3,4-tetrahydroisoquinolin | 1.1 (1) | 392.22 | * |

TABLE II-continued

| Compound | Name | RT | MS | K$_i$ |
|---|---|---|---|---|
| 132 | 2-[2-(4-cyclobutylpiperazin-1-yl)-2-oxoethyl]-6-(1,3-thiazol-5-yl)-1,2,3,4-tetrahydroisoquinoline | 0.6 (3) | 397.22 | * |
| 133 | 6-[2-(4-cyclopentylpiperazin-1-yl)-2-oxoethyl]-5,6,7,8-tetrahydro-1,6-naphthyridin-2(1H)-one | 0.99 (1) | 345.22 | * |
| 134 | 6-[2-(4-cyclobutylpiperazin-1-yl)-2-oxoethyl]-5,6,7,8-tetrahydro-1,6-naphthyridin-2(1H)-one | 0.96 (1) | 331.20 | * |
| 135 | 6-[2-(4-isopropylpiperazin-1-yl)-2-oxoethyl]-5,6,7,8-tetrahydro-1,6-naphthyridin-2(1H)-one | 0.92 (1) | 319.20 | * |
| 136 | 6-[2-(4-cyclohexylpiperazin-1-yl)-2-oxoethyl]-5,6,7,8-tetrahydro-1,6-naphthyridin-2(1H)-one | 1.04 (1) | 359.23 | * |
| 137 | 6-[2-(4-cyclobutylpiperazin-1-yl)-2-oxoethyl]-2-pyridin-4-yl-5,6,7,8-tetrahydropyrido[4,3-d]pyrimidine | 1.05 (1) | 393.23 | * |

TABLE II-continued

| Compound | Name | RT | MS | K$_i$ |
|---|---|---|---|---|
| 138 | 6-[2-(4-cyclopentylpiperazin-1-yl)-2-oxoethyl]-2-pyridin-4-yl-5,6,7,8-tetrahydropyrido[4,3-d]pyrimidine | 1.08 (1) | 407.24 | * |
| 139 | 6-[2-(4-cyclobutylpiperazin-1-yl)-2-oxoethyl]-2-morpholin-4-yl-5,6,7,8-tetrahydropyrido[4,3-d]pyrimidine | 0.31 (3) | 401.29 | * |
| 140 | 6-[2-(4-cyclopentylpiperazin-1-yl)-2-oxoethyl]-2-morpholin-4-yl-5,6,7,8-tetrahydropyrido[4,3-d]pyrimidine | 0.3 (3) | 415.25 | * |
| 141 | 1-{2-[2-(4-isopropylpiperazin-1-yl)-2-oxoethyl]-1,2,3,4-tetrahydroisoquinolin-6-yl}ethanone | 1.05 (1) | 344.22 | * |
| 142 | 1-{2-[2-(6-methyloctahydro-2H-pyrido[1,2-a]pyrazin-2-yl)-2-oxoethyl]-1,2,3,4-tetrahydroisoquinolin-6-yl}ethanone | 0.3 (3) | | * |

TABLE II-continued

| Compound | | Name | RT | MS | $K_i$ |
|---|---|---|---|---|---|
| 143 | (structure) | 6-[2-(4-cyclobutylpiperazin-1-yl)-2-oxoethyl]-2-pyridin-3-yl-5,6,7,8-tetrahydropyrido[4,3-d]pyrimidine | 1.05 (1) | 393.22 | * |
| 144 | (structure) | 6-[2-(4-cyclobutylpiperazin-1-yl)-2-oxoethyl]-2-pyridin-2-yl-5,6,7,8-tetrahydropyrido[4,3-d]pyrimidine | 1.03 (1) | 393.22 | * |
| 145 | (structure) | 2-{2-[4-(1-ethylpropyl)piperazin-1-yl]-2-oxoethyl}-6-pyrimidin-5-yl-1,2,3,4-tetrahydroisoquinoline | 0.58 (3) | 408.27 | * |
| 146 | (structure) | 2-[(6-bromo-3,4-dihydroisoquinolin-2(1H)-yl)acetyl]-6-methyloctahydro-2H-pyrido[1,2-a]pyrazine | 0.93 (3) | 406.14 | * |
| 147 | (structure) | 2-[(2-chloro-6,7-dihydro[1,3]thiazolo[5,4-c]pyridin-5(4H)-yl)acetyl]-6-methyloctahydro-2H-pyrido[1,2-a]pyrazine | 1.1 (1) | 369.13 | * |
| 148 | (structure) | 2-[(6-bromo-3,4-dihydroisoquinolin-2(1H)-yl)acetyl]octahydro-2H-pyrido[1,2-a]pyrazine | 0.89 (3) | 392.14 | * |

TABLE II-continued

| Compound | Name | RT | MS | $K_i$ |
|---|---|---|---|---|
| 149 | 6-methyl-2-[(6-pyrimidin-5-yl-3,4-dihydroisoquinolin-2(1H)-yl)acetyl]octahydro-2H-pyrido[1,2-a]pyrazine | 1.09 (1) | 406.25 | * |
| 150 | 6-methyl-2-[(2-pyrimidin-5-yl-6,7-dihydro[1,3]thiazolo[5,4-c]pyridin-5(4H)-yl)acetyl]octahydro-2H-pyrido[1,2-a]pyrazine | 1.05 (1) | 413.20 | * |
| 151 | 2-[(6-pyrimidin-5-yl-3,4-dihydroisoquinolin-2(1H)-yl)acetyl]octahydro-2H-pyrido[1,2-a]pyrazine | 0.4 (3) | 392.23 | * |
| 152 | 6-methyl-2-{[6-(1H-pyrazol-1-yl)-3,4-dihydroisoquinolin-2(1H)-yl]acetyl}octahydro-2H-pyrido[1,2-a]pyrazine | 0.75 (3) | 394.26 | * |
| 153 | 2-{[6-(1H-pyrazol-1-yl)-3,4-dihydroisoquinolin-2(1H)-yl]acetyl}octahydro-2H-pyrido[1,2-a]pyrazine | 0.37 (3) | 380.23 | * |
| 154 | 1-{2-[2-(octahydro-2H-pyrido[1,2-a]pyrazin-2-yl)-2-oxoethyl]-1,2,3,4-tetrahydroisoquinolin-6-yl}ethanone | 1.06 (1) | 356.22 | * |

TABLE II-continued

| Compound | | Name | RT | MS | $K_i$ |
|---|---|---|---|---|---|
| 155 | | 6-[2-(4-cyclobutylpiperazin-1-yl)-2-oxoethyl]-2-piperidin-1-yl-5,6,7,8-tetrahydropyrido[4,3-d]pyrimidine | 0.97 (3) | 399.31 | * |
| 156 | | 6-[2-(4-cyclopentylpiperazin-1-yl)-2-oxoethyl]-2-piperidin-1-yl-5,6,7,8-tetrahydropyrido[4,3-d]pyrimidine | 1.01 (3) | 413.32 | * |
| 157 | | 2-[2-(4-cyclobutylpiperazin-1-yl)-2-oxoethyl]-6-[3-(trifluoromethyl)-1H-pyrazol-1-yl]-1,2,3,4-tetrahydroisoquinoline | 1.08 (3) | 448.24 | * |
| 158 | | 6-methyl-2-({6-[3-(trifluoromethyl)-1H-pyrazol-1-yl]-3,4-dihydroisoquinolin-2(1H)-yl}acetyl)octahydro-2H-pyrido[1,2-a]pyrazine | 1.09 (3) | 462.25 | * |
| 159 | | 2-({6-[3-(trifluoromethyl)-1H-pyrazol-1-yl]-3,4-dihydroisoquinolin-2(1H)-yl}acetyl)octahydro-2H-pyrido[1,2-a]pyrazine | 1.08 (3) | 448.25 | * |

TABLE II-continued

| Compound | Name | RT | MS | $K_i$ |
|---|---|---|---|---|
| 160 | 6-ethyl-2-[(6-pyrimidin-5-yl-3,4-dihydroisoquinolin-2(1H)-yl)acetyl]octahydro-2H-pyrido[1,2-a]pyrazine | 0.53 (3) | 420.35 | * |
| 161 | 6-ethyl-2-({6-[3-(trifluoromethyl)-1H-pyrazol-1-yl]-3,4-dihydroisoquinolin-2(1H)-yl}acetyl)octahydro-2H-pyrido[1,2-a]pyrazine | 1.09 (3) | 476.10 | * |
| 162 | 2-[(6-bromo-3,4-dihydroisoquinolin-2(1H)-yl)acetyl]-6-ethyloctahydro-2H-pyrido[1,2-a]pyrazine | 0.99 (3) | 420.24 | * |
| 163 | 1-{2-[2-(6-ethyloctahydro-2H-pyrido[1,2-a]pyrazin-2-yl)-2-oxoethyl]-1,2,3,4-tetrahydroisoquinolin-6-yl}ethanone | 0.41 (3) | 384.29 | * |
| 164 | 2-[2-(4-isopropylpiperazin-1-yl)-2-oxoethyl]-6-pyridazin-3-yl-1,2,3,4-tetrahydroisoquinoline | 1.05 (1) | 380.26 | * |

TABLE II-continued

| Compound | | Name | RT | MS | $K_i$ |
|---|---|---|---|---|---|
| 165 | | 6-methyl-2-[(6-pyridazin-3-yl-3,4-dihydroisoquinolin-2(1H)-yl)acetyl]octahydro-2H-pyrido[1,2-a]pyrazine | 1.08 (1) | 406.28 | * |
| 166 | | 2-[2-(4-cyclobutylpiperazin-1-yl)-2-oxoethyl]-6-(6-methylpyridazin-3-yl)-1,2,3,4-tetrahydroisoquinoline | 1.09 (1) | 406.28 | * |
| 167 | | 6-ethyl-2-{[6-(1H-pyrazol-1-yl)-3,4-dihydroisoquinolin-2(1H)-yl]acetyl}octahydro-2H-pyrido[1,2-a]pyrazine | 1.17 (1) | 408.30 | * |
| 168 | | 2-chloro-6-[2-(4-cyclobutylpiperazin-1-yl)-2-oxoethyl]-5,6,7,8-tetrahydro-1,6-naphthyridine | 1.09 (1) | 349.20 | * |
| 169 | | 2-{2-[4-(1-methylcyclobutyl)piperazin-1-yl]-2-oxoethyl}-6-pyrimidin-5-yl-1,2,3,4-tetrahydroisoquinoline | 1.12 (1) | 406.28 | * |

TABLE II-continued

| Compound | | Name | RT | MS | $K_i$ |
|---|---|---|---|---|---|
| 170 | | 6-bromo-2-(2-oxo-2-{4-[1-(trifluoromethyl)propyl]piperazin-1-yl}ethyl)-1,2,3,4-tetrahydroisoquinoline | 1.19 (3) | 447.99 | |
| 171 | | 6-[2-(4-cyclobutylpiperazin-1-yl)-2-oxoethyl]-2-pyrimidin-5-yl-5,6,7,8-tetrahydro-1,6-naphthyridine | 1.05 (1) | 393.26 | * |
| 172 | | 6-[2-(4-cyclobutylpiperazin-1-yl)-2-oxoethyl]-2-pyridazin-3-yl-5,6,7,8-tetrahydro-1,6-naphthyridine | 1.05 (1) | 393.26 | * |
| 173 | | 1-{6-[2-(4-cyclobutylpiperazin-1-yl)-2-oxoethyl]-5,6,7,8-tetrahydro-1,6-naphthyridin-2-yl}ethanone | 1.08 (1) | 357.25 | * |
| 174 | | 2-chloro-6-[2-(6-methyloctahydro-2H-pyrido[1,2-a]pyrazin-2-yl)-2-oxoethyl]-5,6,7,8-tetrahydro-1,6-naphthyridine | 1.08 (1) | 363.23 | * |
| 175 | | 6-[2-(4-cyclobutylpiperazin-1-yl)-2-oxoethyl]-2-morpholin-4-yl-5,6,7,8-tetrahydro-1,6-naphthyridine | 1.08 (1) | 400.29 | * |

TABLE II-continued

| Compound | | Name | RT | MS | K$_i$ |
|---|---|---|---|---|---|
| 176 | | 6-[2-(4-cyclobutylpiperazin-1-yl)-2-oxoethyl]-2-pyrrolidin-1-yl-5,6,7,8-tetrahydro-1,6-naphthyridine | 1.15 (1) | 384.30 | * |
| 177 | | 6-[2-(6-methyloctahydro-2H-pyrido[1,2-a]pyrazin-2-yl)-2-oxoethyl]-2-pyrimidin-5-yl-5,6,7,8-tetrahydro-1,6-naphthyridine | 1.04 (1) | 407.29 | * |
| 178 | | 2-(4-methoxyphenyl)-6-[2-(6-methyloctahydro-2H-pyrido[1,2-a]pyrazin-2-yl)-2-oxoethyl]-5,6,7,8-tetrahydro-1,6-naphthyridine | 1.01 (3) | 435.31 | * |
| 179 | | 2-(2,6-dimethylmorpholin-4-yl)-6-[2-(6-methyloctahydro-2H-pyrido[1,2-a]pyrazin-2-yl)-2-oxoethyl]-5,6,7,8-tetrahydro-1,6-naphthyridine | 0.44 (3) | 442.37 | * |
| 180 | | 2-(4,4-difluoropiperidin-1-yl)-6-[2-(6-methyloctahydro-2H-pyrido[1,2-a]pyrazin-2-yl)-2-oxoethyl]-5,6,7,8-tetrahydro-1,6-naphthyridine | 0.46 (3) | 448.27 | * |

TABLE II-continued

| Compound | | Name | RT | MS | K$_i$ |
|---|---|---|---|---|---|
| 181 | | N-(2-methoxyethyl)-N-methyl-6-[2-(6-methyloctahydro-2H-pyrido[1,2-a]pyrazin-2-yl)-2-oxoethyl]-5,6,7,8-tetrahydro-1,6-naphthyridin-2-amine | 1.13 (1) | 416.17 | * |
| 182 | | 6-[2-(4-cyclobutylpiperazin-1-yl)-2-oxoethyl]-2-(2,6-dimethylmorpholin-4-yl)-5,6,7,8-tetrahydro-1,6-naphthyridine | 0.38 (3) | 428.32 | * |
| 183 | | 6-[2-(4-cyclobutylpiperazin-1-yl)-2-oxoethyl]-2-(4,4-difluoropiperidin-1-yl)-5,6,7,8-tetrahydro-1,6-naphthyridine | 0.38 (3) | 434.28 | * |
| 184 | | 6-[2-(4-cyclobutylpiperazin-1-yl)-2-oxoethyl]-N-(2-methoxyethyl)-N-methyl-5,6,7,8-tetrahydro-1,6-naphthyridin-2-amine | 1.12 (1) | 402.16 | * |
| 185 | | 6-[2-(4-cyclobutylpiperazin-1-yl)-2-oxoethyl]-2-(cyclopentyloxy)-5,6,7,8-tetrahydro-1,6-naphthyridine | 1.06 (3) | 399.30 | * |

TABLE II-continued

| Compound | | Name | RT | MS | $K_i$ |
|---|---|---|---|---|---|
| 186 | | 6-[2-(6-methyloctahydro-2H-pyrido[1,2-a]pyrazin-2-yl)-2-oxoethyl]-2-morpholin-4-yl-5,6,7,8-tetrahydropyrido[4,3-d]pyrimidine | 0.3 (3) | 415.29 | * |
| 187 | | 6-[2-(4-cyclobutylpiperazin-1-yl)-2-oxoethyl]-2-(2,6-dimethylmorpholin-4-yl)-5,6,7,8-tetrahydropyrido[4,3-d]pyrimidine | 0.87 (3) | 429.31 | * |
| 188 | | 2-{2-[(3S)-4-cyclobutyl-3-isopropylpiperazin-1-yl]-2-oxoethyl}-6-pyrimidin-5-yl-1,2,3,4-tetrahydroisoquinoline | 0.93 (3) | 434.52 | |
| 189 | | 2-{2-[(3R)-4-cyclobutyl-3-isopropylpiperazin-1-yl]-2-oxoethyl}-6-pyrimidin-5-yl-1,2,3,4-tetrahydroisoquinoline | 0.96 (3) | 434.31 | * |
| 190 | | 2-{2-[4-(2-methylcyclopentyl)piperazin-1-yl]-2-oxoethyl}-6-(6-methylpyridazin-3-yl)-1,2,3,4-tetrahydroisoquinoline | 0.45 (3) | 434.52 | * |

TABLE II-continued

| Compound | Name | RT | MS | $K_i$ |
|---|---|---|---|---|
| 191 | 2-{2-[4-(2-methylcyclopentyl)piperazin-1-yl]-2-oxoethyl}-6-pyridazin-3-yl-1,2,3,4-tetrahydroisoquinoline | 0.35 (3) | 420.21 | * |
| 192 | 5-{2-[2-(4-cyclobutylpiperazin-1-yl)-2-oxoethyl]-1,2,3,4-tetrahydroisoquinolin-6-yl}-1-methylpyridin-2(1H)-one | 0.45 (3) | | * |
| 193 | 2-{2-[2-(4-cyclobutylpiperazin-1-yl)-2-oxoethyl]-1,2,3,4-tetrahydroisoquinolin-6-yl}pyridazin-3(2H)-one | 1.05 (1) | 408.14 | * |
| 194 | 6-(benzyloxy)-2-[2-(4-cyclobutylpiperazin-1-yl)-2-oxoethyl]-1,2,3,4-tetrahydroisoquinoline | 1.23 (1) | 420.15 | * |
| 195 | 2-[2-(4-cyclobutylpiperazin-1-yl)-2-oxoethyl]-1,2,3,4-tetrahydroisoquinolin-6-ol | 1.04 (1) | 330.14 | * |
| 196 | 2-[2-(4-cyclobutylpiperazin-1-yl)-2-oxoethyl]-6-(cyclopentyloxy)-1,2,3,4-tetrahydroisoquinoline | 1.08 (3) | 398.50 | * |
| 197 | 2-[2-(4-cyclobutylpiperazin-1-yl)-2-oxoethyl]-6-isopropoxy-1,2,3,4-tetrahydroisoquinoline | 0.98 (3) | 372.48 | * |

TABLE II-continued

| Compound | Name | RT | MS | K$_i$ |
|---|---|---|---|---|
| 198 | 2-[2-(4-cyclobutylpiperazin-1-yl)-2-oxoethyl]-6-{[5-(trifluoromethyl)pyridin-2-yl]oxy}-1,2,3,4-tetrahydroisoquinoline | 1.1 (3) | 475.45 | * |
| 199 | 5-[2-(4-cyclobutylpiperazin-1-yl)-2-oxoethyl]-2-(6-methoxypyridazin-3-yl)-4,5,6,7-tetrahydro-2H-pyrazolo[4,3-c]pyridine | 0.47 (3) | 412.16 | * |
| 200 | 5-[2-(4-cyclobutylpiperazin-1-yl)-2-oxoethyl]-2-(6-methylpyridazin-3-yl)-4,5,6,7-tetrahydro-2H-pyrazolo[4,3-c]pyridine | 1.06 (1) | 396.16 | * |
| 201 | 2-(6-chloropyridazin-3-yl)-5-[2-(4-cyclobutylpiperazin-1-yl)-2-oxoethyl]-4,5,6,7-tetrahydro-2H-pyrazolo[4,3-c]pyridine | 0.36 (3) | 416.11 | * |
| 202 | 1-(6-{5-[2-(4-cyclobutylpiperazin 1-yl)-2-oxoethyl]-4,5,6,7-tetrahydro-2H-pyrazolo[4,3-c]pyridin-2-yl}pyridazin-3-yl)ethanone | 0.44 (3) | 424.17 | * |
| 203 | 6-(5-[2-(4-cyclobutylpiperazin-1-yl)-2-oxoethyl]-4,5,6,7-tetrahydro-2H-pyrazolo[4,3-c]pyridin-2-yl}pyridazine-3-carbonitrile | 1.06 (1) | 407.14 | * |
| 204 | 6-[2-(4-cyclobutylpiperazin-1-yl)-2-oxoethyl]-2-pyrrolidin-1-yl-5,6,7,8-tetrahydropyrido[4,3-d]pyrimidine | 0.35 (3) | 385.31 | * |

TABLE II-continued

| Compound | | Name | RT | MS | K$_i$ |
|---|---|---|---|---|---|
| 205 | | 6-{2-[4-(2-methylcyclopentyl)piperazin-1-yl]-2-oxoethyl}-2-morpholin-4-yl-5,6,7,8-tetrahydropyrido[4,3-d]pyrimidine | 0.49 (3) | 429.32 | * |
| 206 | | 1-(2-{2-[4-(2-methylcyclopentyl)piperazin-1-yl]-2-oxoethyl}-1,2,3,4-tetrahydroisoquinolin-6-yl)ethanone | 0.48 (3) | 384.32 | * |
| 207 | | 2-[2-(4-cyclobutylpiperazin-1-yl)-2-oxoethyl]-6-(1H-1,2,4-triazol-1-yl)-1,2,3,4-tetrahydroisoquinoline | 1.07 (1) | 381.14 | * |
| 208 | | 2-[2-(4-cyclobutylpiperazin-1-yl)-2-oxoethyl]-6-(1H-1,2,3-triazol-1-yl)-1,2,3,4-tetrahydroisoquinoline | 1.05 (1) | 381.13 | * |
| 209 | | 2-[2-(4-cyclobutylpiperazin-1-yl)-2-oxoethyl]-6-(2H-1,2,3-triazol-2-yl)-1,2,3,4-tetrahydroisoquinoline | 0.58 (3) | 381.29 | * |
| 210 | | 3-{2-[2-(4-cyclobutylpiperazin-1-yl)-2-oxoethyl]-1,2,3,4-tetrahydroisoquinolin-6-yl}-1,3-oxazolidin-2-one | 1.04 (1) | 399.13 | * |
| 211 | | 1-{2-[2-(4-cyclobutylpiperazin-1-yl)-2-oxoethyl]-1,2,3,4-tetrahydroisoquinolin-6-yl}piperidin-2-one | 1.08 (1) | 411.16 | * |

TABLE II-continued

| Compound | | Name | RT | MS | $K_i$ |
|---|---|---|---|---|---|
| 212 | | 3-{2-[2-(4-cyclobutylpiperazin-1-yl)-2-oxoethyl]-1,2,3,4-tetrahydroisoquinolin-6-yl}-1-methylpyridin-2(1H)-one | 0.63 (3) | 421.29 | * |
| 213 | | 1-{2-[2-(4-cyclobutylpiperazin-1-yl)-2-oxoethyl]-1,2,3,4-tetrahydroisoquinolin-6-yl}pyrimidin-2(1H)-one | 1.02 (1) | 408.12 | * |
| 214 | | 1-(6-chloropyridazin-3-yl)-5-[2-(4-cyclobutylpiperazin-1-yl)-2-oxoethyl]-4,5,6,7-tetrahydro-1H-pyrazolo[4,3-c]pyridine | 0.44 (3) | 416.24 | * |
| 215 | | 6-{5-[2-(4-cyclobutylpiperazin-1-yl)-2-oxoethyl]-4,5,6,7-tetrahydro-1H-pyrazolo[4,3-c]pyridin-1-yl}pyridazine-3-carbonitrile | 1.07 (1) | 407.12 | * |
| 216 | | 1-(6-{5-[2-(4-cyclobutylpiperazin-1-yl)-2-oxoethyl]-4,5,6,7-tetrahydro-1H-pyrazolo[4,3-c]pyridin-1-yl}pyridazin-3-yl)ethanone | 0.44 (3) | 424.30 | * |

TABLE II-continued

| Compound | Name | RT | MS | K$_i$ |
|---|---|---|---|---|
| 217 | 2-[2-(4-cyclobutylpiperazin-1-yl)-2-oxoethyl]-6-(4-methyl-1H-pyrazol-1-yl)-1,2,3,4-tetrahydroisoquinoline | 1 (3) | 394.20 | * |
| 218 | 6-{2-[4-(2-methylcyclopentyl)piperazin-1-yl]-2-oxoethyl}-2-pyrrolidin-1-yl-5,6,7,8-tetrahydropyrido[4,3-d]pyrimidine | 0.73 (3) | 413.34 | * |
| 219 | 1-{2-[2-(4-cyclobutylpiperazin-1-yl)-2-oxoethyl]-1,2,3,4-tetrahydroisoquinolin-6-yl}ethanol | 1.08 (1) | 358.14 | * |
| 220 | 7-[2-(4-cyclobutylpiperazin-1-yl)-2-oxoethyl]-3-morpholin-4-yl-5,6,7,8-tetrahydropyrido[3,4-c]pyridazine | 1.02 (1) | 401.15 | * |
| 221 | 7-[2-(4-cyclobutylpiperazin-1-yl)-2-oxoethyl]-3-pyrrolidin-1-yl-5,6,7,8-tetrahydropyrido[3,4-c]pyridazine | 1.0 (1) | 385.16 | * |
| 222 | 6-[2-(4-cyclobutylpiperazin-1-yl)-2-oxoethyl]-2-piperidin-1-yl-5,6,7,8-tetrahydro-1,6-naphthyridine | 1.18 (1) | 398.17 | * |

TABLE II-continued

| Compound | | Name | RT | MS | $K_i$ |
|---|---|---|---|---|---|
| 223 | | 6-[2-(4-cyclobutylpiperazin-1-yl)-2-oxoethyl]-2-(2-methylpyrrolidin-1-yl)-5,6,7,8-tetrahydro-1,6-naphthyridine | 1.19 (1) | 398.17 | * |
| 224 | | 6-[2-(4-cyclobutylpiperazin-1-yl)-2-oxoethyl]-N,N-dimethyl-5,6,7,8-tetrahydro-1,6-naphthyridin-2-amine | 1.11 (1) | 358.16 | * |
| 225 | | 6-[2-(4-cyclobutylpiperazin-1-yl)-2-oxoethyl]-2-(3-fluoropyrrolidin-1-yl)-5,6,7,8-tetrahydro-1,6-naphthyridine | 1.11 (1) | 402.15 | * |
| 226 | | 1-{6-[2-(4-cyclobutylpiperazin-1-yl)-2-oxoethyl]-5,6,7,8-tetrahydro-1,6-naphthyridin-2-yl}pyrrolidin-3-ol | 1.06 (1) | 400.16 | * |
| 227 | | 6-[2-(4-cyclobutylpiperazin-1-yl)-2-oxoethyl]-2-(1H-pyrrol-1-yl)-5,6,7,8-tetrahydro-1,6-naphthyridine | 0.9 (3) | 380.19 | * |

TABLE II-continued

| Compound | | Name | RT | MS | $K_i$ |
|---|---|---|---|---|---|
| 228 | | 6-[2-(4-cyclobutylpiperazin-1-yl)-2-oxoethyl]-5,6,7,8-tetrahydropyrido[3,4-b]pyrazine | 0.99 (1) | 316.12 | * |
| 229 | | 2-[2-(4-cyclobutylpiperazin-1-yl)-2-oxoethyl]-6-(2H-indazol-2-yl)-1,2,3,4-tetrahydroisoquinoline | 1.07 (3) | 430.30 | * |
| 230 | | 2-[2-(4-cyclobutylpiperazin-1-yl)-2-oxoethyl]-6-(1H-indazol-1-yl)-1,2,3,4-tetrahydroisoquinoline | 1.08 (3) | 430.19 | * |
| 231 | | 2-[2-(4-cyclobutylpiperazin-1-yl)-2-oxoethyl]-6-imidazo[1,2-a]pyridin-6-yl-1,2,3,4-tetrahydroisoquinoline | 1.12 (1) | 430.13 | * |
| 232 | | 7-[2-(4-cyclobutylpiperazin-1-yl)-2-oxoethyl]-3-pyrimidin-5-yl-5,6,7,8-tetrahydropyrido[3,4-c]pyridazine | 0.99 (1) | 394.17 | * |
| 233 | | 7-[2-(4-cyclobutylpiperazin-1-yl)-2-oxoethyl]-3-(3-fluorophenyl)-5,6,7,8-tetrahydropyrido[3,4-c]pyridazine | 0.82 (3) | 410.23 | * |
| 234 | | 5-[2-(4-cyclobutylpiperazin-1-yl)-2-oxoethyl]-1-(4-fluorophenyl)-4,5,6,7-tetrahydro-1H-pyrazolo[4,3-c]pyridine | 0.47 (3) | 398.23 | * |

TABLE II-continued

| Compound | | Name | RT | MS | $K_i$ |
|---|---|---|---|---|---|
| 235 | | 5-[2-(4-cyclobutylpiperazin-1-yl)-2-oxoethyl]-1-(3-fluorophenyl)-4,5,6,7-tetrahydro-1H-pyrazolo[4,3-c]pyridine | 0.51 (3) | 398.23 | * |
| 236 | | 5-[2-(4-cyclobutylpiperazin-1-yl)-2-oxoethyl]-2-(4-fluorophenyl)-4,5,6,7-tetrahydro-2H-pyrazolo[4,3-c]pyridine | 0.84 (3) | 398.23 | * |
| 237 | | 5-[2-(4-cyclobutylpiperazin-1-yl)-2-oxoethyl]-2-[4-(trifluoromethyl)phenyl]-4,5,6,7-tetrahydro-2H-pyrazolo[4,3-c]pyridine | 1.04 (3) | 448.22 | * |
| 238 | | 5-[2-(4-cyclobutylpiperazin-1-yl)-2-oxoethyl]-2-(4-methoxyphenyl)-4,5,6,7-tetrahydro-2H-pyrazolo[4,3-c]pyridine | 0.9 (3) | 410.25 | * |
| 239 | | 6-[2-(4-cyclobutylpiperazin-1-yl)-2-oxoethyl]-8,8-dimethyl-2-morpholin-4-yl-5,6,7,8-tetrahydropyrido[4,3-d]pyrimidine | 0.93 (3) | 429.29 | * |
| 240 | | 6-[2-(4-cyclobutylpiperazin-1-yl)-2-oxoethyl]-2-morpholin-4-yl-5,6,7,8-tetrahydropyrido[3,4-b]pyrazine | 1.06 (1) | 401.21 | * |

TABLE II-continued

| Compound | | Name | RT | MS | $K_i$ |
|---|---|---|---|---|---|
| 241 | | 6-[2-(4-cyclobutylpiperazin-1-yl)-2-oxoethyl]-3-morpholin-4-yl-5,6,7,8-tetrahydropyrido[3,4-b]pyrazine | 1.01 (1) | 401.19 | * |
| 242 | | 6-[2-(4-cyclobutylpiperazin-1-yl)-2-oxoethyl]-2-(3,3-difluoropyrrolidin-1-yl)-5,6,7,8-tetrahydro-1,6-naphthyridine | 1.14 (1) | 420.18 | * |
| 243 | | 1-{2-[2-(4-cyclobutylpiperazin-1-yl)-2-oxoethyl]-1,2,3,4-tetrahydroisoquinolin-6-yl}-1H-pyrazole-4-carboxamide | 1.05 (1) | 423.18 | * |
| 244 | | 1-{2-[2-(4-cyclobutylpiperazin-1-yl)-2-oxoethyl]-1,2,3,4-tetrahydroisoquinolin-6-yl}-1H-pyrazole-4-carbonitrile | 0.6 (3) | 405.24 | * |
| 245 | | 6-[2-(4-cyclobutylpiperazin-1-yl)-2-oxoethyl]-N-ethyl-N-methyl-5,6,7,8-tetrahydro-1,6-naphthyridin-2-amine | 1.14 (1) | 372.20 | * |

TABLE II-continued

| Compound | Name | RT | MS | K$_i$ |
|---|---|---|---|---|
| 246 | 6-[2-(4-cyclobutylpiperazin-1-yl)-2-oxoethyl]-N,N-dimethyl-5,6,7,8-tetrahydropyrido[4,3-d]pyrimidin-2-amine | 1.09 (1) | 359.15 | * |
| 247 | 6-[2-(4-cyclobutylpiperazin-1-yl)-2-oxoethyl]-2-phenyl-5,6,7,8-tetrahydropyrido[4,3-d]pyrimidine | 0.92 (3) | 392.22 | * |
| 248 | 5-[2-(4-cyclobutylpiperazin-1-yl)-2-oxoethyl]-2-pyrimidin-2-yl-4,5,6,7-tetrahydro-2H-pyrazolo[4,3-c]pyridine | 1.04 (1) | 382.12 | * |
| 249 | 1-{2-[2-(4-cyclobutylpiperazin-1-yl)-2-oxoethyl]-1,2,3,4-tetrahydroisoquinolin-6-yl}acetone | 1.08 (1) | 370.12 | * |
| 250 | 1-{2-[2-(4-cyclobutylpiperazin-1-yl)-2-oxoethyl]-1,2,3,4-tetrahydroisoquinolin-6-yl}propan-2-ol | 0.44 (3) | 372.25 | * |
| 251 | 5-[2-(4-cyclobutylpiperazin-1-yl)-2-oxoethyl]-1-pyrimidin-5-yl-4,5,6,7-tetrahydro-1H-pyrazolo[4,3-c]pyridine | 1.02 (1) | 382.11 | * |

TABLE II-continued

| Compound | | Name | RT | MS | $K_i$ |
|---|---|---|---|---|---|
| 252 | | 5-[2-(4-cyclobutylpiperazin-1-yl)-2-oxoethyl]-2-pyrimidin-5-yl-4,5,6,7-tetrahydro-2H-pyrazolo[4,3-c]pyridine | 1.02 (1) | 382.11 | * |
| 253 | | 1-{2-[2-(4-cyclobutylpiperazin-1-yl)-2-oxoethyl]-1,2,3,4-tetrahydroisoquinolin-6-yl}ethanol | 1.07 (1) | 358.14 | * |
| 254 | | 1-{2-[2-(4-cyclobutylpiperazin-1-yl)-2-oxoethyl]-1,2,3,4-tetrahydroisoquinolin-6-yl}ethanol | 1.07 (1) | 358.12 | * |
| 255 | | 5-[2-(4-cyclobutylpiperazin-1-yl)-2-oxoethyl]-2-pyridazin-3-yl-4,5,6,7-tetrahydro-2H-pyrazolo[4,3-c]pyridine | 1.03 (1) | 382.14 | * |
| 256 | | 5-[2-(4-cyclobutylpiperazin-1-yl)-2-oxoethyl]-2-(2-methoxypyrimidin-5-yl)-4,5,6,7-tetrahydro-2H-pyrazolo[4,3-c]pyridine | 1.05 (1) | 412.14 | * |
| 257 | | 5-[2-(4-cyclobutylpiperazin-1-yl)-2-oxoethyl]-1-(2-methoxypyrimidin-5-yl)-4,5,6,7-tetrahydro-1H-pyrazolo[4,3-c]pyridine | 1.04 (1) | 412.14 | * |

TABLE II-continued

| Compound | Name | RT | MS | K_i |
|---|---|---|---|---|
| 258 | 5-[2-(4-cyclobutylpiperazin-1-yl)-2-oxoethyl]-2-(6-pyrrolidin-1-ylpyridazin-3-yl)-4,5,6,7-tetrahydro-2H-pyrazolo[4,3-c]pyridine | 1.1 (1) | 451.19 | * |
| 259 | 6-{5-[2-(4-cyclobutylpiperazin-1-yl)-2-oxoethyl]-4,5,6,7-tetrahydro-2H-pyrazolo[4,3-c]pyridin-2-yl}-N,N-dimethylpyridazin-3-amine | 1.07 (1) | 425.18 | * |
| 260 | 5-[2-(4-cyclobutylpiperazin-1-yl)-2-oxoethyl]-2-(6-cyclopropylpyridazin-3-yl)-4,5,6,7-tetrahydro-2H-pyrazolo[4,3-c]pyridine | 0.83 (3) | 422.22 | * |
| 261 | 5-(8 2-(4-cyclobutylpiperazin-1-yl)-2-oxoethyl]1-2-(5-methylpyridin-2-yl)-4,5,6,7-tetrahydro-2H-pyrazolo[4,3-c]pyridine | 0.91 (3) | 395.23 | * |
| 262 | 5-{5-[2-(4-cyclobutylpiperazin-1-yl)-2-oxoethyl]-4,5,6,7-tetrahydro-2H-pyrazolo[4,3-c]pyridin-2-yl}-1-methylpyridin-2(1H)-one | 1.01 (1) | 411.11 | * |
| 263 | 5-{5-[2-(4-cyclobutylpiperazin-1-yl)-2-oxoethyl]-4,5,6,7-tetrahydro-1H-pyrazolo[4,3-c]pyridin-1-yl}-1-methylpyridin-2(1H)-one | 1 (1) | 411.11 | * |

TABLE II-continued

| Compound | Name | RT | MS | $K_i$ |
|---|---|---|---|---|
| 264 | 6-[2-(4-cyclobutylpiperazin-1-yl)-2-oxoethyl]-2-(6-methylpyridazin-3-yl)-4,5,6,7-tetrahydro-2H-pyrazolo[3,4-c]pyridine | 1.06 (1) | 396.12 | * |
| 265 | 5-[2-(4-cyclobutylpiperazin-1-yl)-2-oxoethyl]-4,5,6,7-tetrahydrothieno[3,2-c]pyridine | 1.13 (1) | 320.08 | * |
| 266 | 5-{2-[2-(4-cyclobutylpiperazin-1-yl)-2-oxoethyl]-1,2,3,4-tetrahydroisoquinolin-6-yl}-1-methylpyrimidin-2(1H)-one | 1.03 (1) | 422.12 | * |
| 267 | 2-(6-chloropyrazin-2-yl)-5-[2-(4-cyclobutylpiperazin-1-yl)-2-oxoethyl]-4,5,6,7-tetrahydro-2H-pyrazolo[4,3-c]pyridine | 0.56 (3) | 416.13 | * |
| 268 | 5-[2-(4-cyclobutylpiperazin-1-yl)-2-oxoethyl]-2-(6-pyrrolidin-1-ylpyrazin-2-yl)-4,5,6,7-tetrahydro-2H-pyrazolo[4,3-c]pyridine | 1.04 (3) | 451.24 | * |
| 269 | 5-[2-(4-cyclobutylpiperazin-1-yl)-2-oxoethyl]-2-pyrimidin-5-yl-4,5,6,7-tetrahydrothieno[3,2-c]pyridine | 0.32 (3) | 398.17 | * |

TABLE II-continued

| Compound | Name | RT | MS | K$_i$ |
|---|---|---|---|---|
| 270 | 5-{5-[2-(4-cyclobutylpiperazin-1-yl)-2-oxoethyl]-4,5,6,7-tetrahydrothieno[3,2-c]pyridin-2-yl}-1-methylpyridin-2(1H)-one | 0.37 (3) | 427.19 | * |
| 271 | 6-{5-[2-(4-cyclobutylpiperazin-1-yl)-2-oxoethyl]-4,5,6,7-tetrahydro-2H-pyrazolo[4,3-c]pyridin-2-yl}pyrazine-2-carbonitrile | 0.32 (3) | 407.21 | * |
| 272 | 5-[2-(4-cyclobutylpiperazin-1-yl)-2-oxoethyl]-2-(6-cyclopropylpyrazin-2-yl)-4,5,6,7-tetrahydro-2H-pyrazolo[4,3-c]pyridine | 0.98 (3) | 422.24 | * |
| 273 | 2-(5-bromopyridin-2-yl)-5-[2-(4-cyclobutylpiperazin-1-yl)-2-oxoethyl]-3-methyl-4,5,6,7-tetrahydro-2H-pyrazolo[4,3-c]pyridine | 1.05 (3) | 473.06 | * |
| 274 | 6-{5-[2-(4-cyclobutylpiperazin-1-yl)-2-oxoethyl]-3-methyl-4,5,6,7-tetrahydro-2H-pyrazolo[4,3-c]pyridin-2-yl}nicotinonitrile | 0.64 (3) | 420.20 | * |
| 275 | 6-[2-(4-cyclobutylpiperazin-1-yl)-2-oxoethyl]-2-(1H-pyrazol-1-yl)-5,6,7,8-tetrahydropyrido[4,3-d]pyrimidine | 1.06 (1) | 382.10 | * |

TABLE II-continued

| Compound | | Name | RT | MS | $K_i$ |
|---|---|---|---|---|---|
| 276 | | 6-[2-(4-cyclobutylpiperazin-1-yl)-2-oxoethyl]-2-cyclopropyl-5,6,7,8-tetrahydropyrido[4,3-d]pyrimidine | 1.07 (1) | 356.12 | * |
| 277 | | 2-tert-butyl-6-[2-(4-cyclobutylpiperazin-1-yl)-2-oxoethyl]-5,6,7,8-tetrahydropyrido[4,3-d]pyrimidine | 0.86 (3) | 372.27 | * |
| 278 | | 6-{2-[2-(4-cyclobutylpiperazin-1-yl)-2-oxoethyl]-1,2,3,4-tetrahydroisoquinolin-6-yl}-1-methylpyridin-2(1H)-one | 0.43 (3) | 421.24 | * |
| 279 | | 5-[2-(4-cyclobutylpiperazin-1-yl)-2-oxoethyl]-2-pyridazin-3-yl-4,5,6,7-tetrahydro[1,3]thiazolo[5,4-c]pyridine | 1.03 (1) | 399.04 | * |
| 280 | | 5-{2-[2-(4-cyclobutylpiperazin-1-yl)-2-oxoethyl]-1,2,3,4-tetrahydroisoquinolin-6-yl}-1-ethylpyridin-2(1H)-one | 0.82 (3) | 435.22 | * |
| 281 | | 5-{2-[2-(4-cyclobutylpiperazin-1-yl)-2-oxoethyl]-1,2,3,4-tetrahydroisoquinolin-6-yl}-1-propylpyridin-2(1H)-one | 0.98 (3) | 449.23 | * |

TABLE II-continued

| Compound | Name | RT | MS | K$_i$ |
|---|---|---|---|---|
| 282 | 5-{2-[2-(4-cyclobutylpiperazin-1-yl)-2-oxoethyl]-1,2,3,4-tetrahydroisoquinolin-6-yl}-1-isopropylpyridin-2(1H)-one | 0.96 (3) | 449.21 | * |
| 283 | 5-{2-[2-(4-cyclobutylpiperazin-1-yl)-2-oxoethyl]-1,2,3,4-tetrahydroisoquinolin-6-yl}-1-(2,2,2-trifluoroethyl)pyridin-2(1H)-one | 0.98 (3) | 489.17 | * |
| 284 | 6-[2-(4-cyclobutylpiperazin-1-yl)-2-oxoethyl]-1-(6-methylpyridazin-3-yl)-4,5,6,7-tetrahydro-1H-pyrazolo[3,4-c]pyridine | 0.36 (3) | 396.25 | * |
| 285 | 5-[2-(4-cyclobutylpiperazin-1-yl)-2-oxoethyl]-1-pyridazin-3-yl-4,5,6,7-tetrahydro-1H-pyrazolo[4,3-c]pyridine | 1.04 (1) | 382.10 | * |
| 286 | 6-[2-(4-cyclobutylpiperazin-1-yl)-2-oxoethyl]-2-(methoxymethyl)-5,6,7,8-tetrahydropyrido[4,3-d]pyrimidine | 1 (1) | 360.13 | * |
| 287 | 2-(5-bromopyrimidin-2-yl)-5-[2-(4-cyclobutylpiperazin-1-yl)-2-oxoethyl]-4,5,6,7-tetrahydro-2H-pyrazolo[4,3-c]pyridine | 0.39 (3) | 460.22 | * |

TABLE II-continued

| Compound | Name | RT | MS | $K_i$ |
|---|---|---|---|---|
| 288 | 5-[2-(4-cyclobutylpiperazin-1-yl)-2-oxoethyl]-1-(6-methylpyridazin-3-yl)-4,5,6,7-tetrahydro-1H-pyrazolo[4,3-c]pyridine | 1.07 (1) | 396.11 | * |
| 289 | 5-[2-(4-cyclobutylpiperazin-1-yl)-2-oxoethyl]-2-(5-methylpyrimidin-2-yl)-4,5,6,7-tetrahydro-2H-pyrazolo[4,3-c]pyridine | 1.07 (1) | 396.12 | * |
| 290 | 5-[2-(4-cyclobutylpiperazin-1-yl)-2-oxoethyl]-1-(6-methoxypyridazin-3-yl)-4,5,6,7-tetrahydro-1H-pyrazolo[4,3-c]pyridine | 0.37 (3) | 412.29 | * |
| 291 | 6-{5-[2-(4-cyclobutylpiperazin-1-yl)-2-oxoethyl]-4,5,6,7-tetrahydro-1H-pyrazolo[4,3-c]pyridin-1-yl}pyridazin-3-ol | 1 (1) | 398.11 | * |

TABLE II-continued

| Compound | Name | RT | MS | $K_i$ |
|---|---|---|---|---|
| 292 | 6-[2-(4-cyclobutylpiperazin-1-yl)-2-oxoethyl]-2-(trifluoromethyl)-5,6,7,8-tetrahydropyrido[4,3-d]pyrimidine | 1.09 (1) | 384.08 | * |
| 293 | 5-[2-(4-cyclobutylpiperazin-1-yl)-2-oxoethyl]-2-methyl-4,5,6,7-tetrahydro-2H-pyrazolo[4,3-c]pyridine | 1.01 (1) | 318.21 | * |
| 294 | 5-[2-(4-cyclobutylpiperazin-1-yl)-2-oxoethyl]-2-phenyl-4,5,6,7-tetrahydro[1,3]thiazolo[5,4-c]pyridine | 1.03 (2) | 397.16 | * |
| 295 | 2-(3-chlorophenyl)-5-[2-(4-cyclobutylpiperazin-1-yl)-2-oxoethyl]-4,5,6,7-tetrahydro[1,3]thiazolo[5,4-c]pyridine | 1.09 (2) | 431.11 | * |
| 296 | 2-(4-chlorophenyl)-5-[2-(4-cyclobutylpiperazin-1-yl)-2-oxoethyl]-4,5,6,7-tetrahydro[1,3]thiazolo[5,4-c]pyridine | 1.09 (2) | 431.11 | * |

TABLE II-continued

| Compound | Name | RT | MS | $K_i$ |
|---|---|---|---|---|
| 297 | 5-[2-(4-cyclobutylpiperazin-1-yl)-2-oxoethyl]-2-(4-fluorophenyl)-4,5,6,7-tetrahydro[1,3]thiazolo[5,4-c]pyridine | 1.04 (2) | 415.14 | * |
| 298 | 5-[2-(4-cyclobutylpiperazin-1-yl)-2-oxoethyl]-2-(3-fluorophenyl)-4,5,6,7-tetrahydro[1,3]thiazolo[5,4-c]pyridine | 1.04 (2) | | * |
| 299 | 5-[2-(4-cyclobutylpiperazin-1-yl)-2-oxoethyl]-2-(2-fluorophenyl)-4,5,6,7-tetrahydro[1,3]thiazolo[5,4-c]pyridine | 1.05 (2) | 415.14 | * |
| 300 | 5-[2-(4-cyclobutylpiperazin-1-yl)-2-oxoethyl]-2-(2-naphthyl)-4,5,6,7-tetrahydro[1,3]thiazolo[5,4-c]pyridine | 1.11 (2) | 447.15 | * |
| 301 | 5-[2-(4-cyclobutylpiperazin-1-yl)-2-oxoethyl]-2-(2-fluoro-4-methylphenyl)-4,5,6,7-tetrahydro[1,3]thiazolo[5,4-c]pyridine | 1.08 (2) | 429.15 | * |

TABLE II-continued

| Compound | Name | RT | MS | $K_i$ |
|---|---|---|---|---|
| 302 | 5-[2-(4-cyclobutylpiperazin-1-yl)-2-oxoethyl]-2-(2-fluoro-5-methylphenyl)-4,5,6,7-tetrahydro[1,3]thiazolo[5,4-c]pyridine | 1.08 (2) | 429.15 | * |
| 303 | 5-[2-(4-cyclobutylpiperazin-1-yl)-2-oxoethyl]-2-(4-fluoro-3-methylphenyl)-4,5,6,7-tetrahydro[1,3]thiazolo[5,4-c]pyridine | 1.1 (2) | 429.15 | * |
| 304 | 5-[2-(4-cyclobutylpiperazin-1-yl)-2-oxoethyl]-2-(3-methylphenyl)-4,5,6,7-tetrahydro[1,3]thiazolo[5,4-c]pyridine | 1.08 (2) | 411.17 | * |
| 305 | 5-[2-(4-cyclobutylpiperazin-1-yl)-2-oxoethyl]-2-(4-methylphenyl)-4,5,6,7-tetrahydro[1,3]thiazolo[5,4-c]pyridine | 1.08 (2) | 411.17 | * |
| 306 | 5-[2-(4-cyclobutylpiperazin-1-yl)-2-oxoethyl]-2-(3-isopropylphenyl)-4,5,6,7-tetrahydro[1,3]thiazolo[5,4-c]pyridine | 1.14 (2) | 439.19 | * |

TABLE II-continued

| Compound | Name | RT | MS | K<sub>i</sub> |
|---|---|---|---|---|
| 307 | 5-[2-(4-cyclobutylpiperazin-1-yl)-2-oxoethyl]-2-(4-isopropylphenyl)-4,5,6,7-tetrahydro[1,3]thiazolo[5,4-c]pyridine | 1.14 (2) | 439.18 | * |
| 308 | 5-[2-(4-cyclobutylpiperazin-1 yl)-2-oxoethyl]-2-(3,4-dimethylphenyl)-4,5,6,7-tetrahydro[1,3]thiazolo[5,4-c]pyridine | 1.11 (2) | 425.18 | * |
| 309 | 2-(4-butylphenyl)-5-[2-(4-cyclobutylpiperazin-1-yl)-2-oxoethyl]-4,5,6,7-tetrahydro[1,3]thiazolo[5,4-c]pyridine | 1.18 (2) | 453.20 | * |
| 310 | 5-[2-(4-cyclobutylpiperazin-1-yl)-2-oxoethyl]-2-(3,5-dimethylphenyl)-4,5,6,7-tetrahydro[1,3]thiazolo[5,4-c]pyridine | 1.12 (2) | 425.18 | * |
| 311 | 5-[2-(4-cyclobutylpiperazin-1-yl)-2-oxoethyl]-2-(4-ethylphenyl)-4,5,6,7-tetrahydro[1,3]thiazolo[5,4-c]pyridine | 1.12 (2) | 425.18 | * |

TABLE II-continued

| Compound | Name | RT | MS | K$_i$ |
|---|---|---|---|---|
| 312 | 5-[2-(4-cyclobutylpiperazin-1-yl)-2-oxoethyl]-2-(4-propylphenyl)-4,5,6,7-tetrahydro[1,3]thiazolo[5,4-c]pyridine | 1.14 (2) | 439.18 | * |
| 313 | 5-[2-(4-cyclobutylpiperazin-1-yl)-2-oxoethyl]-2-(3-ethylphenyl)-4,5,6,7-tetrahydro[1,3]thiazolo[5,4-c]pyridine | 1.11 (2) | 425.18 | * |
| 314 | 2-(4-tert-butylphenyl)-5-[2-(4-cyclobutylpiperazin-1-yl)-2-oxoethyl]-4,5,6,7-tetrahydro[1,3]thiazolo[5,4-c]pyridine | 1.16 (2) | 453.20 | * |
| 315 | 5-[2-(4-cyclobutylpiperazin-1-yl)-2-oxoethyl]-2-(3-methoxyphenyl)-4,5,6,7-tetrahydro[1,3]thiazolo[5,4-c]pyridine | 1.05 (2) | 427.16 | * |
| 316 | 5-[2-(4-cyclobutylpiperazin-1-yl)-2-oxoethyl]-2-[4-(trifluoromethoxy)phenyl]-4,5,6,7-tetrahydro[1,3]thiazolo[5,4-c]pyridine | 1.13 (2) | 481.10 | * |

TABLE II-continued

| Compound | | Name | RT | MS | $K_i$ |
|---|---|---|---|---|---|
| 317 | 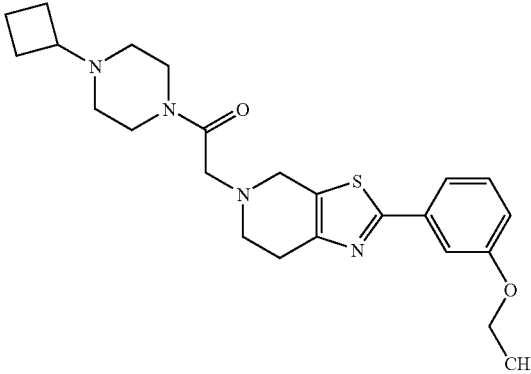 | 5-[2-(4-cyclobutylpiperazin-1-yl)-2-oxoethyl]-2-(3-ethoxyphenyl)-4,5,6,7-tetrahydro[1,3]thiazolo[5,4-c]pyridine | 1.09 (2) | 441.17 | * |
| 318 | 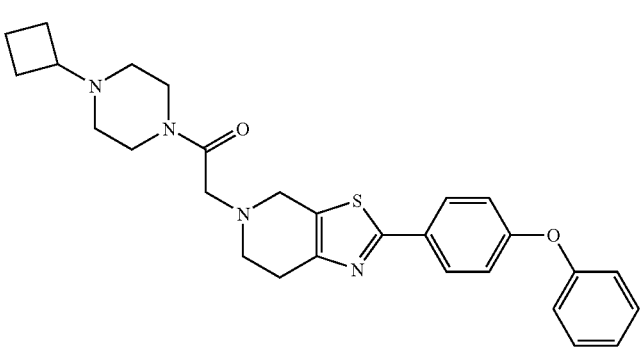 | 5-[2-(4-cyclobutylpiperazin-1-yl)-2-oxoethyl]-2-(4-phenoxyphenyl)-4,5,6,7-tetrahydrol[1,3]thiazolo[5,4-c]pyridine | 1.15 (2) | 489.15 | * |
| 319 | 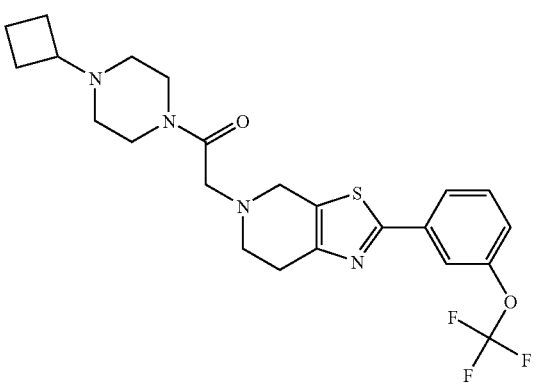 | 5-[2-(4-cyclobutylpiperazin-1-yl)-2-oxoethyl]-2-[3-(trifluoromethoxy)phenyl]-4,5,6,7-tetrahydro[1,3]thiazolo[5,4-c]pyridine | 1.13 (2) | 481.10 | * |
| 320 | 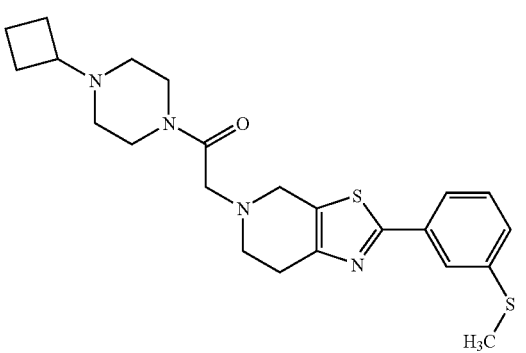 | 5-[2-(4-cyclobutylpiperazin-1-yl)-2-oxoethyl]-2-[3-(methylthio)phenyl]-4,5,6,7-tetrahydro[1,3]thiazolo[5,4-c]pyridine | 1.09 (2) | 443.14 | * |

TABLE II-continued

| Compound | Name | RT | MS | K$_i$ |
|---|---|---|---|---|
| 321 | 5-[2-(4-cyclobutylpiperazin-1-yl)-2-oxoethyl]-2-(4'-methoxybiphenyl-4-yl)-4,5,6,7-tetrahydro[1,3]thiazolo[5,4-c]pyridine | 1.16 (2) | 503.16 | * |
| 322 | 5-[2-(4-cyclobutylpiperazin-1-yl)-2-oxoethyl]-2-(3-fluoro-4-methoxyphenyl)-4,5,6,7-tetrahydro[1,3]thiazolo[5,4-c]pyridine | 1.05 (2) | 445.15 | * |
| 323 | 5-[2-(4-cyclobutylpiperazin-1-yl)-2-oxoethyl]-2-(2,5-difluoro-4-methoxyphenyl)-4,5,6,7-tetrahydro[1,3]thiazolo[5,4-c]pyridine | 1.06 (2) | 463.14 | * |
| 324 | 5-[2-(4-cyclobutylpiperazin-1-yl)-2-oxoethyl]-2-(6-methoxy-2-naphthyl)-4,5,6,7-tetrahydro[1,3]thiazolo[5,4-c]pyridine | 1.15 (2) | 477.16 | * |
| 325 | 5-[2-(4-cyclobutylpiperazin-1-yl)-2-oxoethyl]-2-(3-isopropoxyphenyl)-4,5,6,7-tetrahydro[1,3]thiazolo[5,4-c]pyridine | 1.11 (2) | 455.19 | * |

TABLE II-continued

| Compound | Name | RT | MS | K$_i$ |
|---|---|---|---|---|
| 326 | 5-[2-(4-cyclobutylpiperazin-1-yl)-2-oxoethyl]-2-(3,4,5-trimethoxyphenyl)-4,5,6,7-tetrahydro[1,3]thiazolo[5,4-c]pyridine | 1.04 (2) | 487.16 | * |
| 327 | 5-[2-(4-cyclobutylpiperazin-1-yl)-2-oxoethyl]-2-(4-methoxyphenyl)-4,5,6,7-tetrahydro[1,3]thiazolo[5,4-c]pyridine | 1.05 (2) | 427.16 | * |
| 328 | 2-(1,3-benzodioxol-5-yl)-5-[2-(4-cyclobutylpiperazin-1-yl)-2-oxoethyl]-4,5,6,7-tetrahydro[1,3]thiazolo[5,4-c]pyridine | 1.04 (2) | 441.14 | * |
| 329 | 5-[2-(4-cyclobutylpiperazin-1-yl)-2-oxoethyl]-2-(3,4-dimethoxyphenyl)-4,5,6,7-tetrahydro[1,3]thiazolo[5,4-c]pyridine | 1.02 (2) | 457.17 | * |
| 330 | 5-[2-(4-cyclobutylpiperazin-1-yl)-2-oxoethyl]-2-(4-ethoxyphenyl)-4,5,6,7-tetrahydro[1,3]thiazolo[5,4-c]pyridine | 1.08 (2) | 441.17 | * |

TABLE II-continued

| Compound | Name | RT | MS | $K_i$ |
|---|---|---|---|---|
| 331 | 4-{5-[2-(4-cyclobutylpiperazin-1-yl)-2-oxoethyl]-4,5,6,7-tetrahydro[1,3]thiazolo[5,4-c]pyridin-2-yl}-N,N-dimethylaniline | 1.04 (2) | 440.22 | * |
| 332 | 5-[2-(4-cyclobutylpiperazin-1-yl)-2-oxoethyl]-2-(2,3-dihydro-1,4-benzodioxin-6-yl)-4,5,6,7-tetrahydro[1,3]thiazolo[5,4-c=pyridine | 1.04 (2) | 455.15 | * |
| 333 | 5-[2-(4-cyclobutylpiperazin-1-yl)-2-oxoethyl]-2-(4-methoxy-3-methylphenyl)-4,5,6,7-tetrahydro[1,3]thiazolo[5,4-c]pyridine | 1.1 (2) | 441.17 | * |
| 334 | 5-[2-(4-cyclobutylpiperazin-1-yl)-2-oxoethyl]-2-(4-propoxyphenyl)-4,5,6,7-tetrahydro[1,3]thiazolo[5,4-c]pyridine | 1.12 (2) | 455.18 | * |
| 335 | 5-[2-(4-cyclobutylpiperazin-1-yl)-2-oxoethyl]-2-(4-methoxy-2-methylphenyl)-4,5,6,7-tetrahydro[1,3]thiazolo[5,4-c]pyridine | 1.06 (2) | 441.17 | * |

TABLE II-continued

| Compound | | Name | RT | MS | $K_i$ |
|---|---|---|---|---|---|
| 336 | 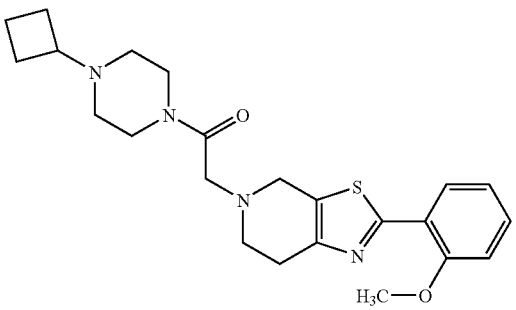 | 5-[2-(4-cyclobutylpiperazin-1-yl)-2-oxoethyl]-2-(2-methoxyphenyl)-4,5,6,7-tetrahydro[1,3]thiazolo[5,4-c]pyridine | 1.05 (2) | 427.17 | * |
| 337 | 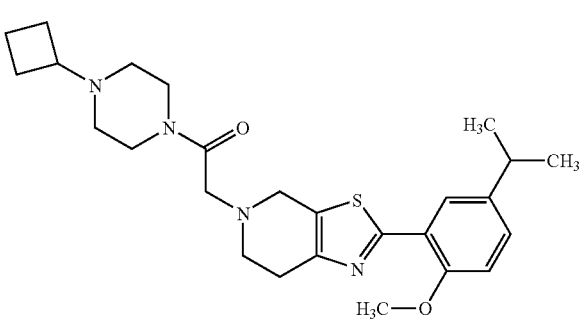 | 5-[2-(4-cyclobutylpiperazin-1-yl)-2-oxoethyl]-2-(5-isopropyl-2-methoxyphenyl)-4,5,6,7-tetrahydro[1,3]thiazolo[5,4-c]pyridine | 1.15 (2) | 469.19 | † |
| 338 | 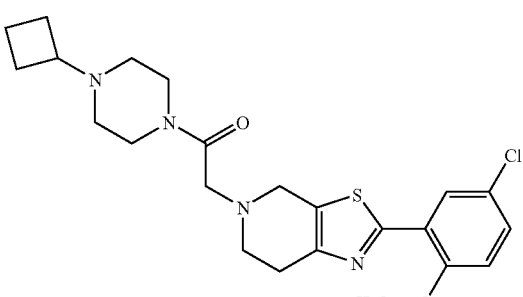 | 2-(5-chloro-2-methoxyphenyl)-5-[2-(4-cyclobutylpiperazin-1-yl)-2-oxoethyl]-4,5,6,7-tetrahydro[1,3]thiazolo[5,4-c]pyridine | 1.1 (2) | 461.12 | * |
| 339 | 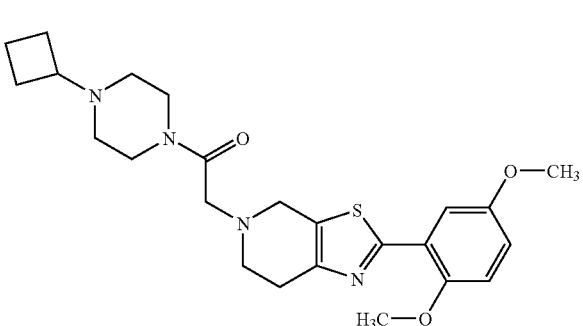 | 5-[2-(4-cyclobutylpiperazin-1-yl)-2-oxoethy]-2-(2,5-dimethoxyphenyl)-4,5,6,7-tetrahydro[1,3]thiazolo[5,4-c]pyridine | 1.06 (2) | 457.16 | * |
| 340 | 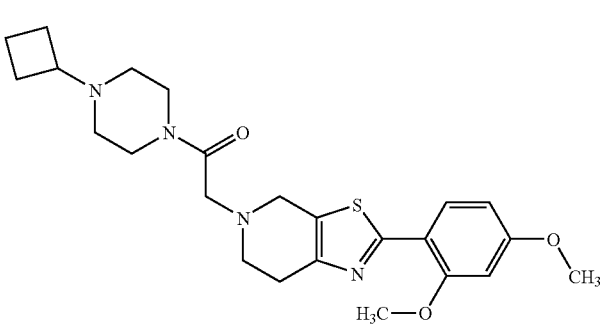 | 5-[2-(4-cyclobutylpiperazin-1-yl)-2-oxoethyl]-2-(2,4-dimethoxyphenyl)-4,5,6,7-tetrahydro[1,3]thiazolo[5,4-c]pyridine | 1.06 (2) | 457.18 | * |

TABLE II-continued

| Compound | | Name | RT | MS | K$_i$ |
|---|---|---|---|---|---|
| 341 | 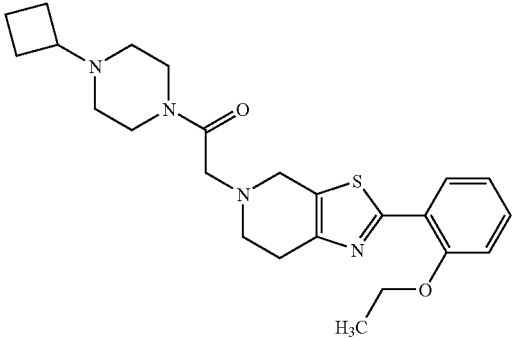 | 5-[2-(4-cyclobutylpiperazin-1-yl)-2-oxoethyl]-2-(2-ethoxyphenyl)-4,5,6,7-tetrahydro[1,3]thiazolo[5,4-c]pyridine | 1.08 (2) | 441.17 | * |
| 342 | 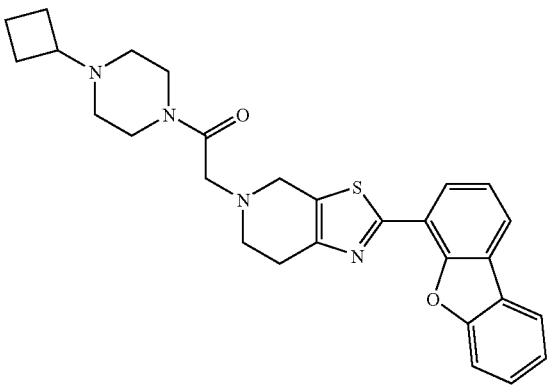 | 5-[2-(4-cyclobutylpiperazin-1-yl)-2-oxoethyl]-2-dibenzo[b,d]furan-4-yl-4,5,6,7-tetrahydro[1,3]thiazolo[5,4-c]pyridine | 1.16 (2) | 487.14 | |
| 343 | 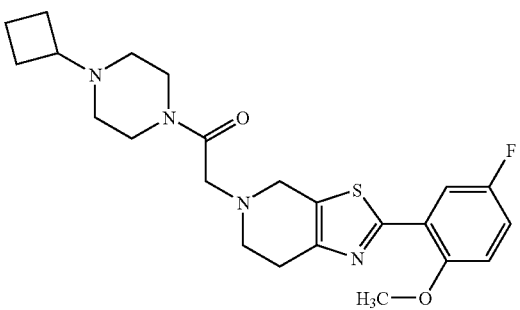 | 5-[2-(4-cyclobutylpiperazin-1-yl)-2-oxoethyl]-2-(5-fluoro-2-methoxyphenyl-4,5,6,7-tetrahydro[1,3]thiazolo[5,4-c]pyridine | 1.07 (2) | 445.15 | † |
| 344 | 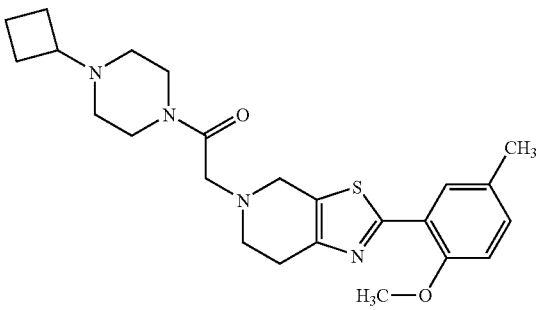 | 5-[2-(4-cyclobutylpiperazin-1-yl)-2-oxoethyl]-2-(2-methoxy-5-methylphenyl)-4,5,6,7-tetrahydro[1,3]thiazolo[5,4-c]pyridine | 1.09 (2) | 441.17 | * |

TABLE II-continued

| Compound | Name | RT | MS | $K_i$ |
|---|---|---|---|---|
| 345 | 5-[2-(4-cyclobutylpiperazin-1-yl)-2-oxoethyl]-2-(2-phenoxyphenyl)-4,5,6,7-tetrahydro[1,3]thiazolo[5,4-c]pyridine | 1.14 (2) | 489.14 | † |
| 346 | 2-(3-chloro-4-fluorophenyl)-5-[2-(4-cyclobutylpiperazin-1-yl)-2-oxoethyl]-4,5,6,7-tetrahydro[1,3]thiazolo[5,4-c]pyridine | 1.1 (2) | 449.09 | * |
| 347 | 5-[2-(4-cyclobutylpiperazin-1-yl)-2-oxoethyl]-2-(2,5-difluorophenyl)-4,5,6,7-tetrahydro[1,3]thiazolo[5,4-c]pyridine | 1.06 (2) | 433.13 | * |
| 348 | 5-[2-(4-cyclobutylpiperazin-1-yl)-2-oxoethyl]-2-(2,4-difluorophenyl)-4,5,6,7-tetrahydro[1,3]thiazolo[5,4-c]pyridine | 1.07 (2) | 433.13 | * |
| 349 | 5-[2-(4-cyclobutylpiperazin-1-yl)-2-oxoethyl]-2-(3,4-difluorophenyl)-4,5,6,7-tetrahydro[1,3]thiazolo[5,4-c]pyridine | 1.07 (2) | 433.13 | * |

TABLE II-continued

| Compound | Name | RT | MS | K$_i$ |
|---|---|---|---|---|
| 350 | 5-[2-(4-cyclobutylpiperazin-1-yl)-2-oxoethyl]-2-(3,5-dichlorophenyl)-4,5,6,7-tetrahydro[1,3]thiazolo[5,4-c]pyridine | 1.15 (2) | 465.07 | * |
| 351 | 2-(4-chloro-2-fluorophenyl)-5-[2-(4-cyclobutylpiperazin-1-yl)-2-oxoethyl]-4,5,6,7-tetrahydro[1,3]thiazolo[5,4-c]pyridine | 1.11 (2) | 449.10 | * |
| 352 | 2-(4-chloro-3-fluorophenyl)-5-[2-(4-cyclobutylpiperazin-1-yl)-2-oxoethyl]-4,5,6,7-tetrahydro[1,3]thiazolo[5,4-c]pyridine | 1.11 (2) | 449.09 | * |
| 353 | 5-[2-(4-cyclobutylpiperazin-1-yl)-2-oxoethyl]-2-(2,6-difluorophenyl)-4,5,6,7-tetrahydro[1,3]thiazolo[5,4-c]pyridine | 1.01 (2) | 433.15 | * |
| 354 | 5-[2-(4-cyclobutylpiperazin-1-yl)-2-oxoethyl]-2-(3,4-dichlorophenyl)-4,5,6,7-tetrahydro[1,3]thiazolo[5,4-c]pyridine | 1.14 (2) | 465.06 | * |

TABLE II-continued

| Compound | | Name | RT | MS | $K_i$ |
|---|---|---|---|---|---|
| 355 | | 5-[2-(4-cyclobutylpiperazin-1-yl)-2-oxoethyl]-2-(3,5-difluorophenyl)-4,5,6,7-tetrahydro[1,3]thiazolo[5,4-c]pyridine | 1.07 (2) | 433.13 | * |
| 356 | | 5-[2-(4-cyclobutylpiperazin-1-yl)-2-oxoethyl]-2-(2,3-difluorophenyl)-4,5,6,7-tetrahydro[1,3]thiazolo[5,4-c]pyridine | 1.06 (2) | 433.14 | * |
| 357 | | 2-(2-chlorophenyl)-5-[2-(4-cyclobutylpiperazin-1-yl)-2-oxoethyl]-4,5,6,7-tetrahydro[1,3]thiazolo[5,4-c]pyridine | 1.06 (2) | 431.13 | * |
| 358 | | 5-[2-(4-cyclobutylpiperazin-1-yl)-2-oxoethyl]-2-(2,3-dichlorophenyl)-4,5,6,7-tetrahydro[1,3]thiazolo[5,4-c]pyridine | 1.12 (2) | 465.08 | * |
| 359 | | 5-[2-(4-cyclobutylpiperazin-1-yl)-2-oxoethyl]-2-(2,4-dichlorophenyl)-4,5,6,7-tetrahydro[1,3]thiazolo[5,4-c]pyridine | 1.13 (2) | 465.07 | * |

TABLE II-continued

| Compound | | Name | RT | MS | $K_i$ |
|---|---|---|---|---|---|
| 360 | 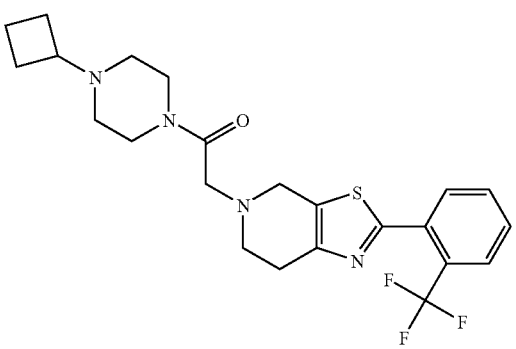 | 5-[2-(4-cyclobutylpiperazin-1-yl)-2-oxoethyl]-2-[2-(trifluoromethyl)phenyl]-4,5,6,7-tetrahydro[1,3]thiazolo[5,4-c]pyridine | 1.07 (2) | 465.13 | * |
| 361 | 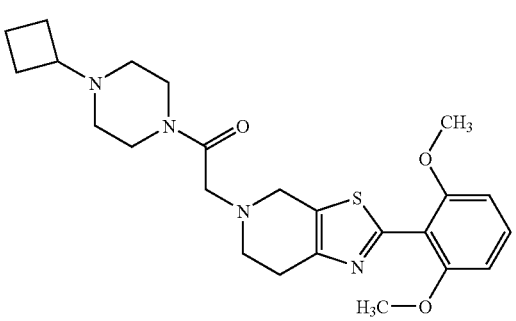 | 5-[2-(4-cyclobutylpiperazin-1-yl)-2-oxoethyl]-2-(2,6-dimethoxyphenyl)-4,5,6,7-tetrahydro[1,3]thiazolo[5,4-c]pyridine | 1.03 (2) | 457.17 | * |
| 362 | 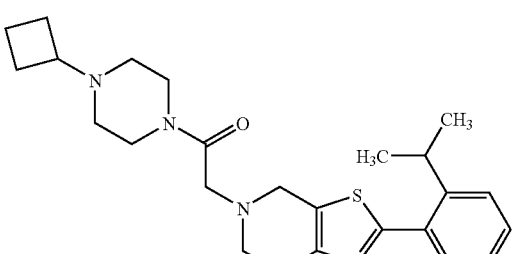 | 5-[2-(4-cyclobutylpiperazin-1-yl)-2-oxoethyl]-2-(2-isopropylphenyl)-4,5,6,7-tetrahydro[1,3]thiazolo[5,4-c]pyridine | 1.12 (2) | 439.21 | * |
| 363 | 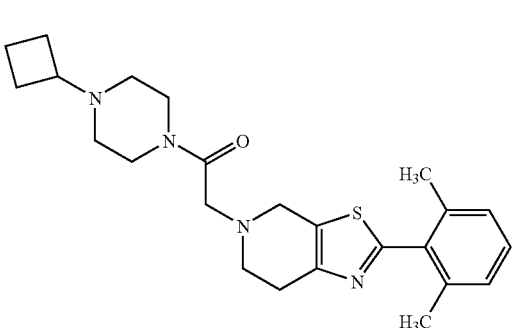 | 5-[2-(4-cyclobutylpiperazin-1-yl)-2-oxoethyl]-2-(2,6-dimethylphenyl)-4,5,6,7-tetrahydro[1,3]thiazolo[5,4-c]pyridine | 1.09 (2) | 425.18 | * |
| 364 | 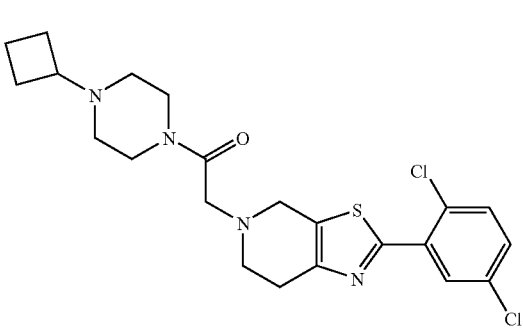 | 5-[2-(4-cyclobutylpiperazin-1-yl)-2-oxoethyl]-2-(2,5-dichlorophenyl)-4,5,6,7-tetrahydro[1,3]thiazolo[5,4-c]pyridine | 1.12 (2) | 465.07 | * |

| Compound | Name | RT | MS | K$_i$ |
|---|---|---|---|---|
| 365 | 2-(2-chloro-6-fluoro-3-methylphenyl)-5-[2-(4-cyclobutylpiperazin-1-yl)-2-oxoethyl]-4,5,6,7-tetrahydro[1,3]thiazolo[5,4-c]pyridine | 1.08 (2) | 463.13 | * |
| 366 | 5-[2-(4-cyclobutylpiperazin-1-yl)-2-oxoethyl]-2-mesityl-4,5,6,7-tetrahydro[1,3]thiazolo[5,4-c]pyridine | 1.12 (2) | 439.19 | * |
| 367 | 3-{5-[2-(4-cyclobutylpiperazin-1-yl)-2-oxoethyl]-4,5,6,7-tetrahydro[1,3]thiazolo[5,4-c]pyridin-2-yl}benzonitrile | 1 (2) | 422.16 | * |
| 368 | 4-{5-[2-(4-cyclobutylpiperazin-1-yl)-2-oxoethyl]-4,5,6,7-tetrahydro[1,3]thiazolo[5,4-c]pyridin-2-yl}benzonitrile | 1 (2) | 422.16 | * |
| 369 | 5-[2-(4-cyclobutylpiperazin-1-yl)-2-oxoethyl]-2-[4-(trifluoromethyl)phenyl]-4,5,6,7-tetrahydro[1,3]thiazolo[5,4-c]pyridine | 1.12 (2) | 465.12 | * |

TABLE II-continued

| Compound | Name | RT | MS | K_i |
|---|---|---|---|---|
| 370 | 1-(3-{5-[2-(4-cyclobutylpiperazin-1-yl)-2-oxoethyl]-4,5,6,7-tetrahydro[1,3]thiazolo[5,4-c]pyridin-2-yl}phenyl)ethanone | 1.02 (2) | 439.16 | * |
| 371 | 2-[3,5-bis(trifluoromethyl)phenyl]-5-[2-(4-cyclobutylpiperazin-1-yl)-2-oxoethyl]-4,5,6,7-tetrahydro[1,3]thiazolo[5,4-c]pyridine | 1.18 (2) | 533.08 | * |
| 372 | 5-[2-(4-cyclobutylpiperazin-1-yl)-2-oxoethyl]-2-[3-(trifluoromethyl)phenyl]-4,5,6,7-tetrahydro[1,3]thiazolo[5,4-c]pyridine | 1.11 (2) | 465.12 | * |
| 373 | 2-[4-chloro-3-(trifluoromethyl)phenyl]-5-[2-(4-cyclobutylpiperazin-1-yl)-2-oxoethyl]-4,5,6,7-tetrahydro[1,3]thiazolo[5,4-c]pyridine | 1.16 (2) | 499.07 | * |

TABLE II-continued

| Compound | Name | RT | MS | K<sub>i</sub> |
|---|---|---|---|---|
| 374 | 2-[2-chloro-5-(trifluoromethyl)phenyl]-5-[2-(4-cyclobutylpiperazin-1-yl)-2-oxoethyl]-4,5,6,7-tetrahydro[1,3]thiazolo[5,4-c]pyridine | 1.13 (2) | 499.07 | * |
| 375 | ethyl 4-{5-[2-(4-cyclobutylpiperazin-1-yl)-2-oxoethyl]-4,5,6,7-tetrahydro[1,3]thiazolo[5,4-c]pyridin-2-yl}benzoate | 1.1 (2) | 469.16 | * |
| 376 | ethyl 3-{5-[2-(4-cyclobutylpiperazin-1-yl)-2-oxoethyl]-4,5,6,7-tetrahydro[1,3]thiazolo[5,4-c]pyridin-2-yl}benzoate | 1.09 (2) | 469.15 | * |
| 377 | 6-(1,3-benzodioxol-5-yl)-2-[2-(4-cyclobutylpiperazin-1-yl)-2-oxoethyl]-1,2,3,4-tetrahydroisoquinoline | 1.25 (1) | 434.24 | * |
| 378 | 6-(1,3-benzodioxol-5-yl)-2-[2-(4-cyclopentylpiperazin-1-yl)-2-oxoethyl]-1,2,3,4-tetrahydroisoquinoline | 1.3 (1) | 448.27 | * |

TABLE II-continued

| Compound | | Name | RT | MS | K$_i$ |
|---|---|---|---|---|---|
| 379 | | 2-[2-(4-cyclopentylpiperazin-1-yl)-2-oxoethyl]-6-dibenzo[b,d]furan-4-yl-1,2,3,4-tetrahydroisoquinoline | 1.13 (3) | 494.32 | † |
| 380 | | 2-[2-(4-cyclobutylpiperazin-1-yl)-2-oxoethyl]-6-(2,3-dihydro-1,4-benzodioxin-6-yl)-1,2,3,4-tetrahydroisoquinoline | 1.23 (1) | 448.29 | * |
| 381 | | 2-[2-(4-cyclopentylpiperazin-1-yl)-2-oxoethyl]-6-(2,3-dihydro-1,4-benzodioxin-6-yl)-1,2,3,4-tetrahydroisoquinoline | 1.04 (2) | 462.36 | * |
| 382 | | 2-[2-(4-isopropylpiperazin-1-yl)-2-oxoethyl]-6-[4-(methylsulfonyl)phenyl]-1,2,3,4-tetrahydroisoquinoline | 0.95 (2) | 456.32 | * |

TABLE II-continued

| Compound | | Name | RT | MS | $K_i$ |
|---|---|---|---|---|---|
| 383 | | 2-[2-(4-sec-butylpiperazin-1-yl)-2-oxoethyl]-6-(6-methoxypyridin-3-yl)-1,2,3,4-tetrahydroisoquinoline | 1.01 (2) | 423.37 | * |
| 384 | | 2-[2-(4-cyclohexylpiperazin-1-yl)-2-oxoethyl]-6-dibenzo[b,d]furan-4-yl-1,2,3,4-tetrahydroisoquinoline | 1.13 (3) | 508.34 | † |
| 385 | | 6-(2,3-dihydro-1,4-benzodioxin-6-yl)-2-[2-(4-isopropylpiperazin-1-yl)-2-oxoethyl]-1,2,3,4-tetrahydroisoquinoline | 1.01 (3) | 436.31 | † |

TABLE II-continued
| Compound | | Name | RT | MS | K_i |
|---|---|---|---|---|---|
| 386 | 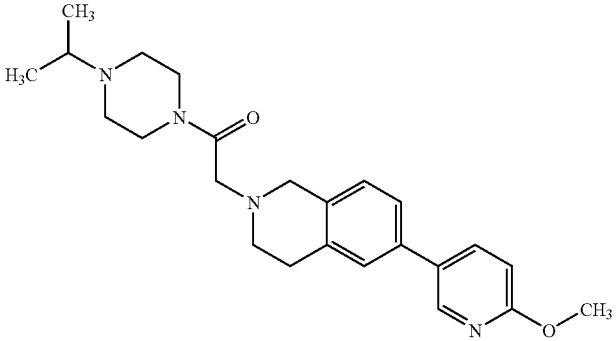 | 2-[2-(4-isopropylpiperazin-1-yl)-2-oxoethyl]-6-(6-methoxypyridin-3-yl)-1,2,3,4-tetrahydroisoquinoline | 1.16 (1) | 409.28 | * |
| 387 | 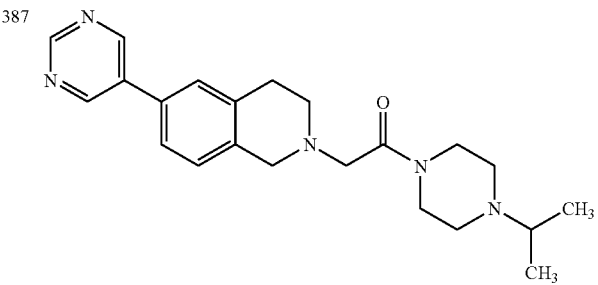 | 2-[2-(4-isopropylpiperazin-1-yl)-2-oxoethyl]-6-pyrimidin-5-yl-1,2,3,4-tetrahydroisoquinoline | 1.06 (1) | 380.23 | * |
| 388 | 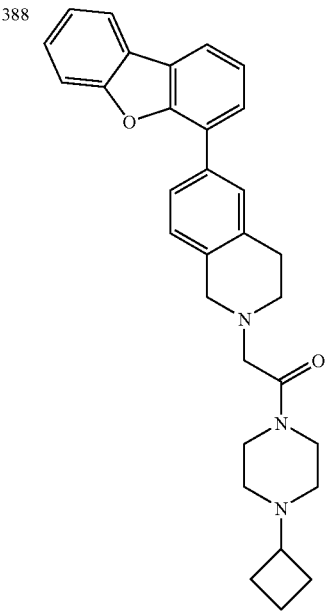 | 2-[2-(4-cyclobutylpiperazin-1-yl)-2-oxoethyl]-6-dibenzo[b,d]furan-4-yl-1,2,3,4-tetrahydroisoquinoline | 1.14 (2) | 480.35 | † |

TABLE II-continued

| Compound | Name | RT | MS | $K_i$ |
|---|---|---|---|---|
| 389 | 2-[2-(4-cyclobutylpiperazin-1-yl)-2-oxoethyl]-6-[4-(methylsulfonyl)phenyl]-1,2,3,4-tetrahydroisoquinoline | 1.1 (1) | 468.27 | * |
| 390 | 2-[2-(4-cyclopentylpiperazin-1-yl)-2-oxoethyl]-6-[4-(methylsulfonyl)phenyl]-1,2,3,4-tetrahydroisoquinoline | 1.14 (1) | 482.29 | * |
| 391 | 2-[2-(4-cyclopentylpiperazin-1-yl)-2-oxoethyl]-6-(6-methoxypyridin-3-yl)-1,2,3,4-tetrahydroisoquinoline | 1.12 (1) | 435.30 | * |
| 392 | 2-[2-(4-cyclopentylpiperazin-1-yl)-2-oxoethyl]-6-pyrimidin-5-yl-1,2,3,4-tetrahydroisoquinoline | 1.12 (1) | 406.18 | * |

TABLE II-continued

| Compound | | Name | RT | MS | $K_i$ |
|---|---|---|---|---|---|
| 393 | | 2-[2-(4-cyclohexylpiperazin-1-yl)-2-oxoethyl]-6-pyrimidin-5-yl-1,2,3,4-tetrahydroisoquinoline | 1.14 (1) | 420.30 | * |
| 394 | | 2-[2-(4-cyclopentylpiperazin-1-yl)-2-oxoethyl]-6-[3-(methylsulfonyl)phenyl]-1,2,3,4-tetrahydroisoquinoline | 1.13 (1) | 482.27 | * |
| 395 | | 2-[2-(4-cyclohexylpiperazin-1-yl)-2-oxoethyl]-6-[3-(methylsulfonyl)phenyl]-1,2,3,4-tetrahydroisoquinoline | 1.15 (1) | 496.29 | * |
| 396 | | 2-[2-(4-sec-butylpiperazin-1-yl)-2-oxoethyl]-6-[4-(methylsulfonyl)phenyl]-1,2,3,4-tetrahydroisoquinoline | 1.13 (1) | 470.24 | * |

TABLE II-continued

| Compound | Name | RT | MS | K$_i$ |
|---|---|---|---|---|
| 397 | 2-[2-(4-sec-butylpiperazin-1-yl)-2-oxoethyl]-6-pyrimidin-5-yl-1,2,3,4-tetrahydroisoquinoline | 1.11 (1) | 394.28 | * |
| 398 | 2-[2-(4-cyclobutylpiperazin-1-yl)-2-oxoethyl]-6-phenyl-1,2,3,4-tetrahydroisoquinoline | 1.03 (3) | 390.25 | † |
| 399 | 2-[2-(4-cyclopentylpiperazin-1-yl)-2-oxoethyl]-6-phenyl-1,2,3,4-tetrahydroisoquinoline | 1.27 (1) | 404.19 | † |
| 400 | 2-[2-(4-cyclohexylpiperazin-1-yl)-2-oxoethyl]-6-phenyl-1,2,3,4-tetrahydroisoquinoline | 1.04 (3) | 418.28 | † |
| 401 | 6-(3-chlorophenyl)-2-[2-(4-cyclobutylpiperazin-1-yl)-2-oxoethyl]-1,2,3,4-tetrahydroisoquinoline | 1.07 (3) | 424.22 | † |

TABLE II-continued

| Compound | | Name | RT | MS | K$_i$ |
|---|---|---|---|---|---|
| 402 | | 6-(3-chlorophenyl)-2-[2-(4-cyclopentylpiperazin-1-yl)-2-oxoethyl]-1,2,3,4-tetrahydroisoquinoline | 1.07 (3) | 438.23 | † |
| 403 | | 6-(3-chlorophenyl)-2-[2-(4-cyclohexylpiperazin-1-yl)-2-oxoethyl]-1,2,3,4-tetrahydroisoquinoline | 1.09 (3) | 452.25 | † |
| 404 | | 6-(4-chlorophenyl)-2-[2-(4-cyclobutylpiperazin-1-yl)-2-oxoethyl]-1,2,3,4-tetrahydroisoquinoline | 1.06 (3) | 424.22 | † |
| 405 | | 6-(4-chlorophenyl)-2-[2-(4-cyclopentylpiperazin-1-yl)-2-oxoethyl]-1,2,3,4-tetrahydroisoquinoline | 1.08 (3) | 438.24 | † |

TABLE II-continued

| Compound | Name | RT | MS | $K_i$ |
|---|---|---|---|---|
| 406 | 6-(4-chlorophenyl)-2-[2-(4-cyclohexylpiperazin-1-yl)-2-oxoethyl]-1,2,3,4-tetrahydroisoquinoline | 1.08 (3) | 452.26 | † |
| 407 | 2-[2-(4-cyclobutylpiperazin-1-yl)-2-oxoethyl]-6-(4-fluorophenyl)-1,2,3,4-tetrahydroisoquinoline | 1.03 (3) | 408.24 | † |
| 408 | 2-[2-(4-cyclopentylpiperazin-1-yl)-2-oxoethyl]-6-(4-fluorophenyl)-1,2,3,4-tetrahydroisoquinoline | 1.04 (3) | 422.26 | † |
| 409 | 2-[2-(4-cyclohexylpiperazin-1-yl)-2-oxoethyl]-6-(4-fluorophenyl)-1,2,3,4-tetrahydroisoquinoline | 1.05 (3) | 436.27 | † |

TABLE II-continued

| Compound | | Name | RT | MS | $K_i$ |
|---|---|---|---|---|---|
| 410 | | 2-[2-(4-cyclobutylpiperazin-1-yl)-2-oxoethyl]-6-(3-fluorophenyl)-1,2,3,4-tetrahydroisoquinoline | 1.24 (1) | 408.18 | † |
| 411 | | 2-[2-(4-cyclopentylpiperazin-1-yl)-2-oxoethyl]-6-(3-fluorophenyl)-1,2,3,4-tetrahydroisoquinoline | 1.04 (3) | 422.28 | † |
| 412 | | 2-[2-(4-cyclohexylpiperazin-1-yl)-2-oxoethyl]-6-(3-fluorophenyl)-1,2,3,4-tetrahydroisoquinoline | 1.05 (3) | 436.30 | † |
| 413 | | 6-(3-fluorophenyl)-2-[2-(4-isopropylpiperazin-1-yl)-2-oxoethyl]-1,2,3,4-tetrahydroisoquinoline | 1.03 (3) | 396.28 | † |

TABLE II-continued

| Compound | Name | RT | MS | $K_i$ |
|---|---|---|---|---|
| 414 | 2-[2-(4-cyclobutylpiperazin-1-yl)-2-oxoethyl]-6-(2-fluorophenyl)-1,2,3,4-tetrahydroisoquinoline | 1.02 (3) | 408.27 | † |
| 415 | 2-[2-(4-cyclopentylpiperazin-1-yl)-2-oxoethyl]-6-(2-fluorophenyl)-1,2,3,4-tetrahydroisoquinoline | 1.04 (3) | 422.29 | † |
| 416 | 2-[2-(4-cyclobutylpiperazin-1-yl)-2-oxoethyl]-6-(2-naphthyl)-1,2,3,4-tetrahydroisoquinoline | 1.09 (3) | 440.30 | † |
| 417 | 2-[2-(4-cyclopentylpiperazin-1-yl)-2-oxoethyl]-6-(2-naphthyl)-1,2,3,4-tetrahydroisoquinoline | 1.09 (3) | 454.31 | † |
| 418 | 2-[2-(4-cyclohexylpiperazin-1-yl)-2-oxoethyl]-6-(2-naphthyl)-1,2,3,4-tetrahydroisoquinoline | 1.1 (3) | 468.33 | † |

TABLE II-continued

| Compound | | Name | RT | MS | K$_i$ |
|---|---|---|---|---|---|
| 419 | | 2-[2-(4-isopropylpiperazin-1-yl)-2-oxoethyl]-6-(2-naphthyl)-1,2,3,4-tetrahydroisoquinoline | 1.09 (3) | 428.29 | † |
| 420 | | 2-[2-(4-cyclobutylpiperazin-1-yl)-2-oxoethyl]-6-(2-fluoro-4-methylphenyl)-1,2,3,4-tetrahydroisoquinoline | 4.06 (3) | 42.28 | † |
| 421 | | 2-[2-(4-cyclopentylpiperazin-1-yl)-2-oxoethyl]-6-(2-fluoro-4-methylphenyl)-1,2,3,4-tetrahydroisoquinoline | 1.07 (3) | 436.30 | † |
| 422 | | 2-[2-(4-cyclohexylpiperazin-1-yl)-2-oxoethyl]-6-(2-fluoro-4-methylphenyl)-1,2,3,4-tetrahydroisoquinoline | 1.08 (3) | 450.32 | † |

TABLE II-continued

| Compound | Name | RT | MS | K$_i$ |
|---|---|---|---|---|
| 423 | 2-[2-(4-cyclobutylpiperazin-1-yl)-2-oxoethyl]-6-(2-fluoro-5-methylphenyl)-1,2,3,4-tetrahydroisoquinoline | 1.07 (3) | 422.29 | † |
| 424 | 2-[2-(4-cyclopentylpiperazin-1-yl)-2-oxoethyl]-6-(2-fluoro-5-methylphenyl)-1,2,3,4-tetrahydroisoquinoline | 1.06 (3) | 436.31 | † |
| 425 | 2-[2-(4-cyclohexylpiperazin-1-yl)-2-oxoethyl]-6-(2-fluoro-5-methylphenyl)-1,2,3,4-tetrahydroisoquinoline | 1.07 (3) | 450.33 | † |
| 426 | 2-[2-(4-cyclobutylpiperazin-1-yl)-2-oxoethyl]-6-(3-fluoro-4-methylphenyl)-1,2,3,4-tetrahydroisoquinoline | 1.07 (3) | 422.29 | † |

TABLE II-continued

| Compound | | Name | RT | MS | $K_i$ |
|---|---|---|---|---|---|
| 427 | | 2-[2-(4-cyclopentylpiperazin-1-yl)-2-oxoethyl]-6-(3-fluoro-4-methylphenyl)-1,2,3,4-tetrahydroisoquinoline | 1.08 (3) | 436.32 | † |
| 428 | | 2-[2-(4-cyclohexylpiperazin-1-yl)-2-oxoethyl]-6-(3-fluoro-4-methylphenyl)-1,2,3,4-tetrahydroisoquinoline | 1.09 (3) | 450.33 | † |
| 429 | | 2-[2-(4-cyclobutylpiperazin-1-yl)-2-oxoethyl]-6-(4-fluoro-3-methylphenyl)-1,2,3,4-tetrahydroisoquinoline | 1.06 (3) | 422.30 | † |
| 430 | | 2-[2-(4-cyclopentylpiperazin-1-yl)-2-oxoethyl]-6-(4-fluoro-3-methylphenyl)-1,2,3,4-tetrahydroisoquinoline | 1.08 (3) | 436.32 | † |

TABLE II-continued

| Compound | | Name | RT | MS | $K_i$ |
|---|---|---|---|---|---|
| 431 | | 2-[2-(4-cyclohexylpiperazin-1-yl)-2-oxoethyl]-6-(4-fluoro-3-methylphenyl)-1,2,3,4-tetrahydroisoquinoline | 1.34 (1) | 450.21 | † |
| 432 | | 2-[2-(4-cyclobutylpiperazin-1-yl)-2-oxoethyl]-6-(3-methylphenyl)-1,2,3,4-tetrahydroisoquinoline | 1.06 (3) | 404.30 | † |
| 433 | | 2-[2-(4-cyclopentylpiperazin-1-yl)-2-oxoethyl]-6-(3-methylphenyl)-1,2,3,4-tetrahydroisoquinoline | 1.06 (3) | 418.33 | † |
| 434 | | 2-[2-(4-cyclohexylpiperazin-1-yl)-2-oxoethyl]-6-(3-methylphenyl)-1,2,3,4-tetrahydroisoquinoline | 1.07 (3) | 432.35 | † |

TABLE II-continued

| Compound | Name | RT | MS | K$_i$ |
|---|---|---|---|---|
| 435 | 2-[2-(4-cyclobutylpiperazin-1-yl)-2-oxoethyl]-6-(4-methylphenyl)-1,2,3,4-tetrahydroisoquinoline | 1.06 (3) | 404.31 | † |
| 436 | 2-[2-(4-cyclopentylpiperazin-1-yl)-2-oxoethyl]-6-(4-methylphenyl)-1,2,3,4-tetrahydroisoquinoline | 1.06 (3) | 418.33 | † |
| 437 | 2-[2-(4-cyclohexylpiperazin-1-yl)-2-oxoethyl]-6-(4-methylphenyl)-1,2,3,4-tetrahydroisoquinoline | 1.07 (3) | 432.34 | † |
| 438 | 2-[2-(4-isopropylpiperazin-1-yl)-2-oxoethyl]-6-(4-methylphenyl)-1,2,3,4-tetrahydroisoquinoline | 1.05 (3) | 393.31 | † |

TABLE II-continued

| Compound | | Name | RT | MS | $K_i$ |
|---|---|---|---|---|---|
| 439 | | 2-[2-(4-cyclobutylpiperazin-1-yl)-2-oxoethyl]-6-(3-isopropylphenyl)-1,2,3,4-tetrahydroisoquinoline | 1.11 (3) | 432.34 | † |
| 440 | | 2-[2-(4-cyclopentylpiperazin-1-yl)-2-oxoethyl]-6-(3-isopropylphenyl)-1,2,3,4-tetrahydroisoquinoline | 1.12 (3) | 446.36 | † |
| 441 | | 2-[2-(4-cyclohexylpiperazin-1-yl)-2-oxoethyl]-6-(3-isopropylphenyl)-1,2,3,4-tetrahydroisoquinoline | 1.12 (3) | 460.37 | † |
| 442 | | 6-(3-isopropylphenyl)-2-[2-(4-isopropylpiperazin-1-yl)-2-oxoethyl]-1,2,3,4-tetrahydroisoquinoline | 1.1 (3) | 420.34 | † |

TABLE II-continued

| Compound | | Name | RT | MS | $K_i$ |
|---|---|---|---|---|---|
| 443 | | 2-[2-(4-cyclobutylpiperazin-1-yl)-2-oxoethyl]-6-(4-isopropylphenyl)-1,2,3,4-tetrahydroisoquinoline | 1.12 (3) | 432.35 | † |
| 444 | | 2-[2-(4-cyclopentylpiperazin-1-yl)-2-oxoethyl]-6-(4-isopropylphenyl)-1,2,3,4-tetrahydroisoquinoline | 1.11 (3) | 446.36 | † |
| 445 | | 2-[2-(4-cyclohexylpiperazin-1-yl)-2-oxoethyl]-6-(4-isopropylphenyl)-1,2,3,4-tetrahydroisoquinoline | 1.12 (3) | 460.37 | † |
| 446 | | 6-(4-isopropylphenyl)-2-[2-(4-isopropylpiperazin-1-yl)-2-oxoethyl]-1,2,3,4-tetrahydroisoquinoline | 1.11 (3) | 420.34 | † |

TABLE II-continued

| Compound | | Name | RT | MS | $K_i$ |
|---|---|---|---|---|---|
| 447 | | 2-[2-(4-cyclobutylpiperazin-1-yl)-2-oxoethyl]-6-(3,4-dimethylphenyl)-1,2,3,4-tetrahydroisoquinoline | 1.09 (3) | 418.33 | † |
| 448 | | 2-[2-(4-cyclopentylpiperazin-1-yl)-2-oxoethyl]-6-(3,4-dimethylphenyl)-1,2,3,4-tetrahydroisoquinoline | 1.08 (3) | 432.34 | † |
| 449 | | 2-[2-(4-cyclohexylpiperazin-1-yl)-2-oxoethyl]-6-(3,4-dimethylphenyl)-1,2,3,4-tetrahydroisoquinoline | 1.1 (3) | 446.36 | † |
| 450 | | 6-(3,4-dimethylphenyl)-2-[2-(4-isopropylpiperazin-1-yl)-2-oxoethyl]-1,2,3,4-tetrahydroisoquinoline | 1.08 (3) | 406.33 | † |

TABLE II-continued

| Compound | | Name | RT | MS | $K_i$ |
|---|---|---|---|---|---|
| 451 | | 6-(4-butylphenyl)-2-[2-(4-cyclobutylpiperazin-1-yl)-2-oxoethyl]-1,2,3,4-tetrahydroisoquinoline | 1.14 (3) | 446.36 | † |
| 452 | | 6-(4-butylphenyl)-2-[2-(4-cyclopentylpiperazin-1-yl)-2-oxoethyl]-1,2,3,4-tetrahydroisoquinoline | 1.15 (3) | 460.38 | † |
| 453 | | 6-(4-butylphenyl)-2-[2-(4-cyclohexylpiperazin-1-yl)-2-oxoethyl]-1,2,3,4-tetrahydroisoquinoline | 1.16 (3) | 474.40 | † |
| 454 | | 6-(4-butylphenyl)-2-[2-(4-isopropylpiperazin-1-yl)-2-oxoethyl]-1,2,3,4-tetrahydroisoquinoline | 1.15 (3) | 434.36 | † |

TABLE II-continued

| Compound | | Name | RT | MS | $K_i$ |
|---|---|---|---|---|---|
| 455 | | 2-[2-(4-cyclobutylpiperazin-1-yl)-2-oxoethyl]-6-(3,5-dimethylphenyl)-1,2,3,4-tetrahydroisoquinoline | 1.09 (3) | 418.33 | † |
| 456 | | 2-[2-(4-cyclopentylpiperazin-1-yl)-2-oxoethyl]-6-(3,5-dimethylphenyl)-1,2,3,4-tetrahydroisoquinoline | 1.1 (3) | 432.35 | † |
| 457 | | 2-[2-(4-cyclohexylpiperazin-1-yl)-2-oxoethyl]-6-(3,5-dimethylphenyl)-1,2,3,4-tetrahydroisoquinoline | 1.1 (3) | 446.36 | † |
| 458 | | 6-(3,5-dimethylphenyl)-2-[2-(4-isopropylpiperazin-1-yl)-2-oxoethyl]-1,2,3,4-tetrahydroisoquinoline | 1.09 (3) | 406.33 | † |

TABLE II-continued

| Compound | Name | RT | MS | $K_i$ |
|---|---|---|---|---|
| 459 | 2-[2-(4-cyclobutylpiperazin-1-yl)-2-oxoethyl]-6-(4-ethylphenyl)-1,2,3,4-tetrahydroisoquinoline | 1.09 (3) | 418.33 | † |
| 460 | 2-[2-(4-cyclopentylpiperazin-1-yl)-2-oxoethyl]-6-(4-ethylphenyl)-1,2,3,4-tetrahydroisoquinoline | 1.09 (3) | 432.35 | † |
| 461 | 2-[2-(4-cyclohexylpiperazin-1-yl)-2-oxoethyl]-6-(4-ethylphenyl)-1,2,3,4-tetrahydroisoquinoline | 1.1 (3) | 446.36 | † |
| 462 | 6-(4-ethylphenyl)-2-[2-(4-isopropylpiperazin-1-yl)-2-oxoethyl]-1,2,3,4-tetrahydroisoquinoline | 1.09 (3) | 406.33 | † |

TABLE II-continued

| Compound | Name | RT | MS | K$_i$ |
|---|---|---|---|---|
| 463 | 2-[2-(4-cyclobutylpiperazin-1-yl)-2-oxoethyl]-6-(4-propylphenyl)-1,2,3,4-tetrahydroisoquinoline | | | † |
| 464 | 2-[2-(4-cyclopentylpiperazin-1-yl)-2-oxoethyl]-6-(4-propylphenyl)-1,2,3,4-tetrahydroisoquinoline | 1.12 (3) | 446.36 | † |
| 465 | 2-[2-(4-cyclohexylpiperazin-1-yl)-2-oxoethyl]-6-(4-propylphenyl)-1,2,3,4-tetrahydroisoquinoline | 1.13 (3) | 460.38 | † |
| 466 | 2-[2-(4-isopropylpiperazin-1-yl)-2-oxoethyl]-6-(4-propylphenyl)-1,2,3,4-tetrahydroisoquinoline | 1.12 (3) | 420.35 | † |

TABLE II-continued
| Compound | | Name | RT | MS | $K_i$ |
|---|---|---|---|---|---|
| 467 | 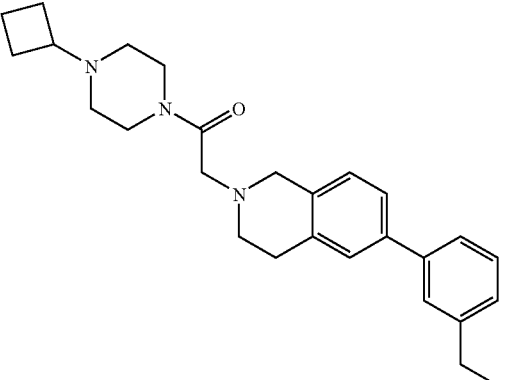 | 2-[2-(4-cyclobutylpiperazin-1-yl)-2-oxoethyl]-6-(3-ethylphenyl)-1,2,3,4-tetrahydroisoquinoline | 1.09 (3) | 418.33 | † |
| 468 | 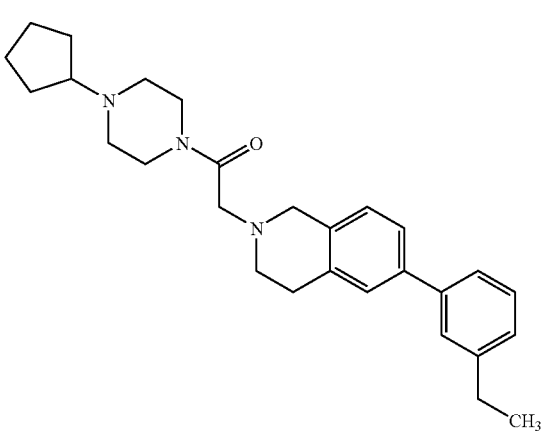 | 2-[2-(4-cyclopentylpiperazin-1-yl)-2-oxoethyl]-6-(3-ethylphenyl)-1,2,3,4-tetrahydroisoquinoline | 1.09 (3) | 432.35 | † |
| 469 | 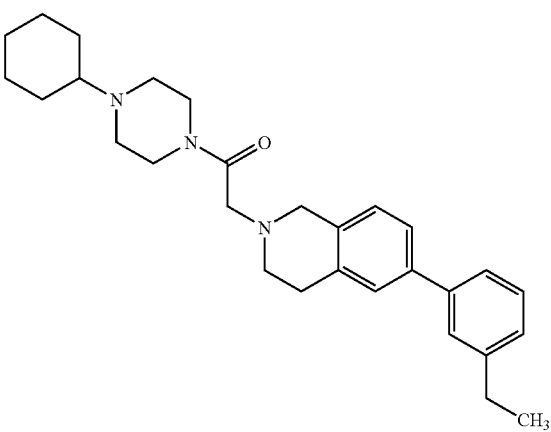 | 2-[2-(4-cyclohexylpiperazin-1-yl)-2-oxoethyl]-6-(3-ethylphenyl)-1,2,3,4-tetrahydroisoquinoline | 1.09 (3) | 446.37 | † |

TABLE II-continued

| Compound | Name | RT | MS | $K_i$ |
|---|---|---|---|---|
| 470 | 6-(3-ethylphenyl)-2-[2-(4-isopropylpiperazin-1-yl)-2-oxoethyl]-1,2,3,4-tetrahydroisoquinoline | 1.08 (3) | 406.33 | † |
| 471 | 6-(4-tert-butylphenyl)-2-[2-(4-cyclobutylpiperazin-1-yl)-2-oxoethyl]-1,2,3,4-tetrahydroisoquinoline | 1.13 (3) | 446.37 | † |
| 472 | 6-(4-tert-butylphenyl)-2-[2-(4-cyclopentylpiperazin-1-yl)-2-oxoethyl]-1,2,3,4-tetrahydroisoquinoline | 1.13 (3) | 460.38 | † |
| 473 | 6-(4-tert-butylphenyl)-2-[2-(4-cyclohexylpiperazin-1-yl)-2-oxoethyl]-1,2,3,4-tetrahydroisoquinoline | 1.14 (3) | 474.40 | † |

TABLE II-continued

| Compound | Name | RT | MS | K$_i$ |
|---|---|---|---|---|
| 474 | 6-(4-tert-butylphenyl)-2-[2-(4-isopropylpiperazin-1-yl)-2-oxoethyl]-1,2,3,4-tetrahydroisoquinoline | 1.13 (3) | 434.37 | † |
| 475 | 2-[2-(4-cyclobutylpiperazin-1-yl)-2-oxoethyl]-6-(3-methoxyphenyl)-1,2,3,4-tetrahydroisoquinoline | 1.02 (3) | 420.32 | * |
| 476 | 2-[2-(4-cyclopentylpiperazin-1-yl)-2-oxoethyl]-6-(3-methoxyphenyl)-1,2,3,4-tetrahydroisoquinoline | 1.03 (3) | 434.34 | * |

TABLE II-continued

| Compound | | Name | RT | MS | $K_i$ |
|---|---|---|---|---|---|
| 477 | | 2-[2-(4-cyclohexylpiperazin-1-yl)-2-oxoethyl]-6-(3-methoxyphenyl)-1,2,3,4-tetrahydroisoquinoline | 1.04 (3) | 448.36 | † |
| 478 | | 2-[2-(4-cyclobutylpiperazin-1-yl)-2-oxoethyl]-6-[4-(trifluoromethoxy)phenyl]-1,2,3,4-tetrahydroisoquinoline | 1.28 (1) | 474.16 | † |
| 479 | | 2-[2-(4-cyclopentylpiperazin-1-yl)-2-oxoethyl]-6-[4-(trifluoromethoxy)phenyl]-1,2,3,4-tetrahydroisoquinoline | 1.1 (3) | 488.32 | † |
| 480 | | 2-[2-(4-cyclohexylpiperazin-1-yl)-2-oxoethyl]-6-[4-(trifluoromethoxy)phenyl]-1,2,3,4-tetrahydroisoquinoline | 1.1 (3) | 502.34 | † |

TABLE II-continued
| Compound | | Name | RT | MS | $K_i$ |
|---|---|---|---|---|---|
| 481 | 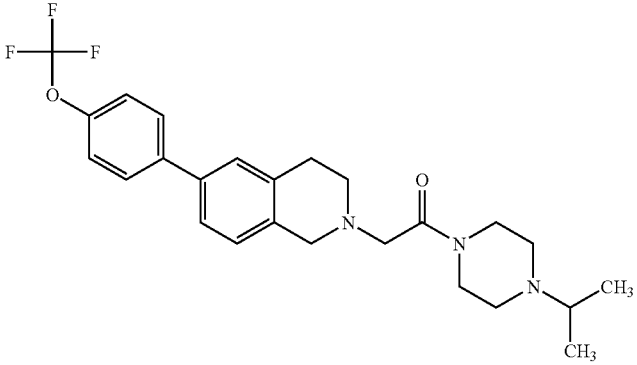 | 2-[2-(4-isopropylpiperazin-1-yl)-2-oxoethyl]-6-[4-(trifluoromethoxy)phenyl]-1,2,3,4-tetrahydroisoquinoline | 1.1 (3) | 462.30 | † |
| 482 | 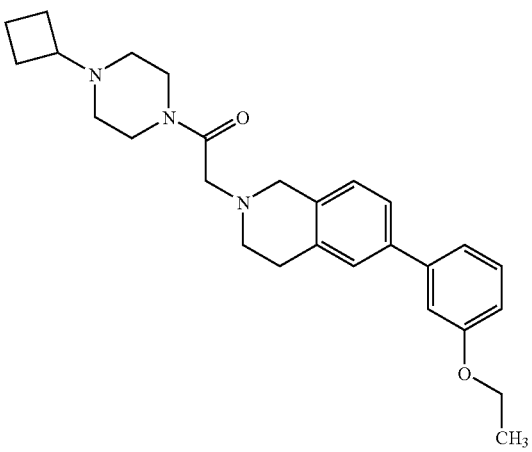 | 2-[2-(4-cyclobutylpiperazin-1-yl)-2-oxoethyl]-6-(3-ethoxyphenyl)-1,2,3,4-tetrahydroisoquinoline | 1.05 (3) | 434.33 | * |
| 483 | 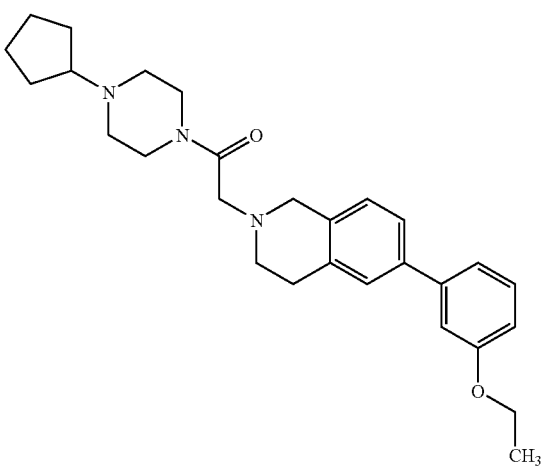 | 2-[2-(4-cyclopentylpiperazin-1-yl)-2-oxoethyl]-6-(3-ethoxyphenyl)-1,2,3,4-tetrahydroisoquinoline | 1.06 (3) | 448.36 | * |

TABLE II-continued
| Compound | | Name | RT | MS | $K_i$ |
|---|---|---|---|---|---|
| 484 | 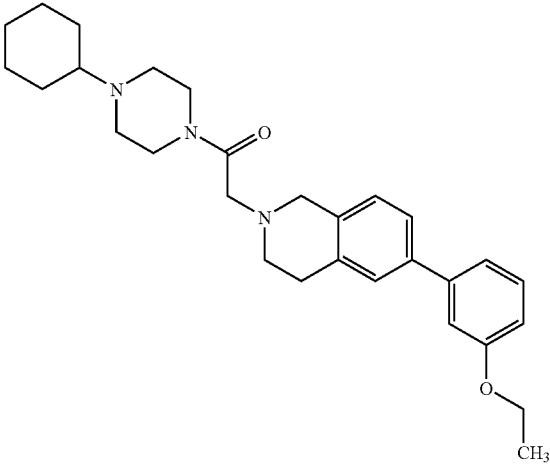 | 2-[2-(4-cyclohexylpiperazin-1-yl)-2-oxoethyl]-6-(3-ethoxyphenyl)-1,2,3,4-tetrahydroisoquinoline | 1.07 (3) | 462.37 | † |
| 485 | 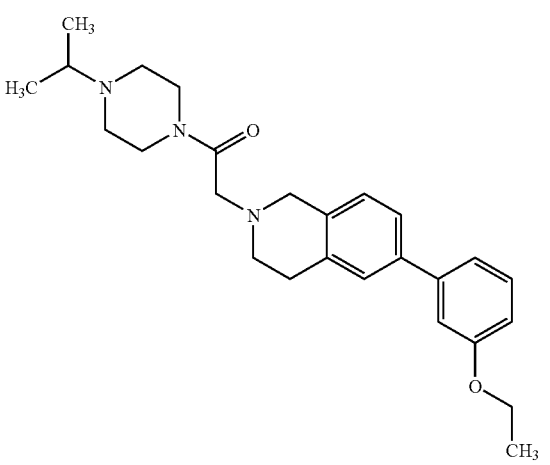 | 6-(3-ethoxyphenyl)-2-[2-(4-isopropylpiperazin-1-yl)-2-oxoethyl]-1,2,3,4-tetrahydroisoquinoline | 1.05 (3) | 422.34 | † |
| 486 | 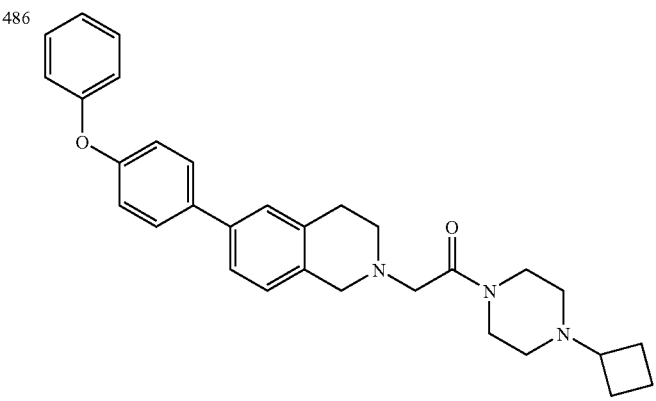 | 2-[2-(4-cyclobutylpiperazin 1-yl)-2-oxoethyl]-6-(4-phenoxyphenyl)-1,2,3,4-tetrahydroisoquinoline | 1.12 (3) | 482.35 | † |

TABLE II-continued
| Compound | | Name | RT | MS | $K_i$ |
|---|---|---|---|---|---|
| 487 | 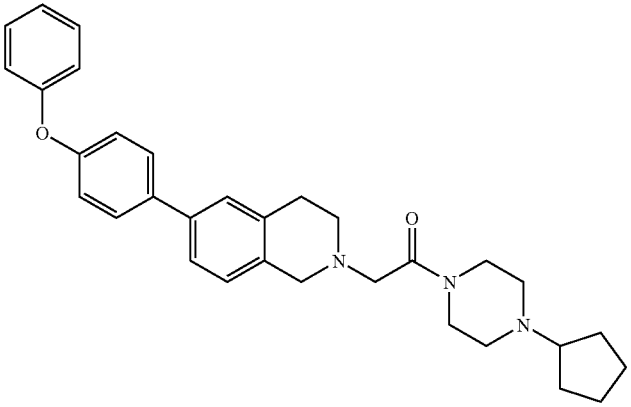 | 2-[2-(4-cyclopentylpiperazin-1-yl)-2-oxoethyl]-6-(4-phenoxyphenyl)-1,2,3,4-tetrahydroisoquinoline | 1.13 (3) | 496.36 | † |
| 488 | 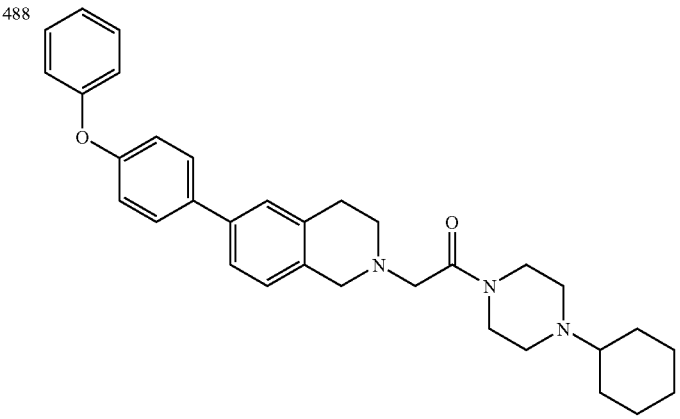 | 2-[2-(4-cyclohexylpiperazin-1-yl)-2-oxoethyl]-6-(4-phenoxyphenyl)-1,2,3,4-tetrahydroisoquinoline | 1.12 (3) | 510.3 | † |
| 489 | 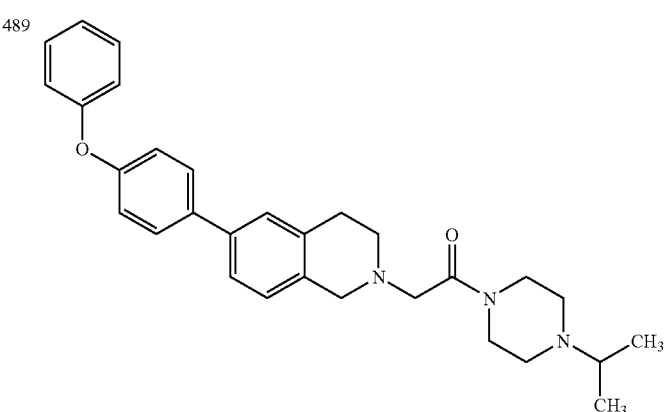 | 2-[2-(4-isopropylpiperazin-1-yl)-2-oxoethyl]-6-(4-phenoxyphenyl)-1,2,3,4-tetrahydroisoquinoline | 1.11 (3) | 470.34 | † |

TABLE II-continued

| Compound | Name | RT | MS | K$_i$ |
|---|---|---|---|---|
| 490 | 2-[2-(4-cyclobutylpiperazin-1-yl)-2-oxoethyl]-6-[3-(trifluoromethoxy)phenyl]-1,2,3,4-tetrahydroisoquinoline | 1.09 (3) | 474.30 | † |
| 491 | 2-[2-(4-cyclopentylpiperazin-1-yl)-2-oxoethyl]-6-[3-(trifluoromethoxy)phenyl]-1,2,3,4-tetrahydroisoquinoline | 1.1 (3) | 488.32 | † |
| 492 | 2-[2-(4-cyclohexylpiperazin-1-yl)-2-oxoethyl]-6-[3-(trifluoromethoxy)phenyl]-1,2,3,4-tetrahydroisoquinoline | 1.1 (3) | 502.33 | † |

TABLE II-continued

| Compound | | Name | RT | MS | $K_i$ |
|---|---|---|---|---|---|
| 493 | 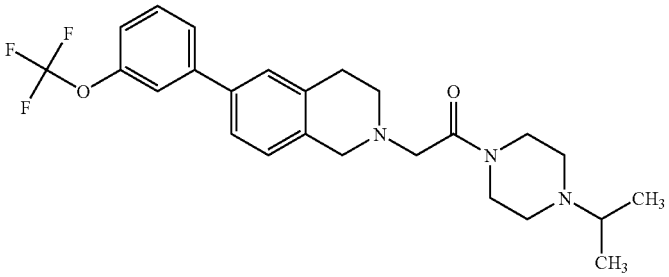 | 2-[2-(4-isopropylpiperazin-1-yl)-2-oxoethyl]-6-[3-(trifluoromethoxy)phenyl]-1,2,3,4-tetrahydroisoquinoline | 1.09 (3) | 462.30 | † |
| 494 | 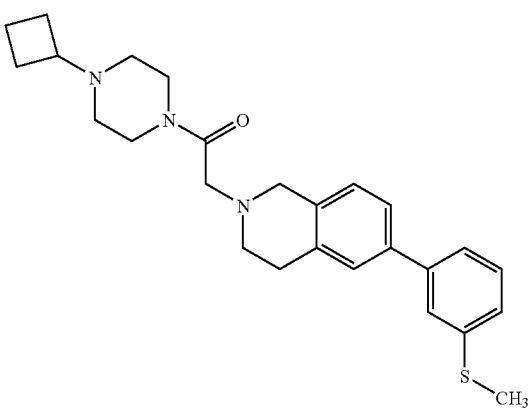 | 2-[2-(4-cyclobutylpiperazin-1-yl)-2-oxoethyl]-6-[3-(methylthio)phenyl]-1,2,3,4-tetrahydroisoquinoline | 1.06 (3) | 436.30 | † |
| 495 | 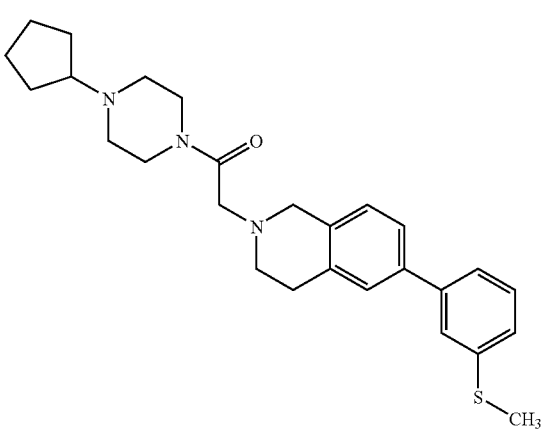 | 2-[2-(4-cyclopentylpiperazin-1-yl)-2-oxoethyl]-6-[3-(methylthio)phenyl]-1,2,3,4-tetrahydroisoquinoline | 1.06 (3) | 450.32 | † |
| 496 | 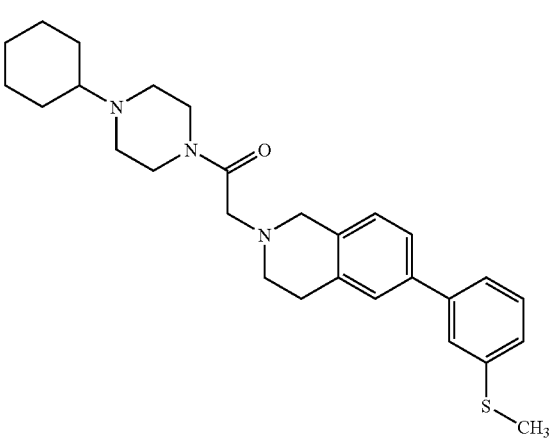 | 2-[2-(4-cyclohexylpiperazin-1-yl)-2-oxoethyl]-6-[3-(methylthio)phenyl]-1,2,3,4-tetrahydroisoquinoline | 1.08 (3) | 464.33 | † |

TABLE II-continued
| Compound | | Name | RT | MS | $K_i$ |
|---|---|---|---|---|---|
| 497 | 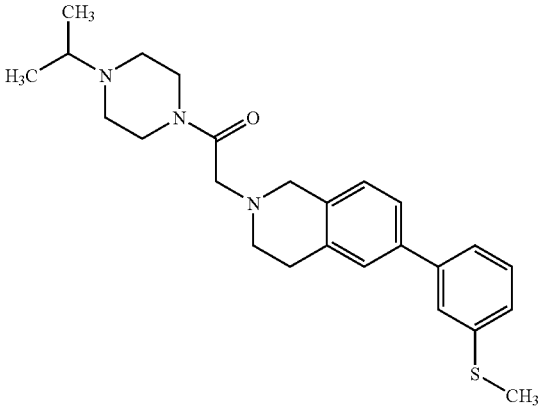 | 2-[2-(4-isopropylpiperazin-1-yl)-2-oxoethyl]-6-[3-(methylthio)phenyl]-1,2,3,4-tetrahydroisoquinoline | 1.06 (3) | 424.30 | † |
| 498 | 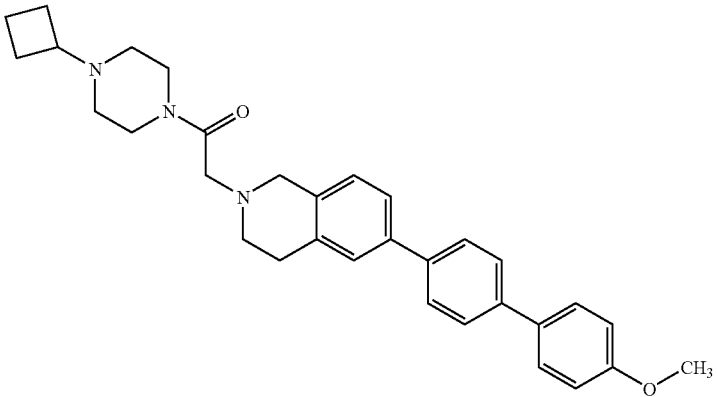 | 2-[2-(4-cyclobutylpiperazin-1-yl)-2-oxoethyl]-6-(4'-methoxybiphenyl-4-yl)-1,2,3,4-tetrahydroisoquinoline | 1.12 (3) | 496.36 | † |
| 499 | 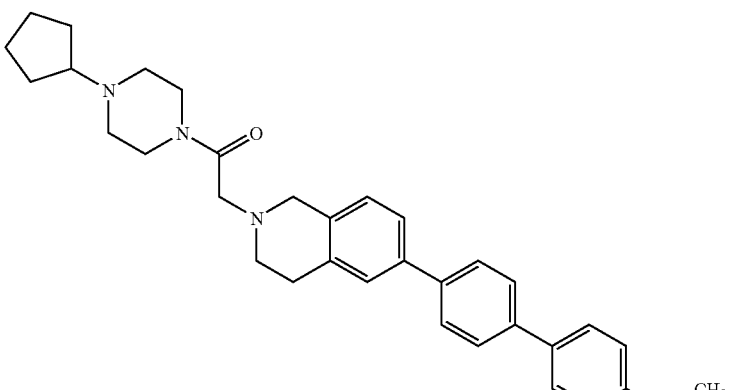 | 2-[2-(4-cyclopentylpiperazin-1-yl)-2-oxoethyl]-6-(4'-methoxybiphenyl-4-yl)-1,2,3,4-tetrahydroisoquinoline | 1.12 (3) | 510.38 | † |

TABLE II-continued
| Compound | | Name | RT | MS | $K_i$ |
|---|---|---|---|---|---|
| 500 | 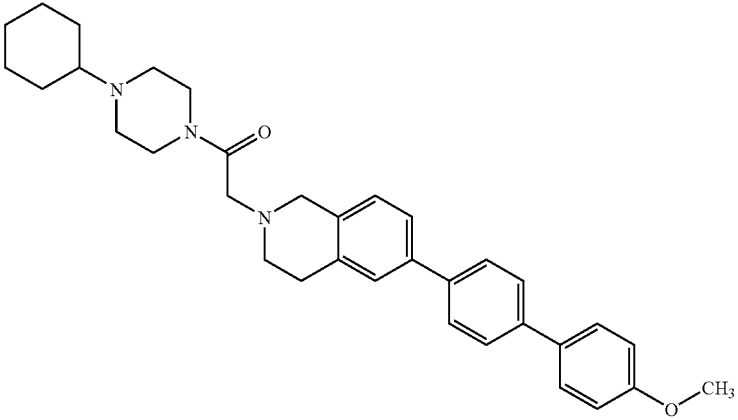 | 2-[2-(4-cyclohexylpiperazin-1-yl)-2-oxoethyl]-6-(4'-methoxybiphenyl-4-yl)-1,2,3,4-tetrahydroisoquinoline | 1.13 (3) | 524.40 | † |
| 501 | 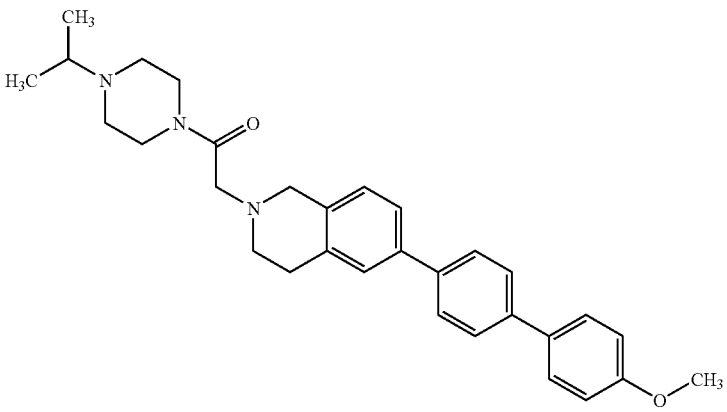 | 2-[2-(4-isopropylpiperazin-1-yl)-2-oxoethyl]-6-(4'-methoxybiphenyl-4-yl)-1,2,3,4-tetrahydroisoquinoline | 1.12 (3) | 484.36 | † |
| 502 | 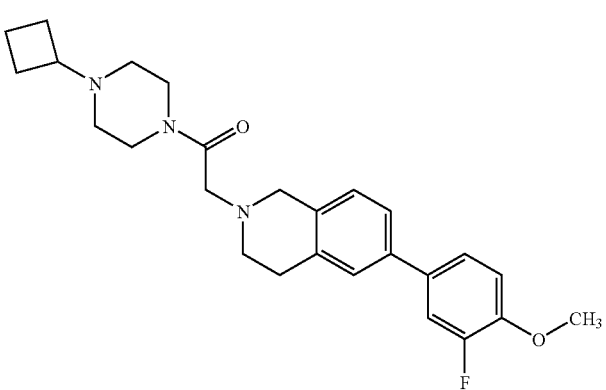 | 2-[2-(4-cyclobutylpiperazin-1-yl)-2-oxoethyl]-6-(3-fluoro-4-methoxyphenyl)-1,2,3,4-tetrahydroisoquinoline | 1.02 (3) | 438.31 | * |

TABLE II-continued

| Compound | | Name | RT | MS | $K_i$ |
|---|---|---|---|---|---|
| 503 | | 2-[2-(4-cyclopentylpiperazin-1-yl)-2-oxoethyl]-6-(3-fluoro-4-methoxyphenyl)-1,2,3,4-tetrahydroisoquinoline | 1.02 (3) | 452.33 | * |
| 504 | | 2-[2-(4-cyclohexylpiperazin-1-yl)-2-oxoethyl]-6-(3-fluoro-4-methoxyphenyl)-1,2,3,4-tetrahydroisoquinoline | 1.03 (3) | 466.35 | † |
| 505 | | 6-(3-fluoro-4-methoxyphenyl)-2-[2-(4-isopropylpiperazin-1-yl)-2-oxoethyl]-1,2,3,4-tetrahydroisoquinoline | 1.02 (3) | 426.31 | † |
| 506 | | 2-[2-(4-cyclobutylpiperazin-1-yl)-2-oxoethyl]-6-(2,5-difluoro-4-methoxyphenyl)-1,2,3,4-tetrahydroisoquinoline | 1.03 (3) | 456.29 | * |

TABLE II-continued

| Compound | | Name | RT | MS | $K_i$ |
|---|---|---|---|---|---|
| 507 | | 2-[2-(4-cyclopentylpiperazin-1-yl)-2-oxoethyl]-6-(2,5-difluoro-4-methoxyphenyl)-1,2,3,4-tetrahydroisoquinoline | 1.03 (3) | 470.32 | * |
| 508 | | 6-(2,5-difluoro-4-methoxyphenyl)-2-[2-(4-isopropylpiperazin-1-yl)-2-oxoethyl]-1,2,3,4-tetrahydroisoquinoline | 1.02 (3) | 444.30 | † |
| 509 | | 2-[2-(4-cyclobutylpiperazin-1-yl)-2-oxoethyl]-6-(6-methoxy-2-naphthyl)-1,2,3,4-tetrahydroisoquinoline | 1.08 (3) | 470.34 | * |
| 510 | | 2-[2-(4-cyclopentylpiperazin-1-yl)-2-oxoethyl]-6-(6-methoxy-2-naphthyl)-1,2,3,4-tetrahydroisoquinoline | 1.09 (3) | 484.36 | † |

TABLE II-continued

| Compound | Name | RT | MS | K_i |
|---|---|---|---|---|
| 511 | 2-[2-(4-cyclohexylpiperazin-1-yl)-2-oxoethyl]-6-(6-methoxy-2-naphthyl)-1,2,3,4-tetrahydroisoquinoline | 1.1 (3) | 498.37 | † |
| 512 | 2-[2-(4-isopropylpiperazin-1-yl)-2-oxoethyl]-6-(6-methoxy-2-naphthyl)-1,2,3,4-tetrahydroisoquinoline | 1.08 (3) | 4584 | † |
| 513 | 2-[2-(4-cyclobutylpiperazin-1-yl)-2-oxoethyl]-6-(3-isopropoxyphenyl)-1,2,3,4-tetrahydroisoquinoline | 1.06 (3) | 448.34 | * |

TABLE II-continued

| Compound | | Name | RT | MS | $K_i$ |
|---|---|---|---|---|---|
| 514 | | 2-[2-(4-cyclopentylpiperazin-1-yl)-2-oxoethyl]-6-(3-isopropoxyphenyl)-1,2,3,4-tetrahydroisoquinoline | 1.08 (3) | 462.36 | † |
| 515 | | 6-(3-isopropoxyphenyl)-2-[2-(4-isopropylpiperazin-1-yl)-2-oxoethyl]-1,2,3,4-tetrahydroisoquinoline | 1.07 (3) | 436.34 | † |
| 516 | | 2-[2-(4-cyclobutylpiperazin-1-yl)-2-oxoethyl]-6-(3,4,5-trimethoxyphenyl)-1,2,3,4-tetrahydroisoquinoline | 0.98 (3) | 480.33 | * |

TABLE II-continued

| Compound | | Name | RT | MS | $K_i$ |
|---|---|---|---|---|---|
| 517 | | 2-[2-(4-cyclopentylpiperazin-1-yl)-2-oxoethyl]-6-(3,4,5-trimethoxyphenyl)-1,2,3,4-tetrahydroisoquinoline | 0.99 (3) | 494.35 | * |
| 518 | | 2-[2-(4-cyclohexylpiperazin-1-yl)-2-oxoethyl]-6-(3,4,5-trimethoxyphenyl)-1,2,3,4-tetrahydroisoquinoline | 1.01 (3) | 508.36 | † |
| 519 | | 2-[2-(4-isopropylpiperazin-1-yl)-2-oxoethyl]-6-(3,4,5-trimethoxyphenyl)-1,2,3,4-tetrahydroisoquinoline | 0.98 (3) | 468.33 | † |

TABLE II-continued

| Compound | | Name | RT | MS | $K_i$ |
|---|---|---|---|---|---|
| 520 | | 2-[2-(4-cyclobutylpiperazin-1-yl)-2-oxoethyl]-6-(4-methoxyphenyl)-1,2,3,4-tetrahydroisoquinoline | 1.01 (3) | 420.30 | * |
| 521 | | 2-[2-(4-cyclopentylpiperazin-1-yl)-2-oxoethyl]-6-(4-methoxyphenyl)-1,2,3,4-tetrahydroisoquinoline | 1.02 (3) | 434.32 | * |
| 522 | | 2-[2-(4-cyclohexylpiperazin-1-yl)-2-oxoethyl]-6-(4-methoxyphenyl)-1,2,3,4-tetrahydroisoquinoline | 1.03 (3) | 448.33 | † |
| 523 | | 2-[2-(4-isopropylpiperazin-1-yl)-2-oxoethyl]-6-(4-methoxyphenyl)-1,2,3,4-tetrahydroisoquinoline | 1.02 (3) | 408.31 | † |

TABLE II-continued

| Compound | Name | RT | MS | K$_i$ |
|---|---|---|---|---|
| 524 | 2-[2-(4-cyclobutylpiperazin-1-yl)-2-oxoethyl]-6-(3,4-dimethoxyphenyl)-1,2,3,4-tetrahydroisoquinoline | 0.98 (3) | 450.32 | * |
| 525 | 2-[2-(4-cyclopentylpiperazin-1-yl)-2-oxoethyl]-6-(3,4-dimethoxyphenyl)-1,2,3,4-tetrahydroisoquinoline | 0.98 (3) | 464.34 | * |
| 526 | 2-[2-(4-cyclohexylpiperazin-1-yl)-2-oxoethyl]-6-(3,4-dimethoxyphenyl)-1,2,3,4-tetrahydroisoquinoline | 1 (3) | 478.35 | * |

TABLE II-continued

| Compound | | Name | RT | MS | K_i |
|---|---|---|---|---|---|
| 527 | (structure) | 6-(3,4-dimethoxyphenyl)-2-[2-(4-isopropylpiperazin-1-yl)-2-oxoethyl]-1,2,3,4-tetrahydroisoquinoline | 0.97 (3) | 438.32 | * |
| 528 | (structure) | 2-[2-(4-cyclobutylpiperazin-1-yl)-2-oxoethyl]-6-(4-ethoxyphenyl)-1,2,3,4-tetrahydroisoquinoline | 1.04 (3) | 434.32 | * |
| 529 | (structure) | 2-[2-(4-cyclopentylpiperazin-1-yl)-2-oxoethyl]-6-(4-ethoxyphenyl)-1,2,3,4-tetrahydroisoquinoline | 1.06 (3) | 448.33 | * |
| 530 | (structure) | 2-[2-(4-cyclohexylpiperazin-1-yl)-2-oxoethyl]-6-(4-ethoxyphenyl)-1,2,3,4-tetrahydroisoquinoline | 1.06 (3) | 462.36 | † |

TABLE II-continued

| Compound | Name | RT | MS | $K_i$ |
|---|---|---|---|---|
| 531 | 6-(4-ethoxyphenyl)-2-[2-(4-isopropylpiperazin-1-yl)-2-oxoethyl]-1,2,3,4-tetrahydroisoquinoline | 1.04 (3) | 422.32 | † |
| 532 | 4-{2-[2-(4-cyclobutylpiperazin-1-yl)-2-oxoethyl]-1,2,3,4-tetrahydroisoquinolin-6-yl}-N,N-dimethylaniline | 1.24 (1) | 433.27 | * |
| 533 | 4-{2-[2-(4-cyclopentylpiperazin-1-yl)-2-oxoethyl]-1,2,3,4-tetrahydroisoquinolin-6-yl}-N,N-dimethylaniline | 1.27 (1) | 447.24 | * |
| 534 | 4-{2-[2-(4-cyclohexylpiperazin-1-yl)-2-oxoethyl]-1,2,3,4-tetrahydroisoquinolin-6-yl}-N,N-dimethylaniline | 1.3 (1) | 461.26 | † |

TABLE II-continued

| Compound | | Name | RT | MS | $K_i$ |
|---|---|---|---|---|---|
| 535 | | 4-{2-[2-(4-isopropylpiperazin-1-yl)-2-oxoethyl]-1,2,3,4-tetrahydroisoquinolin-6-yl}-N,N-dimethylaniline | 1.24 (1) | 421.24 | † |
| 536 | | 3-{2-[2-(4-cyclobutylpiperazin-1-yl)-2-oxoethyl]-1,2,3,4-tetrahydroisoquinolin-6-yl}-N,N-dimethylaniline | 1.24 (1) | 433.25 | * |
| 537 | | 3-{2-[2-(4-cyclopentylpiperazin-1-yl)-2-oxoethyl]-1,2,3,4-tetrahydroisoquinolin-6-yl}-N,N-dimethylaniline | 1.26 (1) | 447.26 | † |
| 538 | | 3-{2-[2-(4-cyclohexylpiperazin-1-yl)-2-oxoethyl]-1,2,3,4-tetrahydroisoquinolin-6-yl}-N,N-dimethylaniline | 1.3 (1) | 461.28 | † |

TABLE II-continued

| Compound | | Name | RT | MS | $K_i$ |
|---|---|---|---|---|---|
| 539 | | 3-{2-[2-(4-isopropylpiperazin-1-yl)-2-oxoethyl]-1-1,2,3,4-tetrahydroisoquinolin-6-yl}-N,N-dimethylaniline | 1.23 (1) | 421.25 | † |
| 540 | | 2-[2-(4-cyclobutylpiperazin-1-yl)-2-oxoethyl]-6-(4-methoxy-3-methylphenyl)-1,2,3,4-tetrahydroisoquinoline | 1.06 (3) | 434.31 | * |
| 541 | | 2-[2-(4-cyclopentylpiperazin-1-yl)-2-oxoethyl]-6-(4-methoxy-3-methylphenyl)-1,2,3,4-tetrahydroisoquinoline | 1.06 (3) | 448.34 | * |
| 542 | | 2-[2-(4-cyclohexylpiperazin-1-yl)-2-oxoethyl]-6-(4-methoxy-3-methylphenyl)-1,2,3,4-tetrahydroisoquinoline | 1.07 (3) | 462.35 | † |

TABLE II-continued

| Compound | Name | RT | MS | K$_i$ |
|---|---|---|---|---|
| 543 | 2-[2-(4-isopropylpiperazin-1-yl)-2-oxoethyl]-6-(4-methoxy-3-methylphenyl)-1,2,3,4-tetrahydroisoquinoline | 1.06 (3) | 422.32 | † |
| 544 | 2-[2-(4-cyclobutylpiperazin-1-yl)-2-oxoethyl]-6-(4-propoxyphenyl)-1,2,3,4-tetrahydroisoquinoline | 1.09 (3) | 448.33 | * |
| 545 | 2-[2-(4-cyclopentylpiperazin-1-yl)-2-oxoethyl]-6-(4-propoxyphenyl)-1,2,3,4-tetrahydroisoquinoline | 1.09 (3) | 462.35 | * |
| 546 | 2-[2-(4-cyclohexylpiperazin-1-yl)-2-oxoethyl]-6-(4-propoxyphenyl)-1,2,3,4-tetrahydroisoquinoline | 1.1 (3) | 476.37 | † |

TABLE II-continued

| Compound | | Name | RT | MS | K_i |
|---|---|---|---|---|---|
| 547 | | 2-[2-(4-isopropylpiperazin-1-yl)-2-oxoethyl]-6-(4-propoxyphenyl)-1,2,3,4-tetrahydroisoquinoline | 1.09 (3) | 436.34 | † |
| 548 | | 2-[2-(4-cyclobutylpiperazin-1-yl)-2-oxoethyl]-6-(4-methoxy-2-methylphenyl)-1,2,3,4-tetrahydroisoquinoline | 1.25 (1) | 434.25 | † |
| 549 | | 2-[2-(4-cyclopentylpiperazin-1-yl)-2-oxoethyhl]-6-(4-methoxy-2-methylphenyl)-1,2,3,4-tetrahydroisoquinoline | 1.05 (3) | 448.34 | † |
| 550 | | 2-[2-(4-cyclohexylpiperazin-1-yl)-2-oxoethyl]-6-(4-methoxy-2-methylphenyl)-1,2,3,4-tetrahydroisoquinoline | 1.06 (3) | 462.36 | † |

TABLE II-continued

| Compound | Name | RT | MS | $K_i$ |
|---|---|---|---|---|
| 551 | 2-[2-(4-cyclobutylpiperazin-1-yl)-2-oxoethyl]-6-(2-methoxyphenyl)-1,2,3,4-tetrahydroisoquinoline | 1.22 (1) | 420.23 | † |
| 552 | 2-[2-(4-cyclopentylpiperazin-1-yl)-2-oxoethyl]-6-(2-methoxyphenyl)-1,2,3,4-tetrahydroisoquinoline | 1.03 (3) | 434.32 | † |
| 553 | 2-[2-(4-cyclohexylpiperazin-1-yl)-2-oxoethyl]-6-(2-methoxyphenyl)-1,2,3,4-tetrahydroisoquinoline | 1.04 (3) | 448.34 | † |
| 554 | 2-[2-(4-cyclobutylpiperazin-1-yl)-2-oxoethyl]-6-(5-isopropyl-2-methoxyphenyl)-1,2,3,4-tetrahydroisoquinoline | 1.1 (3) | 462.36 | † |

TABLE II-continued

| Compound | | Name | RT | MS | $K_i$ |
|---|---|---|---|---|---|
| 555 | | 2-[2-(4-cyclopentylpiperazin-1-yl)-2-oxoethyl]-6-(5-isopropyl-2-methoxyphenyl)-1,2,3,4-tetrahydroisoquinoline | 1.11 (3) | 476.37 | † |
| 556 | | 2-[2-(4-cyclohexylpiperazin-1-yl)-2-oxoethyl]-6-(5-isopropyl-2-methoxyphenyl)-1,2,3,4-tetrahydroisoquinoline | 1.12 (3) | 490.39 | † |
| 557 | | 6-(5-chloro-2-methoxyphenyl)-2-[2-(4-cyclobutylpiperazin-1-yl)-2-oxoethyl]-1,2,3,4-tetrahydroisoquinoline | 1.06 (3) | 454.27 | † |

TABLE II-continued

| Compound | | Name | RT | MS | K_i |
|---|---|---|---|---|---|
| 558 | | 6-(5-chloro-2-methoxyphenyl)-2-[2-(4-cyclohexylpiperazin-1-yl)-2-oxoethyl]-1,2,3,4-tetrahydroisoquinoline | 1.08 (3) | 482.30 | † |
| 559 | | 2-[2-(4-cyclobutylpiperazin-1-yl)-2-oxoethyl]-6-(2,5-dimethoxyphenyl)-1,2,3,4-tetrahydroisoquinoline | 1.25 (1) | 450.25 | † |
| 560 | | 2-[2-(4-cyclopentylpiperazin-1-yl)-2-oxoethyl]-6-(2,5-dimethoxyphenyl)-1,2,3,4-tetrahydroisoquinoline | 1.02 (3) | 464.33 | † |

TABLE II-continued

| Compound | Name | RT | MS | K_i |
|---|---|---|---|---|
| 561 | 2-[2-(4-cyclohexylpiperazin-1-yl)-2-oxoethyl]-6-(2,5-dimethoxyphenyl)-1,2,3,4-tetrahydroisoquinoline | 1.03 (3) | 478.35 | † |
| 562 | 6-(2,5-dimethoxyphenyl)-2-[2-(4-isopropylpiperazin-1-yl)-2-oxoethyl]-1,2,3,4-tetrahydroisoquinoline | 1.01 (3) | 438.32 | † |
| 563 | 2-[2-(4-cyclobutylpiperazin-1-yl)-2-oxoethyl]-6-(2,4-dimethoxyphenyl)-1,2,3,4-tetrahydroisoquinoline | 1.02 (3) | 450.31 | † |
| 564 | 2-[2-(4-cyclopentylpiperazin-1-yl)-2-oxoethyl]-6-(2,4-dimethoxyphenyl)-1,2,3,4-tetrahydroisoquinoline | 1.03 (3) | 464.32 | † |

TABLE II-continued

| Compound | | Name | RT | MS | $K_i$ |
|---|---|---|---|---|---|
| 565 | | 2-[2-(4-cyclohexylpiperazin-1-yl)-2-oxoethyl]-6-(2,4-dimethoxyphenyl)-1,2,3,4-tetrahydroisoquinoline | 1.04 (3) | 478.34 | † |
| 566 | | 2-[2-(4-cyclobutylpiperazin-1-yl)-2-oxoethyl]-6-(2-ethoxyphenyl)-1,2,3,4-tetrahydroisoquinoline | 1.05 (3) | 434.31 | † |
| 567 | | 2-[2-(4-cyclopentylpiperazin-1-yl)-2-oxoethyl]-6-(2-ethoxyphenyl)-1,2,3,4-tetrahydroisoquinoline | 1.05 (3) | 448.33 | † |

TABLE II-continued

| Compound | | Name | RT | MS | $K_i$ |
|---|---|---|---|---|---|
| 568 | | 2-[2-(4-cyclohexylpiperazin-1-yl)-2-oxoethyl]-6-(2-ethoxyphenyl)-1,2,3,4-tetrahydroisoquinoline | 1.07 (3) | 462.35 | † |
| 569 | | 6-(2-ethoxyphenyl)-2-[2-(4-isopropylpiperazin-1-yl)-2-oxoethyl]-1,2,3,4-tetrahydroisoquinoline | 1.05 (3) | 422.32 | † |
| 570 | | 2-[2-(4-cyclobutylpiperazin-1-yl)-2-oxoethyl]-6-(5-fluoro-2-methoxyphenyl)-1,2,3,4-tetrahydroisoquinoline | 1.22 (1) | 438.22 | † |

TABLE II-continued

| Compound | | Name | RT | MS | K$_i$ |
|---|---|---|---|---|---|
| 571 | | 2-[2-(4-cyclopentylpiperazin-1-yl)-2-oxoethyl]-6-(5-fluoro-2-methoxyphenyl)-1,2,3,4-tetrahydroisoquinoline | 1.04 (3) | 452.31 | † |
| 572 | | 2-[2-(4-cyclobutylpiperazin-1-yl)-2-oxoethyl]-6-(2-methoxy-5-methylphenyl)-1,2,3,4-tetrahydroisoquinoline | 1.05 (3) | 434.31 | † |
| 573 | | 2-[2-(4-cyclopentylpiperazin-1-yl)-2-oxoethyl]-6-(2-methoxy-5-methylphenyl)-1,2,3,4-tetrahydroisoquinoline | 1.06 (3) | 448.34 | † |

TABLE II-continued

| Compound | | Name | RT | MS | $K_i$ |
|---|---|---|---|---|---|
| 574 | | 2-[2-(4-cyclohexylpiperazin-1-yl)-2-oxoethyl]-6-(2-methoxy-5-methylphenyl)-1,2,3,4-tetrahydroisoquinoline | 1.07 (3) | 462.36 | † |
| 575 | | 2-[2-(4-cyclobutylpiperazin-1-yl)-2-oxoethyl]-6-(2-phenoxyphenyl)-1,2,3,4-tetrahydroisoquinoline | 1.11 (3) | 482.33 | † |
| 576 | | 2-[2-(4-cyclopentylpiperazin-1-yl)-2-oxoethyl]-6-(2-phenoxyphenyl)-1,2,3,4-tetrahydroisoquinoline | 1.11 (3) | 496.34 | † |
| 577 | | 2-[2-(4-cyclohexylpiperazin-1-yl)-2-oxoethyl]-6-(2-phenoxyphenyl)-1,2,3,4-tetrahydroisoquinoline | 1.11 (3) | 510.37 | † |
| 578 | | 2-[2-(4-isopropylpiperazin-1-yl)-2-oxoethyl]-6-(2-phenoxyphenyl)-1,2,3,4-tetrahydroisoquinoline | 1.11 (3) | 470.33 | † |

TABLE II-continued

| Compound | Name | RT | MS | $K_i$ |
|---|---|---|---|---|
| 579 | 6-(3-chloro-4-fluorophenyl)-2-[2-(4-cyclobutylpiperazin-1-yl)-2-oxoethyl]-1,2,3,4-tetrahydroisoquinoline | 1.06 (3) | 442.24 | † |
| 580 | 6-(3-chloro-4-fluorophenyl)-2-[2-(4-cyclopentylpiperazin-1-yl)-2-oxoethyl]-1,2,3,4-tetrahydroisoquinoline | 1.08 (3) | 456.26 | † |
| 581 | 6-(3-chloro-4-fluorophenyl)-2-[2-(4-cyclohexylpiperazin-1-yl)-2-oxoethyl]-1,2,3,4-tetrahydroisoquinoline | 1.09 (3) | 470.29 | † |
| 582 | 2-[2-(4-cyclobutylpiperazin-1-yl)-2-oxoethyl]-6-(2,5-difluorophenyl)-1,2,3,4-tetrahydroisoquinoline | 1.03 (3) | 426.28 | † |

TABLE II-continued

| Compound | Name | RT | MS | K_i |
|---|---|---|---|---|
| 583 | 2-[2-(4-cyclopentylpiperazin-1-yl)-2-oxoethyl]-6-(2,5-difluorophenyl)-1,2,3,4-tetrahydroisoquinoline | 1.04 (3) | 440.30 | † |
| 584 | 2-[2-(4-cyclohexylpiperazin-1-yl)-2-oxoethyl]-6-(2,5-difluorophenyl)-1,2,3,4-tetrahydroisoquinoline | 1.04 (3) | 454.31 | † |
| 585 | 6-(2,5-difluorophenyl)-2-[2-(4-isopropylpiperazin-1-yl)-2-oxoethyl]-1,2,3,4-tetrahydroisoquinoline | 1.03 (3) | 414.27 | † |
| 586 | 2-[2-(4-cyclobutylpiperazin-1-yl)-2-oxoethyl]-6-(2,4-difluorophenyl)-1,2,3,4-tetrahydroisoquinoline | 1.24 (1) | 426.19 | † |

TABLE II-continued

| Compound | | Name | RT | MS | $K_i$ |
|---|---|---|---|---|---|
| 587 | 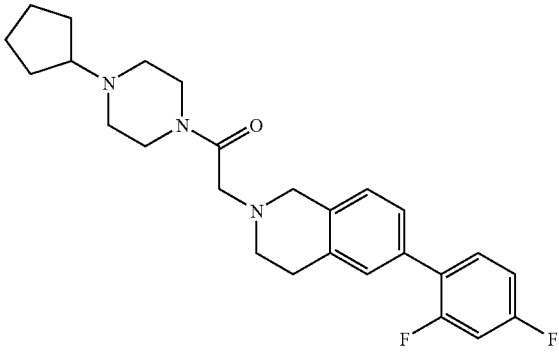 | 2-[2-(4-cyclopentylpiperazin-1-yl)-2-oxoethyl]-6-(2,4-difluorophenyl)-1,2,3,4-tetrahydroisoquinoline | 1.04 (3) | 440.29 | † |
| 588 | 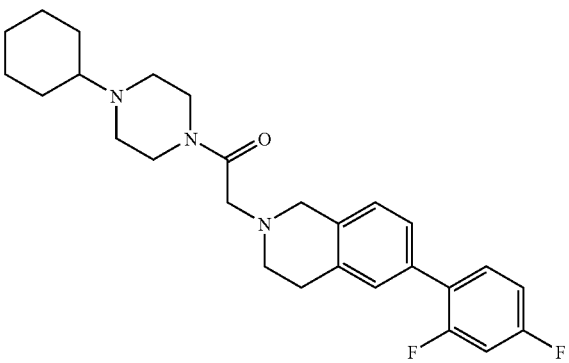 | 2-[2-(4-cyclohexylpiperazin-1-yl)-2-oxoethyl]-6-(2,4-difluorophenyl)-1,2,3,4-tetrahydroisoquinoline | 1.06 (3) | 454.30 | † |
| 589 | 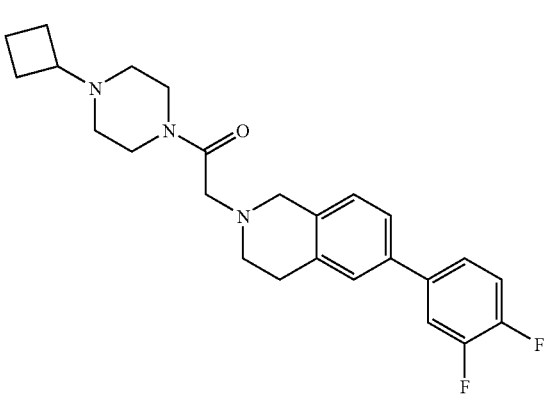 | 2-[2-(4-cyclobutylpiperazin-1-yl)-2-oxoethyl]-6-(3,4-difluorophenyl)-1,2,3,4-tetrahydroisoquinoline | 1.25 (1) | 426.19 | † |
| 590 | 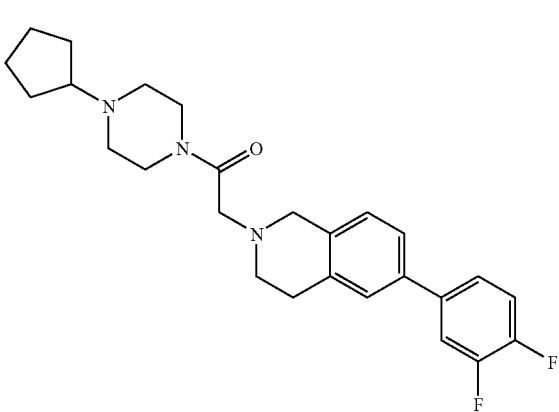 | 2-[2-(4-cyclopentylpiperazin-1-yl)-2-oxoethyl]-6-(3,4-difluorophenyl)-1,2,3,4-tetrahydroisoquinoline | 1.06 (3) | 440.29 | † |

TABLE II-continued

| Compound | Name | RT | MS | K_i |
|---|---|---|---|---|
| 591 | 2-[2-(4-cyclohexylpiperazin-1-yl)-2-oxoethyl]-6-(3,4-difluorophenyl)-1,2,3,4-tetrahydroisoquinoline | 1.06 (3) | 454.31 | † |
| 592 | 2-[2-(4-cyclobutylpiperazin-1-yl)-2-oxoethyl]-6-(3,5-dichlorophenyl)-1,2,3,4-tetrahydroisoquinoline | 1.12 (3) | 458.22 | † |
| 593 | 6-(4-chloro-3-fluorophenyl)-2-[2-(4-cyclohexylpiperazin-1-yl)-2-oxoethyl]-1,2,3,4-tetrahydroisoquinoline | 1.09 (3) | 470.28 | † |
| 594 | 2-[2-(4-cyclobutylpiperazin-1-yl)-2-oxoethyl]-6-(3,4-dichlorophenyl)-1,2,3,4-tetrahydroisoquinoline | 1.1 (3) | 458.21 | † |

TABLE II-continued

| Compound | Name | RT | MS | $K_i$ |
|---|---|---|---|---|
| 595 | 2-[2-(4-cyclopentylpiperazin-1-yl)-2-oxoethyl]-6-(3,4-dichlorophenyl)-1,2,3,4-tetrahydroisoquinoline | 1.1 (3) | 472.22 | † |
| 596 | 2-[2-(4-cyclobutylpiperazin-1-yl)-2-oxoethyl]-6-(3,5-difluorophenyl)-1,2,3,4-tetrahydroisoquinoline | 1.04 (3) | 426.27 | † |
| 597 | 2-[2-(4-cyclopentylpiperazin-1-yl)-2-oxoethyl]-6-(3,5-difluorophenyl)-1,2,3,4-tetrahydroisoquinoline | 1.05 (3) | 440.28 | † |
| 598 | 2-[2-(4-cyclohexylpiperazin-1-yl)-2-oxoethyl]-6-(3,5-difluorophenyl)-1,2,3,4-tetrahydroisoquinoline | 1.06 (3) | 454.31 | † |

TABLE II-continued

| Compound | Name | RT | MS | K$_i$ |
|---|---|---|---|---|
| 599 | 2-[2-(4-cyclobutylpiperazin-1-yl)-2-oxoethyl]-6-(2,3-difluorophenyl)-1,2,3,4-tetrahydroisoquinoline | 1.03 (3) | 426.27 | † |
| 600 | 2-[2-(4-cyclopentylpiperazin-1-yl)-2-oxoethyl]-6-(2,3-difluorophenyl)-1,2,3,4-tetrahydroisoquinoline | 1.04 (3) | 440.29 | † |
| 601 | 2-[2-(4-cyclohexylpiperazin-1-yl)-2-oxoethyl]-6-(2,3-difluorophenyl)-1,2,3,4-tetrahydroisoquinoline | 1.05 (3) | 454.31 | † |
| 602 | 6-(2,3-difluorophenyl)-2-[2-(4-isopropylpiperazin-1-yl)-2-oxoethyl]-1,2,3,4-tetrahydroisoquinoline | 1.02 (3) | 414.27 | † |

TABLE II-continued

| Compound | Name | RT | MS | K$_i$ |
|---|---|---|---|---|
| 603 | 2-[2-(4-ethylpiperazin-1-yl)-2-oxoethyl]-6-1-pyrimidin-5-yl-1,2,3,4-tetrahydroisoquinoline | 1.02 (1) | 366.18 | † |
| 604 | 2-[2-(4-butylpiperazin-1-yl)-2-oxoethyl]-6-pyrimidin-5-yl-1,2,3,4-tetrahydroisoquinoline | 1.11 (1) | 394.21 | † |
| 605 | 2-[2-(4-isobutylpiperazin-1-yl)-2-oxoethyl]-6-pyrimidin-5-yl-1,2,3,4-tetrahydroisoquinoline | 1.13 (1) | 394.21 | † |
| 606 | 2-{2-[(3R)-4-sec-butyl-3-methylpiperazin-1-yl]-2-oxoethyl}-6-pyrimidin-5-yl-1,2,3,4-tetrahydroisoquinoline | 1.12 (1) | 408.30 | † |

TABLE II-continued

| Compound | Name | RT | MS | K$_i$ |
|---|---|---|---|---|
| 607 | 2-{2-[4-(1,2-dimethylpropyl)piperazin-1-yl]-2-oxoethyl}-6-pyrimidin-5-yl-1,2,3,4-tetrahydroisoquinoline | 1.18 (1) | 408.30 | † |
| 608 | 2-{2-[(1S,4S)-5-(1,2-dimethylpropyl)-2,5-diazabicyclo[2.2.1]hept-2-yl]-2-oxoethyl}-6-pyrimidin-5-yl-1,2,3,4-tetrahydroisoquinoline | 0.98 (2) | 420.15 | † |
| 609 | 2-{2-[4-(1-cyclopropylethyl)piperazin-1-yl]-2-oxoethyl}-6-pyrimidin-5-yl-1,2,3,4-tetrahydroisoquinoline | 1.1 (1) | 406.27 | † |
| 610 | 2-{2-[(3S)-4-cyclopentyl-3-methylpiperazin-1-yl]-2-oxoethyl}-6-pyrimidin-5-yl-1,2,3,4-tetrahydroisoquinoline | 1.13 (1) | 420.30 | * |

TABLE II-continued

| Compound | | Name | RT | MS | $K_i$ |
|---|---|---|---|---|---|
| 611 | | 2-{2-[(3R)-4-cyclopentyl-3-methylpiperazin-1-yl]-2-oxoethyl}-6-pyrimidin-5-yl-1,2,3,4-tetrahydroisoquinoline | 1.14 (1) | 420.29 | * |
| 612 | | 2-{2-[(1S,4S)-5-cyclopentyl-2,5-diazabicyclo[2.2.1]hept-2-yl]-2-oxoethyl}-6-pyrimidin-5-yl-1,2,3,4-tetrahydroisoquinoline | 1.08 (1) | 418.27 | † |
| 613 | | 2-{2-[4-(2-methylcyclopentyl)piperazin-1-yl]-2-oxoethyl}-6-pyrimidin-5-yl-1,2,3,4-tetrahydroisoquinoline | 1.17 (1) | 420.29 | * |
| 614 | | 2-{2-[(3S)-3-methyl-4-(2-methylcyclopentyl)piperazin-1-yl]-2-oxoethyl}-6-pyrimidin-5-yl-1,2,3,4-tetrahydroisoquinoline | 1.2 (1) | 434.30 | * |

TABLE II-continued
| Compound | | Name | RT | MS | $K_i$ |
|---|---|---|---|---|---|
| 615 | 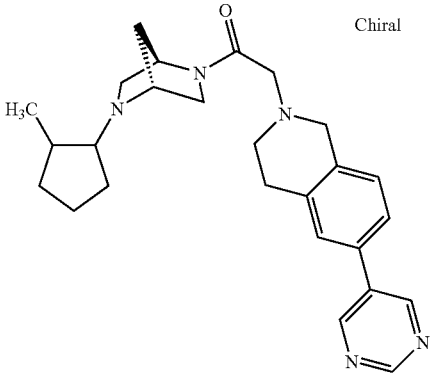 Chiral | 2-{2-[(1S,4S)-5-(2-methylcyclopentyl) 2,5-diazabicyclo [2.2.1]hept-2-yl]-2-oxoethyl}-6-pyrimidin-5-yl-1,2,3,4-tetrahydroisoquinoline | 1.13 (1) | 432.19 | † |
| 616 | 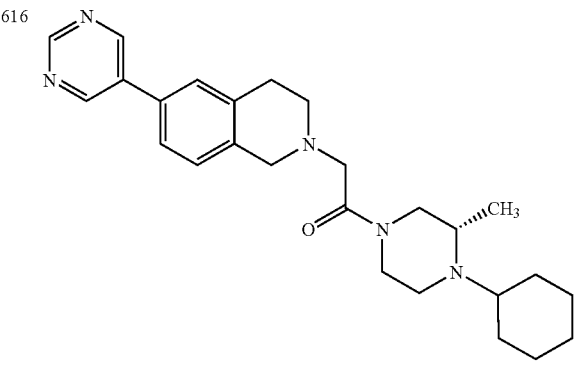 Chiral | 2-{2-[(3S)-4-cyclohexyl-3-methylpiperazin-1-yl]-2-oxoethyl}-6-1-pyrimidin-5-yl-1,2,3,4-tetrahydroisoquinoline | 1.16 (1) | 434.3 | * |
| 617 | 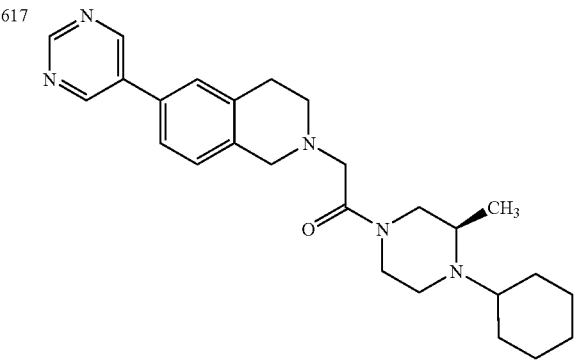 | 2-{2-[(3R)-4-cyclohexyl-3-methylpiperazin-1-yl]-2-oxoethyl}-6-pyrimidin-5-yl-1,2,3,4-tetrahydroisoquinoline | 1.17 (1) | 434.31 | * |

TABLE II-continued

| Compound | Name | RT | MS | K_i |
|---|---|---|---|---|
| 618 | 2-{2-[(1S,4S)-5-cyclohexyl-2,5-diazabicyclo[2.2.1]hept-2-yl]-2-oxoethyl}-6-pyrimidin-5-yl-1,2,3,4-tetrahydroisoquinoline | 1.11 (1) | 432.28 | † |
| 619 | 2-{2-[4-(2-methylcyclohexyl)piperazin-1-yl]-2-oxoethyl}-6-pyrimidin-5-yl-1,2,3,4-tetrahydroisoquinoline | 1.18 (1) | 434.30 | * |
| 620 | 2-{2-[(1S,4S)-5-(2-methoxycyclohexyl)-2,5-diazabicyclo[2.2.1]hept-2-yl]-2-oxoethyl}-6-pyrimidin-5-yl-1,2,3,4-tetrahydroisoquinoline | 1.12 (1) | 462.30 | † |
| 621 | 2-{2-oxo-2-[4-(tetrahydro-2H-pyran-4-yl)piperazin-1-yl]ethyl}-6-pyrimidin-5-yl-1,2,3,4-tetrahydroisoquinoline | 1.05 (1) | 422.28 | † |

TABLE II-continued

| Compound | Name | RT | MS | K_i |
|---|---|---|---|---|
| 622 | 2-{2-[(3S)-3-methyl-4-(tetrahydro-2H-pyran-4-yl)piperazin-1-yl]-2-oxoethyl}-6-pyrimidin-5-yl-1,2,3,4-tetrahydroisoquinolin | 1.05 (1) | 436.29 | † |
| 623 | 2-(2-{4-[(1R,4S)-bicyclo[2.2.1]hept-2-yl]piperazin-1-yl}-2-oxoethyl)-6-pyrimidin-5-yl-1,2,3,4-tetrahydroisoquinoline | 1.19 (1) | 432.29 | † |
| 624 | 2-(2-{(3S)-4-[(1R,4S)-bicyclo[2.2.1]hept-2-yl]-3-methylpiperazin-1-yl}-2-oxoethyl)-6-pyrimidin-5-yl-1,2,3,4-tetrahydroisoquinoline | 1.24 (1) | 446.31 | * |
| 625 | 4-{2-[2-(4-cyclobutylpiperazin-1-yl)-2-oxoethyl]-1,2,3,4-tetrahydroisoquinolin-6-yl}-N,N-diethylaniline | 1.32 (1) | 461.31 | * |

TABLE II-continued

| Compound | Name | RT | MS | K_i |
|---|---|---|---|---|
| 626 | 2-[2-(4-cyclobutylpiperazin-1-yl)-2-oxoethyl]-6-(4-fluoro-2-methylphenyl)-1,2,3,4-tetrahydroisoquinoline | 1.26 (1) | 422.22 | † |
| 627 | 2-{2-[2-(4-cyclobutylpiperazin-1-yl)-2-oxoethyl]-1,2,3,4-tetrahydroisoquinolin-6-yl}benzonitrile | 1.16 (1) | 415.23 | * |
| 628 | 2-[2-(4-cyclobutylpiperazin-1-yl)-2-oxoethyl]-6-(6-methylpyridin-2-yl)-1,2,3,4-tetrahydroisoquinoline | 1.17 (1) | 405.25 | * |
| 629 | 2-[2-(4-cyclobutylpiperazin-1-yl)-2-oxoethyl]-6-(5-methylpyridin-2-yl)-1,2,3,4-tetrahydroisoquinoline | 1.16 (1) | 405.24 | * |
| 630 | 2-[2-(4-cyclobutylpiperazin-1-yl)-2-oxoethyl]-6-(4-methylpyridin-2-yl)-1,2,3,4-tetrahydroisoquinoline | 1.15 (1) | 405.24 | * |

TABLE II-continued

| Compound | | Name | RT | MS | $K_i$ |
|---|---|---|---|---|---|
| 631 | | 6-(5-chloropyridin-2-yl)-2-[2-(4-cyclobutylpiperazin-1-yl)-2-oxoethyl]-1,2,3,4-tetrahydroisoquinoline | 1.2 (1) | 425.19 | * |
| 632 | | 2-[2-(4-cyclobutylpiperazin-1-yl)-2-oxoethyl]-6-[5-(trifluoromethyl)pyridin-2-yl]-1,2,3,4-tetrahydroisoquinoline | 1.21 (1) | 459.19 | * |
| 633 | | 2-[2-(4-cyclobutylpiperazin-1-yl)-2-oxoethyl]-6-(6-methoxypyridin-2-yl)-1,2,3,4-tetrahydroisoquinoline | 1.21 (1) | 421.23 | * |
| 634 | | 2-{2-[2-(4-cyclobutylpiperazin-1-yl)-2-oxoethyl]-1,2,3,4-tetrahydroisoquinolin-6-yl}quinoline | 1.21 (1) | 441.25 | * |
| 635 | | 2-[2-(4-cyclobutylpiperazin-1-yl)-2-oxoethyl]-6-(2,6-dimethoxypyrimidin-4-yl)-1,2,3,4-tetrahydroisoquinoline | 1.18 (1) | 452.24 | * |

TABLE II-continued

| Compound | Name | RT | MS | K_i |
|---|---|---|---|---|
| 636 | 2-[2-(4-cyclobutylpiperazin-1-yl)-2-oxoethyl]-6-[4-(trifluoromethyl)pyrimidin-2-yl]-1,2,3,4-tetrahydroisoquinoline | 1.21 (1) | 460.14 | * |
| 637 | 2'-[2-(4-cyclobutylpiperazin-1-yl)-2-oxoethyl]-1',2',3',4'-tetrahydro-1,6'-biisoquinoline | 1.18 (1) | 441.25 | * |
| 638 | 3-{2-[2-(4-cyclobutylpiperazin-1-yl)-2-oxoethyl]-1,2,3,4-tetrahydroisoquinolin-6-yl}quinoline | 1.19 (1) | 441.25 | * |

TABLE II-continued

| Compound | | Name | RT | MS | K_i |
|---|---|---|---|---|---|
| 639 | | 2-[2-(4-cyclobutylpiperazin-1-yl)-2-oxoethyl]-6-(1H-indol-4-yl)-1,2,3,4-tetrahydroisoquinoline | 1.16 (1) | 429.27 | * |
| 640 | | 1-(2-{2-[2-(4-cyclobutylpiperazin-1-yl)-2-oxoethyl]-1,2,3,4-tetrahydroisoquinolin-6-yl}phenyl)-N,N-dimethylmethanamine | 1.21 (1) | 447.27 | * |
| 641 | | 1-(3-{2-[2-(4-cyclobutylpiperazin-1-yl)-2-oxoethyl]-1,2,3,4-tetrahydroisoquinolin-6-yl}phenyl)-N,N-dimethylmethanamine | 1.21 (1) | 447.27 | * |
| 642 | | 1-(4-{2-[2-(4-cyclobutylpiperazin-1-yl)-2-oxoethyl]-1,2,3,4-tetrahydroisoquinolin-6-yl}phenyl)-N,N-dimethylmethanamine | 1.21 (1) | 447.28 | * |

TABLE II-continued

| Compound | | Name | RT | MS | $K_i$ |
|---|---|---|---|---|---|
| 643 | 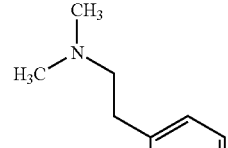 | 2-(2-{2-[2-(4-cyclobutylpiperazin-1-yl)-2-oxoethyl]-1,2,3,4-tetrahydroisoquinolin-6-yl}phenyl)-N,N-dimethylethanamine | 1.22 (1) | 461.29 | * |
| 644 | 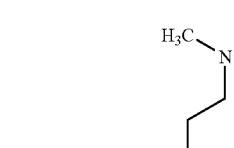 | 2-(3-{2-[2-(4-cyclobutylpiperazin-1-yl)-2-oxoethyl]-1,2,3,4-tetrahydroisoquinolin-6-yl}phenyl)-N,N-dimethylethanamine | 1.22 (1) | 461.29 | * |
| 645 | 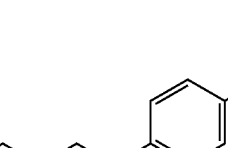 | 2-(4-{2-[2-(4-cyclobutylpiperazin-1-yl)-2-oxoethyl]-1,2,3,4-tetrahydroisoquinolin-6-yl}phenyl)-N,N-dimethylethanamine | 1.22 (1) | 461.29 | * |
| 646 | 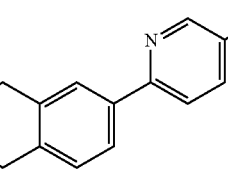 | 2-[2-(4-cyclobutylpiperazin-1-yl)-2-oxoethyl]-6-[5-(methoxymethyl)pyridin-2-yl]-1,2,3,4-tetrahydroisoquinoline | 1.13 (1) | 435.26 | * |

TABLE II-continued

| Compound | | Name | RT | MS | $K_i$ |
|---|---|---|---|---|---|
| 647 | | 2-[2-(4-cyclobutylpiperazin-1-yl)-2-oxoethyl]-6-(5-isopropylpyridin-2-yl)-1,2,3,4-tetrahydroisoquinoline | 1.21 (1) | 433.29 | * |
| 648 | | 2-[2-(4-cyclobutylpiperazin-1-yl)-2-oxoethyl]-6-[6-(trifluoromethyl)pyridin-3-yl]-1,2,3,4-tetrahydroisoquinoline | 1.18 (1) | 459.21 | * |
| 649 | | 2-[2-(4-cyclobutylpiperazin-1-yl)-2-oxoethyl]-6-(6-isopropylpyridin-3-yl)-1,2,3,4-tetrahydroisoquinoline | 1.2 (1) | 433.28 | * |
| 650 | | 6-[2-(4-cyclobutylpiperazin-1-yl)-2-oxoethyl]-N-(cyclopropylmethyl)-5,6,7,8-tetrahydro-1,6-naphthyridin-2-amine | 1.13 (1) | 384.19 | * |
| 651 | | 6-[2-(4-cyclobutylpiperazin-1-yl)-2-oxoethyl]-N-isobutyl-5,6,7,8-tetrahydro-1,6-naphthyridin-2-amine | 1.15 (1) | 386.20 | * |

TABLE II-continued

| Compound | | Name | RT | MS | $K_i$ |
|---|---|---|---|---|---|
| 652 | | 6-[2-(4-cyclobutylpiperazin-1-yl)-2-oxoethyl]-N-(3-methylbutyl)-5,6,7,8-tetrahydro-1,6-naphthyridin-2-amine | 1.18 (1) | 400.22 | * |
| 653 | | 1-[3-({6-[2-(4-cyclobutylpiperazin-1-yl)-2-oxoethyl]-5,6,7,8-tetrahydro-1,6-naphthyridin-2-yl}amino)propyl]pyrrolidin-2-one | 1.05 (1) | 455.20 | * |
| 654 | | N-cyclobutyl-6-[2-(4-cyclobutylpiperazin-1-yl)-2-oxoethyl]-5,6,7,8-tetrahydro-1,6-naphthyridin-2-amine | 1.14 (1) | 384.18 | * |
| 655 | | N-sec-butyl-6-[2-(4-cyclobutylpiperazin-1-yl)-2-oxoethyl]-5,6,7,8-tetrahydro-1,6-naphthyridin-2-amine | 1.15 (1) | 386.19 | * |
| 656 | | 6-[2-(4-cyclobutylpiperazin-1-yl)-2-oxoethyl]-N-cyclopentyl-5,6,7,8-tetrahydro-1,6-naphthyridin-2-amine | 1.17 (1) | 398.19 | * |
| 657 | | 6-[2-(4-cyclobutylpiperazin-1-yl)-2-oxoethyl]-N-(1-methylbutyl)-5,6,7,8-tetrahydro-1,6-naphthyridin-2-amine | 0.43 (3) | 400.30 | * |
| 658 | | 6-[2-(4-cyclobutylpiperazin-1-yl)-2-oxoethyl]-N-cyclohexyl-5,6,7,8-tetrahydro-1,6-naphthyridin-2-amine | 1.2 (1) | 412.21 | * |

TABLE II-continued

| Compound | Name | RT | MS | K$_i$ |
|---|---|---|---|---|
| 659 | 6-[2-(4-cyclobutylpiperazin-1-yl)-2-oxoethyl]-N-(cyclohexylmethyl)-5,6,7,8-tetrahydro-1,6-naphthyridin-2-amine | 1.23 (1) | 426.22 | * |
| 660 | 6-[2-(4-cyclobutylpiperazin-1-yl)-2-oxoethyl]-N-(2-ethylbutyl)-5,6,7,8-tetrahydro-1,6-naphthyridin-2-amine | 1.22 (1) | 414.22 | * |
| 661 | 6-[2-(4-cyclobutylpiperazin-1-yl)-2-oxoethyl]-N-(1,2-dimethylpropyl)-5,6,7,8-tetrahydro-5,6,7,8-tetrahydro-1,6-naphthyridin-2-amine | 1.19 (1) | 400.21 | * |
| 662 | 6-[2-(4-cyclobutylpiperazin-1-yl)-2-oxoethyl]-N-(1-ethylpropyl)-5,6,7,8-tetrahydro-1,6-naphthyridin-2-amine | 1.19 (1) | 400.21 | * |
| 663 | 6-[2-(4-cyclobutylpiperazin-1-yl)-2-oxoethyl]-N-(2-methoxyethyl)-5,6,7,8-tetrahydro-1,6-naphthyridin-2-amine | 1.06 (1) | 388.17 | * |
| 664 | 6-[2-(4-cyclobutylpiperazin-1-yl)-2-oxoethyl]-N-(3-methoxypropyl)-5,6,7,8-tetrahydro-1,6-naphthyridin-2-amine | 1.09 (1) | 402.18 | * |

TABLE II-continued

| Compound | Name | RT | MS | $K_i$ |
|---|---|---|---|---|
| 665 | 6-[2-(4-cyclobutylpiperazin-1-yl)-2-oxoethyl]-N-(2-methoxy-1-methylethyl)-5,6,7,8-tetrahydro-1,6-naphthyridin-2-amine | 1.1 (1) | 402.19 | † |
| 666 | 6-[2-(4-cyclobutylpiperazin-1-yl)-2-oxoethyl]-N-[1-(methoxymethyl)propyl]-5,6,7,8-tetrahydro-1,6-naphthyridin-2-amine | 1.13 (1) | 416.20 | * |
| 667 | 6-[2-(4-cyclobutylpiperazin-1-yl)-2-oxoethyl]-N-(2-ethoxyethyl)-5,6,7,8-tetrahydro-1,6-naphthyridin-2-amine | 1.11 (1) | 402.18 | * |
| 668 | 6-[2-(4-cyclobutylpiperazin-1-yl)-2-oxoethyl]-N-(2-isopropoxyethyl)-5,6,7,8-tetrahydro-1,6-naphthyridin-2-amine | 1.13 (1) | 416.20 | † |
| 669 | 6-[2-(4-cyclobutylpiperazin-1-yl)-2-oxoethyl]-N-(2-propoxyethyl)-5,6,7,8-tetrahydro-1,6-naphthyridin-2-amine | 1.14 (1) | 416.19 | † |
| 670 | 6-[2-(4-cyclobutylpiperazin-1-yl)-2-oxoethyl]-2-[(3S)-3-methoxypyrrolidin-1-yl]-5,6,7,8-tetrahydro-1,6-naphthyridine | 1.12 (1) | 414.19 | * |

TABLE II-continued

| Compound | | Name | RT | MS | $K_i$ |
|---|---|---|---|---|---|
| 671 | | 6-[2-(4-cyclobutylpiperazin-1-yl)-2-oxoethyl]-2-(3-methoxypiperidin-1-yl)-5,6,7,8-tetrahydro-1,6-naphthyridine | 1.15 (1) | 428.22 | † |
| 672 | | 6-[2-(4-cyclobutylpiperazin-1-yl)-2-oxoethyl]-2-[4-(2-methoxyethyl)piperidin-yl]-5,6,7,8-tetrahydro-1,6-naphthyridine | 1.19 (1) | 456.24 | * |
| 673 | | 6-[2-(4-cyclobutylpiperazin-1-yl)-2-oxoethyl]-2-[4-(methoxymethyl)piperdin-1-yl]-5,6,7,8-tetrahydro-1,6-naphthyridine | 1.17 (1) | 442.23 | * |
| 674 | | 6-[2-(4-cyclobutylpiperazin-1-yl)-2-oxoethyl]-2-[3-(2-methoxyethyl)piperidin-1-yl]-5,6,7,8-tetrahydro-1,6-naphthyridine | 1.21 (1) | 456.24 | * |
| 675 | | (1-{6-[2-(4-cyclobutylpiperazin-1-yl)-2-oxoethyl]-5,6,7,8-tetrahydro-1,6-naphthyridin-2-yl}piperidin-4-yl)acetonitrile | 1.12 (1) | 437.21 | * |

TABLE II-continued

| Compound | Name | RT | MS | $K_i$ |
|---|---|---|---|---|
| 676 | 6-[2-(4-cyclobutylpiperazin-1-yl)-2-oxoethyl]-2-(2-methylpiperidin-1-yl)-5,6,7,8-tetrahydro-1,6-naphthyridine | 1.23 (1) | 412.23 | * |
| 677 | 6-[2-(4-cyclobutylpiperazin-1-yl)-2-oxoethyl]-N-cyclohexyl-N-methyl-5,6,7,8-tetrahydro-1,6-naphthyridin-2-amine | 1.27 (1) | 426.24 | * |
| 678 | 6-[2-(4-cyclobutylpiperazin-1-yl)-2-oxoethyl]-2-[(2S)-2-(methoxymethyl)pyrrolidin-1-yl]-5,6,7,8-tetrahydro-1,6-naphthyridine | 1.18 (1) | 428.0 | * |
| 679 | 6-[2-(4-cyclobutylpiperazin-1-yl)-2-oxoethyl]-2-[(2R)-2-(methoxymethyl)pyrrolidin-1-yl]-5,6,7,8-tetrahydro-1,6-naphthyridine | 1.18 (1) | 428.21 | * |
| 680 | [{6-[2-(4-cyclobutylpiperazin-1-yl)-2-oxoethyl]-5,6,7,8-tetrahydro-1,6-naphthyridin-2-yl}(methyl)amino]acetonitrile | | | † |

TABLE II-continued

| Compound | Name | RT | MS | $K_i$ |
|---|---|---|---|---|
| 681 | 6-[2-(4-cyclobutyipiperazin-1-yl)-2-oxoethyl]-2-(4-methoxypiperidin-1-yl)-5,6,7,8-tetrahydro-1,6-naphthyridine | 1.14 (1) | 428.22 | * |
| 682 | 6-[2-(4-cyclobutylpiperazin-1-yl)-2-oxoethyl]-2-[3-(trifluoromethyl)piperidin-1-yl]-5,6,7,8-tetrahydro-1,6-naphthyridine | 1.23 (1) | 466.18 | * |
| 683 | 4-{6-[2-(4-cyclobutylpiperazin-1-yl)-2-oxoethyl]-5,6,7,8-tetrahydropyrido[4,3-d]pyrimidin-2-yl}benzonitrile | 0.78 (1) | 417.23 | * |
| 684 | 5-[2-(4-cyclobutylpiperazin-1-yl)-2-oxoethyl]-2-cyclopentyl-4,5,6,7-tetrahydro-2H-pyrazolo[4,3-c]pyridine | 0.6 (1) | 372.29 | * |
| 685 | 5-[2-(4-cyclobutylpiperazin-1-yl)-2-oxoethyl]-2-(tetrahydro-2H-pyran-4-yl)-4,5,6,7-tetrahydro-2H-pyrazolo[4,3-c]pyridine | 1.02 (1) | 388.3 | * |
| 686 | 2-{5-[2-(4-cyclobutylpiperazin-1-yl)-2-oxoethyl]-4,5,6,7-tetrahydro-2H-pyrazolo[4,3-c]pyridin-2-yl}pyrimidine-5-carbonitrile | 0.86 (1) | 407.2 | * |

TABLE II-continued

| Compound | Name | RT | MS | $K_i$ |
|---|---|---|---|---|
| 687 | 6-{5-[2-(4-cyclobutylpiperazin-1-yl)-2-oxoethyl]-4,5,6,7-tetrahydro-2H-pyrazolo[4,3-c]pyridin-2-yl}nicotinonitrile | 0.42 (1) | 406.34 | * |
| 688 | 6-{5-[2-(4-cyclobutylpiperazin-1-yl)-2-oxoethyl]-4,5,6,7-tetrahydro-2H-pyrazolo[4,3-c]pyridin-2-yl}[1,2,4]triazolo[4,3-b]pyridazine | 0.41 (1) | 422.2 | * |
| 689 | 6-{5-[2-(4-cyclobutylpiperazin-1-yl)-2-oxoethyl]-4,5,6,7-tetrahydro-2H-pyrazolo[4,3-c]pyridin-2-yl}-3-methyl[1,2,4]triazolo[4,3-b]pyridazine | 1.02 (1) | 436.3 | * |
| 690 | 1-{6-[2-(4-cyclobutylpiperazin-1-yl)-2-oxoethyl]-5,6,7,8-tetrahydropyrido[4,3-d]pyrimidin-2-yl}piperidine-4-carbonitrile | | | * |
| 691 | 1-{6-[2-(4-cyclobutylpiperazin-1-yl)-2-oxoethyl]-5,6,7,8-tetrahydropyrido[4,3-d]pyrimidin-2-yl}piperidine-4-carboxamide | | | * |

TABLE II-continued

| Compound | | Name | RT | MS | $K_i$ |
|---|---|---|---|---|---|
| 692 | | 6-[2-(4-cyclobutylpiperazin-1-yl)-2-oxoethyl]-4-methyl-2-morpholin-4-yl-5,6,7,8-tetrahydropyrido[4,3-d]pyrimidine | | | * |

Example 3

Additional Representative Compounds

Using routine modifications, the starting materials may be varied and additional steps employed to produce other compounds provided herein. Compounds listed in Table III are prepared using such methods.

TABLE III

| Compound | | Name |
|---|---|---|
| 693 | | (4-Cyclobutyl-piperazin-1-yl)-(6-pyrimidin-5-yl-3,4-dihydro-1H-isoquinolin-2-yl)-methanone |
| 694 | | 2-[2-(4-Cyclobutyl-piperazin-1-yl)-2-oxo-ethyl]-1,2,3,4-tetrahydro-isoquinoline-6-carboxylic acid methyl ester |
| 695 | | 2-[2-(4-Cyclobutyl-piperazin-1-yl)-2-oxo-ethyl]-1,2,3,4-tetrahydro-isoquinoline-6-carboxylic acid |

TABLE III-continued

| Compound | | Name |
|---|---|---|
| 696 | 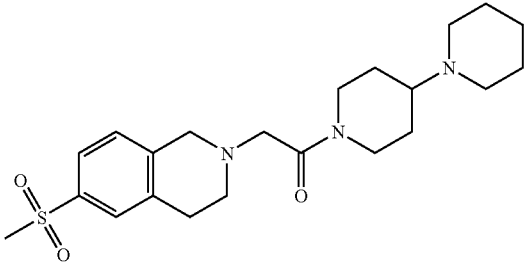 | 1-[1,4']Bipiperidinyl-1'-yl-2-(6-methanesulfonyl-3,4-dihydro-1H-isoquinolin-2-yl)-ethanone |
| 697 | 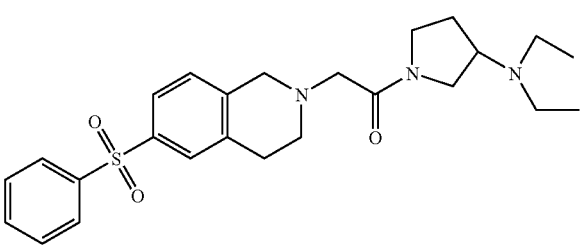 | 2-(6-Benzenesulfonyl-3,4-dihydro-1H-isoquinolin-2-yl)-1-(3-diethylamino-pyrrolidin-1-yl)-ethanone |
| 698 | 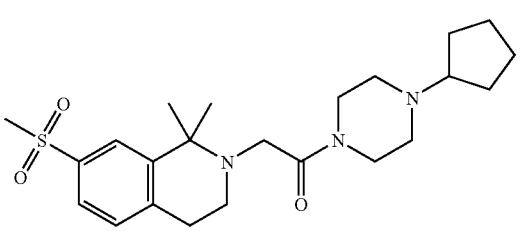 | 1-(4-Cyclopentyl-piperazin-1-yl)-2-(7-methanesulfonyl-1,1-dimethyl-3,4-dihydro-1H-isoquinolin-2-yl)-ethanone |
| 699 | 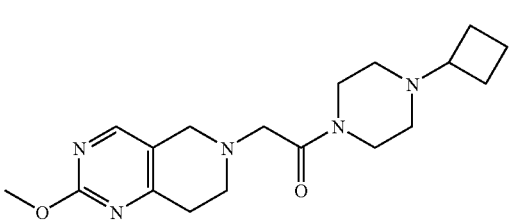 | 1-(4-Cyclobutyl-piperazin-1-yl)-2-(2-methoxy-7,8-dihydro-5H-pyrido[4,3-d]pyrimidin-6-yl)-ethanone |
| 700 | 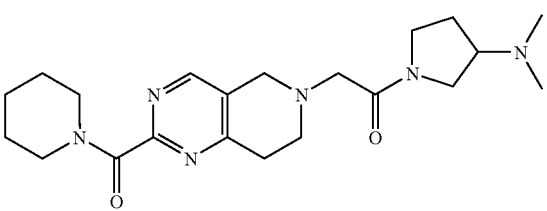 | 1-(3-Dimethylamino-pyrrolidin-1-yl)-2-[2-(piperidine-1-carbonyl)-7,8-dihydro-5H-pyrido[4,3-d]pyrimidin-6-yl]-ethanone |
| 701 | 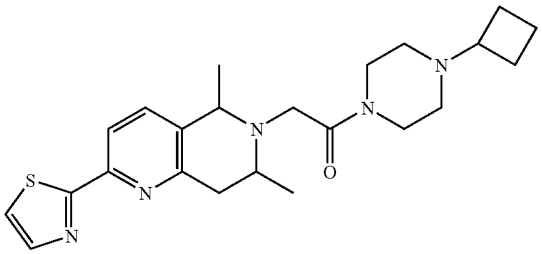 | 1-(4-Cyclobutyl-piperazin-1-yl)-2-(5,7-dimethyl-2-thiazol-2-yl-7,8-dihydro-5H-[1,6]naphthyridin-6-yl)-ethanone |

TABLE III-continued

| Compound | Name |
|---|---|
| 702 | 1-(4-Cyclopentyl-piperazin-1-yl)-2-[2-(6-methoxy-pyridin-3-yl)-5,6,8,9-tetrahydro-pyrimido[4,5-d]azepin-7-yl]-ethanone |
| 703 | 1-(4-Isopropyl-piperazin-1-yl)-2-[2-(tetrahydro-pyran-4-carbonyl)-5,6,8,9-tetrahydro-pyrido[2,3-d]azepin-7-yl]-ethanone |
| 704 | 1-(3-Diethylamino-pyrrolidin-1-yl)-2-(3-phenyl-5,6,8,9-tetrahydro-1,2,7-triaza-benzocyclohepten-7-yl)-ethanone |
| 705 | 1-[1,4']Bipiperidinyl-1'-yl-2-(3-pyridin-4-yl-5,6,8,9-tetrahydro-pyrido[3,4-d]azepin-7-yl)-ethanone |
| 706 | 1-(4-Dimethylamino-piperidin-1-yl)-2-[2-(4-methoxy-phenyl)-5,6,8,9-tetrahydro-pyrazino[2,3-d]azepin-7-yl]-ethanone |
| 707 | 7-[4-(4-Isopropyl-piperazin-1-yl)-4-oxo-butyl]-5,6,7,8-tetrahydro-[1,7]naphthyridine-3-carboxylic acid amide |
| 708 | 7-[3-(4-Isopropyl-piperazin-1-yl)-3-oxo-propyl]-5,6,7,8-tetrahydro-[1,7]naphthyridine-3-carboxylic acid amide |
| 709 | 1-(3-Diethylamino-pyrrolidin-1-yl)-2-[3-(5-methyl-[1,2,4]oxadiazol-3-yl)-5,6,8,9-tetrahydro-pyrido[2,3-d]azepin-7-yl]-ethanone |

TABLE III-continued

| Compound | | Name |
|---|---|---|
| 710 | 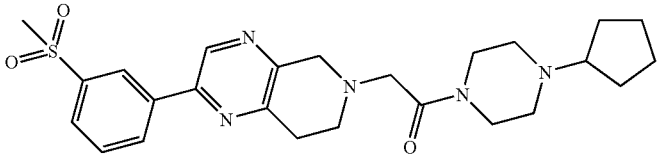 | 1-(4-Cyclopentyl-piperazin-1-yl)-2-[2-(3-methanesulfonyl-phenyl)-7,8-dihydro-5H-pyrido[3,4-b]pyrazin-6-yl]-ethanone |
| 711 | 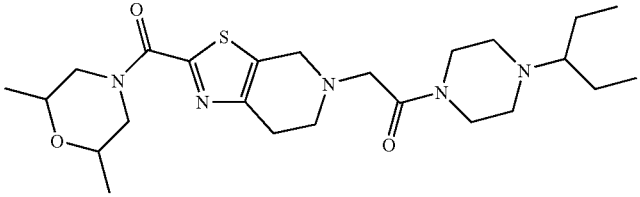 | 2-[2-(2,6-Dimethyl-morpholine-4-carbonyl)-6,7-dihydro-4H-thiazolo[5,4-c]pyridin-5-yl]-1-[4-(1-ethyl-propyl)-piperazin-1-yl]-ethanone |
| 712 | 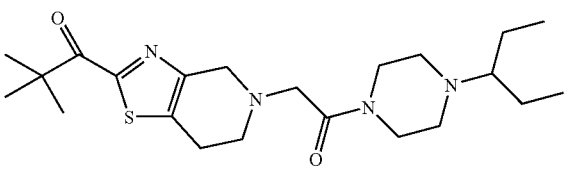 | 1-(5-{2-[4-(1-Ethyl-propyl)-piperazin-1-yl]-2-oxo-ethyl}-4,5,6,7-tetrahydro-thiazolo[4,5-c]pyridin-2-yl)-2,2-dimethyl-propan-1-one |
| 713 | 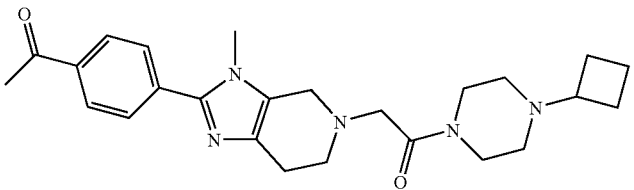 | 2-[2-(4-Acetyl-phenyl)-3-methyl-3,4,6,7-tetrahydro-imidazo[4,5-c]pyridin-5-yl]-1-(4-cyclobutyl-piperazin-1-yl)-ethanone |
| 714 | 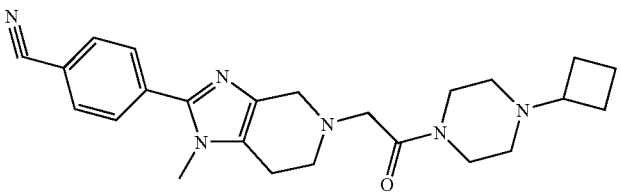 | 4-{5-[2-(4-Cyclobutyl-piperazin-1-yl)-2-oxo-ethyl]-1-methyl-4,5,6,7-tetrahydro-1H-imidazo[4,5-c]pyridin-2-yl}-benzonitrile |
| 715 | 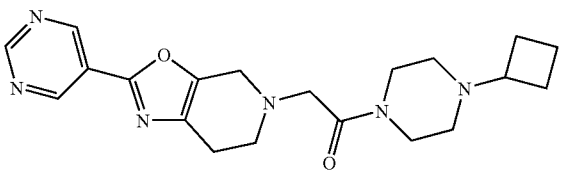 | 1-(4-Cyclobutyl-piperazin-1-yl)-2-(2-pyrimidin-5-yl-6,7-dihydro-4H-oxazolo[5,4-c]pyridin-5-yl)-ethanone |
| 716 | 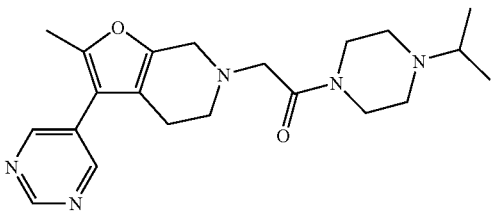 | 1-(4-Isopropyl-piperazin-1-yl)-2-(2-methyl-3-pyrimidin-5-yl-4,7-dihydro-5H-furo[2,3-c]pyridin-6-yl)-ethanone |

TABLE III-continued

| Compound | | Name |
|---|---|---|
| 717 | 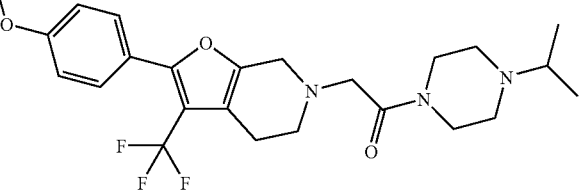 | 1-(4-Isopropyl-piperazin-1-yl)-2-[2-(4-methoxy-phenyl)-3-trifluoromethyl-4,7-dihydro-5H-furo[2,3-c]pyridin-6-yl]-ethanone |
| 718 | 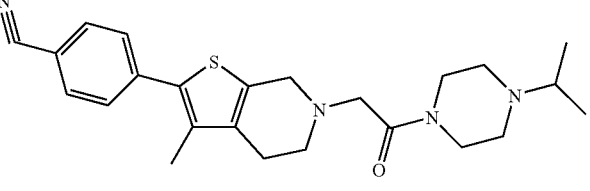 | 4-{6-[2-(4-Isopropyl-piperazin-1-yl)-2-oxo-ethyl]-3-methyl-4,5,6,7-tetrahydro-thieno[2,3-c]pyridin-2-yl}-benzonitrile |
| 719 | 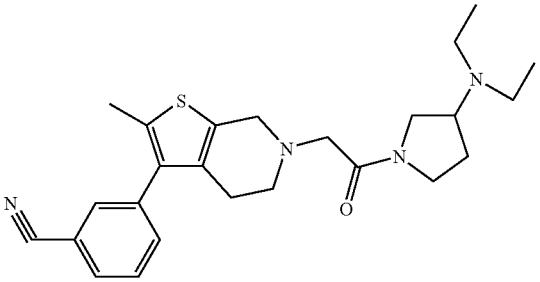 | 3-{6-[2-(3-Diethylamino-pyrrolidin-1-yl)-2-oxo-ethyl]-2-methyl-4,5,6,7-tetrahydro-thieno[2,3-c]pyridin-3-yl}-benzonitrile |
| 720 | 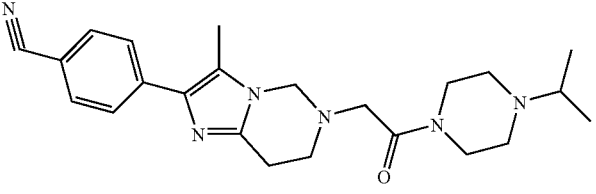 | 4-{6-[2-(4-Isopropyl-piperazin-1-yl)-2-oxo-ethyl]-3-methyl-5,6,7,8-tetrahydro-imidazo[1,2-c]pyrimidin-2-yl}-benzonitrile |
| 721 | 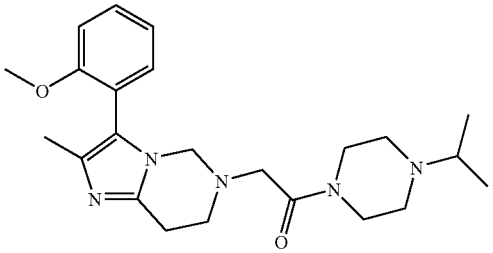 | 1-(4-Isopropyl-piperazin-1-yl)-2-[3-(2-methoxy-phenyl)-2-methyl-7,8-dihydro-imidazo[1,2-c]pyrimidin-6-yl]-ethanone |
| 722 | 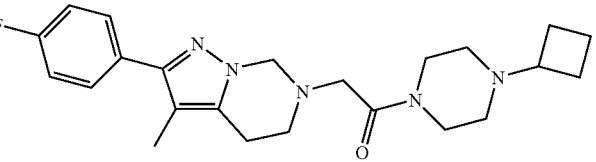 | 1-(4-Cyclobutyl-piperazin-1-yl)-2-[2-(4-fluoro-phenyl)-3-methyl-4,5-dihydro-pyrazolo[1,5-c]pyrimidin-6-yl]-ethanone |
| 723 | 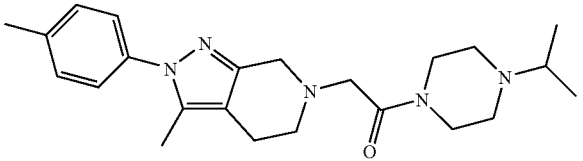 | 1-(4-Isopropyl-piperazin-1-yl)-2-(3-methyl-2-p-tolyl-2,4,5,7-tetrahydro-pyrazolo[3,4-c]pyridin-6-yl)-ethanone |

TABLE III-continued

| Compound | | Name |
|---|---|---|
| 724 | 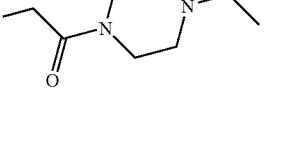 | 1-(4-Isopropyl-piperazin-1-yl)-2-(1-methyl-3-phenyl-1,4,5,7-tetrahydro-pyrazolo[3,4-c]pyridin-6-yl)-ethanone |
| 725 | 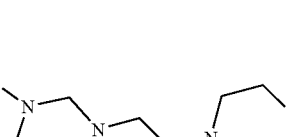 | 2-[2-(4-Acetyl-phenyl)-7,8-dihydro-[1,2,4]triazolo[1,5-c]pyrimidin-6-yl]-1-(4-isopropyl-piperazin-1-yl)-ethanone |
| 726 | 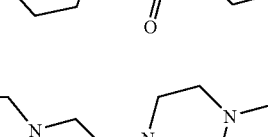 | 1-(4-Cyclobutyl-piperazin-1-yl)-2-(3-methyl-2-phenyl-4,5,7,8-tetrahydro-2H-1,2,6-triaza-azulen-6-yl)-ethanone |
| 727 | 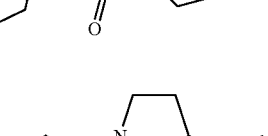 | 1-{2-[2-(3-Dimethylamino-pyrrolidin-1-yl)-2-oxo-ethyl]-2,3,4,5-tetrahydro-1H-benzo[c]azepin-7-yl}-propan-1-one |
| 728 | 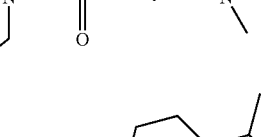 | 3-[2-(4-Isopropyl-piperazin-1-yl)-2-oxo-ethyl]-1,2,3,4,5,6-hexahydro-benzo[d]azocine-8-carbonitrile |
| 729 | 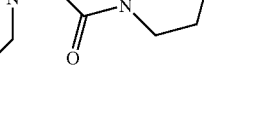 | 6-{5-[2-(4-cyclobutylpiperazin-1-yl)-2-oxoethyl]-4,5,6,7-tetrahydropyrazolo[1,5-a]pyrazin-2-yl}nicotinonitrile |

Example 4

Preparation of Chimeric Human H3 Receptor

Chimeric H3 receptor cDNA from human H3 receptor is generated from three cDNA fragments: (1) a human H3 receptor cDNA 5' fragment; (2) a human H3 receptor cDNA 3' fragment; and (3) a rat $G\alpha_{i2}$ cDNA fragment, each containing appropriate, overlapping linker sequences, as described in Example 1 of U.S. patent application Ser. No. 11/355,711, which published as US 2006/0188960, and is hereby incorporated by reference for its teaching of the preparation of a chimeric human H3 receptor-rat $G\alpha_{i2}$ baculoviral expression construct that has the sequence provided in SEQ ID NO:7 of US 2006/0188960, and encodes a polypeptide that has the sequence provided in SEQ ID NO: 8 of US 2006/0188960.

Example 5

Chimeric Human H3 Receptor Baculovirus Preparation and Infection

The chimeric human H3 receptor-rat $G\alpha_{i2}$ baculoviral expression vector is co-transfected along with BACULOGOLD DNA (BD PHARMINGEN, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City, Kans.) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing $2 \times 10^6$ Sf9 cells in 5 ml of insect medium. After five days of incubation at 27° C., supernatant medium is harvested from each of the T25 infections for use as passage 1 inoculum.

Two of seven recombinant baculoviral clones are chosen for a second round of amplification, using 1 ml of passage 1 stock to infect $1 \times 10^8$ cells in 100 ml of insect medium divided into two T175 flasks. Forty-eight hours post infection, passage 2 medium from each 100 ml prep is harvested and plaque assayed to determine virus titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection, the supernatant medium is harvested to yield passage 3 baculoviral stock.

The remaining cell pellet is assayed for affinity binding using the protocol of DeMartino et al. (1994) J. Biol. Chem. 269(20):14446-50 (which is incorporated herein by reference for its teaching of binding assays at page 14447), adapted as follows. Radioligand ranges from 0.40-40 nM [$^3$H]-N-(a) methylhistamine (Perkin Elmer, Boston, Mass.) and assay buffer contains 50 mM Tris, 1 mM $CaCl_2$, 5 mM $MgCl_2$, 0.1% BSA, 0.1 mM bacitracin, and 100 KIU/ml aprotinin, pH 7.4. Filtration is carried out using GF/C WHATMAN filters (pre-soaked in 1.0% polyethyeneimine for 2 hr prior to use). Filters are washed three times with 5 ml cold assay buffer without BSA, bacitracin, or aprotinin and air dried for 12-16 hr. Radioactivity retained on filters is measured on a beta scintillation counter.

Titer of the passage 3 baculoviral stock is determined by plaque assay and a multiplicity of infection, incubation time course, binding assay experiment is carried out to determine conditions for optimal receptor expression. A multiplicity of infection of 0.5 and a 72-hr incubation period are preferred infection parameters for chimeric human H3 receptor-rat $G\alpha_{i2}$ expression in up to 1-liter Sf9 cell infection cultures.

Log-phase Sf9 cells (INVITROGEN), are infected with one or more stocks of recombinant baculovirus followed by culturing in insect medium at 27° C. Infections are carried out with virus directing the expression of human H3 receptor-rat $G\alpha_{i2}$ in combination with three G-protein subunit-expression virus stocks: 1) rat $G\alpha_{i2}$ G-protein-encoding virus stock (BIOSIGNAL #V5J008), 2) bovine β1 G-protein-encoding virus stock (BIOSIGNAL #V5H012), and 3) human γ2 G-protein-encoding virus stock (BIOSIGNAL #V6B003), which may be obtained from BIOSIGNAL Inc., Montreal.

The infections are conveniently carried out at a multiplicity of infection of 0.5:1.0:0.5:0.5. At 72 hr post-infection, an aliquot of cell suspension is analyzed for viability by trypan blue dye exclusion. If no blue is detected by visual inspection, the Sf9 cells are harvested via centrifugation (3000 rpm/10 min/4° C.).

Example 6

Chimeric Human H3 Receptor Cell Membrane Preparations

Sf9 cell pellets obtained as described in Example 5 are resuspended in homogenization buffer (10 mM HEPES, 250 mM sucrose, 0.5 μg/ml leupeptin, 2 μg/ml Aprotinin, 200 μM PMSF, and 2.5 mM EDTA, pH 7.4) and homogenized using a POLYTRON PT10-35 homogenizer (KINEMATICA AG, Lucerne, Switzerland; setting 5 for 30 seconds). The homogenate is centrifuged (536×g/10 min at 4° C.) to pellet the nuclei and unbroken cells. The supernatant containing the membranes is decanted to a clean centrifuge tube, centrifuged (48,000×g/30 min, 4° C.) and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until used for radioligand binding or functional response assays. The protein concentration of the resulting membrane preparation (hereinafter termed "P2 membranes") is conveniently measured using a Bradford protein assay (BIO-RAD LABORATORIES, Hercules, Calif.). By this measure, a 1-liter culture of cells typically yields 100-150 mg of total membrane protein.

Example 7

Chimeric Human H3 Receptor GTP Binding Assays

This Example illustrates a representative assay for evaluating agonist-stimulated GTP-gamma$^{35}$S binding ("GTP binding") activity. Such GTP binding activity can be used to identify H3 antagonists and to differentiate neutral antagonist compounds from those that possess inverse agonist activity. This agonist-stimulated GTP binding activity can also be used to detect partial agonism mediated by antagonist compounds. A compound analyzed in this assay is referred to herein as a "test compound."

Four independent baculoviral stocks (one directing the expression of the chimeric human H3 receptor and three directing the expression of each of the three subunits of a heterotrimeric G-protein) are used to infect a culture of Sf9 cells as described above. P2 membranes are prepared as described above, and agonist-stimulated GTP binding on the P2 membranes is assessed using histamine (Sigma Chemical Co., St. Louis, Mo.) as agonist in order to ascertain that the receptor/G-protein-alpha-beta-gamma combination(s) yield a functional response as measured by GTP binding. P2 membranes are resuspended by Dounce homogenization (tight pestle) in GTP binding assay buffer (50 mM Tris pH 7.4, 120 mM NaCl, 5 mM $MgCl_2$, 2 mM EGTA, 1 mg/ml BSA, 0.2 mg/ml bacitracin, 0.02 mg/ml aprotinin, 0.01 mg/ml saponin, 10 μM GDP) and added to assay tubes at a concentration of 35 μg protein/reaction tube. After adding increasing doses of histamine at concentrations ranging from $10^{-12}$ M to $10^{-5}$ M, reactions are initiated by the addition of 125 pM GTP-gamma$^{35}$S (PERKIN ELMER; Boston, Mass.) with a final assay volume of 0.20 ml. In competition experiments, non-radiolabeled test compounds are added to separate reactions at concentrations ranging from $10^{-10}$ M to $10^{-6}$ M along with 1 μM histamine to yield a final volume of 0.20 ml.

Neutral antagonists are antagonists that are substantially free of inherent agonist activity, and include those test compounds that reduce the histamine-stimulated GTP binding activity towards, but not below, baseline levels. In contrast, in the absence of added histamine, inverse agonists reduce the GTP binding activity of the receptor-containing membranes below baseline. The elevation of GTP binding activity above baseline by a compound in the absence of added histamine in this assay demonstrates agonist activity.

After a 60-min incubation at room temperature, reactions are terminated by vacuum filtration over WHATMAN GF/C filters (pre-soaked in wash buffer, 0.1% BSA) followed by washing with ice-cold wash buffer (50 mM Tris pH 7.4, 120 mM NaCl). The amount of receptor-bound (and thereby membrane-bound) GTP-gamma$^{35}$S is determined by measuring the filter-bound radioactivity, preferably by liquid scintillation spectrometry of the washed filters. Non-specific binding is determined in parallel assays including 10 μM unlabeled GTP-gammaS and typically represents less than 5 percent of total binding. Data is expressed as percent above basal (baseline). The results of GTP binding experiments are analyzed using SIGMAPLOT software (SPSS Inc., Chicago, Ill.). $IC_{50}$ values are calculated by non-linear regression analysis of dose-response curves using Kaleidograph (Synergy Software, Reading, Pa.).

Alternatively the data is analyzed as follows. First, the average bound radioactivity from negative control wells (no agonist) is subtracted from the bound radioactivity detected for each of the other experimental wells. Second, average bound radioactivity is calculated for the positive control wells (agonist wells). Then, percent inhibition for each compound tested is calculated using the equation:

$$\text{Percent Inhibition} = 100 - 100 \times \left[ \frac{\text{Bound radioactivity in Test Wells}}{\text{Bound radioactivity in Agonist Wells}} \right]$$

The % inhibition data is plotted as a function of test compound concentration and test compound $IC_{50}$ is determined using a linear regression in which x is ln(concentration of test compound) and y is ln(percent inhibition/(100-percent inhibition). Data with a percent inhibition that is greater than 90% or less than 15% are rejected and are not used in the regression. The $IC_{50}$ is $e^{(-intercept/slope)}$.

Calculated $IC_{50}$ values are converted to $K_i$ values by the Cheng-Prusoff correction (Cheng and Prusoff (1973) Biochem. Pharmacol. 22(23):3099-3108). Accordingly, the following equation: $K_i=IC_{50}/(1+[L]/EC_{50})$ is used, where [L] is the histamine concentration in the GTP binding assay, and $EC_{50}$ is the concentration of histamine producing a 50% response, as determined by a dose-response analysis using concentrations of histamine ranging from $10^{-10}$ M to $10^{-6}$ M.

To assess agonist or inverse agonist activity of a test compound, this assay is performed in the absence of added histamine, and $EC_{50}$ values are determined by analogous calculations, where the $EC_{50}$ is the concentration of test compound producing a 50% response.

Example 8

Chimeric Human H3 Receptor Screening: GTP Binding Assays

This Example illustrates a representative screening assay for evaluating inhibition of histamine-stimulated GTP-gamma$^{35}$S binding. Such GTP binding activity can be used to identify H3 antagonists and inverse agonists. A compound analyzed in this assay is referred to herein as a "test compound," and the initial identification of antagonists and inverse agonists is performed using a test compound concentration of 4 μM.

Four independent baculoviral stocks (one directing the expression of the chimeric human H3 receptor and three directing the expression of each of the three subunits of a heterotrimeric G-protein) are used to infect a culture of Sf9 cells as described above. P2 membranes are prepared as described above, and are resuspended by Dounce homogenization (tight pestle) in GTP binding assay buffer (50 mM Tris pH 7.4, 120 mM NaCl, 5 mM MgCl$_2$, 2 mM EGTA, 1 mg/ml BSA, 0.2 mg/ml bacitracin, 0.02 mg/ml aprotinin, 0.01 mg/ml saponin, 10 μM GDP) and added to assay tubes at a concentration of 35 μg protein/reaction tube. Non-radiolabeled test compounds are added to separate reactions at a concentration of 4 μM along with 1 μM histamine (agonist). Reactions are initiated by the addition of 125 pM GTP-gamma$^{35}$S with a final assay volume of 0.20 ml.

After a 60-min incubation at room temperature, reactions are terminated by vacuum filtration over GF/C filters (presoaked in 50 mM Tris pH 7.4, 120 mM NaCl plus 0.1% BSA) followed by washing with ice-cold buffer (50 mM Tris pH 7.4, 120 mM NaCl). The amount of receptor-bound (and thereby membrane-bound) GTP-gamma$^{35}$S is determined by measuring the bound radioactivity, preferably by liquid scintillation spectrometry of the washed filters. Non-specific binding is determined using 10 uM GTP-gammaS and typically represents less than 5 percent of total binding. After subtraction of non-specific binding, data is expressed as percent inhibition of 1 μM histamine signal.

Neutral antagonists are those test compounds that reduce the histamine-stimulated GTP binding activity towards, but not below, baseline levels. In contrast, in the absence of added histamine, inverse agonists reduce the GTP binding activity of the receptor-containing membranes below baseline. Any test compound that elevates GTP binding activity above baseline in the absence of added histamine in this assay is defined as having agonist activity.

What is claimed is:
1. A compound of the formula:

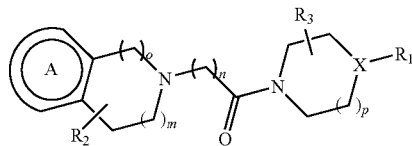

or a pharmaceutically acceptable salt thereof, wherein:
n is 1, 2 or 3;
p is 1;
m and o are independently 1;
X is N;
$R_1$ is $C_1$-$C_6$alkyl, $C_2$-$C_6$alkenyl, $C_2$-$C_6$alkynyl, ($C_3$-$C_8$cycloalkyl)$C_0$-$C_2$alkyl, mono- or di-($C_1$-$C_6$alkyl)amino, or (3- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl;
or $R_1$ and $R_3$ are taken together to form a fused 5- to 7-membered cycloalkyl or heterocycloalkyl ring, each of which is substituted with from 0 to 3 substituents independently chosen from oxo, $C_1$-$C_6$alkyl, $C_1$-$C_6$haloalkyl and $C_1$-$C_6$alkoxy;
$R_2$ represents from 0 to 4 substituents independently chosen from:
(i) $C_1$-$C_6$alkyl, $C_2$-$C_6$alkenyl, $C_2$-$C_6$alkynyl, ($C_3$-$C_8$cycloalkyl)$C_0$-$C_2$alkyl, $C_1$-$C_6$haloalkyl, and groups that are taken together to form a $C_1$-$C_3$alkylene bridge;
(ii) phenyl$C_0$-$C_4$alkyl that is substituted with from 0 to 3 substituents independently chosen from halogen and $C_1$-$C_6$alkyl; and (iii) groups that are taken together to form a spiro $C_3$-$C_7$cycloalkyl or a spiro 4- to 7-membered heterocycloalkyl, each of which is substituted with from 0 to 3 substituents independently chosen from $C_1$-$C_6$alkyl;

$R_3$ represents from 0 to 4 substituents independently chosen from $C_1$-$C_6$alkyl, $C_1$-$C_6$haloalkyl, groups that are taken together to form a $C_1$-$C_3$alkylene bridge and groups that are taken together to form a fused 5- to 7-membered cycloalkyl or heterocycloalkyl ring, each of which is substituted with from 0 to 3 substituents independently chosen from oxo, $C_1$-$C_6$alkyl, and $C_1$-$C_6$alkoxy;

represents a phenyl ring which is substituted with 0 or 1 $R_x$, and which is further substituted with from 0 to 3 substituents independently chosen from $R_y$;

$R_x$ is:
(i) halogen, cyano, aminocarbonyl, or COOH; or
(ii) $C_1$-$C_6$alkyl, $C_2$-$C_6$alkenyl, $C_2$-$C_6$alkynyl, $C_1$-$C_6$alkoxy, $C_1$-$C_6$aminoalkyl, $C_1$-$C_6$alkanoyl, $C_1$-$C_6$alkoxycarbonyl, $C_1$-$C_6$alkylsulfonyl, mono- or di-($C_1$-$C_6$alkyl)aminocarbonyl, mono- or di-($C_1$-$C_6$alkyl)amino$C_0$-$C_4$alkyl, ($C_3$-$C_{10}$cycloalkyl)-J-$C_0$-$C_4$alkyl, (3- to 10-membered heterocycloalkyl)-J-$C_0$-$C_4$alkyl, naphthyl-J-$C_0$-$C_4$alkyl or (5- to 12-membered heteroaryl)-J-$C_0$-$C_4$alkyl, each of which is substituted with from 0 to 4 substituents independently chosen from:
   (a) oxo, halogen, cyano, hydroxy, amino, nitro and aminocarbonyl; and
   (b) groups of the formula D-J-E-
   wherein:
   D represents $C_1$-$C_6$alkyl, $C_2$-$C_6$alkenyl, $C_2$-$C_6$alkynyl, $C_3$-$C_7$cycloalkyl, 3- to 7-membered heterocycloalkyl, phenyl or 5- or 6-membered heteroaryl, each of which is substituted with from 0 to 6 substituents independently chosen from halogen, cyano, hydroxy, amino, nitro, $C_1$-$C_4$alkyl, $C_1$-$C_4$haloalkyl and $C_1$-$C_4$alkoxy;
   Each J is independently absent, O, $CH_2O$, $OCH_2$, C(=O), OC(=O), C(=O)O, $S(O)_m$, $N(R_z)$, C(=O)N($R_z$), $N(R_z)$C(=O), —N($R_z$)$S(O)_m$ or $S(O)_m$N($R_z$), wherein each m is independently 0, 1 or 2 and each $R_z$ is independently hydrogen or $C_1$-$C_6$alkyl; and
   E is absent or represents $C_1$-$C_6$alkylene or $C_1$-$C_6$alkoxy; and Each $R_y$ is independently oxo, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, phenyl$C_0$-$C_2$alkyl or (5- or 6-membered heteroaryl)$C_0$-$C_2$alkyl.

2. A compound or salt according to claim 1, wherein

represents a phenyl ring is substituted with exactly one $R_x$, and which is further substituted with 0 or 1 substituent chosen from $R_y$.

3. A compound or salt according to claim 1, wherein n is 1.

4. A compound or salt according to claim 1, wherein $R_2$ and $R_3$ independently represent 0 substituents or 1 or 2 methyl substituents.

5. A compound or salt according to claim 1, wherein the compound satisfies the formula:

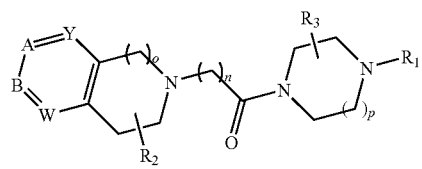

wherein:
exactly one of A, B and Y is $CR_x$; and the others of A, B and Y are independently $CR_4$;
W is $CR_4$;
$R_1$ is $C_1$-$C_6$alkyl, $C_2$-$C_6$alkenyl, $C_2$-$C_6$alkynyl, ($C_3$-$C_8$cycloalkyl)$C_0$-$C_2$alkyl or (4- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl; and each $R_4$ is independently hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, mono- or di-($C_1$-$C_6$alkyl)amino, phenyl$C_0$-$C_2$alkyl or (5- or 6-membered heteroaryl)$C_0$-$C_2$alkyl.

6. A compound or salt according to claim 5, wherein the compound satisfies the formula:

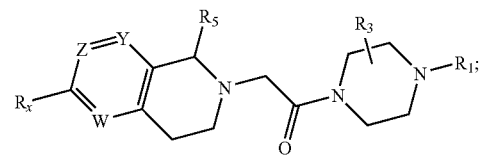

wherein:
W, Y and Z are independently $CR_4$; and
$R_5$ is hydrogen, $C_1$-$C_6$alkyl, ($C_3$-$C_8$cycloalkyl)$C_0$-$C_2$alkyl or phenyl$C_0$-$C_4$alkyl.

7. A compound or salt according to claim 5, wherein the compound satisfies the formula:

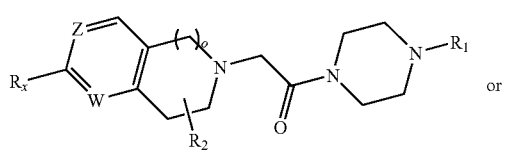

or

-continued

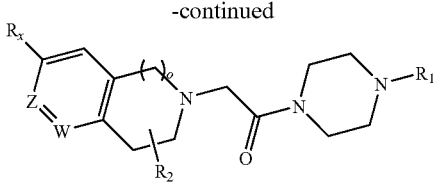

wherein W is CH and Z is $CR_4$.

8. A compound of the formula:

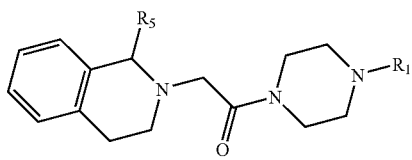

or a pharmaceutically acceptable salt thereof, wherein $R_5$ is hydrogen, $C_1$-$C_6$alkyl, $(C_3$-$C_8$cycloalkyl)$C_0$-$C_2$alkyl or phenyl$C_0$-$C_4$alkyl, and
$R_1$ is $C_1$-$C_6$alkyl, $C_2$-$C_6$alkenyl, $C_2$-$C_6$alkynyl, $(C_3$-$C_8$cycloalkyl)$C_0$-$C_2$alkyl or (4- to 8-membered heterocycloalkyl)$C_0$-$C_2$alkyl, each of which is substituted with from 0 to 4 substituents independently chosen from oxo, nitro, halogen, amino, cyano, hydroxy, aminocarbonyl, $C_1$-$C_6$alkyl, $C_2$-$C_6$alkenyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoyl, $C_3$-$C_6$alkanone, mono- or di-($C_1$-$C_6$alkyl)amino, mono- or di-($C_1$-$C_6$alkyl)aminocarbonyl, $C_3$-$C_7$cycloalkyl and 3- to 7-membered heterocycloalkyl.

9. A compound or salt according to claim 5, wherein the compound satisfies one of the following formulas:

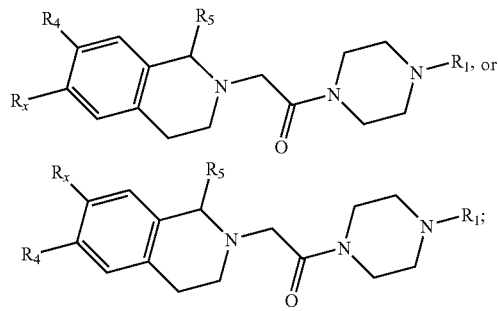

wherein:
$R_x$ is:
(i) halogen, cyano, $C_1$-$C_6$alkoxy, $C_1$-$C_6$alkanoyl, $C_1$-$C_6$alkylsulfonyl, mono- or di-($C_1$-$C_6$alkyl)amino, mono- or di-($C_1$-$C_6$alkyl)aminosulfonyl, mono- or di($C_1$-$C_6$alkyl)aminocarbonyl; or
(ii) $C_1$-$C_8$alkyl, $C_3$-$C_8$cycloalkyl, 4- to 7-membered heterocycloalkyl, phenyl, naphthyl, or 5- to 10-membered heteroaryl, each of which is substituted with from 0 to 3 substituents independently chosen from:
(a) hydroxy, cyano, halogen and oxo; and
(b) $C_1$-$C_8$alkyl, $C_1$-$C_8$haloalkyl, $C_1$-$C_8$cyanoalkyl, $C_1$-$C_8$alkoxy, $C_1$-$C_8$haloalkoxy, $C_1$-$C_8$alkylthio, $C_2$-$C_8$alkyl ether, $C_1$-$C_6$alkylsulfonyl, mono- or di($C_1$-$C_6$alkyl)amino$C_0$-$C_4$alkyl, mono- or di-($C_1$-$C_6$alkyl)aminosulfonyl, phenoxy, phenyl, and 4- to 7-membered heterocycloalkyl, each of which is unsubstituted or substituted with 1 or 2 substituents independently chosen from oxo, $C_1$-$C_4$alkyl and $C_1$-$C_4$alkoxy;
$R_4$ is hydrogen, amino, halogen, cyano, $C_1$-$C_6$alkyl, $C_1$-$C_6$alkoxy, $C_1$-$C_6$haloalkyl, $C_1$-$C_6$alkanoyl, $C_1$-$C_6$alkylsulfonyl, mono- or di-($C_1$-$C_6$alkyl)amino, phenyl$C_0$-$C_2$alkyl or (5- or 6-membered heteroaryl)$C_0$-$C_2$alkyl; and
$R_5$ is hydrogen or $C_1$-$C_6$alkyl.

10. A compound or salt according to claim 9, wherein:
$R_x$ is mono- or di-($C_1$-$C_6$alkyl)amino, 4- to 7-membered heterocycloalkyl, phenyl, naphthyl, or 5- to 10-membered heteroaryl, each of which is substituted with from 0 to 3 substituents independently chosen from:
(a) hydroxy, cyano, halogen and oxo; and
(b) $C_1$-$C_8$alkyl, $C_1$-$C_8$haloalkyl, $C_1$-$C_8$cyanoalkyl, $C_1$-$C_8$alkoxy, $C_1$-$C_8$haloalkoxy, $C_1$-$C_8$alkylthio, $C_2$-$C_8$alkyl ether, $C_1$-$C_6$alkylsulfonyl, mono- or di($C_1$-$C_6$alkyl)amino$C_0$-$C_4$alkyl, mono- or di-($C_1$-$C_6$alkyl) aminosulfonyl, phenoxy, phenyl, and 4- to 7-membered heterocycloalkyl, each of which is unsubstituted or substituted with 1 or 2 substituents independently chosen from oxo, $C_1$-$C_4$alkyl and $C_1$-$C_4$alkoxy; and
$R_1$ is $C_3$-$C_8$cycloalkyl$C_0$-$C_2$alkyl, 4- to 7-membered heterocycloalkyl or $C_2$-$C_8$alkyl, each of which is unsubstituted or substituted with 1 or 2 substituents independently chosen from $C_1$-$C_4$alkyl and $C_1$-$C_4$alkoxy.

11. A compound or salt according to claim 5, wherein:
$R_x$ is:
(i) $C_1$-$C_6$alkanoyl, $C_1$-$C_6$alkylsulfonyl, mono- or di-($C_1$-$C_6$alkyl)aminosulfonyl, or mono- or di($C_1$-$C_6$alkyl)aminocarbonyl; or
(ii) phenyl or 5- or 6-membered heteroaryl, each of which is substituted with from 0 to 3 substituents independently chosen from halogen, cyano, $C_1$-$C_6$alkyl, $C_1$-$C_4$alkoxy, $C_1$-$C_6$alkanoyl, $C_1$-$C_6$alkylsulfonyl, mono- or di-($C_1$-$C_6$alkyl)aminosulfonyl, and mono- or di($C_1$-$C_6$alkyl)aminocarbonyl;
$R_4$ is hydrogen; and
$R_5$ is hydrogen.

12. A compound or salt according to claim 5, wherein $R_x$ is phenyl, pyridyl or pyrimidinyl, each of which is substituted with one substituent chosen from halogen, cyano, $C_1$-$C_4$alkyl, $C_1$-$C_4$alkoxy, and $C_1$-$C_4$alkanoyl.

13. A compound or salt according to claim 5, wherein $R_1$ is $C_3$-$C_6$alkyl, or ($C_3$-$C_6$cycloalkyl)$C_0$-$C_2$alkyl.

14. A compound or salt according to claim 13, wherein $R_1$ is isopropyl, cyclobutyl, cyclopentyl or cyclohexyl.

15. A pharmaceutical composition, comprising at least one compound or salt according to claim 1 in combination with a physiologically acceptable carrier or excipient.

16. A pharmaceutical composition according to claim 15, wherein the composition is formulated as an injectable fluid, an aerosol, a cream, a gel, a pill, a capsule, a syrup or a transdermal patch.

17. A for therapeutically treating a condition in a patient, comprising administering to the patient a therapeutically effective amount of a compound of claim 1, wherein the condition is attention deficit disorder, attention deficit hyperactivity disorder, epilepsy, migraine, excessive daytime sleepiness, shift work sleep disorder, jet lag, narcolepsy, sleep apnea, allergic rhinitis, vertigo, motion sickness, or Parkinson's disease.

18. A method of therapeutically treating a condition in a patient, comprising administering to the patient a therapeutically effective amount of a compound of claim 1, wherein the condition is obesity, an eating disorder or diabetes mellitus.

19. A method according to claim 17, wherein the patient is a human.

20. A packaged pharmaceutical preparation, comprising:
(a) a pharmaceutical composition according to claim 15 in a container; and
(b) instructions for using the composition to treat a condition responsive to H3 receptor modulation in a patient.

21. A compound or salt thereof of claim 1, wherein the compound is 1-(4-Cyclobutyl-piperazin-1-yl)-2-(6-methoxy-3,4-dihydro-1H-isoquinolin-2-yl)-ethanone;
- 2-[2-(4-cyclobutylpiperazin-1-yl)-2-oxoethyl]-6-(cyclopentyloxy)-1,2,3,4-tetrahydroisoquinoline;
- 6-(benzyloxy)-2-[2-(4-cyclobutylpiperazin-1-yl)-2-oxoethyl]-1,2,3,4-tetrahydroisoquinoline;
- 2-[2-(4-cyclobutylpiperazin-1-yl)-2-oxoethyl]-6-{[5-(trifluoromethyl)-pyridin-2-yl]oxy}-1,2,3,4-tetrahydroisoquinoline;
- 2-[2-(4-cyclobutylpiperazin-1-yl)-2-oxoethyl]-6-{[5-(trifluoromethyl)-pyridin-2-yl]oxy}-1,2,3,4-tetrahydroisoquinoline;
- 1-(4-{2-[2-(4-cyclobutylpiperazin-1-yl)-2-oxoethyl]-1,2,3,4-tetrahydroisoquinolin-6-yl}phenyl)ethanone;
- 1-{2-[2-(4-cyclobutylpiperazin-1-yl)-2-oxoethyl]-1,2,3,4-tetrahydroisoquinolin-6-yl}ethanol;
- 2-[6-bromo-1-(2-chloro-phenyl)-3,4-dihydro-1H-isoquinolin-2-yl]-1-(4-cyclobutyl-piperazin-1-yl)-ethanone;
- 2-[6-Acetyl-1-(2-chloro-phenyl)-3,4-dihydro-1H-isoquinolin-2-yl]-1-(4-cyclobutyl-piperazin-1-yl)-ethanone;
- 2-[2-(4-cyclobutyl-piperazin-1-yl)-2-oxo-ethyl]-1,2,3,4-tetrahydro-isoquinoline-7-carboxylic acid methylamide;
- 2-[6-(4-acetyl-phenyl)-3,4-dihydro-1H-isoquinolin-2-yl]-1-(4-cyclobutyl-piperazin-1-yl)-ethanone;
- 1-(4-cyclobutyl-piperazin-1-yl)-2-(6-pyridazin-3-yl-3,4-dihydro-1H-isoquinolin-2-yl)-ethanone;
- 3-{2-[2-(4-cyclobutylpiperazin-1-yl)-2-oxoethyl]-1,2,3,4-tetrahydro-isoquinolin-6-yl}-1,3-oxazolidin-2-one;
- 2-[2-(4-cyclobutylpiperazin-1-yl)-2-oxoethyl]-6-(6-methylpyridazin-3-yl)-1,2,3,4-tetrahydroisoquinoline;
- 2-{2-[2-(4-cyclobutylpiperazin-1-yl)-2-oxoethyl]-1,2,3,4-tetrahydroiso-quinolin-6-yl}pyridazin-3(2H)-one;
- 2.3-{2-[2-(4-cyclobutylpiperazin-1-yl)-2-oxoethyl]-1,2,3,4-tetrahydro-isoquinolin-6-yl}-1,3-oxazolidin-2-one;
- 2-[2-(4-cyclobutylpiperazin-1-yl)-2-oxoethyl]-6-(1H-pyrazol-1-yl)-1,2,3,4-tetrahydroisoquinoline;
- 1-(4-Cyclobutyl-piperazin-1-yl)-2-[6-(pyrrolidine-1-carbonyl)-3,4-dihydro-1H-isoquinolin-2-yl]-ethanone;
- 2-[2-(4-cyclopentylpiperazin-1-yl)-2-oxoethyl]-1,2,3,4-tetrahydroisoquinoline;
- 2-[2-(4-cyclopentylpiperazin-1-yl)-2-oxoethyl]-6,7-dimethoxy-1,2,3,4-tetrahydroisoquinoline;
- 2-[2-(4-cyclopentylpiperazin-1-yl)-2-oxoethyl]-1,2,3,4-tetrahydroisoquinoline;
- 2-[2-(4-cyclopentylpiperazin-1-yl)-2-oxoethyl]-6,7-dimethoxy-1,2,3,4-tetrahydroisoquinoline;
- 2-[2-(4-cyclopentylpiperazin-1-yl)-2-oxoethyl]-1,2,3,4-tetrahydroisoquinoline;
- 2-[2-(4-isopropylpiperazin-1-yl)-2-oxoethyl]-1-phenyl-1,2,3,4-tetrahydroisoquinoline;
- 1-(cyclopentylmethyl)-2-[2-(4-isopropylpiperazin-1-yl)-2-oxoethyl]-1,2,3,4-tetrahydroisoquinoline;
- 1-benzyl-2-[2-(4-isopropylpiperazin-1-yl)-2-oxoethyl]-1,2,3,4-tetrahydroisoquinoline;
- 1-ethyl-2-[2-(4-isopropylpiperazin-1-yl)-2-oxoethyl]-1,2,3,4-tetrahydroisoquinoline;
- 1-isobutyl-2-[2-(4-isopropylpiperazin-1-yl)-2-oxoethyl]-1,2,3,4-tetrahydroisoquinoline;
- 1-(2-fluorophenyl)-2-[2-(4-isopropylpiperazin-1-yl)-2-oxoethyl]-1,2,3,4-tetrahydroisoquinoline;
- 1-(2-chlorophenyl)-2-[2-(4-isopropylpiperazin-1-yl)-2-oxoethyl]-1,2,3,4-tetrahydroisoquinoline;
- 2-[2-(4-cyclobutylpiperazin-1-yl)-2-oxoethyl]-6-methoxy-1,2,3,4-tetrahydroisoquinoline;
- 1-{2-[2-(4-cyclobutylpiperazin-1-yl)-2-oxoethyl]-1,2,3,4-tetrahydroisoquinolin-6-yl}ethanone;
- 1-(2-chlorophenyl)-2-[2-(4-cyclobutylpiperazin-1-yl)-2-oxoethyl]-6-methoxy-1,2,3,4-tetrahydroisoquinoline;
- 6-bromo-1-(2-chlorophenyl)-2-[2-(4-cyclobutylpiperazin-1-yl)-2-oxoethyl]-1,2,3,4-tetrahydroisoquinoline;
- 1-{1-(2-chlorophenyl)-2-[2-(4-cyclobutylpiperazin-1-yl)-2-oxoethyl]-1,2,3,4-tetrahydroisoquinolin-6-yl}ethanone;
- 2-[2-(4-cyclobutylpiperazin-1-yl)-2-oxoethyl]-N-methyl-1,2,3,4-tetrahydroisoquinoline-7-carboxamide;
- 1-(4-{2-[2-(4-cyclobutylpiperazin-1-yl)-2-oxoethyl]-1,2,3,4-tetrahydroisoquinolin-6-yl}phenyl)ethanone;
- 2-[2-(4-cyclobutylpiperazin-1-yl)-2-oxoethyl]-6-(3,5-dimethylisoxazol-4-yl)-1,2,3,4-tetrahydroisoquinoline;
- 2-[2-(4-cyclobutylpiperazin-1-yl)-2-oxoethyl]-1,2,3,4-tetrahydroisoquinoline-6-carbonitrile;
- 2-[2-(4-cyclobutylpiperazin-1-yl)-2-oxoethyl]-6-pyrimidin-5-yl-1,2,3,4-tetrahydroisoquinoline;
- 1-(4-{6-[2-(4-cyclobutylpiperazin-1-yl)-2-oxoethyl]-5,6,7,8-tetrahydropyrido[4,3-d]pyrimidin-2-yl}phenyl)ethanone;
- 4-{2-[2-(4-cyclobutylpiperazin-1-yl)-2-oxoethyl]-1,2,3,4-tetrahydroisoquinolin-6-yl}-N-methylbenzamide;
- 1-{2-[2-(4-cyclobutylpiperazin-1-yl)-2-oxoethyl]-1,2,3,4-tetrahydroisoquinolin-6-yl}propan-1-one;
- 2-[2-(4-cyclobutylpiperazin-1-yl)-2-oxoethyl]-6-[3-(methylsulfonyl)phenyl]-1,2,3,4-tetrahydroisoquinoline;
- 2-[2-(4-cyclobutylpiperazin-1-yl)-2-oxoethyl]-6-pyridin-4-yl-1,2,3,4-tetrahydroisoquinoline;
- 2-[2-(4-cyclobutylpiperazin-1-yl)-2-oxoethyl]-6-[3-(methylsulfonyl)phenyl]-1,2,3,4-tetrahydroisoquinoline;
- 2-[2-(4-cyclobutylpiperazin-1-yl)-2-oxoethyl]-N-methyl-1,2,3,4-tetrahydroisoquinoline-6-carboxamide;
- ethyl 2-[2-(4-cyclobutylpiperazin-1-yl)-2-oxoethyl]-1,2,3,4-tetrahydroisoquinoline-6-carboxylate;
- 2-[2-(4-cyclobutylpiperazin-1-yl)-2-oxoethyl]-6-[(2-methylpyrrolidin-1-yl)carbonyl]-1,2,3,4-tetrahydroisoquinoline;
- 2-[2-(4-cyclobutylpiperazin-1-yl)-2-oxoethyl]-N-cyclopentyl-1,2,3,4-tetrahydroisoquinoline-6-carboxamide;
- 2-[2-(4-cyclobutylpiperazin-1-yl)-2-oxoethyl]-6-(pyrrolidin-1-ylcarbonyl)-1,2,3,4-tetrahydroisoquinoline;
- 2-[2-(4-cyclobutylpiperazin-1-yl)-2-oxoethyl]-6-(6-methoxypyridin-3-yl)-1,2,3,4-tetrahydroisoquinoline;
- 6-bromo-2-[2-(4-cyclobutylpiperazin-1-yl)-2-oxoethyl]-1,2,3,4-tetrahydroisoquinoline;
- 2-[2-(4-cyclobutylpiperazin-1-yl)-2-oxoethyl]-6-(1,3-thiazol-4-yl)-1,2,3,4-tetrahydroisoquinoline;
- 2-[2-(4-cyclobutylpiperazin-1-yl)-2-oxoethyl]-6-(1,3-thiazol-2-yl)-1,2,3,4-tetrahydroisoquinoline;
- 2-[2-(4-cyclobutylpiperazin-1-yl)-2-oxoethyl]-6-(1H-pyrazol-1-yl)-1,2,3,4-tetrahydroisoquinoline;
- 2-[2-(4-cyclobutylpiperazin-1-yl)-2-oxoethyl]-6-(1-methyl-1H-pyrazol-4-yl)-1,2,3,4-tetrahydroisoquinoline;

2-[2-(4-cyclobutylpiperazin-1-yl)-2-oxoethyl]-6-pyrazin-2-yl-1,2,3,4-tetrahydroisoquinoline;
2-[2-(4-cyclobutylpiperazin-1-yl)-2-oxoethyl]-6-pyridazin-3-yl-1,2,3,4-tetrahydroisoquinoline;
2-[2-(4-cyclobutylpiperazin-1-yl)-2-oxoethyl]-6-pyridin-2-yl-1,2,3,4-tetrahydroisoquinoline;
2-[2-(4-cyclobutylpiperazin-1-yl)-2-oxoethyl]-6-pyrimidin-2-yl-1,2,3,4-tetrahydroisoquinoline;
2-[2-(4-cyclobutylpiperazin-1-yl)-2-oxoethyl]-6-(1,3-thiazol-5-yl)-1,2,3,4-tetrahydroisoquinoline;
1-{2-[2-(4-isopropylpiperazin-1-yl)-2-oxoethyl]-1,2,3,4-tetrahydroisoquinolin-6-yl}ethanone;
1-{2-[2-(6-methyloctahydro-2H-pyrido[1,2-a]pyrazin-2-yl)-2-oxoethyl]-1,2,3,4-tetrahydroisoquinolin-6-yl}ethanone;
2-{2-[4-(1-ethylpropyl)piperazin-1-yl]-2-oxoethyl}-6-pyrimidin-5-yl-1,2,3,4-tetrahydroisoquinoline;
2-[2-(4-cyclobutylpiperazin-1-yl)-2-oxoethyl]-6-[3-(trifluoromethyl)-1H-pyrazol-1-yl]-1,2,3,4-tetrahydroisoquinoline;
2-[2-(4-cyclobutylpiperazin-1-yl)-2-oxoethyl]-6-(6-methylpyridazin-3-yl)-1,2,3,4-tetrahydroisoquinoline;
2-{2-[4-(1-methylcyclobutyl)piperazin-1-yl]-2-oxoethyl}-6-pyrimidin-5-yl-1,2,3,4-tetrahydroisoquinoline;
6-bromo-2-(2-oxo-2-{4-[1-(trifluoromethyl)propyl]piperazin-1-yl}ethyl)-1,2,3,4-tetrahydroisoquinoline;
2-{2-[(3S)-4-cyclobutyl-3-isopropylpiperazin-1-yl]-2-oxoethyl}-6-pyrimidin-5-yl-1,2,3,4-tetrahydroisoquinoline;
2-{2-[(3R)-4-cyclobutyl-3-isopropylpiperazin-1-yl]-2-oxoethyl}-6-pyrimidin-5-yl-1,2,3,4-tetrahydroisoquinoline;
2-{2-[4-(2-methylcyclopentyl)piperazin-1-yl]-2-oxoethyl}-6-(6-methylpyridazin-3-yl)-1,2,3,4-tetrahydroisoquinoline;
2-{2-[4-(2-methylcyclopentyl)piperazin-1-yl]-2-oxoethyl}-6-pyridazin-3-yl-1,2,3,4-tetrahydroisoquinoline;
5-{2-[2-(4-cyclobutylpiperazin-1-yl)-2-oxoethyl]-1,2,3,4-tetrahydroisoquinolin-6-yl}-1-methylpyridin-2(1H)-one;
2-{2-[2-(4-cyclobutylpiperazin-1-yl)-2-oxoethyl]-1,2,3,4-tetrahydroisoquinolin-6-yl}pyridazin-3(2H)-one;
6-(benzyloxy)-2-[2-(4-cyclobutylpiperazin-1-yl)-2-oxoethyl]-1,2,3,4-tetrahydroisoquinoline;
2-[2-(4-cyclobutylpiperazin-1-yl)-2-oxoethyl]-1,2,3,4-tetrahydroisoquinolin-6-ol;
2-[2-(4-cyclobutylpiperazin-1-yl)-2-oxoethyl]-6-(cyclopentyloxy)-1,2,3,4-tetrahydroisoquinoline;
2-[2-(4-cyclobutylpiperazin-1-yl)-2-oxoethyl]-6-isopropoxy-1,2,3,4-tetrahydroisoquinoline;
2-[2-(4-cyclobutylpiperazin-1-yl)-2-oxoethyl]-6-{[5-(trifluoromethyl)pyridin-2-yl]oxy}-1,2,3,4-tetrahydroisoquinoline;
1-(2-{2-[4-(2-methylcyclopentyl)piperazin-1-yl]-2-oxoethyl}-1,2,3,4-tetrahydroisoquinolin-6-yl)ethanone;
2-[2-(4-cyclobutylpiperazin-1-yl)-2-oxoethyl]-6-(1H-1,2,4-triazol-1-yl)-1,2,3,4-tetrahydroisoquinoline;
2-[2-(4-cyclobutylpiperazin-1-yl)-2-oxoethyl]-6-(1H-1,2,3-triazol-1-yl)-1,2,3,4-tetrahydroisoquinoline;
2-[2-(4-cyclobutylpiperazin-1-yl)-2-oxoethyl]-6-(2H-1,2,3-triazol-2-yl)-1,2,3,4-tetrahydroisoquinoline;
3-{2-[2-(4-cyclobutylpiperazin-1-yl)-2-oxoethyl]-1,2,3,4-tetrahydroisoquinolin-6-yl}-1,3-oxazolidin-2-one;
1-{2-[2-(4-cyclobutylpiperazin-1-yl)-2-oxoethyl]-1,2,3,4-tetrahydroisoquinolin-6-yl}piperidin-2-one;
3-{2-[2-(4-cyclobutylpiperazin-1-yl)-2-oxoethyl]-1,2,3,4-tetrahydroisoquinolin-6-yl}-1-methylpyridin-2(1H)-one;
1-{2-[2-(4-cyclobutylpiperazin-1-yl)-2-oxoethyl]-1,2,3,4-tetrahydroisoquinolin-6-yl}pyrimidin-2(1H)-one;
2-[2-(4-cyclobutylpiperazin-1-yl)-2-oxoethyl]-6-(4-methyl-1H-pyrazol-1-yl)-1,2,3,4-tetrahydroisoquinoline;
1-{2-[2-(4-cyclobutylpiperazin-1-yl)-2-oxoethyl]-1,2,3,4-tetrahydroisoquinolin-6-yl}ethanol;
2-[2-(4-cyclobutylpiperazin-1-yl)-2-oxoethyl]-6-(2H-indazol-2-yl)-1,2,3,4-tetrahydroisoquinoline;
2-[2-(4-cyclobutylpiperazin-1-yl)-2-oxoethyl]-6-(1H-indazol-1-yl)-1,2,3,4-tetrahydroisoquinoline;
2-[2-(4-cyclobutylpiperazin-1-yl)-2-oxoethyl]-6-imidazo[1,2-a]pyridin-6-yl-1,2,3,4-tetrahydroisoquinoline;
1-{2-[2-(4-cyclobutylpiperazin-1-yl)-2-oxoethyl]-1,2,3,4-tetrahydroisoquinolin-6-yl}-1H-pyrazole-4-carboxamide;
1-{2-[2-(4-cyclobutylpiperazin-1-yl)-2-oxoethyl]-1,2,3,4-tetrahydroisoquinolin-6-yl}-1H-pyrazole-4-carbonitrile;
1-{2-[2-(4-cyclobutylpiperazin-1-yl)-2-oxoethyl]-1,2,3,4-tetrahydroisoquinolin-6-yl}acetone;
1-{2-[2-(4-cyclobutylpiperazin-1-yl)-2-oxoethyl]-1,2,3,4-tetrahydroisoquinolin-6-yl}propan-2-ol;
1-{2-[2-(4-cyclobutylpiperazin-1-yl)-2-oxoethyl]-1,2,3,4-tetrahydroisoquinolin-6-yl}ethanol;
1-{2-[2-(4-cyclobutylpiperazin-1-yl)-2-oxoethyl]-1,2,3,4-tetrahydroisoquinolin-6-yl}ethanol;
5-{2-[2-(4-cyclobutylpiperazin-1-yl)-2-oxoethyl]-1,2,3,4-tetrahydroisoquinolin-6-yl}-1-methylpyrimidin-2(1H)-one;
6-{2-[2-(4-cyclobutylpiperazin-1-yl)-2-oxoethyl]-1,2,3,4-tetrahydroisoquinolin-6-yl}-1-methylpyridin-2(1H)-one;
5-{2-[2-(4-cyclobutylpiperazin-1-yl)-2-oxoethyl]-1,2,3,4-tetrahydroisoquinolin-6-yl}-1-ethylpyridin-2(1H)-one;
5-{2-[2-(4-cyclobutylpiperazin-1-yl)-2-oxoethyl]-1,2,3,4-tetrahydroisoquinolin-6-yl}-1-propylpyridin-2(1H)-one;
5-{2-[2-(4-cyclobutylpiperazin-1-yl)-2-oxoethyl]-1,2,3,4-tetrahydroisoquinolin-6-yl}-1-isopropylpyridin-2(1H)-one;
5-{2-[2-(4-cyclobutylpiperazin-1-yl)-2-oxoethyl]-1,2,3,4-tetrahydroisoquinolin-6-yl}-1-(2,2,2-trifluoroethyl)pyridin-2(1H)-one;
6-(1,3-benzodioxol-5-yl)-2-[2-(4-cyclobutylpiperazin-1-yl)-2-oxoethyl]-1,2,3,4-tetrahydroisoquinoline;
6-(1,3-benzodioxol-5-yl)-2-[2-(4-cyclopentylpiperazin-1-yl)-2-oxoethyl]-1,2,3,4-tetrahydroisoquinoline;
2-[2-(4-cyclopentylpiperazin-1-yl)-2-oxoethyl]-6-dibenzo[b,d]furan-4-yl-1,2,3,4-tetrahydroisoquinoline;
2-[2-(4-cyclobutylpiperazin-1-yl)-2-oxoethyl]-6-(2,3-dihydro-1,4-benzodioxin-6-yl)-1,2,3,4-tetrahydroisoquinoline;
2-[2-(4-cyclopentylpiperazin-1-yl)-2-oxoethyl]-6-(2,3-dihydro-1,4-benzodioxin-6-yl)-1,2,3,4-tetrahydroisoquinoline;
2-[2-(4-isopropylpiperazin-1-yl)-2-oxoethyl]-6-[4-(methylsulfonyl)phenyl]-1,2,3,4-tetrahydroisoquinoline;
2-[2-(4-sec-butylpiperazin-1-yl)-2-oxoethyl]-6-(6-methoxypyridin-3-yl)-1,2,3,4-tetrahydroisoquinoline;
2-[2-(4-cyclohexylpiperazin-1-yl)-2-oxoethyl]-6-dibenzo[b,d]furan-4-yl-1,2,3,4-tetrahydroisoquinoline;

6-(2,3-dihydro-1,4-benzodioxin-6-yl)-2-[2-(4-isopropylpiperazin-1-yl)-2-oxoethyl]-1,2,3,4-tetrahydroisoquinoline;

2-[2-(4-isopropylpiperazin-1-yl)-2-oxoethyl]-6-(6-methoxypyridin-3-yl)-1,2,3,4-tetrahydroisoquinoline;

2-[2-(4-isopropylpiperazin-1-yl)-2-oxoethyl]-6-pyrimidin-5-yl-1,2,3,4-tetrahydroisoquinoline;

2-[2-(4-cyclobutylpiperazin-1-yl)-2-oxoethyl]-6-dibenzo[b,d]furan-4-yl-1,2,3,4-tetrahydroisoquinoline;

2-[2-(4-cyclobutylpiperazin-1-yl)-2-oxoethyl]-6-[4-(methylsulfonyl)phenyl]-1,2,3,4-tetrahydroisoquinoline;

2-[2-(4-cyclopentylpiperazin-1-yl)-2-oxoethyl]-6-[4-(methylsulfonyl)phenyl]-1,2,3,4-tetrahydroisoquinoline;

2-[2-(4-cyclopentylpiperazin-1-yl)-2-oxoethyl]-6-(6-methoxypyridin-3-yl)-1,2,3,4-tetrahydroisoquinoline;

2-[2-(4-cyclopentylpiperazin-1-yl)-2-oxoethyl]-6-pyrimidin-5-yl-1,2,3,4-tetrahydroisoquinoline;

2-[2-(4-cyclohexylpiperazin-1-yl)-2-oxoethyl]-6-pyrimidin-5-yl-1,2,3,4-tetrahydroisoquinoline;

2-[2-(4-cyclopentylpiperazin-1-yl)-2-oxoethyl]-6-[3-(methylsulfonyl)phenyl]-1,2,3,4-tetrahydroisoquinoline;

2-[2-(4-cyclohexylpiperazin-1-yl)-2-oxoethyl]-6-[3-(methylsulfonyl)phenyl]-1,2,3,4-tetrahydroisoquinoline;

2-[2-(4-sec-butylpiperazin-1-yl)-2-oxoethyl]-6-[4-(methylsulfonyl)phenyl]-1,2,3,4-tetrahydroisoquinoline;

2-[2-(4-sec-butylpiperazin-1-yl)-2-oxoethyl]-6-pyrimidin-5-yl-1,2,3,4-tetrahydroisoquinoline;

2-[2-(4-cyclobutylpiperazin-1-yl)-2-oxoethyl]-6-phenyl-1,2,3,4-tetrahydroisoquinoline;

2-[2-(4-cyclopentylpiperazin-1-yl)-2-oxoethyl]-6-phenyl-1,2,3,4-tetrahydroisoquinoline;

2-[2-(4-cyclohexylpiperazin-1-yl)-2-oxoethyl]-6-phenyl-1,2,3,4-tetrahydroisoquinoline;

6-(3-chlorophenyl)-2-[2-(4-cyclobutylpiperazin-1-yl)-2-oxoethyl]-1,2,3,4-tetrahydroisoquinoline;

6-(3-chlorophenyl)-2-[2-(4-cyclopentylpiperazin-1-yl)-2-oxoethyl]-1,2,3,4-tetrahydroisoquinoline;

6-(3-chlorophenyl)-2-[2-(4-cyclohexylpiperazin-1-yl)-2-oxoethyl]-1,2,3,4-tetrahydroisoquinoline;

6-(4-chlorophenyl)-2-[2-(4-cyclobutylpiperazin-1-yl)-2-oxoethyl]-1,2,3,4-tetrahydroisoquinoline;

6-(4-chlorophenyl)-2-[2-(4-cyclopentylpiperazin-1-yl)-2-oxoethyl]-1,2,3,4-tetrahydroisoquinoline;

6-(4-chlorophenyl)-2-[2-(4-cyclohexylpiperazin-1-yl)-2-oxoethyl]-1,2,3,4-tetrahydroisoquinoline;

2-[2-(4-cyclobutylpiperazin-1-yl)-2-oxoethyl]-6-(4-fluorophenyl)-1,2,3,4-tetrahydroisoquinoline;

2-[2-(4-cyclopentylpiperazin-1-yl)-2-oxoethyl]-6-(4-fluorophenyl)-1,2,3,4-tetrahydroisoquinoline;

2-[2-(4-cyclohexylpiperazin-1-yl)-2-oxoethyl]-6-(4-fluorophenyl)-1,2,3,4-tetrahydroisoquinoline;

2-[2-(4-cyclobutylpiperazin-1-yl)-2-oxoethyl]-6-(3-fluorophenyl)-1,2,3,4-tetrahydroisoquinoline;

2-[2-(4-cyclopentylpiperazin-1-yl)-2-oxoethyl]-6-(3-fluorophenyl)-1,2,3,4-tetrahydroisoquinoline;

2-[2-(4-cyclohexylpiperazin-1-yl)-2-oxoethyl]-6-(3-fluorophenyl)-1,2,3,4-tetrahydroisoquinoline;

6-(3-fluorophenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(2-fluorophenyl)-1,2,3,4-tetrahydroisoquinoline;

2-[2-(4-cyclopentylpiperazin-1-yl)-2-oxoethyl]-6-(2-fluorophenyl)-1,2,3,4-tetrahydroisoquinoline;

2-[2-(4-cyclobutylpiperazin-1-yl)-2-oxoethyl]-6-(2-naphthyl)-1,2,3,4-tetrahydroisoquinoline;

2-[2-(4-cyclopentylpiperazin-1-yl)-2-oxoethyl]-6-(2-naphthyl)-1,2,3,4-tetrahydroisoquinoline;

2-[2-(4-cyclohexylpiperazin-1-yl)-2-oxoethyl]-6-(2-naphthyl)-1,2,3,4-tetrahydroisoquinoline;

2-[2-(4-isopropylpiperazin-1-yl)-2-oxoethyl]-6-(2-naphthyl)-1,2,3,4-tetrahydroisoquinoline;

2-[2-(4-cyclobutylpiperazin-1-yl)-2-oxoethyl]-6-(2-fluoro-4-methylphenyl)-1,2,3,4-tetrahydroisoquinoline;

2-[2-(4-cyclopentylpiperazin-1-yl)-2-oxoethyl]-6-(2-fluoro-4-methylphenyl)-1,2,3,4-tetrahydroisoquinoline;

2-[2-(4-cyclohexylpiperazin-1-yl)-2-oxoethyl]-6-(2-fluoro-4-methylphenyl)-1,2,3,4-tetrahydroisoquinoline;

2-[2-(4-cyclobutylpiperazin-1-yl)-2-oxoethyl]-6-(2-fluoro-5-methylphenyl)-1,2,3,4-tetrahydroisoquinoline;

2-[2-(4-cyclopentylpiperazin-1-yl)-2-oxoethyl]-6-(2-fluoro-5-methylphenyl)-1,2,3,4-tetrahydroisoquinoline;

2-[2-(4-cyclohexylpiperazin-1-yl)-2-oxoethyl]-6-(2-fluoro-5-methylphenyl)-1,2,3,4-tetrahydroisoquinoline;

2-[2-(4-cyclobutylpiperazin-1-yl)-2-oxoethyl]-6-(3-fluoro-4-methylphenyl)-1,2,3,4-tetrahydroisoquinoline;

2-[2-(4-cyclopentylpiperazin-1-yl)-2-oxoethyl]-6-(3-fluoro-4-methylphenyl)-1,2,3,4-tetrahydroisoquinoline;

2-[2-(4-cyclohexylpiperazin-1-yl)-2-oxoethyl]-6-(3-fluoro-4-methylphenyl)-1,2,3,4-tetrahydroisoquinoline;

2-[2-(4-cyclobutylpiperazin-1-yl)-2-oxoethyl]-6-(4-fluoro-3-methylphenyl)-1,2,3,4-tetrahydroisoquinoline;

2-[2-(4-cyclopentylpiperazin-1-yl)-2-oxoethyl]-6-(4-fluoro-3-methylphenyl)-1,2,3,4-tetrahydroisoquinoline;

2-[2-(4-cyclohexylpiperazin-1-yl)-2-oxoethyl]-6-(4-fluoro-3-methylphenyl)-1,2,3,4-tetrahydroisoquinoline;

2-[2-(4-cyclobutylpiperazin-1-yl)-2-oxoethyl]-6-(3-methylphenyl)-1,2,3,4-tetrahydroisoquinoline;

2-[2-(4-cyclopentylpiperazin-1-yl)-2-oxoethyl]-6-(3-methylphenyl)-1,2,3,4-tetrahydroisoquinoline;

2-[2-(4-cyclohexylpiperazin-1-yl)-2-oxoethyl]-6-(3-methylphenyl)-1,2,3,4-tetrahydroisoquinoline;

2-[2-(4-cyclobutylpiperazin-1-yl)-2-oxoethyl]-6-(4-methylphenyl)-1,2,3,4-tetrahydroisoquinoline;

2-[2-(4-cyclopentylpiperazin-1-yl)-2-oxoethyl]-6-(4-methylphenyl)-1,2,3,4-tetrahydroisoquinoline;

2-[2-(4-cyclohexylpiperazin-1-yl)-2-oxoethyl]-6-(4-methylphenyl)-1,2,3,4-tetrahydroisoquinoline;

2-[2-(4-isopropylpiperazin-1-yl)-2-oxoethyl]-6-(4-methylphenyl)-1,2,3,4-tetrahydroisoquinoline;

2-[2-(4-cyclobutylpiperazin-1-yl)-2-oxoethyl]-6-(3-isopropylphenyl)-1,2,3,4-tetrahydroisoquinoline;

2-[2-(4-cyclopentylpiperazin-1-yl)-2-oxoethyl]-6-(3-isopropylphenyl)-1,2,3,4-tetrahydroisoquinoline;

2-[2-(4-cyclohexylpiperazin-1-yl)-2-oxoethyl]-6-(3-isopropylphenyl)-1,2,3,4-tetrahydroisoquinoline;

6-(3-isopropylphenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(4-isopropylphenyl)-1,2,3,4-tetrahydroisoquinoline;

2-[2-(4-cyclopentylpiperazin-1-yl)-2-oxoethyl]-6-(4-isopropylphenyl)-1,2,3,4-tetrahydroisoquinoline;
2-[2-(4-cyclohexylpiperazin-1-yl)-2-oxoethyl]-6-(4-isopropylphenyl)-1,2,3,4-tetrahydroisoquinoline;
6-(4-isopropylphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(3,4-dimethylphenyl)-1,2,3,4-tetrahydroisoquinoline;
2-[2-(4-cyclopentylpiperazin-1-yl)-2-oxoethyl]-6-(3,4-dimethylphenyl)-1,2,3,4-tetrahydroisoquinoline;
2-[2-(4-cyclohexylpiperazin-1-yl)-2-oxoethyl]-6-(3,4-dimethylphenyl)-1,2,3,4-tetrahydroisoquinoline;
6-(3,4-dimethylphenyl)-2-[2-(4-isopropylpiperazin-1-yl)-2-oxoethyl]-1,2,3,4-tetrahydroisoquinoline;
6-(4-butylphenyl)-2-[2-(4-cyclobutylpiperazin-1-yl)-2-oxoethyl]-1,2,3,4-tetrahydroisoquinoline;
6-(4-butylphenyl)-2-[2-(4-cyclopentylpiperazin-1-yl)-2-oxoethyl]-1,2,3,4-tetrahydroisoquinoline;
6-(4-butylphenyl)-2-[2-(4-cyclohexylpiperazin-1-yl)-2-oxoethyl]-1,2,3,4-tetrahydroisoquinoline;
6-(4-butylphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(3,5-dimethylphenyl)-1,2,3,4-tetrahydroisoquinoline;
2-[2-(4-cyclopentylpiperazin-1-yl)-2-oxoethyl]-6-(3,5-dimethylphenyl)-1,2,3,4-tetrahydroisoquinoline;
2-[2-(4-cyclohexylpiperazin-1-yl)-2-oxoethyl]-6-(3,5-dimethylphenyl)-1,2,3,4-tetrahydroisoquinoline;
6-(3,5-dimethylphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(4-ethylphenyl)-1,2,3,4-tetrahydroisoquinoline;
2-[2-(4-cyclopentylpiperazin-1-yl)-2-oxoethyl]-6-(4-ethylphenyl)-1,2,3,4-tetrahydroisoquinoline;
2-[2-(4-cyclohexylpiperazin-1-yl)-2-oxoethyl]-6-(4-ethylphenyl)-1,2,3,4-tetrahydroisoquinoline;
6-(4-ethylphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(4-propylphenyl)-1,2,3,4-tetrahydroisoquinoline;
2-[2-(4-cyclopentylpiperazin-1-yl)-2-oxoethyl]-6-(4-propylphenyl)-1,2,3,4-tetrahydroisoquinoline;
2-[2-(4-cyclohexylpiperazin-1-yl)-2-oxoethyl]-6-(4-propylphenyl)-1,2,3,4-tetrahydroisoquinoline;
2-[2-(4-isopropylpiperazin-1-yl)-2-oxoethyl]-6-(4-propylphenyl)-1,2,3,4-tetrahydroisoquinoline;
2-[2-(4-cyclobutylpiperazin-1-yl)-2-oxoethyl]-6-(3-ethylphenyl)-1,2,3,4-tetrahydroisoquinoline;
2-[2-(4-cyclopentylpiperazin-1-yl)-2-oxoethyl]-6-(3-ethylphenyl)-1,2,3,4-tetrahydroisoquinoline;
2-[2-(4-cyclohexylpiperazin-1-yl)-2-oxoethyl]-6-(3-ethylphenyl)-1,2,3,4-tetrahydroisoquinoline;
6-(3-ethylphenyl)-2-[2-(4-isopropylpiperazin-1-yl)-2-oxoethyl]-1,2,3,4-tetrahydroisoquinoline;
6-(4-tert-butylphenyl)-2-[2-(4-cyclobutylpiperazin-1-yl)-2-oxoethyl]-1,2,3,4-tetrahydroisoquinoline;
6-(4-tert-butylphenyl)-2-[2-(4-cyclopentylpiperazin-1-yl)-2-oxoethyl]-1,2,3,4-tetrahydroisoquinoline;
6-(4-tert-butylphenyl)-2-[2-(4-cyclohexylpiperazin-1-yl)-2-oxoethyl]-1,2,3,4-tetrahydroisoquinoline;
6-(4-tert-butylphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(3-methoxyphenyl)-1,2,3,4-tetrahydroisoquinoline;
2-[2-(4-cyclopentylpiperazin-1-yl)-2-oxoethyl]-6-(3-methoxyphenyl)-1,2,3,4-tetrahydroisoquinoline;
2-[2-(4-cyclohexylpiperazin-1-yl)-2-oxoethyl]-6-(3-methoxyphenyl)-1,2,3,4-tetrahydroisoquinoline;
2-[2-(4-cyclobutylpiperazin-1-yl)-2-oxoethyl]-6-[4-(trifluoromethoxy)phenyl]-1,2,3,4-tetrahydroisoquinoline;
2-[2-(4-cyclopentylpiperazin-1-yl)-2-oxoethyl]-6-[4-(trifluoromethoxy)phenyl]-1,2,3,4-tetrahydroisoquinoline;
2-[2-(4-cyclohexylpiperazin-1-yl)-2-oxoethyl]-6-[4-(trifluoromethoxy)phenyl]-1,2,3,4-tetrahydroisoquinoline;
2-[2-(4-isopropylpiperazin-1-yl)-2-oxoethyl]-6-[4-(trifluoromethoxy)phenyl]-1,2,3,4-tetrahydroisoquinoline;
2-[2-(4-cyclobutylpiperazin-1-yl)-2-oxoethyl]-6-(3-ethoxyphenyl)-1,2,3,4-tetrahydroisoquinoline;
2-[2-(4-cyclopentylpiperazin-1-yl)-2-oxoethyl]-6-(3-ethoxyphenyl)-1,2,3,4-tetrahydroisoquinoline;
2-[2-(4-cyclohexylpiperazin-1-yl)-2-oxoethyl]-6-(3-ethoxyphenyl)-1,2,3,4-tetrahydroisoquinoline;
6-(3-ethoxyphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(4-phenoxyphenyl)-1,2,3,4-tetrahydroisoquinoline;
2-[2-(4-cyclopentylpiperazin-1-yl)-2-oxoethyl]-6-(4-phenoxyphenyl)-1,2,3,4-tetrahydroisoquinoline;
2-[2-(4-cyclohexylpiperazin-1-yl)-2-oxoethyl]-6-(4-phenoxyphenyl)-1,2,3,4-tetrahydroisoquinoline;
2-[2-(4-isopropylpiperazin-1-yl)-2-oxoethyl]-6-(4-phenoxyphenyl)-1,2,3,4-tetrahydroisoquinoline;
2-[2-(4-cyclobutylpiperazin-1-yl)-2-oxoethyl]-6-[3-(trifluoromethoxy)phenyl]-1,2,3,4-tetrahydroisoquinoline;
2-[2-(4-cyclopentylpiperazin-1-yl)-2-oxoethyl]-6-[3-(trifluoromethoxy)phenyl]-1,2,3,4-tetrahydroisoquinoline;
2-[2-(4-cyclohexylpiperazin-1-yl)-2-oxoethyl]-6-[3-(trifluoromethoxy)phenyl]-1,2,3,4-tetrahydroisoquinoline;
2-[2-(4-isopropylpiperazin-1-yl)-2-oxoethyl]-6-[3-(trifluoromethoxy)phenyl]-1,2,3,4-tetrahydroisoquinoline;
2-[2-(4-cyclobutylpiperazin-1-yl)-2-oxoethyl]-6-[3-(methylthio)phenyl]-1,2,3,4-tetrahydroisoquinoline;
2-[2-(4-cyclopentylpiperazin-1-yl)-2-oxoethyl]-6-[3-(methylthio)phenyl]-1,2,3,4-tetrahydroisoquinoline;
2-[2-(4-cyclohexylpiperazin-1-yl)-2-oxoethyl]-6-[3-(methylthio)phenyl]-1,2,3,4-tetrahydroisoquinoline;
2-[2-(4-isopropylpiperazin-1-yl)-2-oxoethyl]-6-[3-(methylthio)phenyl]-1,2,3,4-tetrahydroisoquinoline;
2-[2-(4-cyclobutylpiperazin-1-yl)-2-oxoethyl]-6-(4'-methoxybiphenyl-4-yl)-1,2,3,4-tetrahydroisoquinoline;
2-[2-(4-cyclopentylpiperazin-1-yl)-2-oxoethyl]-6-(4'-methoxybiphenyl-4-yl)-1,2,3,4-tetrahydroisoquinoline;
2-[2-(4-cyclohexylpiperazin-1-yl)-2-oxoethyl]-6-(4'-methoxybiphenyl-4-yl)-1,2,3,4-tetrahydroisoquinoline;
2-[2-(4-isopropylpiperazin-1-yl)-2-oxoethyl]-6-(4'-methoxybiphenyl-4-yl)-1,2,3,4-tetrahydroisoquinoline;
2-[2-(4-cyclobutylpiperazin-1-yl)-2-oxoethyl]-6-(3-fluoro-4-methoxyphenyl)-1,2,3,4-tetrahydroisoquinoline;
2-[2-(4-cyclopentylpiperazin-1-yl)-2-oxoethyl]-6-(3-fluoro-4-methoxyphenyl)-1,2,3,4-tetrahydroisoquinoline;
2-[2-(4-cyclohexylpiperazin-1-yl)-2-oxoethyl]-6-(3-fluoro-4-methoxyphenyl)-1,2,3,4-tetrahydroisoquinoline;
6-(3-fluoro-4-methoxyphenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(2,5-difluoro-4-methoxyphenyl)-1,2,3,4-tetrahydroisoquinoline;

2-[2-(4-cyclopentylpiperazin-1-yl)-2-oxoethyl]-6-(2,5-difluoro-4-methoxyphenyl)-1,2,3,4-tetrahydroisoquinoline;

6-(2,5-difluoro-4-methoxyphenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(6-methoxy-2-naphthyl)-1,2,3,4-tetrahydroisoquinoline;

2-[2-(4-cyclopentylpiperazin-1-yl)-2-oxoethyl]-6-(6-methoxy-2-naphthyl)-1,2,3,4-tetrahydroisoquinoline;

2-[2-(4-cyclohexylpiperazin-1-yl)-2-oxoethyl]-6-(6-methoxy-2-naphthyl)-1,2,3,4-tetrahydroisoquinoline;

2-[2-(4-isopropylpiperazin-1-yl)-2-oxoethyl]-6-(6-methoxy-2-naphthyl)-1,2,3,4-tetrahydroisoquinoline;

2-[2-(4-cyclobutylpiperazin-1-yl)-2-oxoethyl]-6-(3-isopropoxyphenyl)-1,2,3,4-tetrahydroisoquinoline;

2-[2-(4-cyclopentylpiperazin-1-yl)-2-oxoethyl]-6-(3-isopropoxyphenyl)-1,2,3,4-tetrahydroisoquinoline;

6-(3-isopropoxyphenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(3,4,5-trimethoxyphenyl)-1,2,3,4-tetrahydroisoquinoline;

2-[2-(4-cyclopentylpiperazin-1-yl)-2-oxoethyl]-6-(3,4,5-trimethoxyphenyl)-1,2,3,4-tetrahydroisoquinoline;

2-[2-(4-cyclohexylpiperazin-1-yl)-2-oxoethyl]-6-(3,4,5-trimethoxyphenyl)-1,2,3,4-tetrahydroisoquinoline;

2-[2-(4-isopropylpiperazin-1-yl)-2-oxoethyl]-6-(3,4,5-trimethoxyphenyl)-1,2,3,4-tetrahydroisoquinoline;

2-[2-(4-cyclobutylpiperazin-1-yl)-2-oxoethyl]-6-(4-methoxyphenyl)-1,2,3,4-tetrahydroisoquinoline;

2-[2-(4-cyclopentylpiperazin-1-yl)-2-oxoethyl]-6-(4-methoxyphenyl)-1,2,3,4-tetrahydroisoquinoline;

2-[2-(4-cyclohexylpiperazin-1-yl)-2-oxoethyl]-6-(4-methoxyphenyl)-1,2,3,4-tetrahydroisoquinoline;

2-[2-(4-isopropylpiperazin-1-yl)-2-oxoethyl]-6-(4-methoxyphenyl)-1,2,3,4-tetrahydroisoquinoline;

2-[2-(4-cyclobutylpiperazin-1-yl)-2-oxoethyl]-6-(3,4-dimethoxyphenyl)-1,2,3,4-tetrahydroisoquinoline;

2-[2-(4-cyclopentylpiperazin-1-yl)-2-oxoethyl]-6-(3,4-dimethoxyphenyl)-1,2,3,4-tetrahydroisoquinoline;

2-[2-(4-cyclohexylpiperazin-1-yl)-2-oxoethyl]-6-(3,4-dimethoxyphenyl)-1,2,3,4-tetrahydroisoquinoline;

6-(3,4-dimethoxyphenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(4-ethoxyphenyl)-1,2,3,4-tetrahydroisoquinoline;

2-[2-(4-cyclopentylpiperazin-1-yl)-2-oxoethyl]-6-(4-ethoxyphenyl)-1,2,3,4-tetrahydroisoquinoline;

2-[2-(4-cyclohexylpiperazin-1-yl)-2-oxoethyl]-6-(4-ethoxyphenyl)-1,2,3,4-tetrahydroisoquinoline;

6-(4-ethoxyphenyl)-2-[2-(4-isopropylpiperazin-1-yl)-2-oxoethyl]-1,2,3,4-tetrahydroisoquinoline;

4-{2-[2-(4-cyclobutylpiperazin-1-yl)-2-oxoethyl]-1,2,3,4-tetrahydroisoquinolin-6-yl}-N,N-dimethylaniline;

4-{2-[2-(4-cyclopentylpiperazin-1-yl)-2-oxoethyl]-1,2,3,4-tetrahydroisoquinolin-6-yl}-N,N-dimethylaniline;

4-{2-[2-(4-cyclohexylpiperazin-1-yl)-2-oxoethyl]-1,2,3,4-tetrahydroisoquinolin-6-yl}-N,N-dimethylaniline;

4-{2-[2-(4-isopropylpiperazin-1-yl)-2-oxoethyl]-1,2,3,4-tetrahydroisoquinolin-6-yl}-N,N-dimethylaniline;

3-{2-[2-(4-cyclobutylpiperazin-1-yl)-2-oxoethyl]-1,2,3,4-tetrahydroisoquinolin-6-yl}-N,N-dimethylaniline;

3-{2-[2-(4-cyclopentylpiperazin-1-yl)-2-oxoethyl]-1,2,3,4-tetrahydroisoquinolin-6-yl}-N,N-dimethylaniline;

3-{2-[2-(4-cyclohexylpiperazin-1-yl)-2-oxoethyl]-1,2,3,4-tetrahydroisoquinolin-6-yl}-N,N-dimethylaniline;

3-{2-[2-(4-isopropylpiperazin-1-yl)-2-oxoethyl]-1,2,3,4-tetrahydroisoquinolin-6-yl}-N,N-dimethylaniline;

2-[2-(4-cyclobutylpiperazin-1-yl)-2-oxoethyl]-6-(4-methoxy-3-methylphenyl)-1,2,3,4-tetrahydroisoquinoline;

2-[2-(4-cyclopentylpiperazin-1-yl)-2-oxoethyl]-6-(4-methoxy-3-methylphenyl)-1,2,3,4-tetrahydroisoquinoline;

2-[2-(4-cyclohexylpiperazin-1-yl)-2-oxoethyl]-6-(4-methoxy-3-methylphenyl)-1,2,3,4-tetrahydroisoquinoline;

2-[2-(4-isopropylpiperazin-1-yl)-2-oxoethyl]-6-(4-methoxy-3-methylphenyl)-1,2,3,4-tetrahydroisoquinoline;

2-[2-(4-cyclobutylpiperazin-1-yl)-2-oxoethyl]-6-(4-propoxyphenyl)-1,2,3,4-tetrahydroisoquinoline;

2-[2-(4-cyclopentylpiperazin-1-yl)-2-oxoethyl]-6-(4-propoxyphenyl)-1,2,3,4-tetrahydroisoquinoline;

2-[2-(4-cyclohexylpiperazin-1-yl)-2-oxoethyl]-6-(4-propoxyphenyl)-1,2,3,4-tetrahydroisoquinoline;

2-[2-(4-isopropylpiperazin-1-yl)-2-oxoethyl]-6-(4-propoxyphenyl)-1,2,3,4-tetrahydroisoquinoline;

2-[2-(4-cyclobutylpiperazin-1-yl)-2-oxoethyl]-6-(4-methoxy-2-methylphenyl)-1,2,3,4-tetrahydroisoquinoline;

2-[2-(4-cyclopentylpiperazin-1-yl)-2-oxoethyl]-6-(4-methoxy-2-methylphenyl)-1,2,3,4-tetrahydroisoquinoline;

2-[2-(4-cyclohexylpiperazin-1-yl)-2-oxoethyl]-6-(4-methoxy-2-methylphenyl)-1,2,3,4-tetrahydroisoquinoline;

2-[2-(4-cyclobutylpiperazin-1-yl)-2-oxoethyl]-6-(2-methoxyphenyl)-1,2,3,4-tetrahydroisoquinoline;

2-[2-(4-cyclopentylpiperazin-1-yl)-2-oxoethyl]-6-(2-methoxyphenyl)-1,2,3,4-tetrahydroisoquinoline;

2-[2-(4-cyclohexylpiperazin-1-yl)-2-oxoethyl]-6-(2-methoxyphenyl)-1,2,3,4-tetrahydroisoquinoline;

2-[2-(4-cyclobutylpiperazin-1-yl)-2-oxoethyl]-6-(5-isopropyl-2-methoxyphenyl)-1,2,3,4-tetrahydroisoquinoline;

2-[2-(4-cyclopentylpiperazin-1-yl)-2-oxoethyl]-6-(5-isopropyl-2-methoxyphenyl)-1,2,3,4-tetrahydroisoquinoline;

2-[2-(4-cyclohexylpiperazin-1-yl)-2-oxoethyl]-6-(5-isopropyl-2-methoxyphenyl)-1,2,3,4-tetrahydroisoquinoline;

6-(5-chloro-2-methoxyphenyl)-2-[2-(4-cyclobutylpiperazin-1-yl)-2-oxoethyl]-1,2,3,4-tetrahydroisoquinoline;

6-(5-chloro-2-methoxyphenyl)-2-[2-(4-cyclohexylpiperazin-1-yl)-2-oxoethyl]-1,2,3,4-tetrahydroisoquinoline;

2-[2-(4-cyclobutylpiperazin-1-yl)-2-oxoethyl]-6-(2,5-dimethoxyphenyl)-1,2,3,4-tetrahydroisoquinoline;

2-[2-(4-cyclopentylpiperazin-1-yl)-2-oxoethyl]-6-(2,5-dimethoxyphenyl)-1,2,3,4-tetrahydroisoquinoline;

2-[2-(4-cyclohexylpiperazin-1-yl)-2-oxoethyl]-6-(2,5-dimethoxyphenyl)-1,2,3,4-tetrahydroisoquinoline;

6-(2,5-dimethoxyphenyl)-2-[2-(4-isopropylpiperazin-1-yl)-2-oxoethyl]-1,2,3,4-tetrahydroisoquinoline;

2-[2-(4-cyclobutylpiperazin-1-yl)-2-oxoethyl]-6-(2,4-dimethoxyphenyl)-1,2,3,4-tetrahydroisoquinoline;

2-[2-(4-cyclopentylpiperazin-1-yl)-2-oxoethyl]-6-(2,4-dimethoxyphenyl)-1,2,3,4-tetrahydroisoquinoline;

2-[2-(4-cyclohexylpiperazin-1-yl)-2-oxoethyl]-6-(2,4-dimethoxyphenyl)-1,2,3,4-tetrahydroisoquinoline;

2-[2-(4-cyclobutylpiperazin-1-yl)-2-oxoethyl]-6-(2-ethoxyphenyl)-1,2,3,4-tetrahydroisoquinoline;

2-[2-(4-cyclopentylpiperazin-1-yl)-2-oxoethyl]-6-(2-ethoxyphenyl)-1,2,3,4-tetrahydroisoquinoline;
2-[2-(4-cyclohexylpiperazin-1-yl)-2-oxoethyl]-6-(2-ethoxyphenyl)-1,2,3,4-tetrahydroisoquinoline;
6-(2-ethoxyphenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(5-fluoro-2-methoxyphenyl)-1,2,3,4-tetrahydroisoquinoline;
2-[2-(4-cyclopentylpiperazin-1-yl)-2-oxoethyl]-6-(5-fluoro-2-methoxyphenyl)-1,2,3,4-tetrahydroisoquinoline;
2-[2-(4-cyclobutylpiperazin-1-yl)-2-oxoethyl]-6-(2-methoxy-5-methylphenyl)-1,2,3,4-tetrahydroisoquinoline;
2-[2-(4-cyclopentylpiperazin-1-yl)-2-oxoethyl]-6-(2-methoxy-5-methylphenyl)-1,2,3,4-tetrahydroisoquinoline;
2-[2-(4-cyclohexylpiperazin-1-yl)-2-oxoethyl]-6-(2-methoxy-5-methylphenyl)-1,2,3,4-tetrahydroisoquinoline;
2-[2-(4-cyclobutylpiperazin-1-yl)-2-oxoethyl]-6-(2-phenoxyphenyl)-1,2,3,4-tetrahydroisoquinoline;
2-[2-(4-cyclopentylpiperazin-1-yl)-2-oxoethyl]-6-(2-phenoxyphenyl)-1,2,3,4-tetrahydroisoquinoline;
2-[2-(4-cyclohexylpiperazin-1-yl)-2-oxoethyl]-6-(2-phenoxyphenyl)-1,2,3,4-tetrahydroisoquinoline;
2-[2-(4-isopropylpiperazin-1-yl)-2-oxoethyl]-6-(2-phenoxyphenyl)-1,2,3,4-tetrahydroisoquinoline;
6-(3-chloro-4-fluorophenyl)-2-[2-(4-cyclobutylpiperazin-1-yl)-2-oxoethyl]-1,2,3,4-tetrahydroisoquinoline;
6-(3-chloro-4-fluorophenyl)-2-[2-(4-cyclopentylpiperazin-1-yl)-2-oxoethyl]-1,2,3,4-tetrahydroisoquinoline;
6-(3-chloro-4-fluorophenyl)-2-[2-(4-cyclohexylpiperazin-1-yl)-2-oxoethyl]-1,2,3,4-tetrahydroisoquinoline;
2-[2-(4-cyclobutylpiperazin-1-yl)-2-oxoethyl]-6-(2,5-difluorophenyl)-1,2,3,4-tetrahydroisoquinoline;
2-[2-(4-cyclopentylpiperazin-1-yl)-2-oxoethyl]-6-(2,5-difluorophenyl)-1,2,3,4-tetrahydroisoquinoline;
2-[2-(4-cyclohexylpiperazin-1-yl)-2-oxoethyl]-6-(2,5-difluorophenyl)-1,2,3,4-tetrahydroisoquinoline;
6-(2,5-difluorophenyl)-2-[2-(4-isopropylpiperazin-1-yl)-2-oxoethyl]-1,2,3,4-tetrahydroisoquinoline;
2-[2-(4-cyclobutylpiperazin-1-yl)-2-oxoethyl]-6-(2,4-difluorophenyl)-1,2,3,4-tetrahydroisoquinoline;
2-[2-(4-cyclopentylpiperazin-1-yl)-2-oxoethyl]-6-(2,4-difluorophenyl)-1,2,3,4-tetrahydroisoquinoline;
2-[2-(4-cyclohexylpiperazin-1-yl)-2-oxoethyl]-6-(2,4-difluorophenyl)-1,2,3,4-tetrahydroisoquinoline;
2-[2-(4-cyclobutylpiperazin-1-yl)-2-oxoethyl]-6-(3,4-difluorophenyl)-1,2,3,4-tetrahydroisoquinoline;
2-[2-(4-cyclopentylpiperazin-1-yl)-2-oxoethyl]-6-(3,4-difluorophenyl)-1,2,3,4-tetrahydroisoquinoline;
2-[2-(4-cyclohexylpiperazin-1-yl)-2-oxoethyl]-6-(3,4-difluorophenyl)-1,2,3,4-tetrahydroisoquinoline;
2-[2-(4-cyclobutylpiperazin-1-yl)-2-oxoethyl]-6-(3,5-dichlorophenyl)-1,2,3,4-tetrahydroisoquinoline;
6-(4-chloro-3-fluorophenyl)-2-[2-(4-cyclohexylpiperazin-1-yl)-2-oxoethyl]-1,2,3,4-tetrahydroisoquinoline;
2-[2-(4-cyclobutylpiperazin-1-yl)-2-oxoethyl]-6-(3,4-dichlorophenyl)-1,2,3,4-tetrahydroisoquinoline;
2-[2-(4-cyclopentylpiperazin-1-yl)-2-oxoethyl]-6-(3,4-dichlorophenyl)-1,2,3,4-tetrahydroisoquinoline;
2-[2-(4-cyclobutylpiperazin-1-yl)-2-oxoethyl]-6-(3,5-difluorophenyl)-1,2,3,4-tetrahydroisoquinoline;
2-[2-(4-cyclopentylpiperazin-1-yl)-2-oxoethyl]-6-(3,5-difluorophenyl)-1,2,3,4-tetrahydroisoquinoline;
2-[2-(4-cyclohexylpiperazin-1-yl)-2-oxoethyl]-6-(3,5-difluorophenyl)-1,2,3,4-tetrahydroisoquinoline;
2-[2-(4-cyclobutylpiperazin-1-yl)-2-oxoethyl]-6-(2,3-difluorophenyl)-1,2,3,4-tetrahydroisoquinoline;
2-[2-(4-cyclopentylpiperazin-1-yl)-2-oxoethyl]-6-(2,3-difluorophenyl)-1,2,3,4-tetrahydroisoquinoline;
2-[2-(4-cyclohexylpiperazin-1-yl)-2-oxoethyl]-6-(2,3-difluorophenyl)-1,2,3,4-tetrahydroisoquinoline;
6-(2,3-difluorophenyl)-2-[2-(4-isopropylpiperazin-1-yl)-2-oxoethyl]-1,2,3,4-tetrahydroisoquinoline;
2-[2-(4-ethylpiperazin-1-yl)-2-oxoethyl]-6-pyrimidin-5-yl-1,2,3,4-tetrahydroisoquinoline;
2-[2-(4-butylpiperazin-1-yl)-2-oxoethyl]-6-pyrimidin-5-yl-1,2,3,4-tetrahydroisoquinoline;
2-[2-(4-isobutylpiperazin-1-yl)-2-oxoethyl]-6-pyrimidin-5-yl-1,2,3,4-tetrahydroisoquinoline;
2-{2-[(3R)-4-sec-butyl-3-methylpiperazin-1-yl]-2-oxoethyl}-6-pyrimidin-5-yl-1,2,3,4-tetrahydroisoquinoline;
2-{2-[4-(1,2-dimethylpropyl)piperazin-1-yl]-2-oxoethyl}-6-pyrimidin-5-yl-1,2,3,4-tetrahydroisoquinoline;
2-{2-[4-(1-cyclopropylethyl)piperazin-1-yl]-2-oxoethyl}-6-pyrimidin-5-yl-1,2,3,4-tetrahydroisoquinoline;
2-{2-[(3S)-4-cyclopentyl-3-methylpiperazin-1-yl]-2-oxoethyl}-6-pyrimidin-5-yl-1,2,3,4-tetrahydroisoquinoline;
2-{2-[(3R)-4-cyclopentyl-3-methylpiperazin-1-yl]-2-oxoethyl}-6-pyrimidin-5-yl-1,2,3,4-tetrahydroisoquinoline;
2-{2-[4-(2-methylcyclopentyl)piperazin-1-yl]-2-oxoethyl}-6-pyrimidin-5-yl-1,2,3,4-tetrahydroisoquinoline;
2-{2-[(3S)-3-methyl-4-(2-methylcyclopentyl)piperazin-1-yl]-2-oxoethyl}-6-pyrimidin-5-yl-1,2,3,4-tetrahydroisoquinoline;
2-{2-[(3S)-4-cyclohexyl-3-methylpiperazin-1-yl]-2-oxoethyl}-6-pyrimidin-5-yl-1,2,3,4-tetrahydroisoquinoline;
2-{2-[(3R)-4-cyclo hexyl-3-methylpiperazin-1-yl]-2-oxoethyl}-6-pyrimidin-5-yl-1,2,3,4-tetrahydroisoquinoline;
2-{2-[4-(2-methylcyclohexyl)piperazin-1-yl]-2-oxoethyl}-6-pyrimidin-5-yl-1,2,3,4-tetrahydroisoquinoline;
2-{2-oxo-2-[4-(tetrahydro-2H-pyran-4-yl)piperazin-1-yl]ethyl}-6-pyrimidin-5-yl-1,2,3,4-tetrahydroisoquinoline;
2-{2-[(3S)-3-methyl-4-(tetrahydro-2H-pyran-4-yl)piperazin-1-yl]-2-oxoethyl}-6-pyrimidin-5-yl-1,2,3,4-tetrahydroisoquinoline;
2-(2-{4-[(1R,4S)-bicyclo[2.2.1]hept-2-yl]piperazin-1-yl}-2-oxoethyl)-6-pyrimidin-5-yl-1,2,3,4-tetrahydroisoquinoline;
2-(2-{(3S)-4-[(1R,4S)-bicyclo[2.2.1]hept-2-yl]-3-methylpiperazin-1-yl}-2-oxoethyl)-6-pyrimidin-5-yl-1,2,3,4-tetrahydroisoquinoline;
4-{2-[2-(4-cyclobutylpiperazin-1-yl)-2-oxoethyl]-1,2,3,4-tetrahydroisoquinolin-6-yl}-N,N-diethylaniline;
2-[2-(4-cyclobutylpiperazin-1-yl)-2-oxoethyl]-6-(4-fluoro-2-methylphenyl)-1,2,3,4-tetrahydroisoquinoline;
2-{2-[2-(4-cyclobutylpiperazin-1-yl)-2-oxoethyl]-1,2,3,4-tetrahydroisoquinolin-6-yl}benzonitrile;
2-[2-(4-cyclobutylpiperazin-1-yl)-2-oxoethyl]-6-(6-methylpyridin-2-yl)-1,2,3,4-tetrahydroisoquinoline;
2-[2-(4-cyclobutylpiperazin-1-yl)-2-oxoethyl]-6-(5-methylpyridin-2-yl)-1,2,3,4-tetrahydroisoquinoline;
2-[2-(4-cyclobutylpiperazin-1-yl)-2-oxoethyl]-6-(4-methylpyridin-2-yl)-1,2,3,4-tetrahydroisoquinoline;

6-(5-chloropyridin-2-yl)-2-[2-(4-cyclobutylpiperazin-1-yl)-2-oxoethyl]-1,2,3,4-tetrahydroisoquinoline;
2-[2-(4-cyclobutylpiperazin-1-yl)-2-oxoethyl]-6-[5-(trifluoromethyl)pyridin-2-yl]-1,2,3,4-tetrahydroisoquinoline;
2-[2-(4-cyclobutylpiperazin-1-yl)-2-oxoethyl]-6-(6-methoxypyridin-2-yl)-1,2,3,4-tetrahydroisoquinoline;
2-{2-[2-(4-cyclobutylpiperazin-1-yl)-2-oxoethyl]-1,2,3,4-tetrahydroisoquinolin-6-yl}quinoline;
2-[2-(4-cyclobutylpiperazin-1-yl)-2-oxoethyl]-6-(2,6-dimethoxypyrimidin-4-yl)-1,2,3,4-tetrahydroisoquinoline;
2-[2-(4-cyclobutylpiperazin-1-yl)-2-oxoethyl]-6-[4-(trifluoromethyl)pyrimidin-2-yl]-1,2,3,4-tetrahydroisoquinoline;
2'-[2-(4-cyclobutylpiperazin-1-yl)-2-oxoethyl]-1',2',3',4'-tetrahydro-1,6'-biisoquinoline;
3-{2-[2-(4-cyclobutylpiperazin-1-yl)-2-oxoethyl]-1,2,3,4-tetrahydroisoquinolin-6-yl}quinoline;
2-[2-(4-cyclobutylpiperazin-1-yl)-2-oxoethyl]-6-(1H-indol-4-yl)-1,2,3,4-tetrahydroisoquinoline;
1-(2-{2-[2-(4-cyclobutylpiperazin-1-yl)-2-oxoethyl]-1,2,3,4-tetrahydroisoquinolin-6-yl}phenyl)-N,N-dimethylmethanamine;
1-(3-{2-[2-(4-cyclobutylpiperazin-1-yl)-2-oxoethyl]-1,2,3,4-tetrahydroisoquinolin-6-yl}phenyl)-N,N-dimethylmethanamine;
1-(4-{2-[2-(4-cyclobutylpiperazin-1-yl)-2-oxoethyl]-1,2,3,4-tetrahydroisoquinolin-6-yl}phenyl)-N,N-dimethylmethanamine;
2-(2-{2-[2-(4-cyclobutylpiperazin-1-yl)-2-oxoethyl]-1,2,3,4-tetrahydroisoquinolin-6-yl}phenyl)-N,N-dimethylethanamine;
2-(3-{2-[2-(4-cyclobutylpiperazin-1-yl)-2-oxoethyl]-1,2,3,4-tetrahydroisoquinolin-6-yl}phenyl)-N,N-dimethylethanamine;
2-(4-{2-[2-(4-cyclobutylpiperazin-1-yl)-2-oxoethyl]-1,2,3,4-tetrahydroisoquinolin-6-yl}phenyl)-N,N-dimethylethanamine;
2-[2-(4-cyclobutylpiperazin-1-yl)-2-oxoethyl]-6-[5-(methoxymethyl)pyridin-2-yl]-1,2,3,4-tetrahydroisoquinoline;
2-[2-(4-cyclobutylpiperazin-1-yl)-2-oxoethyl]-6-(5-isopropylpyridin-2-yl)-1,2,3,4-tetrahydroisoquinoline;
2-[2-(4-cyclobutylpiperazin-1-yl)-2-oxoethyl]-6-[6-(trifluoromethyl)pyridin-3-yl]-1,2,3,4-tetrahydroisoquinoline;
2-[2-(4-cyclobutylpiperazin-1-yl)-2-oxoethyl]-6-(6-isopropylpyridin-3-yl)-1,2,3,4-tetrahydroisoquinoline;
(4-Cyclobutyl-piperazin-1-yl)-(6-pyrimidin-5-yl-3,4-dihydro-1H-isoquinolin-2-yl)-methanone;
2-[2-(4-Cyclobutyl-piperazin-1-yl)-2-oxo-ethyl]-1,2,3,4-tetrahydro-isoquinoline-6-carboxylic acid methyl ester;
2-[2-(4-Cyclobutyl-piperazin-1-yl)-2-oxo-ethyl]-1,2,3,4-tetrahydro-isoquinoline-6-carboxylic acid; or
1-[1,4]Bipiperidinyl-1'-yl-2-(6-methanesulfonyl-3,4-dihydro-1H-isoquinolin-2-yl)-ethanone.

* * * * *